United States Patent
Callahan et al.

(10) Patent No.: US 10,351,530 B2
(45) Date of Patent: Jul. 16, 2019

(54) ARYLCYCLOHEXYL PYRAZOLES AS NRF2 REGULATORS

(71) Applicants: GlaxoSmithKline Intellectual Property Development Limited, Brentford, Middlesex (GB); Astex Therapeutics Limited, Cambridge, Cambridgeshire (GB)

(72) Inventors: James Callahan, King of Prussia, PA (US); Jeffrey K. Kerns, King of Prussia, PA (US); Tindy Li, King of Prussia, PA (US); Brent W. McCleland, King of Prussia, PA (US); Hong Nie, King of Prussia, PA (US); Joseph E. Pero, Anderson, SC (US); Thomas Glanmor Davies, Cambridge (GB); Charlotte Mary Griffiths-Jones, Cambridge (GB); Thomas Daniel Heightman, Cambridge (GB); Steven Howard, Cambridge (GB); David Norton, Cambridge (GB); Marinus Leendert Verdonk, Cambridge (GB); Alison Jo-Anne Woolford, Cambridge (GB)

(73) Assignees: GlaxoSmithKline Intellectual Property Development Limited, Brentford, Middlesex (GB); Astex Therapeutics Limited, Cambridge, Cambridgeshire (GB)

( * ) Notice: Subject to any disclaimer, the term of this patent is extended or adjusted under 35 U.S.C. 154(b) by 0 days.

(21) Appl. No.: 15/765,377

(22) PCT Filed: Oct. 6, 2016

(86) PCT No.: PCT/IB2016/055997
§ 371 (c)(1),
(2) Date: Apr. 2, 2018

(87) PCT Pub. No.: WO2017/060855
PCT Pub. Date: Apr. 13, 2017

(65) Prior Publication Data
US 2018/0282283 A1    Oct. 4, 2018

Related U.S. Application Data

(60) Provisional application No. 62/237,659, filed on Oct. 6, 2015.

(51) Int. Cl.
| | | |
|---|---|---|
| C07D 231/14 | (2006.01) | |
| C07D 401/04 | (2006.01) | |
| C07D 401/06 | (2006.01) | |
| C07D 401/10 | (2006.01) | |
| C07D 401/12 | (2006.01) | |
| C07D 401/14 | (2006.01) | |
| C07D 403/08 | (2006.01) | |
| C07D 403/10 | (2006.01) | |
| C07D 403/14 | (2006.01) | |

(52) U.S. Cl.
CPC ......... C07D 231/14 (2013.01); C07D 401/04 (2013.01); C07D 401/06 (2013.01); C07D 401/10 (2013.01); C07D 401/12 (2013.01); C07D 401/14 (2013.01); C07D 403/08 (2013.01); C07D 403/10 (2013.01); C07D 403/14 (2013.01)

(58) Field of Classification Search
CPC .. C07D 231/14; C07D 401/10; C07D 401/14; C07D 403/08; C07D 403/10; C07D 403/14
USPC .................................................. 514/217.09
See application file for complete search history.

(56) References Cited

U.S. PATENT DOCUMENTS

| | | | |
|---|---|---|---|
| 2016/0318917 A1* | 11/2016 | Boehm | C07D 417/10 |
| 2018/0169110 A1* | 6/2018 | Kerns | C07D 403/06 |
| 2018/0179167 A1* | 6/2018 | Kerns | C07D 249/18 |
| 2018/0179187 A1* | 6/2018 | Kerns | C07D 401/14 |

FOREIGN PATENT DOCUMENTS

| | | | | |
|---|---|---|---|---|
| WO | WO-2004092140 A1 * | 10/2004 | | C07D 231/14 |
| WO | WO-2009032249 A1 * | 3/2009 | | C07D 401/04 |
| WO | WO-2010099054 A2 * | 9/2010 | | C07D 401/04 |
| WO | WO 2016/001876 A1 | 1/2016 | | |
| WO | WO-2016001878 A1 * | 1/2016 | ......... | A61K 31/4545 |
| WO | WO-2017060854 A1 * | 4/2017 | | C07D 401/14 |

OTHER PUBLICATIONS

Biswal; Proc Am Thorac Soc 2012, 9, 47-51. (Year: 2012).*

(Continued)

*Primary Examiner* — Daniel R Carcanague
(74) *Attorney, Agent, or Firm* — Nora L. Stein; Fang Qian; Edward R. Gimmi

(57) ABSTRACT

The present invention relates to arylcyclohexyl pyrazole compounds of Formula (I)

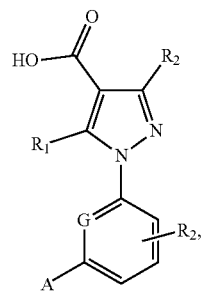

Formula (I)

methods of making them, pharmaceutical compositions containing them and their use as NRF2 regulators.

8 Claims, No Drawings

(56) References Cited

OTHER PUBLICATIONS

Layzer; Section Five-Degenerative Diseases of the Nervous System, Cecil Textbook of Medicine, 20th edition (1996),vol. 2, pp. 2050-2057. (Year: 1996).*

Damasio; Alzheimer's Disease and Related Dementias, Cecil Textbook of Medicine, 20th edition (1996), vol. 2, pp. 1992-1996. (Year: 1996).*

"FDA mulls drug to slow late-stage Alzheimer's," [retrieved on Sep. 23, 2003], Retrieved online via Internet, URL: http://www.cnn.com/2003/HEALTH/conditions/09/24/alzheimers.drug.ap/index.html (Year: 2003).*

* cited by examiner

ARYLCYCLOHEXYL PYRAZOLES AS NRF2 REGULATORS

This application is a 371 national phase entry of International Application No. PCT/IB2016/055997, filed Oct. 6, 2016, which claims the benefit of U.S. Provisional Application No. 62/237,659, filed Oct. 6, 2015, which is incorporated herein in its entirety.

FIELD OF THE INVENTION

The present invention relates to arylcyclohexyl pyrazole compounds, methods of making them, pharmaceutical compositions containing them and their use as NRF2 regulators.

BACKGROUND OF THE INVENTION

NRF2 (NF-E2 related factor 2) is a member of the cap-n-collar family of transcription factors containing a characteristic basic-leucine zipper motif. Under basal conditions, NRF2 levels are tightly controlled by the cytosolic actin-bound repressor, KEAP1 (Kelch-like ECH associating protein 1), which binds to NRF2 and targets it for ubiquitylation and proteasomal degradation via the Cul3-based E3-ubiquitin ligase complex. Under conditions of oxidative stress, DJ1 (PARK7) is activated and stabilizes NRF2 protein by preventing NRF2 from interacting with KEAP1. Also, modification of reactive cysteines on KEAP1 can cause a conformational change in KEAP1 that alters NRF2 binding and promotes NRF2 stabilization. Thus, the levels of NRF2 in the cell are usually kept low in normal conditions but the system is designed to respond quickly to environmental stress by increasing NRF2 levels and thus downstream NRF2 activity.

Inappropriately low NRF2 activity in the face of on-going oxidative stress appears to be a pathological mechanism underlying chronic obstructive pulmonary disease (COPD). Yamada, K., et al. *BMC Pulmonary Medicine*, 2016, 16: 27. This may be a result of an altered equilibrium between NRF2 regulators with both inappropriate lack of positive regulators such as DJ1, and overabundance of negative regulators such as Keap1 and Bach1. Therefore, restoration of NRF2 activity in the lungs of COPD patients should result in repair of the imbalance and mitigation of deleterious processes such as apoptosis of structural cells (including alveolar epithelial and endothelial cells) and inflammation. The results of these effects would be enhanced cytoprotection, preservation of lung structure, and structural repair in the COPD lung, thus slowing disease progression. Therefore, NRF2 modulators may treat COPD (Boutten, A., et al. 2011. *Trends Mol. Med.* 17:363-371) and other respiratory diseases, including asthma and pulmonary fibrosis (Cho, H. Y., and Kleeberger, S. R. 2010. *Toxicol. Appl. Pharmacol.* 244:43-56).

The therapeutic potential of an NRF2 activator is exemplified in pulmonary macrophages from COPD patients where NRF2 pathway appears maladaptive. These cells have impaired bacterial phagocytosis compared with similar cells from control patients, and this effect is reversed by the addition of NRF2 activators in vitro. Therefore, in addition to the effects mentioned above, restoration of appropriate NRF2 activity could also rescue COPD exacerbations by reducing lung infection.

This is demonstrated by the NRF2 activator, Sulforaphane, which increases the expression of Macrophage Receptor with Collagenous structure (MARCO) by COPD macrophages and alveolar macrophages from cigarette smoke-exposed mice, thereby improving in these cells bacterial phagocytosis (Pseudomonas aeruginosa, non-typable *Haemophilus influenzae*) and bacterial clearance both ex vivo and in vivo. (Harvey, C. J., et al. 2011. *Sci. Transl. Med.* 3:78ra32).

The therapeutic potential of targeting NRF2 in the lung is not limited to COPD. Rather, targeting the NRF2 pathway could provide treatments for other human lung and respiratory diseases that exhibit oxidative stress components such as chronic asthma and acute asthma, lung disease secondary to environmental exposures including but not limited to ozone, diesel exhaust and occupational exposures, fibrosis, acute lung infection (e.g., viral (Noah, T. L. et al. 2014. *PLoS ONE* 9(6): e98671), bacterial or fungal), chronic lung infection, α1 antitrypsin disease, and cystic fibrosis (C F, Chen, J. et al. 2008. *PLoS One*. 2008; 3(10):e3367).

A therapy that targets the NRF2 pathway also has many potential uses outside the lung and respiratory system. Many of the diseases for which an NRF2 activator may be useful are autoimmune diseases (psoriasis, IBD, MS), suggesting that an NRF2 activator may be useful in autoimmune diseases in general.

In the clinic, a drug targeting the NRF2 pathway (bardoxolone methyl) has shown efficacy in diabetic patients with diabetic nephropathy/chronic kidney disease (CKD) (Aleksunes, L. M., et al. 2010. *J. Pharmacol. Exp. Ther.* 335:2-12), though phase III trials with this drug in patients with the most severe stage of CKD were terminated. Furthermore, there is evidence to suspect that such a therapy would be effective in sepsis-induced acute kidney injury, other acute kidney injury (AKI) (Shelton, L. M., et al. 2013. *Kidney International*. June 19. doi: 10.1038/ki0.2013.248.), and kidney disease or malfunction seen during kidney transplantation.

In the cardiac area, bardoxolone methyl is currently under investigation in patients 30 with Pulmonary Arterial Hypertension and so a drug targeting NRF2 by other mechanisms may also be useful in this disease area. Oxidative stress is increased in the diseased myocardium, resulting in accumulation of reactive oxygen species (ROS) which impairs cardiac function [*Circ* (1987) 76(2); 458-468] and increases susceptibility to arrhythmia [*J of Mol & Cell Cardio* (1991) 23(8); 899-918] by a direct toxic effect of increased necrosis and apoptosis [*Circ Res* (2000) 87(12); 1172-1179]. In a mouse model of pressure overload (TAC), NRF2 gene and protein expression is increased during the early stage of cardiac adaptive hypertrophy, but decreased in the later stage of maladaptive cardiac remodeling associated with systolic dysfunction [*Arterioscler Thromb Vasc Biol* (2009) 29(11); 1843-5 1850; *PLOS ONE* (2012) 7(9); e44899]. In addition, NRF2 activation has been shown to suppress myocardial oxidative stress as well as cardiac apoptosis, fibrosis, hypertrophy, and dysfunction in mouse models of pressure overload [*Arterioscler Thromb Vasc Biol* (2009) 29(11); *J of Mol & Cell Cardio* (2014) 72; 305-315; and 1843-1850; *PLOS ONE* (2012) 7(9); e44899]. NRF2 activation has also been shown to protect against cardiac I/R injury in mice 10 [*Circ Res* (2009) 105(4); 365-374; *J of Mol & Cell Cardio* (2010) 49(4); 576-586] and reduce myocardial oxidative damage following cardiac I/R injury in rat. Therefore, a drug targeting NRF2 by other mechanisms may be useful in a variety of cardiovascular diseases including but not limited to atherosclerosis, hypertension, and heart failure (Oxidative Medicine and Cellular Longevity Volume 2013 (2013), Article ID 104308, 10 pages), acute coronary 15 syndrome, myocardial infarction, myocardial repair, cardiac remodeling, cardiac arrhythmias, heart failure with preserved ejection fraction, heart failure with reduced ejection fraction and diabetic cardiomyopathy.

A drug activating the NRF2 pathway could also be useful for treatment of several neurodegenerative diseases including Parkinson's disease (PD), Alzheimer's disease (AD), amyotrophic lateral sclerosis (ALS) (Brain Res. 2012 Mar. 29; 1446:109-18. 2011.12.064. Epub 2012 Jan. 12.) and multiple sclerosis (MS). Multiple in vivo models have shown that NRF2 KO mice are more sensitive to neurotoxic insults than their wild-type counterparts. Treatment of rats with the NRF2 activator tert-butylhydroquinone (tBHQ) reduced cortical damage in rats in a cerebral ischemia-reperfusion model, and cortical glutathione levels were increased in NRF2 wild-type but not KO mice after administration of tBHQ (Shih, A. Y., et al. 2005. *J. Neurosci.* 25: 10321-10335). Tecfidera™ (dimethyl fumarate), which activates NRF2 among other targets, is approved in the U.S. to treat relapsing-remitting multiple sclerosis (MS). Activation of NRF2 may also help treat cases of Friedreich's Ataxia, where increased sensitivity to oxidative stress and impaired NRF2 activation has been reported (Paupe V., et al, 2009. PLoS One; 4(1):e4253. Omaveloxolone (RTA-408) is also in clinical trials for Friedreich's Ataxia.

There is preclinical evidence of the specific protective role of the NRF2 pathway in models of inflammatory bowel disease (IBD, Crohn's Disease and Ulcerative Colitis) and/or colon cancer (Khor, T. O., et al 2008. *Cancer Prev. Res.* (*Phila*) 1:187-191).

Age-related macular degeneration (AMD) is a common cause of vision loss in people over the age of 50. Cigarette smoking is a major risk factor for the development of non-neovascular (dry) AMD and perhaps also neovascular (wet) AMD. Findings in vitro and in preclinical species support the notion that the NRF2 pathway is involved in the anti-oxidant response of retinal epithelial cells and modulation of inflammation in preclinical models of eye injury (Schimel, et al. 2011. *Am. J. Pathol.* 178:2032-2043). Fuchs Endothelial Corneal Dystrophy (FECD) is a progressive, blinding disease characterized by corneal endothelial cells apoptosis. It is a disease of aging and increased oxidative stress related to low levels of NRF2 expression and/or function (Bitar, M. S., et al. 2012. *Invest Ophthalmol. Vis. Sci.* Aug. 24, 2012 vol. 53 no. 9 5806-5813). In addition, an NRF2 activator may be useful in uveitis or other inflammatory eye conditions.

Non-alcoholic steatohepatitis (NASH) is a disease of fat deposition, inflammation, and damage in the liver that occurs in patients who drink little or no alcohol. In preclinical models, development of NASH is greatly accelerated in KO mice lacking NRF2 when challenged with a methionine- and choline-deficient diet (Chowdhry S., et al. 2010. *Free Rad. Biol. & Med.* 48:357-371). Administration of the NRF2 activators oltipraz and NK-252 in rats on a choline-deficient L-amino acid-defined diet significantly attenuated progression of histologic abnormalities, especially hepatic fibrosis (Shimozono R. et al. 2012. *Molecular Pharmacology.* 84:62-70). Other liver diseases that may be amenable to NRF2 modulation are toxin-induced liver disease (e.g., acetaminophen-induced hepatic disease), viral hepatitis, and cirrhosis (Oxidative Medicine and Cellular Longevity Volume 2013 (2013), Article ID 763257, 9 page).

Recent studies have also begun to elucidate the role of ROS in skin diseases such as psoriasis. A study in psoriasis patients showed an increase in serum malondialdehyde and nitric oxide end products and a decrease in erythrocyte-superoxide dismutase activity, catalase activity, and total antioxidant status that correlated in each case with disease severity index (Dipali P. K., et al. Indian J Clin Biochem. 2010 October; 25(4): 388-392). Also, an NRF2 modulator may be useful in treating the dermatitis/topical effects of radiation (Schäfer, M. et al. 2010. *Genes & Devl.* 24:1045-1058), and the immunosuppression due to radiation exposure (Kim, J. H. et al., J. Clin. Invest. 2014 Feb. 3; 124(2): 730-41).

There are also data suggesting that an NRF2 activator may be beneficial in preeclampsia, a disease that occurs in 2-5% of pregnancies and involves hypertension and proteinuria (*Annals of Anatomy—Anatomischer Anzeiger Volume* 196, *Issue* 5, September 2014, Pages 268-277).

Preclinical data has shown that compounds with NRF2 activating activity are better at reversing high altitude-induced damage than compounds without NRF2 activity, using animal and cellular models of Acute Mountain Sickness (Lisk C. et al, 2013, Free Radic Biol Med. October 2013; 63: 264-273.)

SUMMARY OF THE INVENTION

In one aspect, this invention provides for arylcyclohexyl pyrazole analogs, or a salt, particularly a pharmaceutically acceptable salt thereof, and pharmaceutical compositions containing them. In particular, the compounds of this invention include a compound of Formula (I) and Formula (Ia).

In a second aspect, this invention provides for the use of the compounds of Formula (I) and Formula (Ia) as NRF2 regulators.

Accordingly, the present invention is also directed to a method of regulating NRF2 which method comprises contacting a cell with a compound according to Formula (I) and Formula (Ia), or a salt, particularly a pharmaceutically acceptable salt, thereof.

In another aspect, this invention provides for the use of the compounds of Formula (I) and Formula (Ia) for treating and preventing conditions associated with NRF2 imbalance.

In one aspect, the invention is provides a pharmaceutical composition comprising a compound of the invention according to Formula (I) and Formula (Ia), or a salt, particularly a pharmaceutically acceptable salt thereof, and a pharmaceutically acceptable excipient. Particularly, this invention is directed to a pharmaceutical composition for the treatment of an NRF2 regulated disease or disorder, wherein the composition comprises a compound according to Formula (I) and Formula (Ia), or a salt, particularly a pharmaceutically acceptable salt thereof, and a pharmaceutically acceptable excipient.

In a further aspect, this invention provides for a method of treating a respiratory or non-respiratory disorder, including COPD, asthma, fibrosis, chronic asthma and acute asthma, lung disease secondary to environmental exposures, acute lung infection, chronic lung infection, $\alpha 1$ antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodeling, cardiac arrhythmias, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness, which comprises administering to a human in need thereof, a compound of Formula (I) and Formula (Ia).

In one aspect, this invention relates to a method of treating COPD, which comprises administering to a human in need thereof, a compound of Formula (I) and Formula (Ia), or a salt, particularly a pharmaceutically acceptable salt thereof.

In one aspect, this invention relates to a method of treating heart failure, which comprises administering to a human in need thereof, a compound of Formula (I) and Formula (Ia), or a salt, particularly a pharmaceutically acceptable salt thereof.

In yet another aspect, this invention provides for the use of a compound of Formula (I) and Formula (Ia), or a salt, particularly a pharmaceutically acceptable salt thereof, for the treatment of a respiratory or non-respiratory disorder, including COPD, asthma, fibrosis, chronic asthma and acute asthma, lung disease secondary to environmental exposures, acute lung infection, chronic lung infection, α1 antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodeling, cardiac arrhythmias, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

In one aspect, this invention relates to the use of a compound of Formula (I) and Formula (Ia), or a salt, particularly a pharmaceutically acceptable salt thereof, for the treatment of COPD.

In one aspect, this invention relates to the use of a compound of Formula (I) and Formula (Ia), or a salt, particularly a pharmaceutically acceptable salt thereof, for the treatment of heart failure.

In a further aspect, this invention relates to use of a compound of Formula (I) and Formula (Ia), or a salt, particularly a pharmaceutically acceptable salt thereof, in the manufacture of a medicament for use in the treatment of a respiratory or non-respiratory disorder, including COPD, asthma, fibrosis, chronic asthma and acute asthma, lung disease secondary to environmental exposures, acute lung infection, chronic lung infection, α1 antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodeling, cardiac arrhythmias, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

In one aspect, this invention relates to use of a compound of Formula (I) and Formula (Ia), or a salt, particularly a pharmaceutically acceptable salt thereof, in the manufacture of a medicament for the treatment of COPD.

In one aspect, this invention relates to use of a compound of Formula (I) and Formula (Ia), or a salt, particularly a pharmaceutically acceptable salt thereof, in the manufacture of a medicament for the treatment of heart failure.

In a further aspect, this invention relates to a compound of Formula (I) and Formula (Ia), or a salt, particularly a pharmaceutically acceptable salt thereof, for use in medical therapy. This invention relates to a compound of Formula (I) and Formula (Ia), or a salt, particularly a pharmaceutically acceptable salt thereof, for use in therapy, specifically for use in the treatment of a respiratory or non-respiratory disorder, including COPD, asthma, fibrosis, chronic asthma and acute asthma, lung disease secondary to environmental exposures, acute lung infection, chronic lung infection, α1 antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodeling, cardiac arrhythmias, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

In one aspect, this invention relates to a compound of Formula (I) and Formula (Ia), or a salt, particularly a pharmaceutically acceptable salt thereof, for use in the treatment of COPD.

In one aspect, this invention relates to a compound of Formula (I) and Formula (Ia), or a salt, particularly a pharmaceutically acceptable salt thereof, for use in the treatment of heart failure.

The compounds of Formula (I) and Formula (Ia) and pharmaceutically acceptable salts thereof may be used in combination with one or more other agents which may be useful in the prevention or treatment of allergic disease, inflammatory disease, autoimmune disease, for example; antigen immunotherapy, anti-histamines, corticosteroids, (e.g., fluticasone propionate, fluticasone furoate, beclomethasone dipropionate, budesonide, ciclesonide, mometasone furoate, triamcinolone, flunisolide), NSAIDs, leukotriene modulators (e.g., montelukast, zafirlukast, pranlukast), iNOS inhibitors, tryptase inhibitors, IKK2 inhibitors, p38 inhibitors, Syk inhibitors, protease inhibitors such as elastase inhibitors, integrin antagonists (e.g., beta-2 integrin antagonists), adenosine A2a agonists, mediator release inhibitors such as sodium chromoglycate, 5-lipoxygenase inhibitors (zyflo), DP1 antagonists, DP2 antagonists, PI3K delta inhibitors, ITK inhibitors, LP (lysophosphatidic) inhibitors or FLAP (5-lipoxygenase activating protein) inhibitors (e.g., sodium 3-(3-(tert-butylthio)-1-(4-(6-ethoxy-pyridin-3-yl)benzyl)-5-((5-methylpyridin-2-yl)methoxy)-1H-indol-2-yl)-2,2-dimethylpropanoate), bronchodilators (e.g., muscarinic antagonists, beta-2 agonists), methotrexate, and similar agents; monoclonal antibody therapy such as anti-IgE, anti-TNF, anti-IL-5, anti-IL-6, anti-IL-12, anti-IL-1 and similar agents; cytokine receptor therapies e.g. etanercept and similar agents; antigen non-specific immunotherapies (e.g. interferon or other cytokines/chemokines, chemokine receptor modulators such as CCR3, CCR4 or CXCR2 antagonists, other cytokine/chemokine agonists or antagonists, TLR agonists and similar agents).

Suitably, for the treatment of asthma, compounds or pharmaceutical formulations of the invention may be administered together with an anti-inflammatory agent such as, for example, a corticosteroid, or a pharmaceutical formulation thereof. For example, a compound of the invention may be formulated together with an anti-inflammatory agent, such as a corticosteroid, in a single formulation, such as a dry powder formulation for inhalation. Alternatively, a pharmaceutical formulation comprising a compound of the invention may be administered in conjunction with a pharmaceutical formulation comprising an anti-inflammatory agent, such as a corticosteroid, either simultaneously or sequentially. In one embodiment, a pharmaceutical formulation comprising a compound of the invention and a pharmaceutical formulation comprising an anti-inflammatory agent, such as a corticosteroid, may each be held in device suitable for the simultaneous administration of both formulations via inhalation.

Suitable corticosteroids for administration together with a compound of the invention include, but are not limited to, fluticasone furoate, fluticasone propionate, beclomethasone diproprionate, budesonide, ciclesonide, mometasone furoate, triamcinolone, flunisolide and prednisilone. In one embodiment of the invention a corticosteroids for administration together with a compound of the invention via inhalation includes fluticasone furoate, fluticasone propionate, beclomethasone diproprionate, budesonide, ciclesonide, mometasone furoate, and, flunisolide.

Suitably, for the treatment of COPD, compounds or pharmaceutical formulations of the invention may be administered together with one or more bronchodilators, or pharmaceutical formulations thereof. For example, a compound of the invention may be formulated together with one or more bronchodilators in a single formulation, such as a dry powder formulation for inhalation. Alternatively, a pharmaceutical formulation comprising a compound of the invention may be administered in conjunction with a pharmaceutical formulation comprising one or more bronchodilators, either simultaneously or sequentially. In a further alternative, a formulation comprising a compound of the invention and a bronchodilator may be administered in conjunction with a pharmaceutical formulation comprising a further bronchodilator. In one embodiment, a pharmaceutical formulation comprising a compound of the invention and a pharmaceutical formulation comprising one or more bronchodilators may each be held in device suitable for the simultaneous administration of both formulations via inhalation. In a further embodiment, a pharmaceutical formulation comprising a compound of the invention together with a bronchodilator and a pharmaceutical formulation comprising a further bronchodilator may each be held in one or more devices suitable for the simultaneous administration of both formulations via inhalation.

Suitable bronchodilators for administration together with a compound of the invention include, but are not limited to, $\beta_2$-adrenoreceptor agonists and anticholinergic agents. Examples of $\beta_2$-adrenoreceptor agonists, include, for example, vilanterol, salmeterol, salbutamol, formoterol, salmefamol, fenoterol carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt of salbutamol or the fumarate salt of formoterol. Suitable anticholinergic agents include umeclidinium (for example, as the bromide), ipratropium (for example, as the bromide), oxitropium (for example, as the bromide) and tiotropium (for example, as the bromide). In one embodiment of the invention, a compound of the invention may be administered together with a $\beta_2$-adrenoreceptor agonist, such as vilanterol, and an anticholinergic agent, such as, umeclidinium.

The compounds may also be used in combination with agents for aiding transplantation including Cyclosporines, Tacrolimus, Mycophenolate mofetil, Prednisone, Azathioprine, Sirolimus, Daclizumab, Basiliximab and OKT3.

They may also be used in combination with agents for Diabetes: metformin (biguanides), meglitinides, sulfonylureas, DPP-4 inhibitors, Thiazolidinediones, Alpha-glucosidase inhibitors, Amylin mimetics, Incretin mimetics and insulin.

The compounds may be used in combination with antihypertensives such as diuretics, ACE inhibitors, ARBS, calcium channel blockers, and beta blockers.

Other aspects and advantages of the present invention are described further in the following detailed description of the preferred embodiments thereof.

DETAILED DESCRIPTION OF THE INVENTION

The present invention provides for compounds of Formula (I):

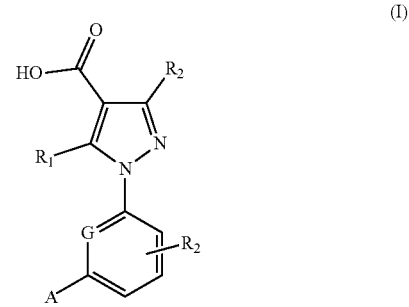

wherein:
$R_1$ is —$CF_3$, —$C_{3-7}$cycloalkyl, or —$C_{4-7}$heterocycloalkyl, wherein the —$C_{3-7}$cycloalkyl, and —$C_{4-7}$heterocycloalkyl is unsubstituted or substituted by one or two substituents independently selected from —$C_{1-3}$alkyl, phenyl, triazolyl, pyridyl, pyridazinyl, imidazolyl, pyrazolyl, isoxazolyl, halo, —$NR_9$—C(O)—$R_{10}$ and —C(O)$R_{10}$, and wherein the phenyl, triazolyl, pyridyl, pyridazinyl, imidazolyl, pyrazolyl and isoxazolyl is substituted by one or two substituents independently selected from —$C_{1-3}$alkyl or halo; or $R_1$ is —$C_{2-3}$alkyl-$R_{11}$;

Each $R_2$ is independently hydrogen, halo, or —$C_{1-3}$alkyl;

G is CH or N;

A is

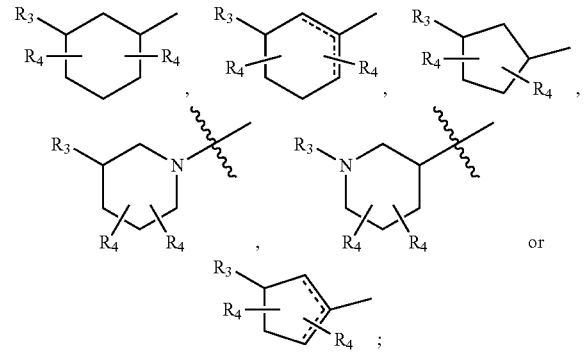

$R_3$ is —$(CH_2)_n$—$C(O)N(R_5)(R_6)$,

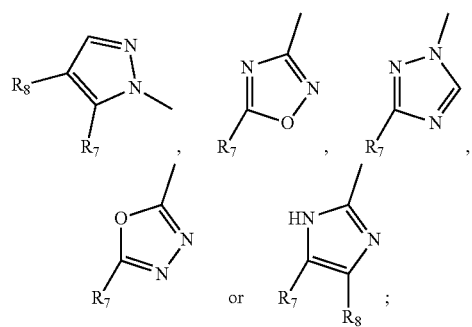

or $R_3$ is —O—$C_{1-3}$alkyl, —$C_{1-6}$alkyl, —$C_{4-7}$heterocycloalkyl, —O—$C_{4-7}$heterocycloalkyl, —$C_{3-7}$cycloalkyl, —O—$C_{3-7}$cycloalkyl, —C(O)—$C_{1-5}$alkyl, —C(O)—O—$C_{1-5}$ alkyl, —C(O)-aryl, —S—$C_{1-3}$alkyl, —S—$C_{4-7}$heterocycloalkyl, —S—$C_{3-7}$cycloalkyl, —S(O)—$C_{1-3}$alkyl, —S(O)—$C_{4-7}$heterocycloalkyl, —S(O)—$C_{3-7}$cycloalkyl, —S(O)$_2$—$C_{1-3}$alkyl, —S(O)$_2$—$C_{4-7}$heterocycloalkyl, —S(O)$_2$—$C_{3-7}$cycloalkyl, —S(O)$_2$-aryl, wherein each of —O—$C_{1-3}$alkyl, —$C_{1-6}$ alkyl, —$C_{4-7}$heterocycloalkyl, —O—$C_{4-7}$heterocycloalkyl, —$C_{3-7}$cycloalkyl, —O—$C_{3-7}$cycloalkyl, —C(O)—$C_{1-5}$alkyl, —C(O)-aryl, —S—$C_{1-3}$alkyl, —S—$C_{4-7}$heterocycloalkyl, —S—$C_{3-7}$cycloalkyl, —S(O)—$C_{1-3}$alkyl, —S(O)—$C_{4-7}$heterocycloalkyl, —S(O)—$C_{3-7}$cycloalkyl, —S(O)$_2$—$C_{1-3}$alkyl, —S(O)$_2$—$C_{4-7}$heterocycloalkyl, —S(O)$_2$—$C_{3-7}$cycloalkyl-S(O)$_2$-aryl, is unsubstituted or substituted by one or two substituents independently selected from —$C_{1-7}$alkyl, —$C_{3-7}$cycloalkyl, —OH, =O, —O—$C_{1-5}$alkyl, —$C_{4-7}$heterocycloalkyl, phenyl, pyridyl, pyrazolyl, pyridazinyl, pyrimidinyl, pyrazinyl, or triazolyl, and wherein the —$C_{1-7}$alkyl, —$C_{3-7}$cycloalkyl, —O—$C_{1-3}$alkyl, —$C_{4-7}$heterocycloalkyl, phenyl, pyridyl, pyrazolyl, pyridazinyl, pyrimidinyl, pyrazinyl, or triazolyl is further unsubstituted or substituted by one or two substituents independently selected from $C_{1-5}$ alkyl and halo;

Each $R_4$ is independently hydrogen, halo or —$C_{1-3}$alkyl.

$R_5$ and $R_6$ are independently H, —$C_{1-6}$alkyl, —$C_{3-7}$cycloalkyl or —$C_{4-7}$heterocycloalkyl, wherein each of —$C_{1-6}$alkyl, —$C_{3-7}$cycloalkyl or —$C_{4-7}$heterocycloalkyl is unsubstituted or substituted by one or two substituents independently selected from F, —CH—F$_2$, —CF$_3$, —$(CH_2)_n$—O—$(CH_2)_m$—$CH_3$, or —$C_{3-7}$cycloalkyl;

or $R_5$ and $R_6$ together with the nitrogen atom to which they are attached form a 5-8-membered ring or an 8-10-membered bicyclic ring or a 9-10-membered bridged bicyclic ring, wherein each 5-8-membered ring, 8-11-membered bicyclic ring, or 9-10-membered bridged bicyclic ring optionally includes one or more oxygen ring atoms or another nitrogen ring atom, and wherein each 5-8-membered ring, 8-11-membered bicyclic ring, or 9-10-membered bridged bicyclic ring is unsubstituted or substituted by one or two substituents independently selected from —$C_{1-5}$alkyl, —$C_{3-7}$cycloalkyl, —$C_{4-7}$heterocycloalkyl, F, —CHF$_2$, —CF$_3$, and —$(CH_2)_n$—O—$(CH_2)_m$—$CH_3$;

$R_5$ and $R_6$ together with the nitrogen atom to which they are attached form 4-azaspiro[2.5]octane, 7-azaspiro[4.5]decane, 2-oxa-8-azaspiro[5.5]undecane, 6-oxa-9-azaspiro[4.5]decane, 2-oxa-8-azaspiro[5.5]undecane, or 1-azaspiro[4.5]decane;

$R_7$ and $R_8$ are independently H, —$C_{1-6}$alkyl, —$C_{3-7}$cycloalkyl or —$C_{4-7}$heterocycloalkyl wherein each of —$C_{1-6}$ alkyl, —$C_{3-7}$ cycloalkyl or —$C_{4-7}$ heterocycloalkyl is unsubstituted or substituted by one or two substituents independently selected from F, CHF$_2$, CF$_3$, and $(CH_2)_n$—O—$(CH_2)_m$—$CH_3$;

or $R_7$ and $R_8$ together with the carbon atoms to which they are attached form a 5-8-membered ring, which optionally includes one or more oxygen or nitrogen atoms as ring atoms, and wherein the 5-8-membered ring is unsubstituted or substituted by one or two substituents independently selected from —$C_{1-5}$alkyl, —$C_{3-7}$cycloalkyl, —$C_{4-7}$heterocycloalkyl, F, —CHF$_2$, —CF$_3$, =O, and —$(CH_2)_n$—O—$(CH_2)_m$—$CH_3$;

$R_9$ is H or —$C_{1-3}$alkyl;

$R_{10}$ is —$C_{1-3}$ alkyl;

$R_{11}$ is phenyl, triazolyl, pyridyl, pyridazinyl, imidazolyl, or pyrazolyl, wherein each of phenyl, triazolyl, pyridyl, pyridazinyl, imidazolyl, or pyrazolyl is unsubstituted or substituted by one or two substituents independently selected from $C_{1-3}$alkyl and halo;

Each n is independently 0 or 1;

Each m is independently 0 or 1;

or a pharmaceutically acceptable salt thereof.

"Alkyl" refers to a monovalent saturated hydrocarbon chain having the specified number of carbon member atoms. For example, $C_{1-4}$ alkyl refers to an alkyl group having from 1 to 4 carbon member atoms. Alkyl groups may be straight or branched. Representative branched alkyl groups have one, two, or three branches. Alkyl includes methyl, ethyl, propyl, (n-propyl and isopropyl), and butyl (n-butyl, isobutyl, s-butyl, and t-butyl).

"Cycloalkyl" refers to a monovalent saturated or unsaturated hydrocarbon ring having the specified number of carbon member atoms. For example, $C_{3-6}$cycloalkyl refers to a cycloalkyl group having from 3 to 6 carbon member atoms. Unsaturated cycloalkyl groups have one or more carbon-carbon double bonds within the ring. Cycloalkyl groups are not aromatic. Cycloalkyl includes cyclopropyl, cyclopropenyl, cyclobutyl, cyclobutenyl, cyclopentyl, cyclopentenyl, cyclohexyl, and cyclohexenyl.

"$C_{4-7}$heterocycloalkyl" refers to a 4- to 7-membered ring that contains up to 4 hetero atoms, for example, oxygen, nitrogen or sulfur. Examples are azetidine, thietane, thietane 1-oxide, thietane 1,1-dioxide, tetrahydrofuran, pyrrolidine, tetrahydrothiophene, tetrahydrothiophene 1-oxide, tetrahydrothiophene 1, 2-dioxide, piperidine, morpholine, thiomorpholine, thiomorpholine 1-oxide, thiomorpholine 1,1-dioxide, tetrahydropyran, tetrahydrothiopyran, tetrahydrothiopyran 1-oxide, tetrahydrothiopyran 1-1 dioxide, piperidine-2-one, azepan-2-one, pyrrolidin-2-one, azepane, oxepane, oxazepane, thiepane, thiepane 1-oxide, thiepane 1,1-dioxide, and thiazepane.

When used herein, the terms 'halogen' and 'halo' include fluorine, chlorine, bromine and iodine, and fluoro, chloro, bromo, and iodo, respectively.

When used herein, the terms "5-8-membered ring or an 8-10-membered bicyclic ring or a 9-10-membered bridged bicyclic ring" include both saturated and unsaturated ring structures containing the indicated number of carbon atoms. The terms "8-10-membered bicyclic ring or a 9-10-membered bridged bicyclic ring" can be aryl or heteroaryl, and also encompass bicyclic aryl groups containing an aryl ring moiety fused to a cycloalkyl ring moiety.

"Substituted" in reference to a group indicates that one or more hydrogen atom attached to a member atom within the group is replaced with a substituent selected from the group of defined substituents. It should be understood that the term "substituted" includes the implicit provision that such substitution be in accordance with the permitted valence of the substituted atom and the substituent and that the substitution results in a stable compound (i.e., one that does not spontaneously undergo transformation such as by rearrangement, cyclization, or elimination and that is sufficiently robust to survive isolation from a reaction mixture). When it is stated that a group may contain one or more substituents, one or more (as appropriate) member atoms within the group may be substituted. In addition, a single member atom within the group may be substituted with more than one substituent as long as such substitution is in accordance with the permitted valence of the atom. Suitable substituents are defined herein for each substituted or optionally substituted group.

The term "independently" means that where more than one substituent is selected from a number of possible substituents, those substituents may be the same or different. That is, each substituent is separately selected from the entire group of recited possible substituents.

The dotted line indicates that a double bond is present in one of the locations.

The invention also includes various isomers of the compounds of Formula (I) and Formula (Ia) and mixtures thereof. "Isomer" refers to compounds that have the same composition and molecular weight but differ in physical and/or chemical properties. The structural difference may be in constitution (geometric isomers) or in the ability to rotate the plane of polarized light (stereoisomers). The compounds according to Formula (I) and Formula (Ia) contain one or more asymmetric centers, also referred to as chiral centers, and may, therefore, exist as individual enantiomers, diastereomers, or other stereoisomeric forms, or as mixtures thereof. All such isomeric forms are included within the present invention, including mixtures thereof.

Chiral centers may also be present in a substituent such as an alkyl group. Where the stereochemistry of a chiral center present in Formula (I) and Formula (Ia), or in any chemical structure illustrated herein, is not specified the structure is intended to encompass any stereoisomer and all mixtures thereof. Thus, compounds according to Formula (I) and Formula (Ia) containing one or more chiral centers may be used as racemic mixtures, enantiomerically enriched mixtures, or as enantiomerically pure individual stereoisomers.

Individual stereoisomers of a compound according to Formula (I) and Formula (Ia) which contain one or more asymmetric centers may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

As used herein, "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

The skilled artisan will appreciate that pharmaceutically acceptable salts of the compounds according to Formula (I) and Formula (Ia) may be prepared. These pharmaceutically acceptable salts may be prepared in situ during the final isolation and purification of the compound, or by separately treating the purified compound in its free acid or free base form with a suitable base or acid, respectively.

In certain embodiments, compounds according to Formula (I) and Formula (Ia) may contain a basic functional group and are therefore capable of forming pharmaceutically acceptable acid addition salts by treatment with a suitable acid. Suitable acids include pharmaceutically acceptable inorganic acids and organic acids. Representative pharmaceutically acceptable acids include hydrogen chloride, hydrogen bromide, nitric acid, sulfuric acid, sulfonic acid, phosphoric acid, acetic acid, hydroxyacetic acid, phenylacetic acid, propionic acid, butyric acid, valeric acid, maleic acid, acrylic acid, fumaric acid, succinic acid, malic acid, malonic acid, tartaric acid, citric acid, salicylic acid, benzoic acid, tannic acid, formic acid, stearic acid, lactic acid, ascorbic acid, methylsulfonic acid, p-toluenesulfonic acid, oleic acid, lauric acid, and the like.

As used herein, the term "a compound of Formula (I) and Formula (Ia)" or "the compound of Formula (I) and Formula (Ia)" refers to one or more compounds according to Formula (I) and Formula (Ia). The compound of Formula (I) and Formula (Ia) may exist in solid or liquid form. In the solid state, it may exist in crystalline or noncrystalline form, or as a mixture thereof. The skilled artisan will appreciate that pharmaceutically acceptable solvates may be formed from crystalline compounds wherein solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates."

Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e., the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The subject invention also includes isotopically-labelled compounds, which are identical to those recited in Formula (I) and Formula (Ia) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{36}$Cl, $^{123}$I and $^{125}$I.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^{18}$F isotopes are particularly useful in PET (positron emission tomography), and $^{125}$I isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of Formula (I) and Formula (Ia) and following of this invention can generally be prepared by carrying out the procedures disclosed in the Schemes and/or in the Examples below, by substituting a readily available isotopically labeled reagent for a non-isotopically labeled reagent.

Representative Embodiments

In one embodiment, the compound of Formula (I) is substituted as follows:
$R_1$ is —$CF_3$, —$C_{3-7}$cycloalkyl, or —$C_{4-7}$heterocycloalkyl, wherein the —$C_{3-7}$cycloalkyl, and —$C_{4-7}$heterocycloalkyl is unsubstituted or substituted by one or two substituents independently selected from —$C_{1-3}$alkyl, phenyl, triazolyl, pyridyl, pyridazinyl, imidazolyl, pyrazolyl, isoxazolyl, halo, —$NR_9$—C(O)—$R_{10}$ and —C(O)$R_{10}$, and wherein the phenyl, triazolyl, pyridyl, pyridazinyl, imidazolyl, pyrazolyl and isoxazolyl is substituted by one or two substituents independently selected from —$C_{1-3}$alkyl and halo; or
$R_1$ is —$C_{2-3}$alkyl-$R_{11}$;
Each $R_2$ is independently hydrogen, halo, or —$C_{1-3}$alkyl;
G is CH or N;
A is

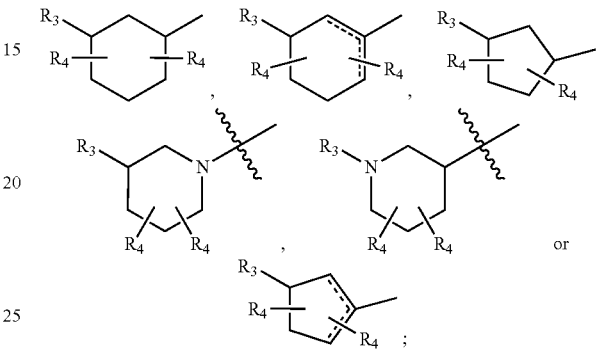

$R_3$ is —$(CH_2)_n$—C(O)N($R_5$)($R_6$),

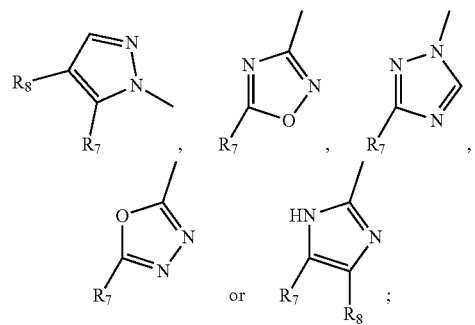

or $R_3$ is —O—$C_{1-3}$alkyl, —$C_{1-6}$alkyl, —$C_{4-7}$heterocycloalkyl, —O—$C_{4-7}$heterocycloalkyl, —$C_{3-7}$cycloalkyl, —O—$C_{3-7}$cycloalkyl, —C(O)—O—$C_{1-5}$ alkyl, —C(O)—$C_{1-5}$alkyl, —C(O)-aryl, —S—$C_{1-3}$alkyl, —S—$C_{4-7}$heterocycloalkyl, —S—$C_{3-7}$cycloalkyl, —S(O)—$C_{1-3}$alkyl, —S(O)—$C_{4-7}$heterocycloalkyl, —S(O)—$C_{3-7}$cycloalkyl, —S(O)$_2$—$C_{1-3}$alkyl, —S(O)$_2$—$C_{4-7}$heterocycloalkyl, —S(O)$_2$—$C_{3-7}$cycloalkyl, —S(O)$_2$-aryl, wherein each of —O—$C_{1-3}$alkyl, —$C_{1-6}$alkyl, —$C_{4-7}$heterocycloalkyl, —O—$C_{4-7}$heterocycloalkyl, —$C_{3-7}$cycloalkyl, —O—$C_{3-7}$cycloalkyl, —C(O)—$C_{1-5}$alkyl, —C(O)-aryl, —S—$C_{1-3}$alkyl, —S—$C_{4-7}$heterocycloalkyl, —S—$C_{3-7}$cycloalkyl, —S(O)—$C_{1-3}$alkyl, —S(O)—$C_{4-7}$heterocycloalkyl, —S(O)—$C_{3-7}$cycloalkyl, —S(O)$_2$—$C_{1-3}$alkyl, —S(O)$_2$—$C_{4-7}$heterocycloalkyl, —S(O)$_2$—$C_{3-7}$cycloalkyl-S(O)$_2$-aryl, is unsubstituted or substituted by one or two substituents independently selected from —$C_{1-7}$alkyl, —$C_{3-7}$cycloalkyl, —OH, =O, —O—$C_{1-5}$alkyl, —$C_{4-7}$heterocycloalkyl, phenyl, pyridyl, pyrazolyl, pyridazinyl, pyrimidinyl, pyrazinyl, or triazolyl, and wherein the —$C_{1-7}$alkyl, —$C_{3-7}$cycloalkyl, —O—$C_{1-3}$alkyl, —$C_{4-7}$heterocycloalkyl, phenyl, pyridyl, pyrazolyl, pyridazinyl, pyrimidinyl, pyrazinyl, or triazolyl is further unsubstituted or substituted by one or two substituents independently selected from $C_{1-5}$ alkyl and halo;

Each $R_4$ is independently hydrogen, halo or —$C_{1-3}$alkyl.

$R_5$ and $R_6$ are independently H, —$C_{1-6}$alkyl, —$C_{3-7}$cycloalkyl or —$C_{4-7}$heterocycloalkyl, wherein each of —$C_{1-6}$alkyl, —$C_{3-7}$cycloalkyl or —$C_{4-7}$heterocycloalkyl is unsubstituted or substituted by one or two substituents independently selected from F, —CH—$F_2$, —$CF_3$, —$(CH_2)_n$—O—$(CH_2)_m$—$CH_3$, or —$C_{3-7}$cycloalkyl;

or $R_5$ and $R_6$ together with the nitrogen atom to which they are attached form a 5-8-membered ring or an 8-10-membered bicyclic ring or a 9-10-membered bridged bicyclic ring, wherein each 5-8-membered ring, 8-11-membered bicyclic ring, or 9-10-membered bridged bicyclic ring optionally includes one or more oxygen ring atoms or another nitrogen ring atom, and wherein each 5-8-membered ring, 8-11-membered bicyclic ring, or 9-10-membered bridged bicyclic ring is unsubstituted or substituted by one or two substituents independently selected from —$C_{1-5}$alkyl, —$C_{3-7}$cycloalkyl, —$C_{4-7}$heterocycloalkyl, F, —$CHF_2$, —$CF_3$, and —$(CH_2)_n$—O—$(CH_2)_m$—$CH_3$;

$R_5$ and $R_6$ together with the nitrogen atom to which they are attached form 4-azaspiro[2.5]octane, 7-azaspiro[4.5]decane, 2-oxa-8-azaspiro[5.5]undecane, 6-oxa-9-azaspiro[4.5]decane, 2-oxa-8-azaspiro[5.5]undecane, or 1-azaspiro[4.5]decane;

$R_7$ and $R_8$ are independently H, —$C_{1-6}$alkyl, —$C_{3-7}$cycloalkyl or —$C_{4-7}$heterocycloalkyl wherein each of —$C_{1-6}$ alkyl, —$C_{3-7}$ cycloalkyl or —$C_{4-7}$ heterocycloalkyl is unsubstituted or substituted by one or two substituents independently selected from F, $CHF_2$, $CF_3$, and $(CH_2)_n$—O—$(CH_2)_m$—$CH_3$;

or $R_7$ and $R_8$ together with the carbon atoms to which they are attached form a 5-8-membered ring, which optionally includes one or more oxygen or nitrogen atoms as ring atoms, and wherein the 5-8-membered ring is unsubstituted or substituted by one or two substituents independently selected from —$C_{1-5}$alkyl, —$C_{3-7}$cycloalkyl, —$C_{4-7}$heterocycloalkyl, F, —$CHF_2$, —$CF_3$, =O, and —$(CH_2)_n$—O—$(CH_2)_m$—$CH_3$;

$R_9$ is H or —$C_{1-3}$alkyl;

$R_{10}$ is —$C_{1-3}$ alkyl;

$R_{11}$ is phenyl, triazolyl, pyridyl, pyridazinyl, imidazolyl, or pyrazolyl, wherein each of phenyl, triazolyl, pyridyl, pyridazinyl, imidazolyl, or pyrazolyl is unsubstituted or substituted by one or two substituents independently selected from $C_{1-3}$alkyl and halo;

Each n is independently 0 or 1;

Each m is independently 0 or 1;

or a pharmaceutically acceptable salt thereof.

In another embodiment, the compound of Formula (I) is substituted as follows:

$R_1$ is —$CF_3$, $C_{3-7}$cycloalkyl, wherein the —$C_{3-7}$ cycloalkyl, is unsubstituted or substituted by one or two substituents selected from —$C_{1-3}$alkyl and halo, or wherein the —$C_{3-7}$ cycloalkyl is substituted by one substituent selected from triazolyl, pyridyl, pyridazinyl, imidazolyl, pyrazolyl and isoxazolyl, and wherein the triazolyl, pyridyl, pyridazinyl, imidazolyl, pyrazolyl and isoxazolyl is unsubstituted or substituted by one or two substituents selected from —$C_{1-3}$alkyl and halo;

$R_2$ is hydrogen;

G is CH;

A is

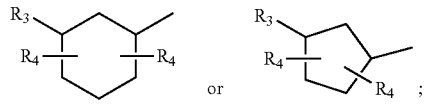

$R_3$ is —$(CH_2)_n$—C(O)N($R_5$)($R_6$), or

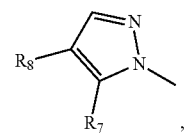

$R_3$ is —O—$C_{1-3}$alkyl, —$C_{1-6}$alkyl, —$C_{4-7}$heterocycloalkyl, —O—$C_{4-7}$heterocycloalkyl, —$C_{3-7}$cycloalkyl, or —O—$C_{3-7}$cycloalkyl, wherein each of —O—$C_{1-3}$alkyl, —$C_{1-6}$alkyl, —$C_{4-7}$heterocycloalkyl, —O—$C_{4-7}$heterocycloalkyl, —$C_{3-7}$cycloalkyl, —O—$C_{3-7}$cycloalkyl, is unsubstituted or substituted by one or two substituents selected from —$C_{1-7}$alkyl, —$C_{3-7}$cycloalkyl, —OH, =O, —O—$C_{1-5}$alkyl, —$C_{4-7}$heterocycloalkyl, phenyl, pyridyl, pyrazolyl, pyridazinyl, pyrimidinyl, pyrazinyl, and triazolyl, and wherein the —$C_{1-7}$alkyl, —$C_{3-7}$cycloalkyl, —O—$C_{1-3}$alkyl, —$C_{4-7}$heterocycloalkyl, phenyl, pyridyl, pyrazolyl, pyridazinyl, pyrimidinyl, pyrazinyl, or triazolyl is unsubstituted or further substituted by one or two substituents independently selected from —$C_{1-5}$alkyl and halo;

Each $R_4$ is independently hydrogen, halo or —$C_{1-3}$ alkyl;

$R_5$ and $R_6$ are independently H, —$C_{1-6}$alkyl, —$C_{3-7}$cycloalkyl or —$C_{4-7}$heterocycloalkyl, wherein each of —$C_{1-6}$alkyl, —$C_{3-7}$cycloalkyl or —$C_{4-7}$heterocycloalkyl is unsubstituted or substituted by one or two substituents independently selected from F, —CH—$F_2$, —$CF_3$, —$(CH_2)_n$—O—$(CH_2)_m$—$CH_3$, and —$C_{3-7}$cycloalkyl;

or $R_5$ and $R_6$ together with the nitrogen atom to which they are attached form a 5-8-membered ring or an 8-10-membered bicyclic ring or a 9-10-membered bridged bicyclic ring, wherein each 5-8-membered ring, 8-11-membered bicyclic ring, or 9-10-membered bridged bicyclic ring optionally includes one or more oxygen ring atoms or another nitrogen ring atom, and wherein each 5-8-membered ring, 8-11-membered bicyclic ring, or 9-10-membered bridged bicyclic ring is unsubstituted or substituted by one or two substituents independently selected from —$C_{1-5}$alkyl, —$C_{3-7}$cycloalkyl, —$C_{4-7}$heterocycloalkyl, F, —$CHF_2$, —$CF_3$, and —$(CH_2)_n$—O—$(CH_2)_m$—$CH_3$;

$R_5$ and $R_6$ together with the nitrogen atom to which they are attached form 4-azaspiro[2.5]octane, 7-azaspiro[4.5]decane, 2-oxa-8-azaspiro[5.5]undecane, 6-oxa-9-azaspiro[4.5]decane, 2-oxa-8-azaspiro[5.5]undecane, or 1-azaspiro[4.5]decane;

$R_7$ and $R_8$ are independently H, —$C_{1-6}$alkyl, —$C_{3-7}$cycloalkyl or —$C_{4-7}$heterocycloalkyl wherein each of —$C_{1-6}$ alkyl, —$C_{3-7}$ cycloalkyl or —$C_{4-7}$ heterocycloalkyl is unsubstituted or substituted by one or two substituents independently selected from F, —$CHF_2$, —$CF_3$, and —$(CH_2)_n$—O—$(CH_2)_m$—$CH_3$;

or $R_7$ and $R_8$ together with the carbon atoms to which they are attached form a 5-8-membered ring, which optionally includes one or more oxygen or nitrogen atoms as ring atoms, and wherein the 5-8-membered ring is unsubstituted or substituted by one or two substituents independently selected from —$C_{1-5}$alkyl, —$C_{3-7}$cycloalkyl, —$C_{4-7}$heterocycloalkyl, F, —$CHF_2$, —$CF_3$, =O, and —$(CH_2)_n$—O—$(CH_2)_m$—$CH_3$;

Each n is independently 0 or 1;
Each m is independently 0 or 1;
or a pharmaceutically acceptable salt thereof.

In one embodiment, the compound of Formula (I) is substituted as follows:

$R_1$ is $CF_3$, $C_{3-7}$ cycloalkyl, or $C_{4-7}$ heterocycloalkyl, wherein the $C_{3-7}$ cycloalkyl, or
$C_{4-7}$ heterocycloalkyl may be unsubstituted or substituted by one or two substituents chosen from: $C_{1-3}$alkyl, phenyl, triazolyl, pyridyl, pyridazinyl, imidazolyl, pyrazolyl, isoxazolyl, halo,
$NR_9$—C(O)—$R_{10}$ or C(O)$R_{10}$, and the phenyl, triazolyl, pyridyl, pyridazinyl, imidazolyl, pyrazolyl and isoxazolyl may be substituted by $C_{1-3}$alkyl or halo; or
$R_1$ is —$C_{2-3}$alkyl-$R_{11}$;
Each $R_2$ is independently hydrogen, halo, or $C_{1-3}$alkyl;
G is CH or N;
A is

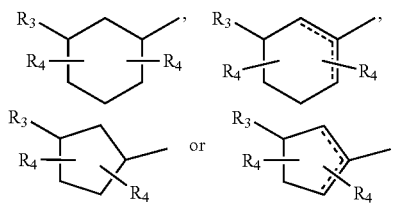

$R_3$ is —$(CH_2)_n$—C(O)N($R_5$)($R_6$),

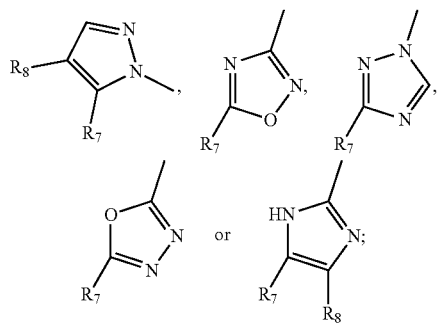

or $R_3$ is O—$C_{1-3}$alkyl, $C_{1-6}$ alkyl, $C_{4-7}$ heterocycloalkyl, O—$C_{4-7}$ heterocycloalkyl,
$C_{3-7}$ cycloalkyl, O—$C_{3-7}$ cycloalkyl, S—$C_{1-3}$alkyl, S—$C_{4-7}$ heterocycloalkyl, S—$C_{3-7}$ cycloalkyl, S(O)—$C_{1-3}$alkyl, S(O)—$C_{4-7}$ heterocycloalkyl, S(O)—$C_{3-7}$ cycloalkyl, S(O)$_2$—$C_{1-3}$alkyl, S(O)$_2$—$C_{4-7}$ heterocycloalkyl, S(O)$_2$—$C_{3-7}$ cycloalkyl, all of which may be substituted by one or two substituents chosen from: $C_{1-7}$ alkyl, $C_{3-7}$ cycloalkyl, OH, =O, —O—$C_{1-5}$ alkyl,
$C_{4-7}$ heterocycloalkyl, phenyl, pyridyl, pyrazolyl, pyridazinyl, pyrimidinyl, pyrazinyl, or triazolyl, and the $C_{1-7}$ alkyl, $C_{3-7}$ cycloalkyl, —O—$C_{1-3}$ alkyl, $C_{4-7}$ heterocycloalkyl, phenyl, pyridyl, pyrazolyl, pyridazinyl, pyrimidinyl, pyrazinyl, or triazolyl may be further substituted by $C_{1-5}$ alkyl or halo;
Each $R_4$ is independently hydrogen, halo or $C_{1-3}$ alkyl;
$R_5$ and $R_6$ are independently H, $C_{1-6}$ alkyl, $C_{3-7}$ cycloalkyl or $C_{4-7}$ heterocycloalkyl, all of which may be substituted by F, CH—$F_2$, $CF_3$, $(CH_2)_n$—O—$(CH_2)_m$—$CH_3$, or $C_{3-7}$ cycloalkyl;

or $R_5$ and $R_6$ together with the nitrogen atom can form a 5-8 member ring or a 8-10 member bicyclic ring or a 9 or 10-membered bridged bicyclic ring, all of which can optionally include oxygen or another nitrogen as ring atoms, and all of which may be substituted by one or two $C_{1-5}$ alkyl, $C_{3-7}$ cycloalkyl, $C_{4-7}$ heterocycloalkyl, F, $CHF_2$, $CF_3$, or $(CH_2)_n$—O—$(CH_2)_m$—$CH_3$; or
$R_5$ and $R_6$ together with the nitrogen atom can form 4-azaspiro[2.5]octane, 7-azaspiro[4.5]decane, 2-oxa-8-azaspiro[5.5]undecane, 6-oxa-9-azaspiro[4.5]decane, 2-oxa-8-azaspiro[5.5]undecane, or 1-azaspiro[4.5]decane;
$R_7$ and $R_8$ are independently H, $C_{1-6}$ alkyl, $C_{3-7}$cycloalkyl or $C_{4-7}$ heterocycloalkyl, of which the $C_{1-6}$ alkyl, $C_{3-7}$ cycloalkyl or $C_{4-7}$ heterocycloalkyl may be substituted by F, $CHF_2$, $CF_3$, $(CH_2)_n$—O—$(CH_2)_m$—$CH_3$, or
$R_7$ and $R_8$ together with the carbon atoms to which they are attached form a 5-8 member ring, which can optionally include oxygen or nitrogen as ring atoms, which may be substituted by one or two $C_{1-5}$ alkyl, $C_{3-7}$ cycloalkyl, $C_{4-7}$ heterocycloalkyl, F, $CHF_2$, $CF_3$, =O, or $(CH_2)_n$—O—$(CH_2)_m$—$CH_3$;
$R_9$ is H or $C_{1-3}$ alkyl;
$R_{10}$ is $C_{1-3}$ alkyl;
$R_{11}$ is phenyl, triazolyl, pyridyl, pyridazinyl, imidazolyl, or pyrazolyl, all of which may be substituted by $C_{1-3}$alkyl or halo;
Each n is independently 0 or 1;
Each m is independently 0 or 1;
or a pharmaceutically acceptable salt thereof.

In one embodiment, the compound of Formula (Ia) is substituted as follows:

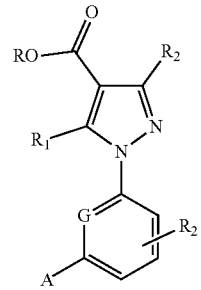

(Ia)

wherein:
R is hydrogen or $C_{1-5}$alkyl;
$R_1$ is —$CF_3$, —$C_{3-7}$cycloalkyl, or —$C_{4-7}$heterocycloalkyl, wherein the —$C_{3-7}$cycloalkyl, and —$C_{4-7}$heterocycloalkyl is unsubstituted or substituted by one or two substituents independently selected from —$C_{1-3}$alkyl, phenyl, triazolyl, pyridyl, pyridazinyl, imidazolyl, pyrazolyl, isoxazolyl, halo, —$NR_9$—C(O)—$R_{10}$ and —C(O)$R_{10}$, and wherein the phenyl, triazolyl, pyridyl, pyridazinyl, imidazolyl, pyrazolyl and isoxazolyl is substituted by one or two substituents independently selected from —$C_{1-3}$alkyl or halo; or
$R_1$ is —$C_{2-3}$alkyl-$R_{11}$;
Each $R_2$ is independently hydrogen, halo, or —$C_{1-3}$alkyl;
G is CH or N;
A is

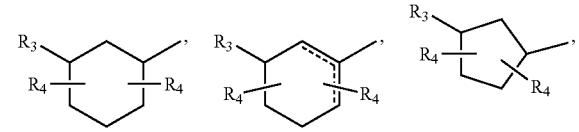

-continued

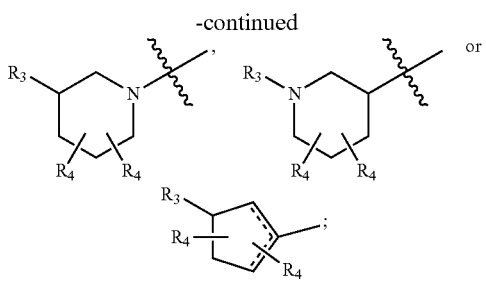

R$_3$ is —(CH$_2$)$_n$—C(O)N(R$_5$)(R$_6$),

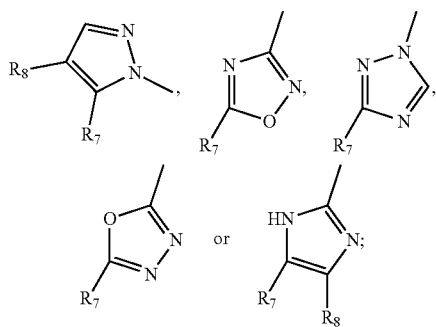

or R$_3$ is —O—C$_{1-3}$alkyl, —C$_{1-6}$alkyl, —C$_{4-7}$heterocycloalkyl, —O—C$_{4-7}$heterocycloalkyl, —C$_{5-7}$cycloalkyl, —O—C$_{3-7}$cycloalkyl, —C(O)—C$_{1-5}$alkyl, —C(O)-aryl, —S—C$_{1-3}$alkyl, —S—C$_{4-7}$heterocycloalkyl, —S—C$_{3-7}$cycloalkyl, —S(O)—C$_{1-3}$alkyl, —S(O)—C$_{4-7}$heterocycloalkyl, —S(O)—C$_{3-7}$cycloalkyl, —S(O)$_2$—C$_{1-3}$alkyl, —S(O)$_2$—C$_{4-7}$heterocycloalkyl, —S(O)$_2$—C$_{3-7}$cycloalkyl, —S(O)$_2$-aryl, wherein each of —O—C$_{1-3}$alkyl, —C$_{1-6}$alkyl, —C$_{4-7}$heterocycloalkyl, —O—C$_{4-7}$heterocycloalkyl, —C$_{3-7}$cycloalkyl, —O—C$_{3-7}$cycloalkyl, —C(O)—C$_{1-5}$alkyl, —C(O)-aryl, —S—C$_{1-3}$alkyl, —S—C$_{4-7}$heterocycloalkyl, —S—C$_{3-7}$cycloalkyl, —S(O)—C$_{1-3}$alkyl, —S(O)—C$_{4-7}$heterocycloalkyl, —S(O)—C$_{3-7}$cycloalkyl, —S(O)$_2$—C$_{1-3}$alkyl, —S(O)$_2$—C$_{4-7}$heterocycloalkyl, —S(O)$_2$—C$_{3-7}$cycloalkyl-S(O)$_2$-aryl, is unsubstituted or substituted by one or two substituents independently selected from —C$_{1-7}$alkyl, —C$_{3-7}$cycloalkyl, —OH, =O, —O—C$_{1-5}$alkyl, —C$_{4-7}$heterocycloalkyl, phenyl, pyridyl, pyrazolyl, pyridazinyl, pyrimidinyl, pyrazinyl, or triazolyl, and wherein the —C$_{1-7}$alkyl, —C$_{3-7}$cycloalkyl, —O—C$_{1-3}$alkyl, —C$_{4-7}$heterocycloalkyl, phenyl, pyridyl, pyrazolyl, pyridazinyl, pyrimidinyl, pyrazinyl, or triazolyl is further unsubstituted or substituted by one or two substituents independently selected from C$_{1-5}$ alkyl and halo;

Each R$_4$ is independently hydrogen, halo or —C$_{1-3}$alkyl;

R$_5$ and R$_6$ are independently H, —C$_{1-6}$alkyl, —C$_{3-7}$cycloalkyl or —C$_{4-7}$heterocycloalkyl, wherein each of —C$_{1-6}$alkyl, —C$_{3-7}$cycloalkyl or —C$_{4-7}$heterocycloalkyl is unsubstituted or substituted by one or two substituents independently selected from F, —CH—F$_2$, —CF$_3$, —(CH$_2$)$_n$—O—(CH$_2$)$_m$—CH$_3$, or —C$_{3-7}$cycloalkyl;

or R$_5$ and R$_6$ together with the nitrogen atom to which they are attached form a 5-8-membered ring or an 8-10-membered bicyclic ring or a 9-10-membered bridged bicyclic ring, wherein each 5-8-membered ring, 8-11-membered bicyclic ring, or 9-10-membered bridged bicyclic ring optionally includes one or more oxygen ring atoms or another nitrogen ring atom, and wherein each 5-8-membered ring, 8-11-membered bicyclic ring, or 9-10-membered bridged bicyclic ring is unsubstituted or substituted by one or two substituents independently selected from —C$_{1-5}$alkyl, —C$_{3-7}$cycloalkyl, —C$_{4-7}$heterocycloalkyl, F, —CHF$_2$, —CF$_3$, and —(CH$_2$)$_n$—O—(CH$_2$)$_m$—CH$_3$;

R$_5$ and R$_6$ together with the nitrogen atom to which they are attached form 4-azaspiro[2.5]octane, 7-azaspiro[4.5]decane, 2-oxa-8-azaspiro[5.5]undecane, 6-oxa-9-azaspiro[4.5]decane, 2-oxa-8-azaspiro[5.5]undecane, or 1-azaspiro[4.5]decane;

R$_7$ and R$_8$ are independently H, —C$_{1-6}$alkyl, —C$_{3-7}$cycloalkyl or —C$_{4-7}$heterocycloalkyl wherein each of —C$_{1-6}$ alkyl, —C$_{3-7}$ cycloalkyl or —C$_{4-7}$ heterocycloalkyl is unsubstituted or substituted by one or two substituents independently selected from F, CHF$_2$, CF$_3$, and (CH$_2$)$_n$—O—(CH$_2$)$_m$—CH$_3$;

or R$_7$ and R$_8$ together with the carbon atoms to which they are attached form a 5-8-membered ring, which optionally includes one or more oxygen or nitrogen atoms as ring atoms, and wherein the 5-8-membered ring is unsubstituted or substituted by one or two substituents independently selected from —C$_{1-5}$alkyl, —C$_{3-7}$cycloalkyl, —C$_{4-7}$heterocycloalkyl, F, —CHF$_2$, —CF$_3$, =O, and —(CH$_2$)$_n$—O—(CH$_2$)$_m$—CH$_3$;

R$_9$ is H or —C$_{1-3}$alkyl;

R$_{10}$ is —C$_{1-3}$ alkyl;

R$_{11}$ is phenyl, triazolyl, pyridyl, pyridazinyl, imidazolyl, or pyrazolyl, wherein each of phenyl, triazolyl, pyridyl, pyridazinyl, imidazolyl, or pyrazolyl is unsubstituted or substituted by one or two substituents independently selected from C$_{1-3}$alkyl and halo;

Each n is independently 0 or 1;

Each m is independently 0 or 1;

or a pharmaceutically acceptable salt thereof.

It is to be understood that the present invention covers all combinations of the embodiments and particular groups described hereinabove Specific examples of compounds of the present invention include the following:

5-Cyclopropyl-1-{3-[3-(dimethylcarbamoyl)cyclohexyl]phenyl}-1H-pyrazole-4-carboxylic acid (cis-racemate);

5-Cyclopropyl-1-{3-[3-(4,5,6,7-tetrahydro-1H-indazol-1-yl)cyclohexyl]phenyl}-1H-pyrazole-4-carboxylic acid;

5-Cyclopropyl-1-{3-[3-(piperidine-1-carbonyl)cyclohexyl]phenyl}-1H-pyrazole-4-carboxylic acid (cis-racemate);

1-[3-(3-{7-Azaspiro[4.5]decane-7-carbonyl}cyclohexyl)phenyl]-5-cyclopropyl-1H-pyrazole-4-carboxylic acid (cis-racemate);

5-Cyclopropyl-1-{3-[3-(2-propylpiperidine-1-carbonyl)cyclohexyl]phenyl}-1H-pyrazole-4-carboxylic acid;

5-cyclopropyl-1-{3-[3-(2,2-dimethylpyrrolidine-1-carbonyl)cyclohexyl]phenyl}-1H-pyrazole-4-carboxylic acid;

1-[3-(3-{1-Azaspiro[4.5]decane-1-carbonyl}cyclohexyl)phenyl]-5-cyclopropyl-1H-pyrazole-4-carboxylic acid;

1-{3-[3-(2-butylpyrrolidine-1-carbonyl)cyclohexyl]phenyl}-5-cyclopropyl-1H-pyrazole-4-carboxylic acid;

1-[3-(3-{1H,4H,5H,6H,7H,8H-cyclohepta[c]pyrazol-1-yl}cyclohexyl)phenyl)-5-cyclopropyl-1H-pyrazole-4-carboxylic acid;

1-[3-(3-{1H,4H,5H,6H-cyclopenta[c]pyrazol-1-yl}cyclopentyl)phenyl]-5-cyclopropyl-1H-pyrazole-4-carboxylic acid;

5-Cyclopropyl-1-(3-{3-[2-(3-methylbutyl)pyrrolidine-1-carbonyl]cyclohexyl}phenyl)-1H-pyrazole-4-carboxylic acid;

5-Cyclopropyl-1-{3-[3-(2-cyclopropylpyrrolidine-1-carbonyl)cyclohexyl]phenyl}-1H-pyrazole-4-carboxylic acid;

1-{3-[3-(2-cyclobutylpyrrolidine-1-carbonyl)cyclohexyl]phenyl}-5-cyclopropyl-1H-pyrazole-4-carboxylic acid;

5-Cyclopropyl-1-{3-[(cis)-3-(6-methyl-5,6-dihydro-4H-cyclopentapyrazol-1-yl)-cyclohexyl]-phenyl}-1H-pyrazole-4-carboxylic acid (cis racemic);

5-Cyclopropyl-1-{3-[3-(4-oxo-4,5,6,7-tetrahydro-indazol-1-yl)-cyclopentyl]-phenyl}-1H-pyrazole-4-carboxylic acid;
5-Cyclopropyl-1-[3-(3-{6-propyl-1H,4H,5H,6H-cyclopenta[c]pyrazol-1-yl}cyclohexyl)phenyl]-1H-pyrazole-4-carboxylic acid (cis racemic);
1-{3-3-[2-butylpyrrolidine-1-carbonyl]cyclohexyl]phenyl}-5-cyclopropyl-1H-pyrazole-4-carboxylic acid;
5-Cyclopropyl-1-(3-{[(2S)-2-(ethoxymethyl)pyrrolidine-1-carbonyl]cyclohexyl}phenyl)-1H-pyrazole-4-carboxylic acid (Resolved cis diastereoisomers);
5-Cyclopropyl-1-(3-{[(2S)-2-(ethoxymethyl)pyrrolidine-1-carbonyl]cyclohexyl}phenyl)-1H-pyrazole-4-carboxylic acid (Resolved cis diastereoisomers);
1-(5'-(Azepane-1-carbonyl)-2',3',4',5'-tetrahydro-[1,1'-biphenyl]-3-yl)-5-cyclopropyl-1H-pyrazole-4-carboxylic acid;
1-(3-(3-(Azepane-1-carbonyl)cyclohexyl)phenyl)-5-cyclopropyl-1H-pyrazole-4-carboxylic acid;
1-(3-(3-(Cyclohexyl(methyl)carbamoyl)cyclohexyl)phenyl)-5-cyclopropyl-1H-pyrazole-4-carboxylic acid;
5-Cyclopropyl-1-(3-(3-(methyl(2-propylcyclohexyl)carbamoyl)cyclohexyl) phenyl)-1H-pyrazole-4-carboxylic acid;
5-Cyclopropyl-1-(3-(t-3-(6,6-dimethyl-5,6-dihydrocyclopenta[c]pyrazol-1(4H)-yl)cyclohexyl)phenyl)-1H-pyrazole-4-carboxylic acid (trans racemic);
5-Cyclopropyl-1-(3-(-3-(6,6-dimethyl-5,6-dihydrocyclopenta[c]pyrazol-1(4H)-yl)cyclohexyl)phenyl)-1H-pyrazole-4-carboxylic acid (cis racemate);
5-Cyclopropyl-1-{3-[3-(3-methyl-pyrrolidine-1-carbonyl)-cyclohexyl]-phenyl}-1H-pyrazole-4-carboxylic acid;
1-(3-(1-(tert-butoxycarbonyl)piperidin-3-yl)phenyl)-5-((1R,2R)-2-(1-methyl-1H-1,2,3-triazol-4-yl)cyclopropyl)-1H-pyrazole-4-carboxylic acid;
1-(3-(1-(tert-Butoxycarbonyl)piperidin-3-yl)phenyl)-5-cyclopropyl-1H-pyrazole-4-carboxylic acid;
1-(3-(1-(cyclohexylmethyl)piperidin-3-yl)phenyl)-5-cyclopropyl-1H-pyrazole-4-carboxylic acid, Hydrochloride;
5-((1R,2R)-2-(1-Methyl-1H-1,2,3-triazol-4-yl)cyclopropyl)-1-(3-(1-phenethylpiperidin-3-yl)phenyl)-1H-pyrazole-4-carboxylic acid, Hydrochloride;
5-((1R,2R)-2-(1-methyl-1H-1,2,3-triazol-4-yl)cyclopropyl)-1-(3-(1-(phenylsulfonyl)piperidin-3-yl)phenyl)-1H-pyrazole-4-carboxylic acid;
1-(3-(1-(2-cyclohexylacetyl)piperidin-3-yl)phenyl)-5-((1R,2R)-2-(1-methyl-1H-1,2,3-triazol-4-yl)cyclopropyl)-1H-pyrazole-4-carboxylic acid;
5-((1R,2R)-2-(1-methyl-1H-1,2,3-triazol-4-yl)cyclopropyl)-1-(3-(1-pivaloylpiperidin-3-yl)phenyl)-1H-pyrazole-4-carboxylic acid;
1-(3-(1-benzoylpiperidin-3-yl)phenyl)-5-((1R,2R)-2-(1-methyl-1H-1,2,3-triazol-4-yl)cyclopropyl)-1H-pyrazole-4-carboxylic acid
5-((1R,2R)-2-(1-Methyl-1H-1,2,3-triazol-4-yl)cyclopropyl)-1-(3-(1-((R)-2-propylpiperidine-1-carbonyl)piperidin-3-yl)phenyl)-1H-pyrazole-4-carboxylic acid;
1-(3-(3-(2-cyclohexylethyl)piperidin-1-yl)phenyl)-5-((1R,2R)-2-(1-methyl-1H-1,2,3-triazol-4-yl)cyclopropyl)-1H-pyrazole-4-carboxylic acid;
1-(3-((S)-3-(2-Cyclohexylethyl)piperidin-1-yl)phenyl)-5-((1R,2R)-2-(1-methyl-1H-1,2,3-triazol-4-yl)cyclopropyl)-1H-pyrazole-4-carboxylic acid;
1-(3-((R)-3-(2-cyclohexylethyl)piperidin-1-yl)phenyl)-5-((1R,2R)-2-(1-methyl-1H-1,2,3-triazol-4-yl)cyclopropyl)-1H-pyrazole-4-carboxylic acid;
1-(3-((1R,3S)-3-(6-Butyl-5,6-dihydrocyclopenta[c]pyrazol-1(4H)-yl)cyclohexyl)phenyl)-5-cyclopropyl-1H-pyrazole-4-carboxylic acid;
1-(3-((1,3-trans)-3-(6-Butyl-5,6-dihydrocyclopenta[c]pyrazol-1(4H)-yl)cyclohexyl)phenyl)-5-cyclopropyl-1H-pyrazole-4-carboxylic acid;
1-(3-((1,3-cis)-3-(6,6-Dimethyl-5,6-dihydrocyclopenta[c]pyrazol-1(4H)-yl)cyclohexyl)phenyl)-5-(2-(1-methyl-1H-1,2,3-triazol-4-yl)cyclopropyl)-1H-pyrazole-4-carboxylic acid;
1-(3-((1,3-trans)-3-(6,6-Dimethyl-5,6-dihydrocyclopenta[c]pyrazol-1(4H)-yl)cyclohexyl)phenyl)-5-(2-(1-methyl-1H-1,2,3-triazol-4-yl)cyclopropyl)-1H-pyrazole-4-carboxylic acid;
1-(3-(3-((2-Butylcyclopentyl)(methyl)carbamoyl)cyclohexyl)phenyl)-5-cyclopropyl-1H-pyrazole-4-carboxylic acid;
1-(3-(3-(2-Butylpyrrolidine-1-carbonyl)cyclohexyl)phenyl)-5-(2-(1-methyl-1H-1,2,3-triazol-4-yl)cyclopropyl)-1H-pyrazole-4-carboxylic acid; and
1-(3-((R)-3-(Cyclohexylmethoxy)piperidin-1-yl)phenyl)-5-((1R,2R)-2-(1-methyl-1H-1,2,3-triazol-4-yl)cyclopropyl)-1H-pyrazole-4-carboxylic acid.

In one embodiment, the invention is directed to compounds of Formula (I) as follows:
1-(3-(3-(2-cyclohexylethyl)piperidin-1-yl)phenyl)-5-((1R,2R)-2-(1-methyl-1H-1,2,3-triazol-4-yl)cyclopropyl)-1H-pyrazole-4-carboxylic acid;
5-((1R,2R)-2-(1-methyl-1H-1,2,3-triazol-4-yl)cyclopropyl)-1-(3-(1-pivaloylpiperidin-3-yl)phenyl)-1H-pyrazole-4-carboxylic acid;
5-Cyclopropyl-1-(3-(t-3-(6,6-dimethyl-5,6-dihydrocyclopenta[c]pyrazol-1(4H)-yl)cyclohexyl)phenyl)-1H-pyrazole-4-carboxylic acid (trans racemic); and
1-(3-((R)-3-(Cyclohexylmethoxy)piperidin-1-yl)phenyl)-5-((1R,2R)-2-(1-methyl-1H-1,2,3-triazol-4-yl)cyclopropyl)-1H-pyrazole-4-carboxylic acid.

Compound Preparation

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

The synthesis of the compounds of the general Formula (I) and pharmaceutically acceptable derivatives and salts thereof may be accomplished as outlined below in Schemes 1-12. In the following description, the groups are as defined above for compounds of Formula (I) unless otherwise indicated. Abbreviations are as defined in the Examples section. Starting materials are commercially available or are made from commercially available starting materials using methods known to those skilled in the art.

Scheme 1: Synthesis of Pyrazole Core

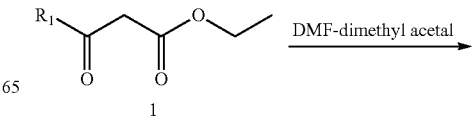

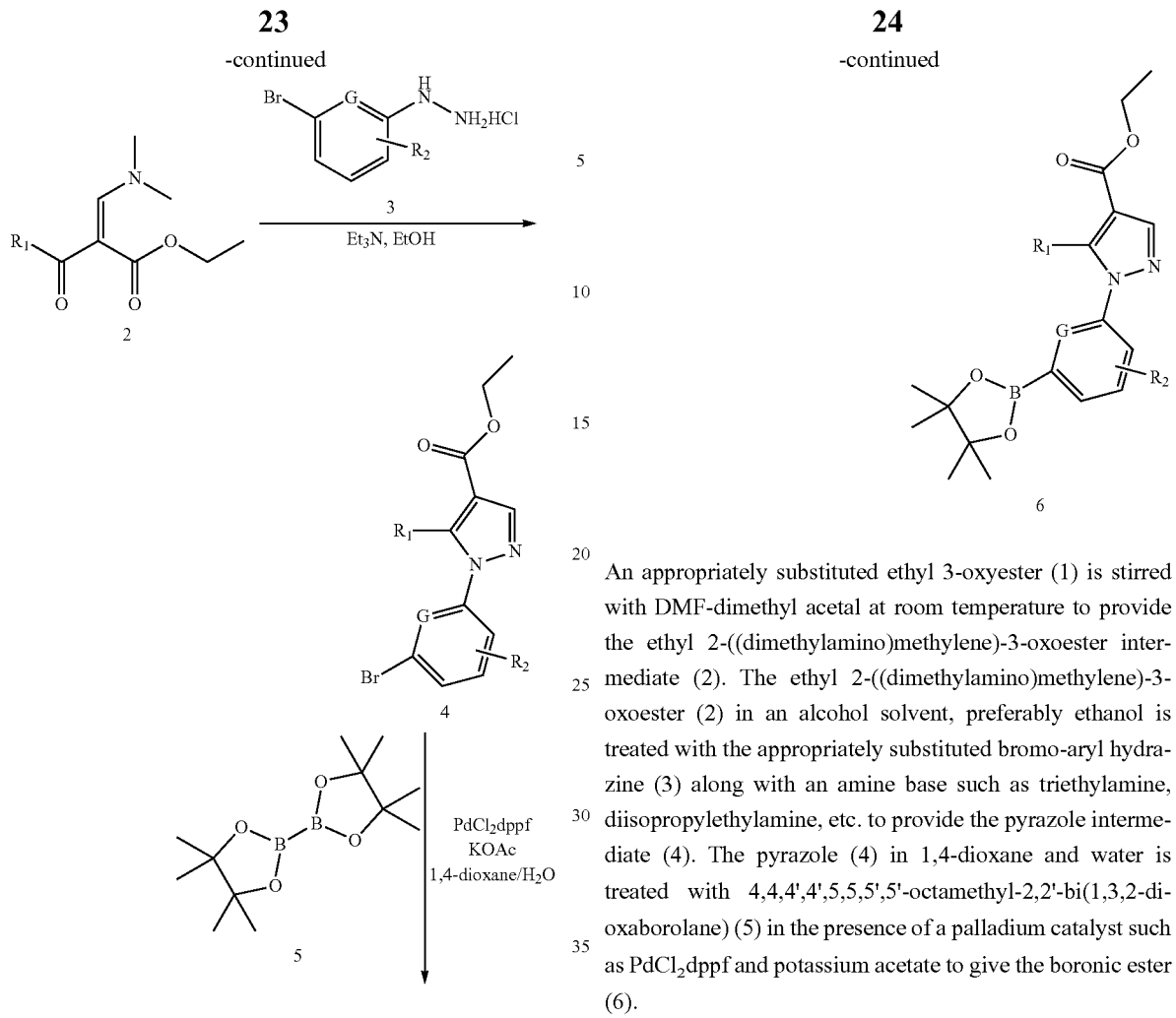

An appropriately substituted ethyl 3-oxyester (1) is stirred with DMF-dimethyl acetal at room temperature to provide the ethyl 2-((dimethylamino)methylene)-3-oxoester intermediate (2). The ethyl 2-((dimethylamino)methylene)-3-oxoester (2) in an alcohol solvent, preferably ethanol is treated with the appropriately substituted bromo-aryl hydrazine (3) along with an amine base such as triethylamine, diisopropylethylamine, etc. to provide the pyrazole intermediate (4). The pyrazole (4) in 1,4-dioxane and water is treated with 4,4,4',4',5,5,5',5'-octamethyl-2,2'-bi(1,3,2-dioxaborolane) (5) in the presence of a palladium catalyst such as PdCl$_2$dppf and potassium acetate to give the boronic ester (6).

Scheme 2: Synthesis of Amide Analogues-1

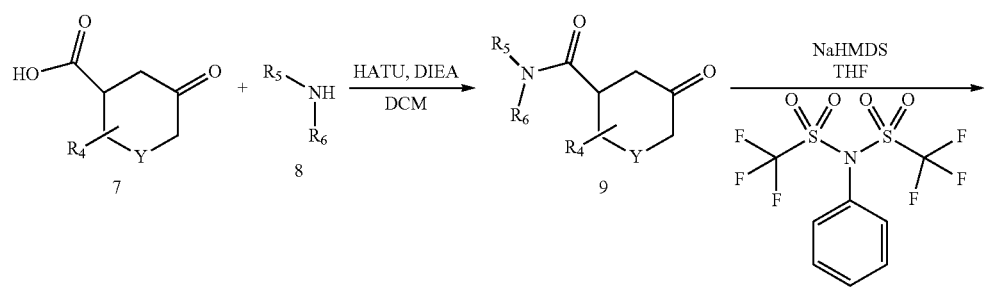

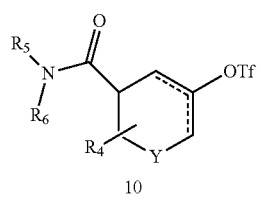

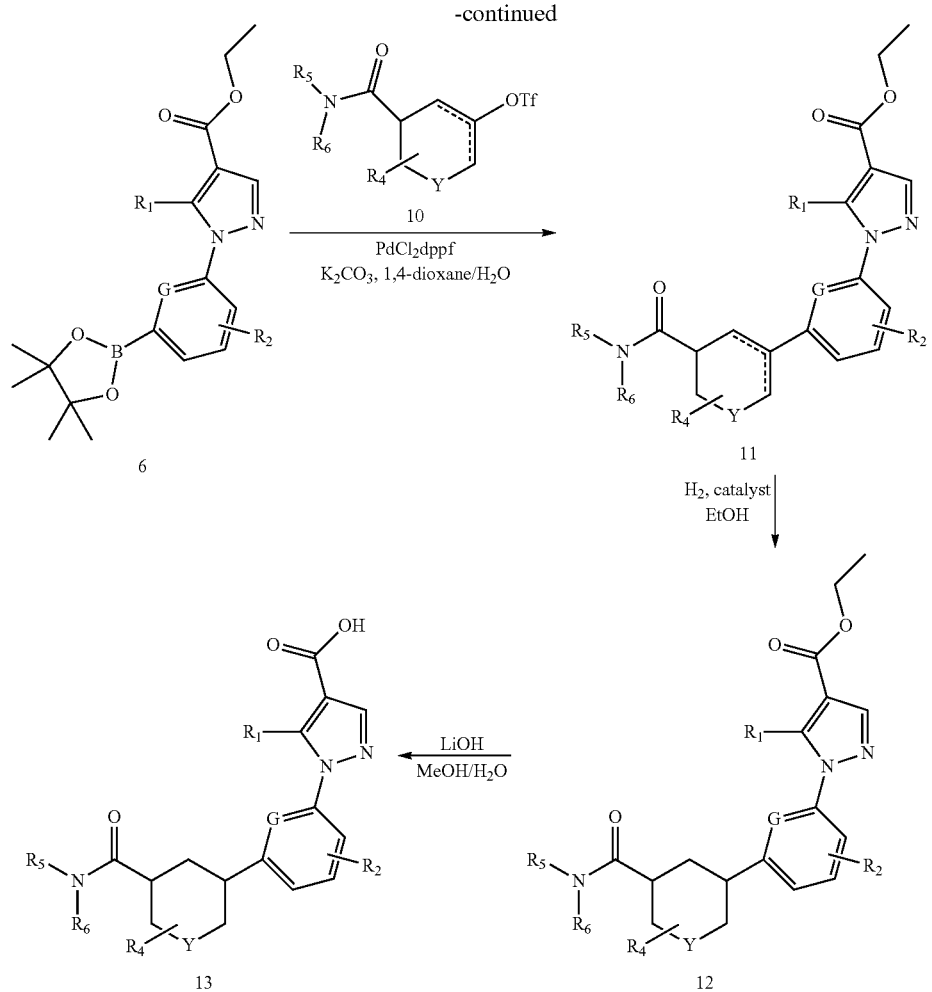

The substituted ketoacid (7) is dissolved in an appropriate solvent such as DCM, DMF or a mixture of DCM and DMF and treated with a substituted amine (8) in the presence of a coupling agent like HATU or EDC and an amine base such as triethylamine, diisopropylethylamine, etc. to provide the ketoacid amide (9). The ketoacid amide (9) in THF is treated with a base such as sodium hexamethyldisilazide, lithium hexamethyldisilazide or lithium diisopropyl amine followed by 1,1,1-trifluoro-N-phenyl-N-((trifluoromethyl)sulfonyl)-methanesulfonamide to give the triflate (10) as a mixture of region isomers that are used without separation in the next step. The triflate (10) and the pyrazole boronic ester (6) are dissolved in a mixture of 1,4-dioxane and water with an inorganic base, such as $K_2CO_3$ and treated with a catalytic amount of a palladium catalyst such as $PdCl_2dppf$ to give the unsaturated pyrazole ethyl ester (11) as a mixture of region isomers that are used without separation in the next step. The unsaturated pyrazole ethyl ester (11) is then dissolved in an alcohol solvent preferably ethanol and reduced using $H_2$ and a catalyst such as Pd on carbon to give the pyrazole ester (12). Base hydrolysis of the ethyl ester with an inorganic base such as LiOH or NaOH in a mixture of an alcohol such as methanol or ethanol and water provides the pyrazole acid (13).

Scheme 3: Synthesis of Amide Analogues-2

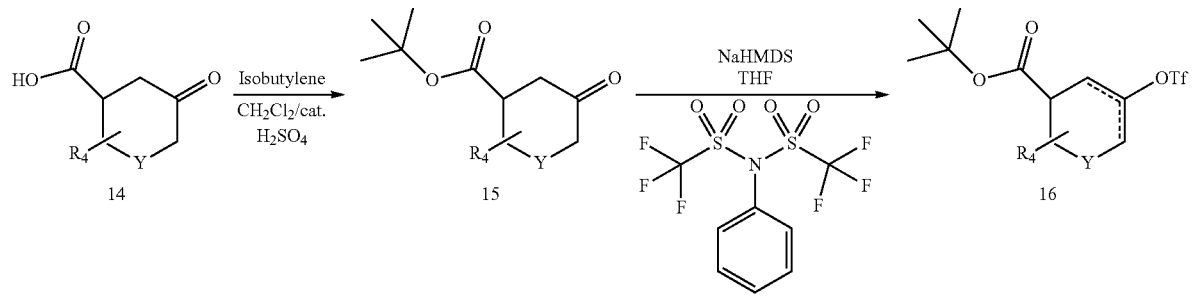

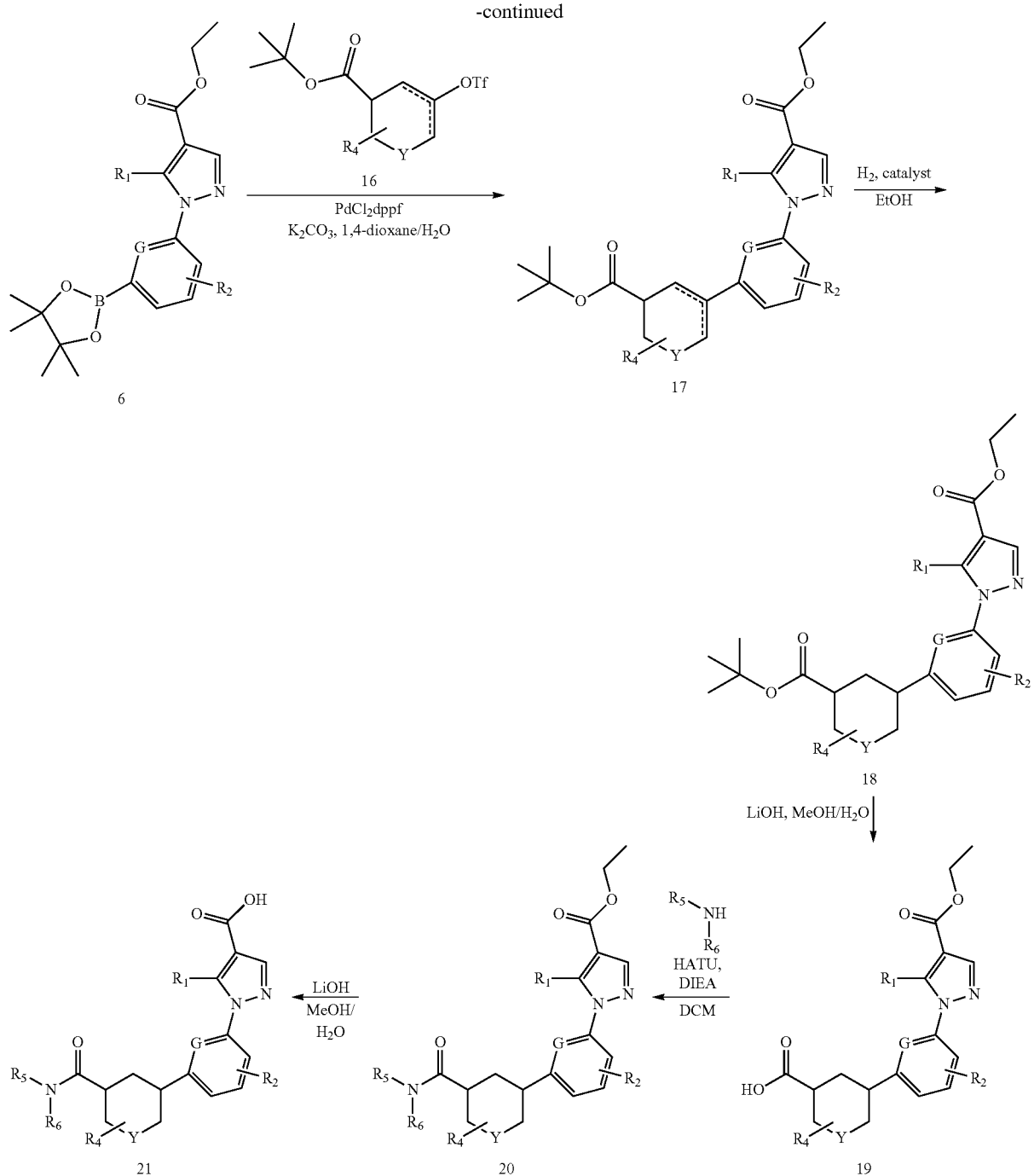

The ketoacid (14) is dissolved in an appropriate solvent such as CH$_2$Cl$_2$ and treated with isobutylene in She presence of an acid catalyst such as H$_2$SO$_4$ to give the ketoacid ester (15). The ketoacid ester (15) in THF is treated with a base such as sodium hexamethyldisilazide, lithium hexamethyldisilazide or lithium diisopropyl amine followed by 1,1,1-trifluoro-N-phenyl-N-(((trifluoromethyl)sulfonyl)methanesulfonamide to give the triflate (16) as a mixture of region isomers that are used without separation in the next step. The triflate (16) and the pyrazole boronic ester (6) are dissolved in a mixture of 1,4-dioxane and water with an inorganic base, such as K$_2$CO$_3$ and treated with a catalytic amount of a palladium catalyst such as PdCl$_2$dppf to give the unsaturated pyrazole (17) as a mixture of region isomers that are used without separation in the next step. The unsaturated pyrazole diester (17) is then dissolved in an alcohol solvent preferably ethanol and reduced using H$_2$ and a catalyst such as Pd on carbon to give the pyrazole diester (18). The pyrazole diester (18) is selectively deprotected in acid conditions such as HCl in 1,4-dioxane to provide the pyrazole acid ester (19). The pyrazole acid ester (19) is dissolved in an appropriate solvent such as DCM, DMF or a mixture of DCM and DMF and treated with a substituted amine (8) in the presence of a coupling agent like HATU or EDC and an amine base such as triethylamine, diisopropylethylamine, etc. to provide the pyrazole amide ester (20). Base hydrolysis of the ethyl ester with an inorganic base such as LiOH or NaOH in a mixture of an alcohol such as methanol or ethanol and water provides the pyrazole acid (21).

Scheme 4: Synthesis of Ether Analogues

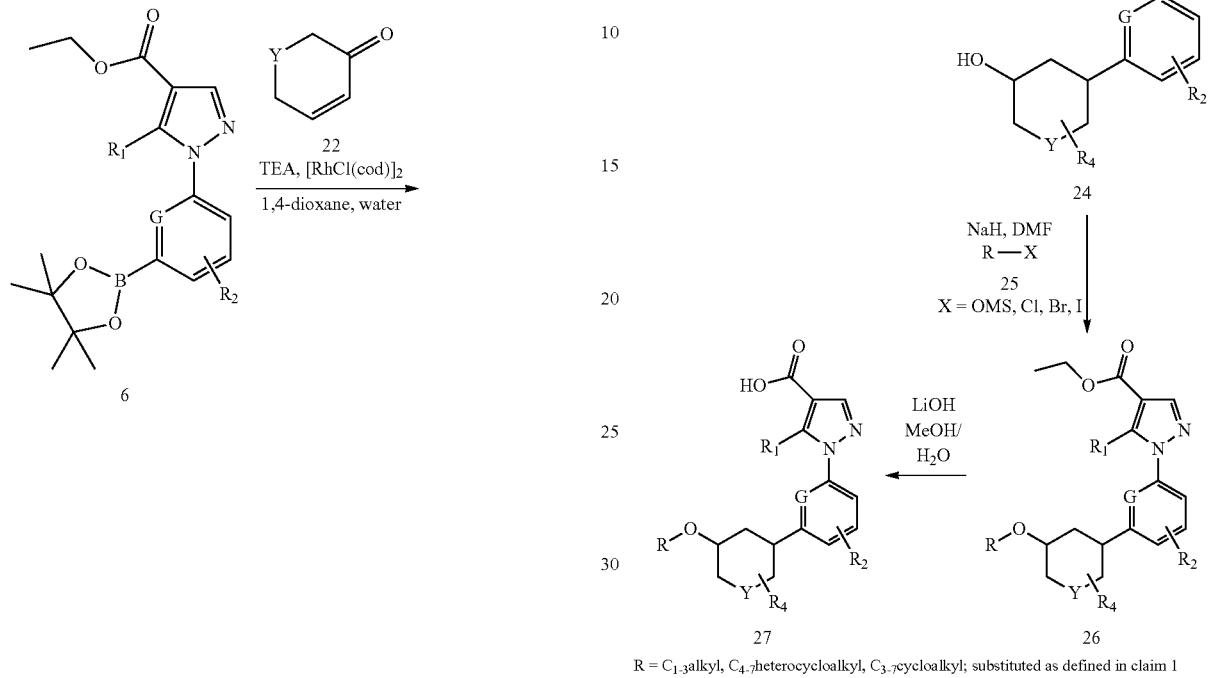

R = $C_{1-3}$alkyl, $C_{4-7}$heterocycloalkyl, $C_{3-7}$cycloalkyl; substituted as defined in claim 1

The pyrazole boronic ester (6) is dissolved in a mixture of 1,4-dioxane and water with an organic base, such as triethyl amine or diisopropylethyl amine and an appropriately substituted cyclohexenone (22) and treated with a catalytic amount of a rhodium catalyst such [RhCl(cod)]$_2$ to give the pyrazole ketone (23). The pyrazole ketone (23) is selectivity reduced with for example NaBH$_4$ in methanol or ethanol to give the pyrazole alcohol (24). The pyrazole alcohol (24) and an alkyl, cycloalkyl or heterocycloalkyl chloride, bromide, iodide or mesylate (25) is dissolved in an appropriate solvent, such as DMF, THF or dioxane and treated with a base, such as NaH to give the pyrazole ether (26). Base hydrolysis of the ethyl ester with an inorganic base such as LiOH or NaOH in a mixture of an alcohol, such as methanol or ethanol, and water provides the pyrazole ether acid (27).

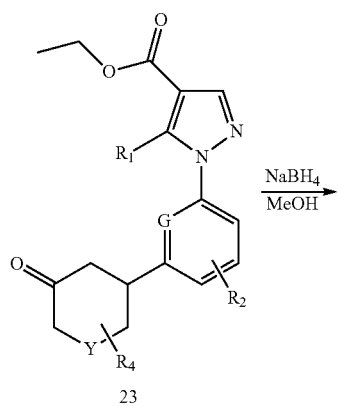

Scheme 5: Synthesis of Alkyl Alcohol Analogues

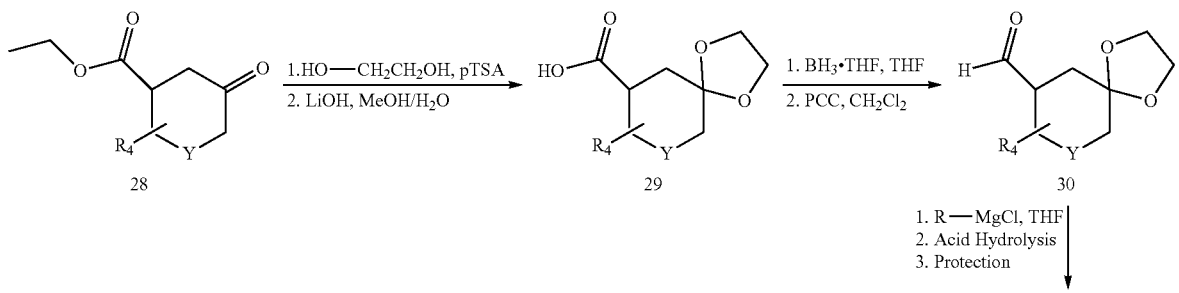

-continued
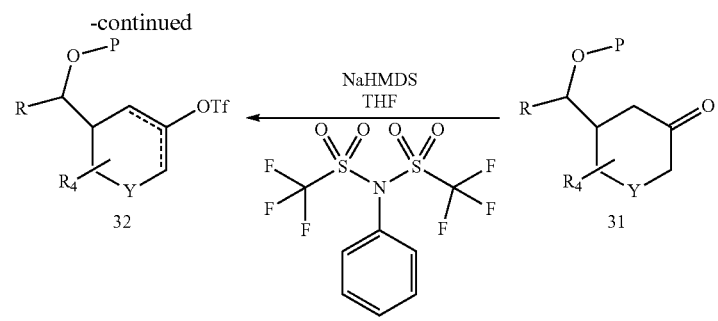
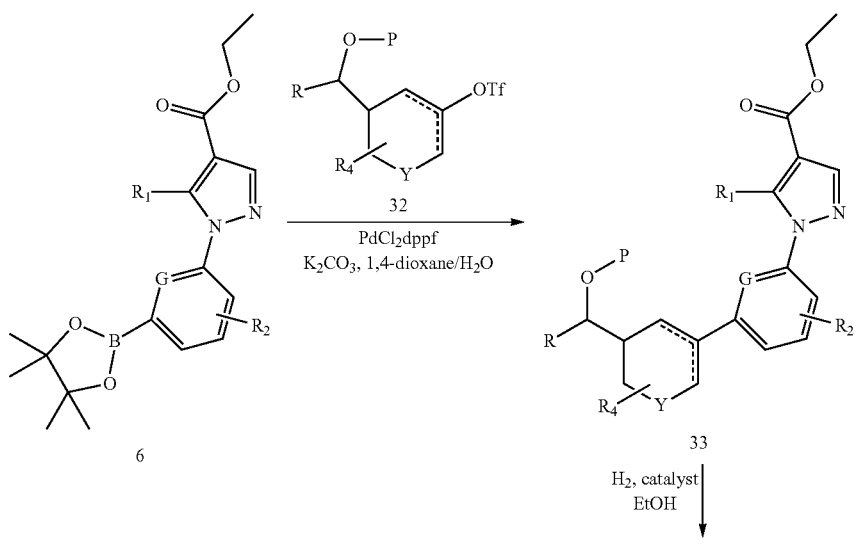
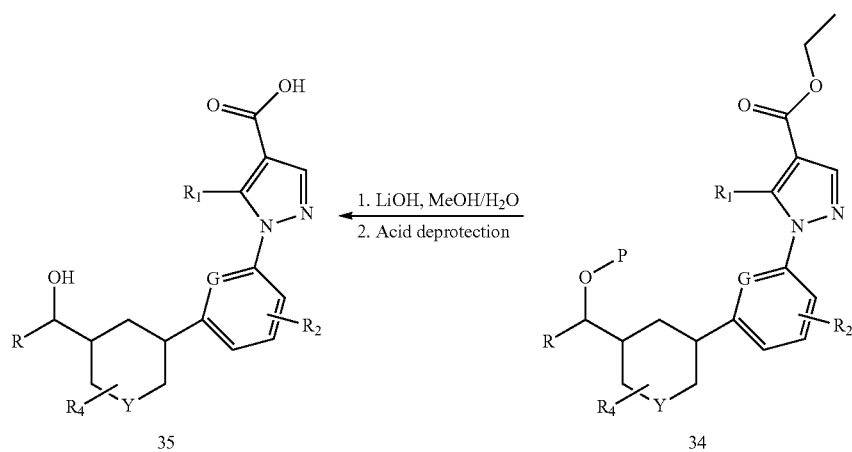
P = acid labile protecting group
R = C$_{1-7}$alkyl, C$_{3-7}$cycloalkyl, C$_{4-7}$heterocycloalkyl, triazolyl; substituted as defined in claim 1

The ketoester (28) is treated with ethane-1,2-diol and an acid catalyst such as pTSA followed by base hydrolysis with LiOH or NaOH in MeOH or EtOH to give the protected keto-acid (29). The protected keto-acid (29) is reduced with $BH_3 \cdot THF$ in THF and then oxidized using pyridinium chlorochromate in $CH_2Cl_2$ to give the differentially protected ketone aldehyde (30). The differentially protected ketone-aldehyde (30) is dissolved in an ethereal solvent such as diethyl ether or THF and treated with a $C_{1-7}$alkyl, $C_{3-7}$cycloalkyl, $C_{3-7}$hetercycloalkyl, triazolyl Grignard reagent followed by hydrolysis of the cyclic ketal with an alcohol acid such as HCl in MeOH and protection of the alcohol with an acid labile protecting group such as THP to provide the ketone (31). The ketone (31) in THF is treated with a base such as sodium hexamethyldisilazide, lithium hexamethyldisilazide or lithium diisopropyl amine followed by 1,1,1-trifluoro-N-phenyl-N-((trifluoromethyl)-sulfonyl)methanesulfonamide to give the triflate (32) as a mixture of regioisomers that are used without separation in the next step. The triflate (32) and the pyrazole boronic ester (6) are dissolved in a mixture of 1,4-dioxane and water with an inorganic base, such as $K_2CO_3$ and treated with a catalytic amount of a palladium catalyst such as $PdCl_2dppf$ to give the unsaturated pyrazole (33) as a mixture of region isomers that are used without separation in the next step. The unsaturated pyrazole (34) is then dissolved in an alcohol solvent preferably ethanol and reduced using $H_2$ and a catalyst such as Pd on carbon to give the pyrazole ester (26). Base hydrolysis of the ethyl ester with an inorganic base such as LiOH or NaOH in a mixture of an alcohol such as methanol or ethanol and water followed by treatment of the reaction product with an aqueous acid such as HCl in an ethereal solvent such as diethyl ether, THF or 1,4-dioxane to give the pyrazole alcohol acid (35).

Scheme 6: Synthesis of Alkyl Ketone Analogues

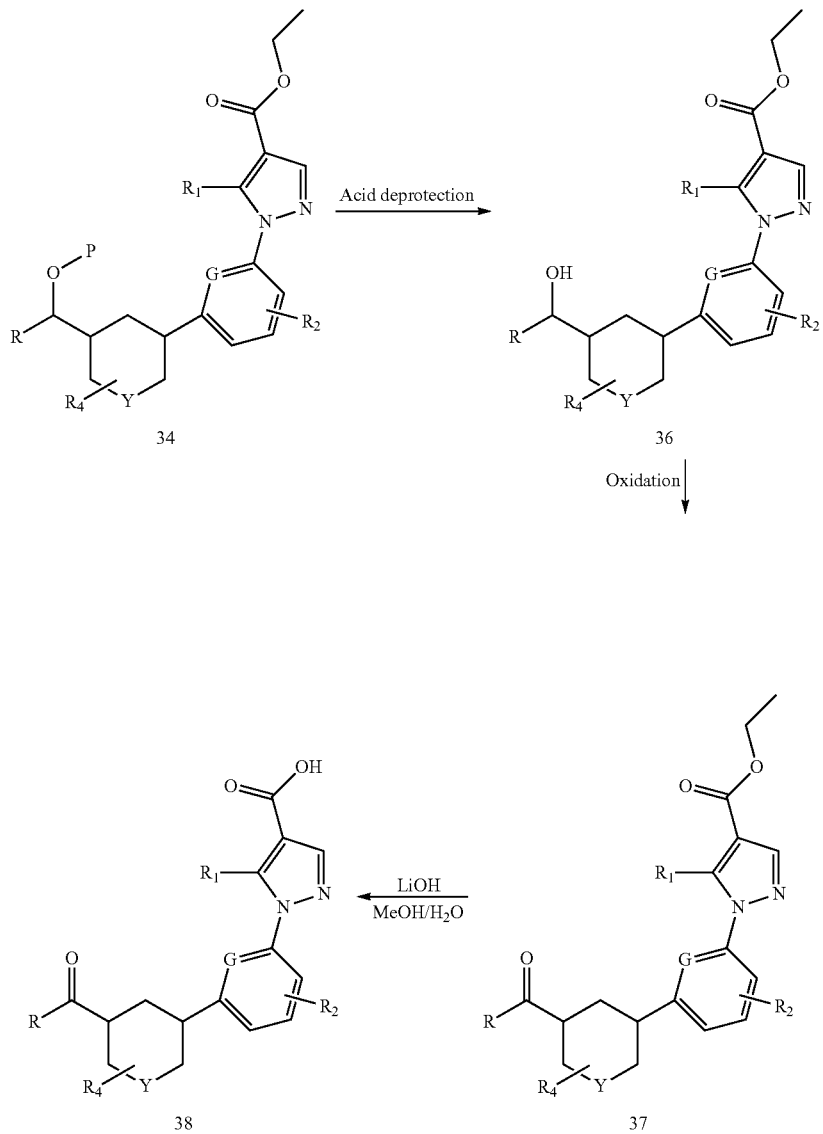

P = acid labile protecting group
R = $C_{1-7}$alkyl, $C_{3-7}$cycloalkyl, $C_{4-7}$heterocycloalkyl, triazolyl; substituted as defined in claim 1

The protected pyrazole alcohol (34) is treated with an aqueous acid such as HCl in an ethereal solvent such as diethyl ether, THF or 1,4-dioxane or an alcoholic solvent preferably ethanol to give the pyrazole alcohol (36). Oxidation of the pyrazole alcohol (36) with an oxidizing agent such as pyridinium dichromate in $CH_2Cl_2$ or Jones reagent in acetone provides the pyrazole ketone (37). Base hydrolysis of the ethyl ester with an inorganic base such as LiOH or NaOH in a mixture of an alcohol such as methanol or ethanol and water provides the pyrazole ketone acid (38).

Scheme 7: Synthesis of Alkyl Ether Analogues

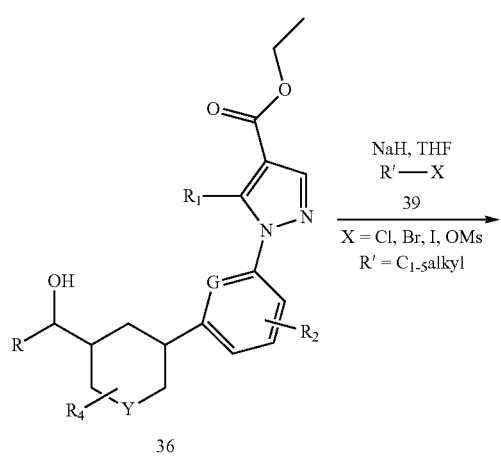

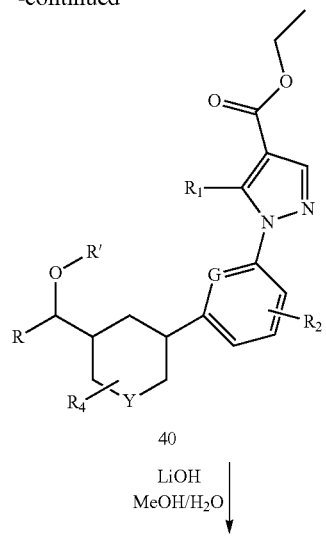

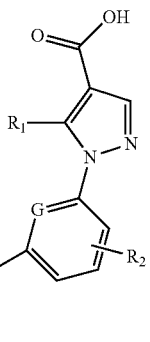

R = $C_{1-7}$alkyl, $C_{3-7}$cycloalkyl, $C_{4-7}$heterocycloalkyl, triazolyl; substituted as defined in claim 1

The pyrazole alcohol (36) is dissolved in THF, 1,4-dioxane or DMF and treated with an alkyl chloride, bromide, iodide or mesylate (40) to provide the pyrazole ether (41). Base hydrolysis of the ethyl ester with an inorganic base such as LiOH or NaOH in a mixture of an alcohol, such as methanol or ethanol, and water provides the pyrazole ether acid (42).

Scheme 8: Synthesis of Heterocyclic Analogues-1

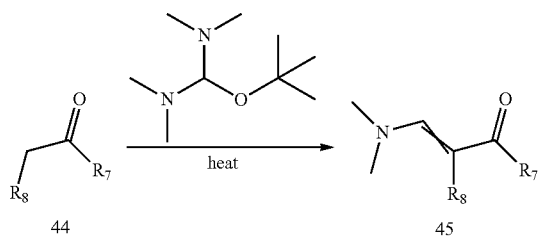

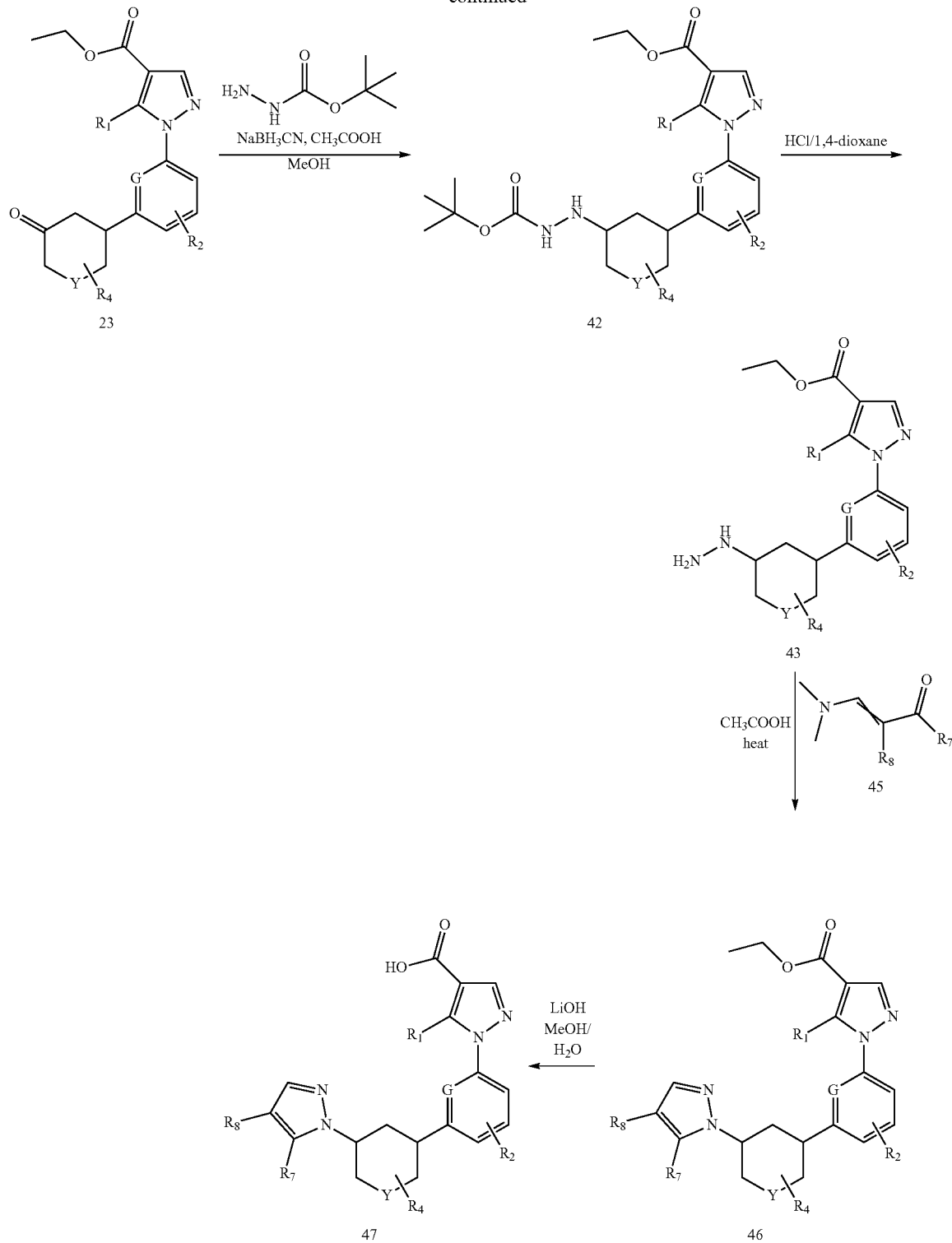

The pyrazole ketone (23) and tert-butyl hydrazinecarboxylate are dissolved in methanol and treated with sodium cyanoborohydride and acetic acid to give the protected hydrazine pyrazole (42). The protected hydrazine pyrazole (42) is treated with HCl in 1,4-dioxane to give the hydrazine pyrazole (43). The ketone (44) is heated with 1-tert-butoxy-N,N,N',N'-tetramethylmethanediamine to give the dimethylamino ketone (45). The hydrazine pyrazole ethyl ester (43) is heated with the dimethylamino ketone (45) in acidic acid to give the pyrazole pyrazole ester (46). Base hydrolysis of the ethyl ester with an inorganic base such as LiOH or NaOH in a mixture of an alcohol, such as methanol or ethanol, and water provides the pyrazole pyrazole acid (47).

Scheme 9: Synthesis of Heterocyclic Analogues-2
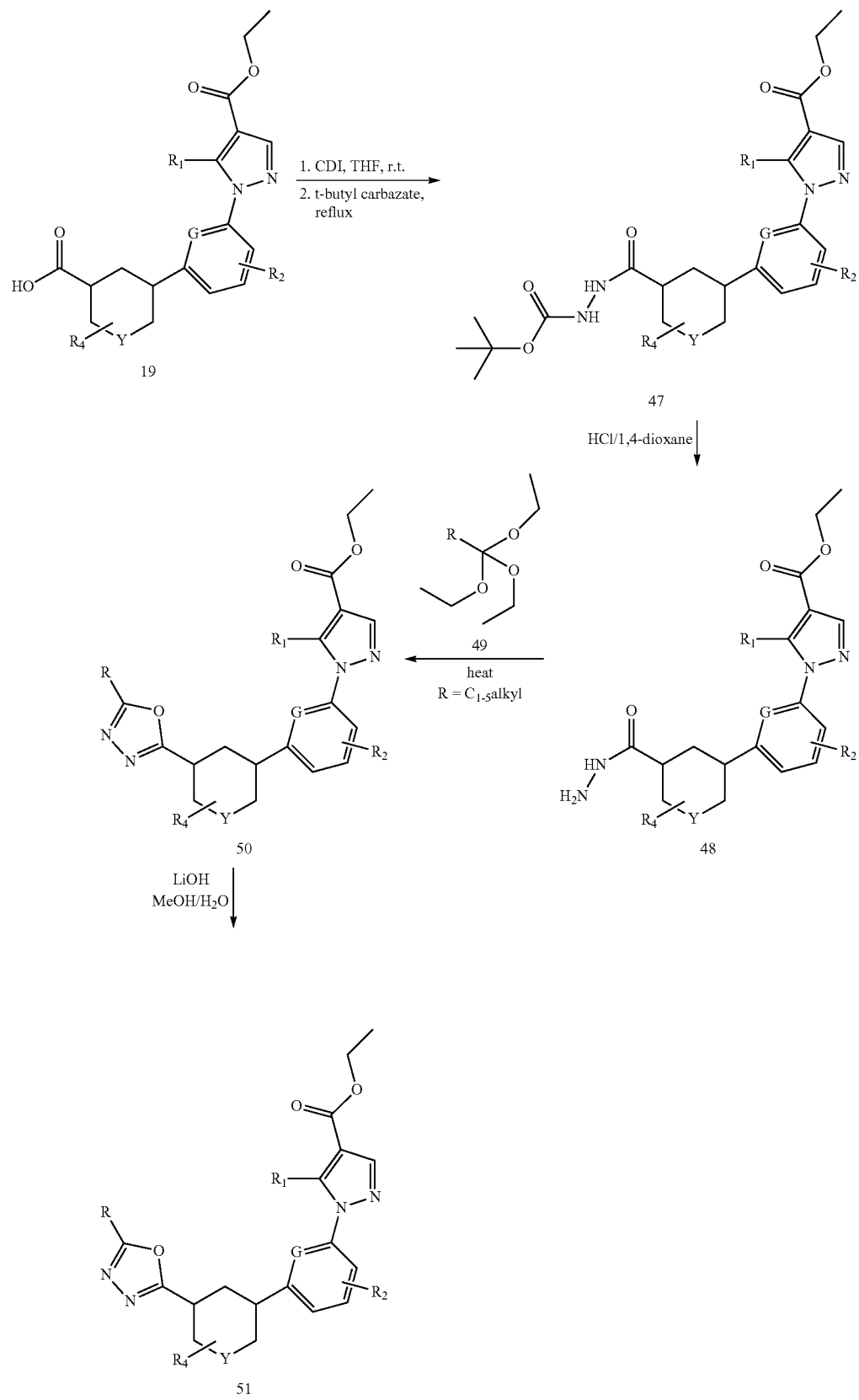

The pyrazole acid (19) is treated with CDI in THF followed by heating with t-butyl carbazate to give the Boc-protected hydrazine carboxylate (47). The Boc-protected pyrazolo hydrazine carboxylate (47) is treated with acid in an appropriate solvent such as HCl in 1,4-dioxane or TFA in $CH_2Cl_2$ to give the pyrazole hydrazine carboxylate (48). The pyrazole hydrazine carboxylate (48) is then heated with the appropriate orthoester (49) to give the pyrazole 1, 3, 4-oxadiazole ester (50). Base hydrolysis of the ethyl ester with an inorganic base such as LiOH or NaOH in a mixture of an alcohol such as methanol or ethanol and water followed by treatment of the reaction product with an aqueous acid such as HCl in an ethereal solvent such as diethyl ether, THF or 1,4-dioxane to give the pyrazole acid (51).

Scheme 1: Synthesis of Pyrazole Core

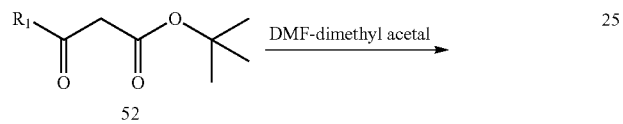

52

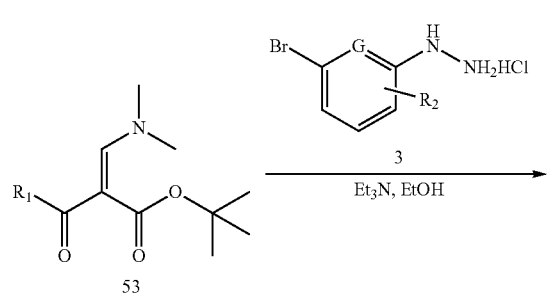

53

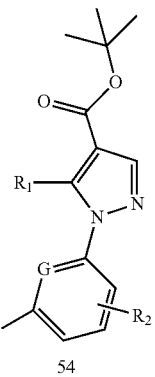

54

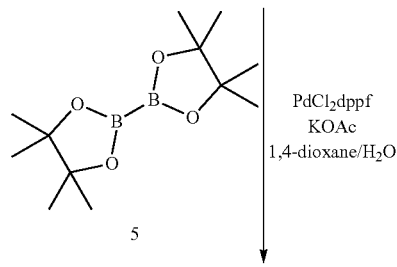

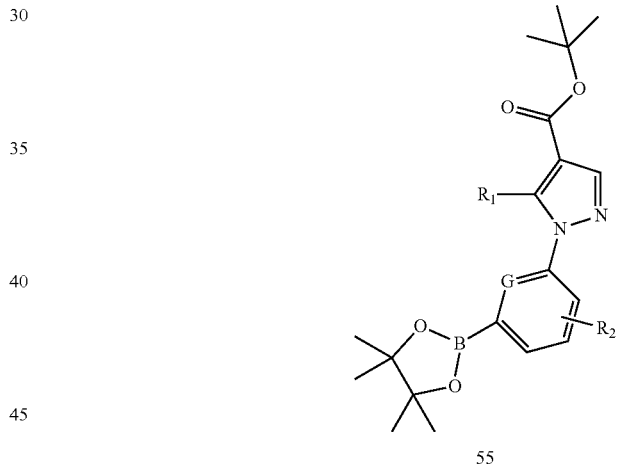

55

An appropriately substituted t-butyl 3-oxyester (52) is stirred with DMF-dimethyl acetal at room temperature to provide the t-butyl 2-((dimethylamino)methylene)-3-oxoester intermediate (53). The t-butyl 2-((dimethylamino) methylene)-3-oxoester (53) in an alcohol solvent, preferably ethanol is treated with the appropriately substituted bromoaryl hydrazine (3) along with an amine base such as triethylamine, diisopropylethylamine, etc. to provide the pyrazole intermediate (54). The pyrazole (54) in 1,4-dioxane and water is treated with 4,4,4',4',5,5,5',5'-octamethyl-2,2'-bi(1,3,2-dioxaborolane) (5) in the presence of a palladium catalyst such as $PdCl_2dppf$ and potassium acetate to give the boronic ester (55).

Scheme 11: Synthesis of Heterocycle Analogues - 3
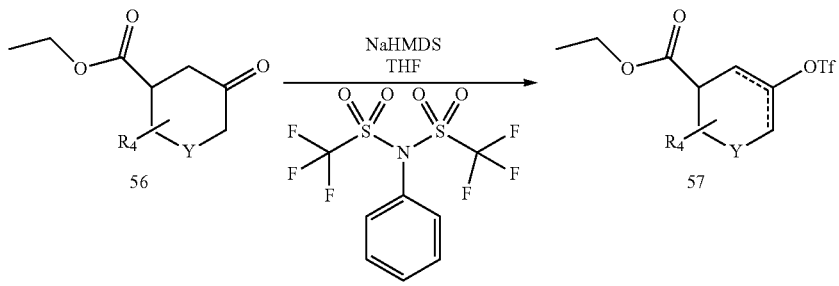
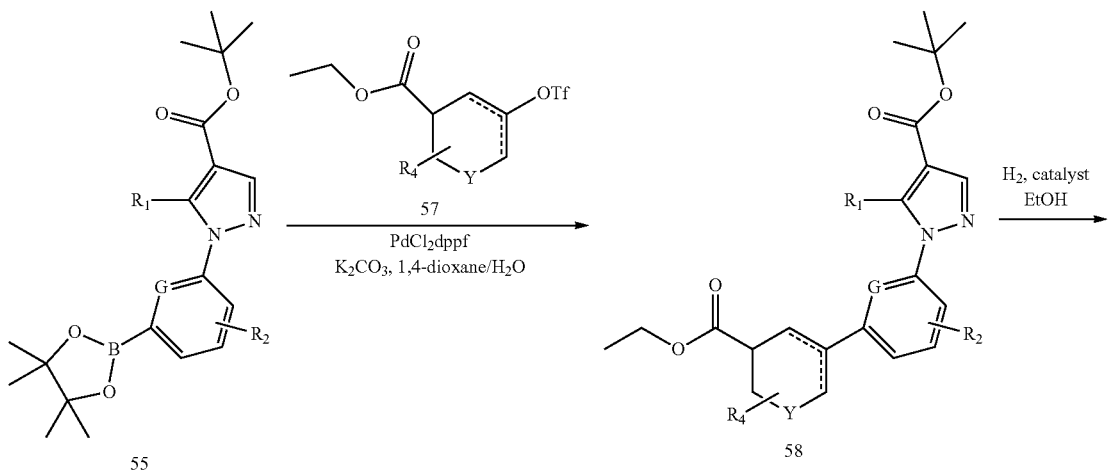
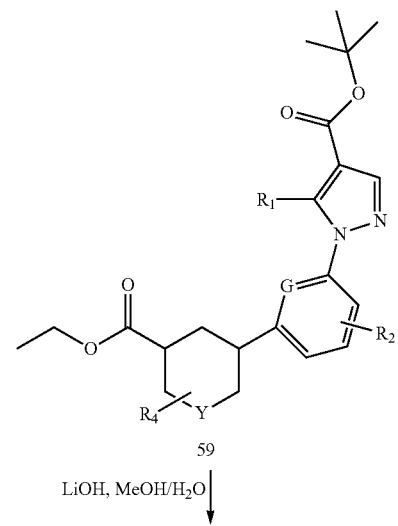

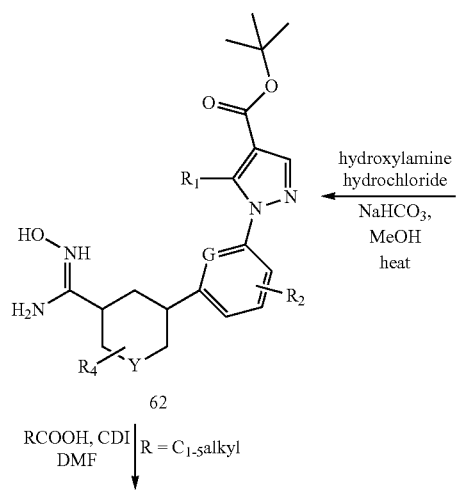
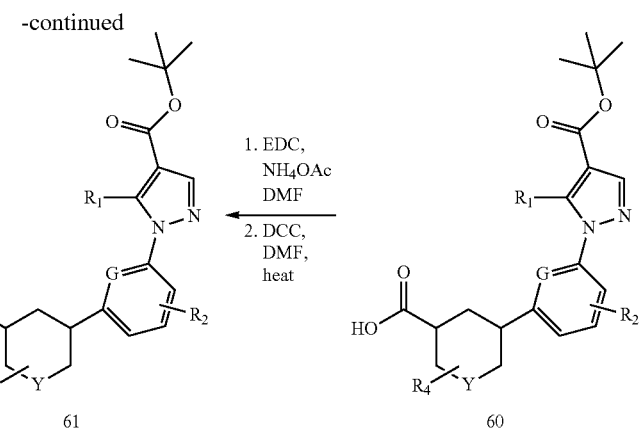

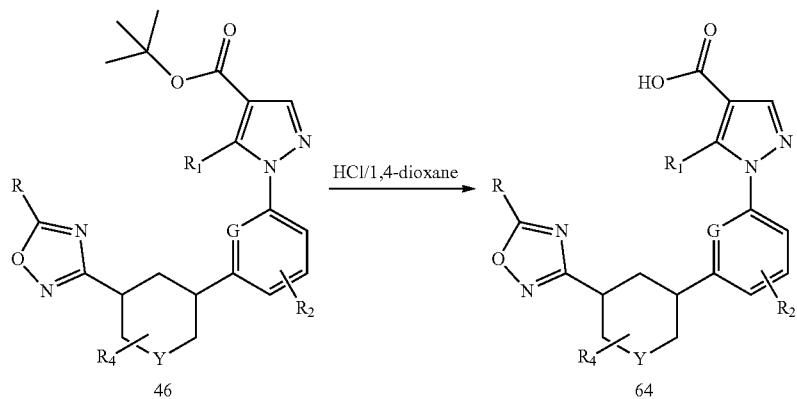

The ketoacid ester (56) in THF is treated with a base such as sodium hexamethyldisilazide, lithium hexamethyldisilazide or lithium diisopropyl amine followed by 1,1,1-trifluoro-N-phenyl-N-((trifluoromethyl)-sulfonyl)methanesulfonamide to give the triflate (57) as a mixture of regio-isomers that are used without separation in the next step. The triflate (57) and the pyrazole boronic ester (55) are dissolved in a mixture of 1,4-dioxane and water with an inorganic base, such as $K_2CO_3$ and treated with a catalytic amount of a palladium catalyst such as $PdCl_2$dppf to give the unsaturated pyrazole (58) as a mixture of region isomers that are used without separation in the next step. The unsaturated pyrazole diester (58) is then dissolved in an alcohol solvent preferably ethanol and reduced using $H_2$ and a catalyst such as Pd on carbon to give the pyrazole diester (59). Base hydrolysis of the pyrazole diester (59) with an inorganic base such as LiOH or NaOH in a mixture of an alcohol, such as methanol or ethanol, and water provides the pyrazole acid-ester (60).

The pyrazole acid-ester (60) is converted to a primary amide using a coupling agent such as DCC or EDC HCl and an ammonia source such as $NH_4Cl$ or $NH_4OH$ and a trialkyl amine such as triethyl amine or diisopropyl ethyl amine in an appropriate solvent such as $CH_2Cl_2$ or DMF and the amide is dehydrated by heating in DMF with a carbodiimide such as DCC to provide the pyrazole nitrile (61). The pyrazole nitrile (61) in an alcohol solvent like methanol or ethanol is heated with hydroxylamine-hydrochloride in the presence of an inorganic base such as $NaHCO_3$ to give the pyrazole N'-hydroxybenzimidamide (62). The pyrazole N'-hydroxybenzimidamide (62) is dissolved in DMF along with an alkylcarboxylic acid such as acetic acid or propionic acid in the presence of CDI to give the pyrazole-1,2,4-oxadiazole ester (63). Acid hydrolysis of the t-butyl ester with an acid such as HCl in 1,4-dioxane provides the pyrazole-1,2,4-oxadiazole ester (64).

Scheme 12: Synthesis of Heterocyclic Analogues-4

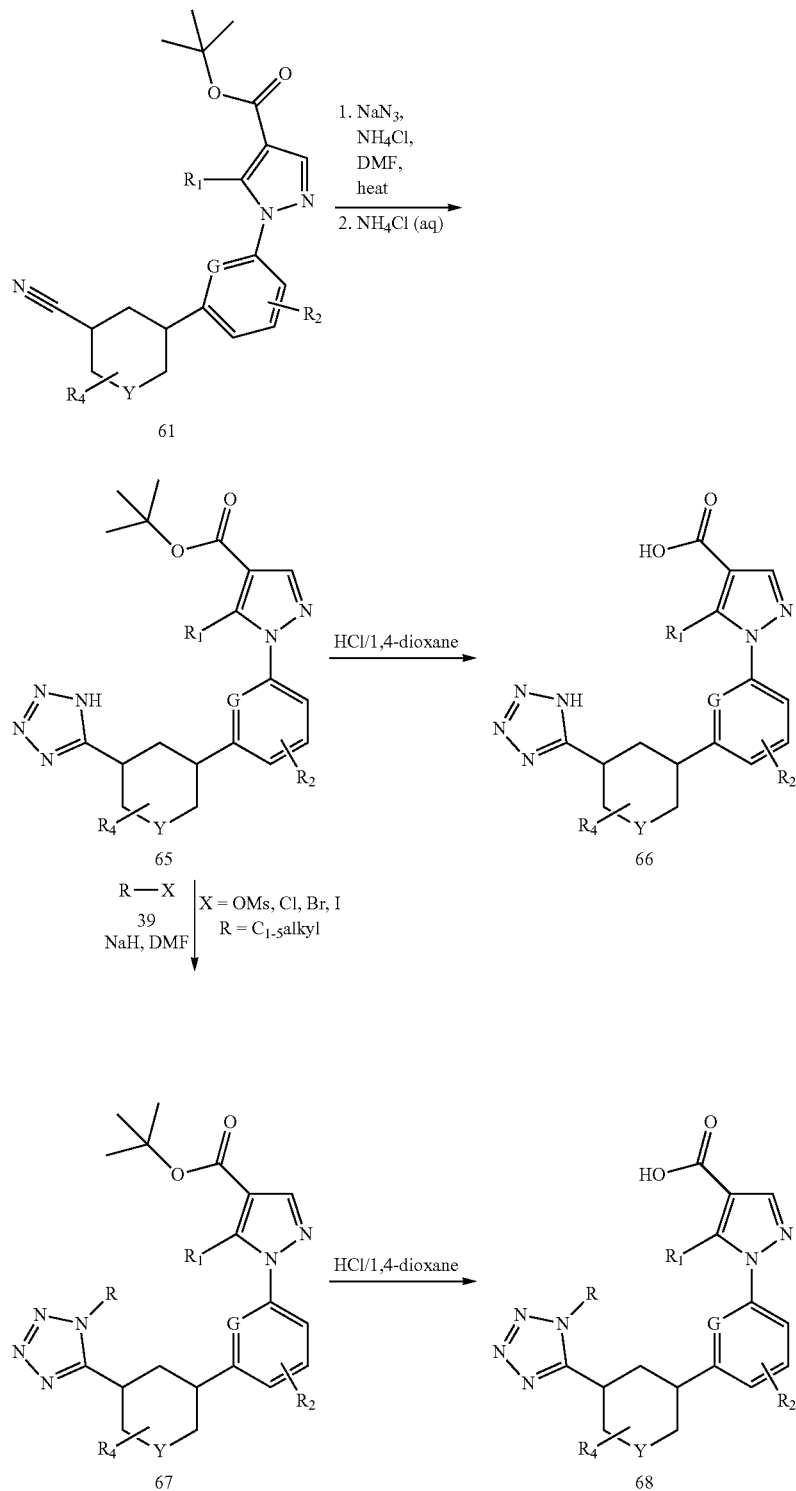

The pyrazolenitrile ester (61) is heated with NaN₃ and NH₄Cl followed by aqueous NH₄Cl to give the pyrazole tetrazole ester (65). Acid hydrolysis of the t-butyl ester (65) with an acid such as HCl in 1,4-dioxane provides the pyrazole tetrazole acid (66). Alternatively, the pyrazole tetrazole ester (65) is dissolved in an appropriate solvent like THF, 1,4-dioxane or DMF with an alkyl bromide, iodide or mesylate (39) in the presence of a base such as NaH to give the pyrazole alkyl tetrazole t-butyl ester (67). Acid hydrolysis of the t-butyl ester (67) with an acid such as HCl in 1,4-dioxane provides the pyrazole tetrazole acid (68).

Scheme 13: Synthesis of Ester for Formula (Ia)

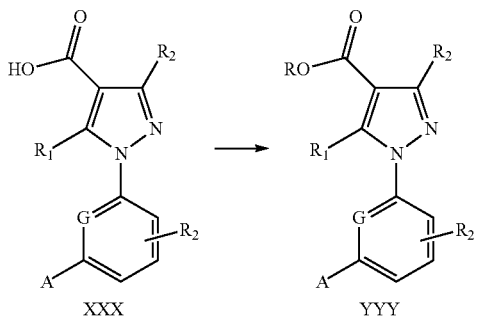

The acid XXX is treated with oxalyl or thionyl chloride to provide the intermediate acid chloride that can be further reacted with an alcohol, R—OH, in the presence of an organic (e.g., Et$_3$N, DIEA) or inorganic base (e.g., potassium carbonate, sodium carbonate) in a suitable solvent (e.g., DCM) to provide the ester YYY. Alternatively, the acid XXX is treated with an inorganic base (e.g., potassium carbonate, sodium carbonate) in an appropriate solvent (e.g., 1,4-dioxane) to provide the intermediate acid salt that can be further reacted with R—X where X represents an appropriate leaving group (e.g., Cl, Br, I) to provide the ester YYY.

Biological Activity

As stated above, the compounds according to Formula I are NRF2 regulators, and are useful in the treatment or prevention of human diseases that exhibit oxidative stress components such as respiratory and non-respiratory disorders, including COPD, asthma, fibrosis, chronic asthma and acute asthma, lung disease secondary to environmental exposures, acute lung infection, chronic lung infection, α1 antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodeling, cardiac arrhythmias, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

The biological activity of the compounds according to Formula I can be determined using any suitable assay for determining the activity of a candidate compound as a NRF2 antagonist, as well as tissue and in vivo models.

The biological activity of the compounds of Formula (I) and Formula (Ia) are demonstrated by the following tests.

BEAS-2B NQO1 MTT Assay

NAD(P)H:quinone oxidoreductase 1 (NQO1), also called DT diaphorase, is a homodimeric FAD-containing enzyme that catalyzes obligatory NAD(P)H-dependent two-electron reductions of quinones and protects cells against the toxic and neoplastic effects of free radicals and reactive oxygen species arising from one-electron reductions. The transcription of NQO1 is finely regulated by NRF$_2$, and thus NQO1 activity is a good marker for NRF2 activation. On day one, frozen BEAS-2B cells (ATCC) are thawed in a water bath, counted, and re-suspended at a concentration of 250,000 cells/mL. Fifty microliters of cells are plated in 384 well black clear-bottomed plates. Plates are incubated at 37° C., 5% CO$_2$ overnight. On day two, plates are centrifuged and 50 nL of compound or controls are added to the cells. Plates are then incubated at 37° C., 5% CO$_2$ for 48 hours. On day four, medium is aspirated from the plate and crude cell lysates are made by adding 13 uL of 1× Cell Signaling Technologies lysis buffer with 1 Complete, Mini, EDTA-free Protease Inhibitor Tablet (Roche) for each 10 mL of lysis buffer. After lysis plates are incubated for 20 minutes at room temperature. Two microliters of lysate are removed for use in Cell Titer Glo assay (Promega) and MTT cocktail is prepared (Prochaska et. al. 1998) for measurement of NQO1 activity. Fifty microliters of MTT cocktail is added to each well, plate is centrifuged, and analyzed on an Envision plate reader (Perkin Elmer) using Absorbance 570 nm label for 30 minutes. Product formation is measured kinetically and the pEC$_{50}$ of NQO1 specific activity induction is calculated by plotting the change in absorbance (Delta OD/min) versus the log of compound concentration followed by 3-parameter fitting.

Beas2B NQO1 MTT Assay

All examples described herein possessed NQO1 specific enzyme activity in BEAS-2B cells with EC$_{50}$s between >10 μM-<1 nM unless otherwise noted (see table below). EC$_{50}$s<1 nM (+++++), EC$_{50}$s 1-10 nM (++++), EC$_{50}$s 10-100 nM (+++), EC$_{50}$s 100 nM-1 μM (++), EC$_{50}$s 1-10 μM (+), EC$_{50}$s>10 μM (−), or were not determined (ND).

| Ex # | EC50 |
|---|---|
| *1 | + |
| 2 | + |
| 3 | + |
| 4 | + |
| 5 | + |
| 6 | + |
| 7 | + |
| 8c | ++ |
| 9 | + |
| 10 | + |
| 11 | ++ |
| 12 | ++ |
| 13 | + |
| *14 | + |
| *15 | + |
| *16 | + |
| 17f | +++ |
| 18g | ++ |
| *18h | + |
| 19 | + |
| 20 | + |
| 21 | + |
| *22 | + |
| 23 | ++ |
| 24 | + |
| *25 | + |
| 26 | + |
| 27 | + |
| 28 | + |
| 29 | + |
| 30 | + |
| *31 | ++ |
| 32 | ++ |
| φ33 | + |
| 34 | + |
| 35 | ++++ |
| 36c | +++ |
| 36d | ++++ |
| 37 | + |

-continued

| Ex # | EC50 |
|---|---|
| *38 | ++ |
| 39 | ++ |
| 40 | + |
| 41 | ++ |
| 42 | + |
| 43 | ++ |

*in some determinations EC$_{50}$ values were >10 μM
ϕtwo determinations for Example 33 did not result in an EC$_{50}$ being calculated NRF2-Keap1 FP Assay One model for the NRF2-Keap1 interaction is through two binding sites in the Neh2 domain on NRF2. The two sites are referred to as the DLG binding motif (latch domain, uM affinity) and the ETGE binding motif (hinge domain, nM affinity). The Keap1 protein consists of an N-terminal region (NTR), a broad complex, tramtrack, and brick a' brac domain (BTB), an intervening region (IVR), a double glycine repeat domain (DGR or Kelch), and a C-terminal region. The DLG and ETGE motifs of NRF2's Neh2 domain bind to the Kelch domain of Keap1 at different affinities. In the Keap1 Kelch fluorescence polarization (FP) assay, a TAMRA-labeled 16 mer peptide (AFFAQLQLDEETGEFL) containing the ETGE motif of NRF2 and the Kelch domain (321-609) of Keap1 is used. The assay determines if a compound interferes with the binding between Keap1 (361-609) and the TAMRA-labeled peptide. Binding of TAMRA-labeled NRF2 peptide to Keap1 (321-609) results in a high FP signal. If a compound interferes with the binding between the peptide and the protein, it will cause the assay signal to decrease. Thus, assay signal is inversely proportional to binding inhibition.

FP Assay:

100 nl of 100× compound dose response curves (serial 3-fold dilutions) in DMSO are stamped using an Echo liquid handling system (Labcyte) into 384-well low volume black assay plates (Greiner, #784076), with DMSO in columns 6 and 18. The top concentration of compound is located in columns 1 and 13. Keap1 (321-609) is diluted to 40 nM (2×) in 1× assay buffer (50 mM Tris, pH 8.0, 100 mM NaCl, 5 mM MgCl$_2$, 1 mM DTT, 2 mM CHAPS, and 0.005% BSA) and 5 ul is added using a Multidrop Combi (Thermo Electron Corporation) equipped with a metal tip dispenser to all wells of the compound plate, except column 18. Column 18 receives only 5 ul of assay buffer. Immediately, 5 uL of 16 nM (2×) of Tamra labeled peptide (AFFAQLQLDEET-GEFL, 21$^{st}$ Century Biochemicals) is added to all wells of the plate. The plates are spun at 500 rpm for 1 min, incubated for 1 hr at room temperature, and read on an Analyst GT (Molecular Devices) equipped with excitation (530/25 nm) and emission (580/10 nm) filters designed for Tamra probes. A 561 nm dichroic mirror is also used in the Analyst. The final assay concentrations of Keap1 (321-609) and Tamra labeled peptide are 20 nM and 8 nM, respectively. Fluorescence measurements, represented as mP, are used in the transformation of the data. Compound activity is calculated based on percent inhibition, normalized against controls in the assay (Control 1 contains the Tamra peptide and Keap1 (321-609) together (0% response) and control 2 contains the Tamra peptide alone (100% response)). Data analysis is handled using the software package Abase XE (Surrey, United Kingdom). The % inhibition values are calculated by the equation:

100−(100*((compound response−average control 2)/(average control 1−average control 2))).

For calculation of pIC$_{50}$s, Abase XE uses a four parameter equation.

All examples described herein possessed activity in the Keap1/NRF2 FP assay as listed (see table below) unless otherwise noted. IC$_{50}$s<1 nM (+++++), IC$_{50}$s 1 nM-10 nM (++++), IC$_{50}$s 10-100 nM (+++), IC$_{50}$s 100 nM-1 μM (++), IC$_{50}$s 1-10 μM (+), IC$_{50}$s>10 μM (−), or were not determined (ND).

| Ex # | IC$_{50}$ |
|---|---|
| 1 | ++ |
| 2 | ++ |
| 3 | ++ |
| 4 | ++ |
| 5 | ++ |
| 6 | ++ |
| 7 | ++ |
| 8c | +++ |
| 9 | ++ |
| 10 | ++ |
| 11 | +++ |
| 12 | +++ |
| 13 | +++ |
| 14 | ++ |
| 15 | ++ |
| 16 | ++ |
| 17f | +++ |
| 18g | +++ |
| 18h | + |
| 19 | ++ |
| 20 | ++ |
| 21 | ++ |
| 22 | ++ |
| 23 | + |
| 24 | ++ |
| 25 | ++ |
| 26 | +++ |
| 27 | − |
| *28 | − |
| 29 | ++ |
| 30 | +++ |
| 31 | ++ |
| 32 | +++ |
| 33 | ++ |
| 34 | ++ |
| 35 | +++ |
| 36c | +++ |
| 36d | +++ |
| 37 | ++ |
| 38 | + |
| 39 | +++ |
| 40 | +++ |
| 41 | ++ |
| 42 | +++ |
| 43 | ++ |

*in some determinations IC$_{50}$ values were >10 μM

NRF2-Keap1 TR-FRET Assay

In the NRF2-Keap1 TR-FRET (time-resolved fluorescence resonance energy transfer) assay, full length NRF2 protein and full length Keap1 protein (Keap1 exists a dimer) are used. The assay detects the ability of compound to displace the binding of FlagHis-tagged Keap1 with biotinylated, Avi-tagged NRF2 protein. Biotin-NRF2 binds to streptavidin-europium (a component of the detection mix) and Keap1-FlagHis is recognized by anti-Flag APC (allophycocyanin) antibody (also a component of the detection mix). If binding occurs between the two proteins, there will be an energy transfer from the Eu+3 (donor) at 615 nm to the APC (acceptor) at 665 nm. A potential Keap1 inhibitor will cause a reduction in the TR-FRET signal by interfering with the binding of Keap1 to NRF2.

One hundred nanoliters of 100× compound dose response curves (serial 3-fold dilutions) in DMSO are stamped using an Echo liquid handling system (Labcyte) into 384-well, low volume, black assay plates (Greiner, #784076), with DMSO in columns 6 and 18. The top concentration of compound is located in columns 1 and 13. All reagents are diluted in assay buffer (50 mM Tris, pH 8.0, 5 mM MgCl2, 100 mM NaCl, 0.005% BSA, 1 mM DTT, and 2 mM CHAPS). The BSA, DTT, and CHAPS are added to the assay buffer on the day of assay. Using a Multidrop Combi (Thermo Electron Corporation) equipped with a metal tip dispenser, 5 ul of 25 nM Keap1-FlagHis protein is added to all wells of the compound plate, with the exception of the wells in column 18. Wells in column 18 receive 5 ul of assay buffer instead. Plates are centrifuged at 500 rpm for 1 minute, covered with a plate lid, and incubated at 37° C. for 2.25 hours. Plates are then removed from the incubator and allowed to cool to RT for 15 minutes. Five microliters of 50 nM biotin-NRF2 protein is then added to all wells of the plates and the plates are spun at 500 rpm for 1 minute, followed by incubating at 4° C. for 1.25 hours. The plates are then allowed to warm to RT for 15 minutes, followed by the addition of 10 ul of detection mix (1 nM Streptavidin Eu+ W1024 and 5 ug/ml mouse anti-DYKDDDDK IgG conjugated to SureLight APC antibody; both from Columbia Biosciences) to all wells. Plates are spun at 500 rpm for 1 minute, incubated for 1 hour at RT, and read on an Envision plate reader using a 320 nm excitation filter and 615 nm and 665 nm emission filters. Compound response (% inhibition) and potency (pIC50) are calculated based on the ratio of the two emissions (665 nm/615 nm) and then the transformed data is normalized against controls in the assay (control 1=1% DMSO in the presence of NRF2 and Keap1 protein and control 2=1% DMSO in the absence of protein). Data analysis is handled using the software package Abase XE (Surrey, United Kingdom). The % inhibition values are calculated from the ratio (transformed) data by the equation:

100−(100*(compound response−average control 2)/(average control 1−average control 2)).

For calculation of pIC50s, Abase XE uses a four parameter equation.

All examples described herein possessed activity in the NRF2/Keap1 TR-FRET assay as listed (see table below) unless otherwise noted. $IC_{50}s<10$ nM (+++++), $IC_{50}s$ 10-100 nM (++++), $IC_{50}s$ 100 nM-1 μM (+++), $IC_{50}s$ 1-10 μM (++). and $IC_{50}s$ 10-100 μM (+), $IC_{50}s>100$ μM (−), or were not determined (ND).

| Ex # | IC$_{50}$ |
|---|---|
| 1 | ++ |
| 2 | ++ |
| 3 | ++ |
| 4 | ++ |
| 5 | ++ |
| 6 | ++ |
| 7 | ++ |
| 8c | +++ |
| 9 | ++ |
| 10 | + |
| 11 | +++ |
| 12 | +++ |
| 13 | +++ |
| 14 | ++ |
| 15 | ++ |
| 16 | ++ |
| 17f | ++++ |
| 18g | ++++ |
| 18h | ++ |
| 19 | ++ |
| 20 | ++ |

-continued

| Ex # | IC$_{50}$ |
|---|---|
| 21 | ++ |
| 22 | ++ |
| 23 | + |
| 24 | ++ |
| 25 | ++ |
| 26 | ND |
| 27 | ND |
| 28 | ND |
| 29 | ND |
| 30 | ND |
| 31 | ND |
| 32 | ND |
| 33 | ND |
| 34 | ND |
| 35 | ND |
| 36c | ND |
| 36d | ND |
| 37 | ++ |
| *38 | + |
| 39 | ++++ |
| 40 | +++ |
| 41 | ++ |
| 42 | +++ |
| 43 | ND |

*in some determinations IC$_{50}$ values were >100 μM

NRF2-Keap1 TR-FRET Low Protein Assay

In the NRF2-Keap1 TR-FRET (time-resolved fluorescence resonance energy transfer) low protein assay, full length NRF2 protein and full length Keap1 protein (Keap1 exists a dimer) are used. The assay detects a compound's ability to displace the binding of Keap1 FlagHis with biotinylated Avi-NRF2 protein. Biotin-NRF2 binds to streptavidin-europium (a component of the detection mix) and Keap1 FlagHis is recognized by anti-Flag APC (allophycocyanin) antibody (also a component of the detection mix). If binding occurs between the two proteins, there will be an energy transfer from the Eu+3 (donor) at 615 nm to the APC (acceptor) at 665 nm. A potential NRF2 inhibitor will cause a reduction in the TR-FRET signal by interfering with the binding of Keap1 to NRF2.

Ten nanoliters of 100× compound dose response curves (serial 3-fold dilutions) in DMSO are stamped using an Echo liquid handling system (Labcyte) into 384-well, low volume, black assay plates (Greiner, #784076), with DMSO in columns 6 and 18. An additional 90 nl DMSO is added to each well, to bring the total volume to 100 nl per well. The top concentration of compound is located in columns 1 and 13, with the serial dilutions going across the row. All reagents are diluted in assay buffer (50 mM Tris, pH 8.0, 5 mM MgCl$_2$, 100 mM NaCl, 0.005% BSA, 1 mM DTT, and 2 mM CHAPS. The BSA, DTT, and CHAPS are added to the assay buffer on the day of assay. Using a Multidrop Combi (Thermo Electron Corporation) equipped with a metal tip dispenser, 5 ul of 1.25 nM Keap1 FlagHis protein is added to all wells of the compound plate, with the exception of the wells in column 18. Wells in column 18 receive 5 ul of assay buffer instead. Plates are centrifuged at 500 rpm for 1 minute, covered with a plate lid, and incubated at 37° C. for 2.25 hours. Plates are then removed from the incubator and allowed to cool to RT for 15 minutes. Five microliters of 2.5 nM biotin-NRF2 protein is then added to all wells of the plates and the plates are spun at 500 rpm for 1 minute, followed by incubating at 4° C. for 1.25 hours. The plates are then allowed to warm to RT for 15 minutes, followed by the addition of 10 ul of detection mix (1 nM Streptavidin Eu+ W1024 and 5 ug/ml mouse anti-DYKDDDDK IgG conjugated to SureLight APC antibody; both from Columbia Biosciences) to all wells. Plates are spun at 500 rpm for 1 minute, incubated for 1 hour at RT, and read on an Envision plate reader using a 320 nm excitation filter and 615 nm and 665 nm emission filters. Compound response (% inhibition) and potency (pIC50) are calculated based on the ratio of the two emissions (665 nm/615 nm) and then the transformed data is normalized against controls in the assay (control 1=1% DMSO in the presence of NRF2 and Keap1 protein and control 2=1% DMSO in the presence of only the NRF2 protein). Data analysis is handled using the software package Abase XE (Surrey, United Kingdom). The % inhibition values are calculated from the ratio (transformed) data by the equation:

100−(100*(compound response−average control 2)/
(average control 1−average control 2)).

For calculation of $pIC_{50}$s, Abase XE uses a four parameter equation.

All examples described herein possessed activity in the NRF2/Keap1 Low Protein

TR-FRET assay as listed (see table below) unless otherwise noted. $IC_{50}$s<10 nM (+++++), $IC_{50}$s 10-100 nM (++++), $IC_{50}$s 100 nM-1 uM (+++), $IC_{50}$s 1-10 uM (++). & $IC_{50}$s 10 uM-100 uM (+), $IC_{50}$s>100 uM (−), or were not determined (ND).

| Ex # | $IC_{50}$ |
|---|---|
| 1 | ND |
| 2 | ND |
| 3 | ND |
| 4 | ND |
| 5 | ND |
| 6 | ND |
| 7 | ND |
| 8c | ++++ |
| 9 | ND |
| 10 | ND |
| 11 | ++++ |
| 12 | ++++ |
| 13 | ND |
| 14 | ND |
| 15 | ND |
| 16 | ND |
| 17f | +++++ |
| 18g | +++++ |
| 18h | ND |
| 19 | +++ |
| 20 | ND |
| 21 | ND |
| 22 | ND |
| 23 | ++ |
| 24 | ND |
| 25 | ND |
| 26 | ++++ |
| *27 | ++ |
| *28 | ++ |
| 29 | ++++ |
| 30 | +++++ |
| 31 | ++++ |
| 32 | ++++ |
| 33 | ++++ |
| 34 | ++++ |
| 35 | ++++ |
| 36c | ++++ |
| 36d | ++++ |
| 37 | ND |
| 38 | + |
| 39 | +++++ |
| 40 | ++++ |
| 41 | +++ |
| 42 | +++++ |
| 43 | ++++ |

*in some determinations $IC_{50}$ values were >100 μM

Rat Model of Myocardial Ischemia and Prolonged Reperfusion

Oxidative stress is increased in the diseased myocardium, resulting in accumulation of reactive oxygen species (ROS) which impairs cardiac function [Circ (1987) 76(2); 458-468] and increases susceptibility to arrhythmia [J of Mol & Cell Cardio (1991) 23(8); 899-918] by a direct toxic effect of increased necrosis and apoptosis [Circ Res (2000) 87(12); 1172-1179]. The present study determines whether a small molecule activator of NRF2 that targets the Kelch-domain of Keap1, improves cardiac function in a rodent model of established cardiac dysfunction following myocardial ischemia/reperfusion (I/R) injury.

Cardiac dysfunction is established in rats by 30 minutes of myocardial ischemia induced by occlusion of the left anterior descending coronary artery (LAD) followed by 4 weeks of reperfusion. Compound is administered once a day via subcutaneous injection for 28 days starting 2 hours post-reperfusion at 0.5, 5 and 50 mg/kg/d. Ejection fraction (EF), a measure of cardiac function, is measured as well as cardiac antioxidant enzyme activity, left ventricular fibrosis] and oxidative damage in the heart.

Methods of Use

The compounds of the invention are NRF2 regulators, and are useful in the treatment or prevention of respiratory disorders, including COPD, asthma, fibrosis, lung infection, diabetic nephropathy/chronic kidney disease, autoimmune diseases (e.g., multiple sclerosis and inflammatory bowel disease), eye diseases (e.g., AMD, Fuchs, and uveitis), cardiovascular diseases, Non-alcoholic steatohepatitis (NASH), Parkinson's, Alzheimer's, psoriasis, acute kidney injury, topical effects of radiation, and kidney transplant.

Accordingly, in another aspect the invention is directed to methods of treating such conditions.

The methods of treatment of the invention comprise administering a safe and effective amount of a compound according to Formula I or a pharmaceutically-acceptable salt thereof to a patient in need thereof.

As used herein, "treat" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "safe and effective amount" in reference to a compound of the invention or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the condition being treated; the severity of the condition being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" refers to a human or other animal.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin as well as intraocular, otic, intravaginal, and intranasal administration.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical dosages for oral administration range from 1 mg to 1000 mg per person per day. Preferred dosages are 1-500 mg once daily, more preferred is 1-100 mg per person per day. IV dosages range form 0.1-000 mg/day, preferred is 0.1-500 mg/day, and more preferred is 0.1-100 mg/day. Inhaled daily dosages range from 10 ug-10 mg/day, with preferred 10 ug-2 mg/day, and more preferred 50 uug-500 ug/day.

Additionally, the compounds of the invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, ethers, esters, thioesters, carbonates, and carbamates, are well known to those skilled in the art.

Compositions

The compounds of the invention will normally, but not necessarily, be formulated into pharmaceutical compositions prior to administration to a patient. Accordingly, in another aspect the invention is directed to pharmaceutical compositions comprising a compound of the invention and one or more pharmaceutically-acceptable excipient.

The pharmaceutical compositions of the invention may be prepared and packaged in bulk form wherein a safe and effective amount of a compound of the invention can be extracted and then given to the patient such as with powders or syrups. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically contain from 1 mg to 1000 mg.

The pharmaceutical compositions of the invention typically contain one compound of the invention. However, in certain embodiments, the pharmaceutical compositions of the invention contain more than one compound of the invention. For example, in certain embodiments the pharmaceutical compositions of the invention contain two compounds of the invention. In addition, the pharmaceutical compositions of the invention may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically-acceptable.

The compound of the invention and the pharmaceutically-acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as dry powders, aerosols, suspensions, and solutions; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting of the compound or compounds of the invention once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

In another aspect, the invention is directed to a dosage form adapted for administration to a patient parenterally including subcutaneous, intramuscular, intravenous or intradermal. Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

In another aspect, the invention is directed to a dosage form adapted for administration to a patient by inhalation. For example, the compound of the invention may be inhaled into the lungs as a dry powder, an aerosol, a suspension, or a solution.

Dry powder compositions for delivery to the lung by inhalation typically comprise a compound of the invention as a finely divided powder together with one or more pharmaceutically acceptable excipients as finely divided powders. Pharmaceutically acceptable excipients particularly suited for use in dry powders are known to those skilled in the art and include lactose, starch, mannitol, and mono-, di-, and polysaccharides.

The dry powder compositions for use in accordance with the present invention are administered via inhalation devices. As an example, such devices can encompass capsules and cartridges of for example gelatin, or blisters of, for example, laminated aluminum foil. In various embodiments, each capsule, cartridge or blister may contain doses of composition according to the teachings presented herein. Examples of inhalation devices can include those intended for unit dose or multi-dose delivery of composition, including all of the devices set forth herein. As an example, in the case of multi-dose delivery, the formulation can be pre-metered (e.g., as in Diskus®, see GB2242134, U.S. Pat. Nos. 6,032,666, 5,860,419, 5,873,360, 5,590,645, 6,378,519 and 6,536,427 or Diskhaler, see GB 2178965, 2129691 and 2169265, U.S. Pat. Nos. 4,778,054, 4,811,731, 5,035,237) or metered in use (e.g., as in Turbuhaler, see EP 69715, or in the devices described in U.S. Pat. No. 6,321,747). An example of a unit-dose device is Rotahaler (see GB 2064336). In one embodiment, the Diskus® inhalation device comprises an elongate strip formed from a base sheet having a plurality of recesses spaced along its length and a lid sheet peelably sealed thereto to define a plurality of containers, each container having therein an inhalable formulation containing the compound optionally with other excipients and additive taught herein. The peelable seal is an engineered seal, and in one embodiment the engineered seal is a hermetic seal. Preferably, the strip is sufficiently flexible to be wound into a roll. The lid sheet and base sheet will preferably have leading end portions which are not sealed to one another and at least one of the leading end portions is constructed to be attached to a winding means. Also, preferably the engineered seal between the base and lid sheets extends over their whole width. The lid sheet may preferably be peeled from the base sheet in a longitudinal direction from a first end of the base sheet.

A dry powder composition may also be presented in an inhalation device which permits separate containment of two different components of the composition. Thus, for example, these components are administrable simultaneously but are stored separately, e.g., in separate pharmaceutical compositions, for example as described in WO 03/061743 A1 WO 2007/012871 A1 and/or WO2007/068896, as well as U.S. Pat. Nos. 8,113,199, 8,161,968, 8,511,304, 8,534,281, 8,746,242 and 9,333,310.

In one embodiment an inhalation device permitting separate containment of components is an inhaler device having two peelable blister strips, each strip containing pre-metered doses in blister pockets arranged along its length, e.g., multiple containers within each blister strip, e.g., as found in ELLIPTA®. Said device has an internal indexing mechanism which, each time the device is actuated, peels opens a pocket of each strip and positions the blisters so that each newly exposed dose of each strip is adjacent to the manifold which communicates with the mouthpiece of the device. When the patient inhales at the mouthpiece, each dose is simultaneously drawn out of its associated pocket into the manifold and entrained via the mouthpiece into the patient's respiratory tract. A further device that permits separate containment of different components is DUOHALER™ of Innovata. In addition, various structures of inhalation devices provide for the sequential or separate delivery of the pharmaceutical composition(s) from the device, in addition to simultaneous delivery.

Aerosols may be formed by suspending or dissolving a compound of the invention in a liquefied propellant. Suitable propellants include halocarbons, hydrocarbons, and other liquefied gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of the invention will typically be administered to a patient via a metered dose inhaler (MDI). Such devices are known to those skilled in the art.

The aerosol may contain additional pharmaceutically acceptable excipients typically used with multiple dose inhalers such as surfactants, lubricants, cosolvents and other excipients to improve the physical stability of the formulation, to improve valve performance, to improve solubility, or to improve taste.

Suspensions and solutions comprising a compound of the invention may also be administered to a patient via a nebulizer. The solvent or suspension agent utilized for nebulization may be any pharmaceutically acceptable liquid such as water, aqueous saline, alcohols or glycols, e.g., ethanol, isopropyl alcohol, glycerol, propylene glycol, polyethylene glycol, etc. or mixtures thereof. Saline solutions utilize salts which display little or no pharmacological activity after administration. Both organic salts, such as alkali metal or ammonium halogen salts, e.g., sodium chloride, potassium chloride or organic salts, such as potassium, sodium and ammonium salts or organic acids, e.g., ascorbic acid, citric acid, acetic acid, tartaric acid, etc. may be used for this purpose.

Other pharmaceutically acceptable excipients may be added to the suspension or solution. The compound of the invention may be stabilized by the addition of an inorganic acid, e.g., hydrochloric acid, nitric acid, sulfuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the compound of the invention. Preservatives may be added such as benzalkonium chloride or benzoic acid and salts thereof. Surfactant may be added particularly to improve the physical stability of suspensions. These include lecithin, disodium dioctylsulphosuccinate, oleic acid and sorbitan esters.

The compounds of Formula (I) and Formula (Ia) and pharmaceutically acceptable salts thereof may be used in combination with one or more other agents which may be useful in the prevention or treatment of allergic disease, inflammatory disease, autoimmune disease, for example; antigen immunotherapy, anti-histamines, corticosteroids, (eg fluticasone propionate, fluticasone furoate, beclomethasone dipropionate, budesonide, ciclesonide, mometasone furoate, triamcinolone, flunisolide), NSAIDs, leukotriene modulators (e.g. montelukast, zafirlukast, pranlukast), iNOS inhibitors, tryptase inhibitors, IKK2 inhibitors, p38 inhibitors, Syk inhibitors, protease inhibitors such as elastase inhibitors, integrin antagonists (e.g., beta-2 integrin antagonists), adenosine A2a agonists, mediator release inhibitors such as sodium chromoglycate, 5-lipoxygenase inhibitors (zyflo), DP1 antagonists, DP2 antagonists, PI3K delta inhibitors, ITK inhibitors, LP (lysophosphatidic) inhibitors or FLAP (5-lipoxygenase activating protein) inhibitors (e.g. sodium 3-(3-(tert-butylthio)-1-(4-(6-ethoxypyridin-3-yl)benzyl)-5-((5-methylpyridin-2-yl)methoxy)-1H-indol-2-yl)-2,2-dimethylpropanoate), bronchodilators (e.g., muscarinic antagonists, beta-2 agonists), methotrexate, and similar agents; monoclonal antibody therapy such as anti-IgE, anti-TNF, anti-IL-5, anti-IL-6, anti-IL-12, anti-IL-1 and similar agents; cytokine receptor therapies e.g. etanercept and similar agents; antigen non-specific immunotherapies (e.g. interferon or other cytokines/chemokines, chemokine receptor modulators such as CCR3, CCR4 or CXCR2 antagonists, other cytokine/chemokine agonists or antagonists, TLR agonists and similar agents).

The compounds may also be used in combination with agents for aiding transplantation including Cyclosporines, Tacrolimus, Mycophenolate mofetil, Prednisone, Azathioprine, Sirolimus, Daclizumab, Basiliximab, or OKT3.

They may also be used in combination with agents for Diabetes: metformin (biguanides), meglitinides, sulfonylureas, DPP-4 inhibitors, Thiazolidinediones, Alpha-glucosidase inhibitors, Amylin mimetics, Incretin mimetics, insulin.

The compounds may be used in combination with anti-hypertensives such as diuretics, ACE inhibitors, ARBS, calcium channel blockers, and beta blockers.

One embodiment of the invention encompasses combinations comprising one or two other therapeutic agents. It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates to optimize the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical formulation and thus pharmaceutical formulations comprising a combination as defined above together with a pharmaceutically acceptable diluent or carrier represent a further aspect of the invention.

The individual compounds of such combinations may be administered either sequentially or simultaneously in separate or combined pharmaceutical formulations. In one embodiment, the individual compounds will be administered simultaneously in a combined pharmaceutical formulation.

Appropriate doses of known therapeutic agents will readily be appreciated by those skilled in the art.

The invention thus provides, in a further aspect, a pharmaceutical composition comprising a combination of a compound of the invention together with another therapeutically active agent.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

All temperatures are given in degrees Celsius, all solvents are highest available purity and all reactions run under anhydrous conditions in an argon (Ar) or nitrogen ($N_2$) atmosphere where necessary.

Analtech Silica Gel GF and E. Merck Silica Gel 60 F-254 thin layer plates were used for thin layer chromatography. Both flash and gravity chromatography were carried out on E. Merck Kieselgel 60 (230-400 mesh) silica gel. The CombiFlash® system used for purification in this application was purchased from Isco, Inc. CombiFlash® purification was carried out using prepacked silica gel columns, a detector with UV wavelength at 254 nm and a variety of solvents or solvent combinations.

Preparative HPLC was performed using a Gilson Preparative System with variable wavelength UV detection or an Agilent Mass Directed AutoPrep (MDAP) system with both mass and variable wavelength UV detection or Waters Preparative System with UV/PDA detection or an Shimadzu PREP LC 20AP. A variety of reverse phase columns, e.g., Luna 5m C18(2) 100A, SunFire C18, XBridge C18, Atlantics T3 were used in the purification with the choice of column support dependent upon the conditions used in the purification. The compounds are eluted using a gradient of $CH_3CN$ and water. Neutral conditions used an $CH_3CN$ and water gradient with no additional modifier, acidic conditions used an acid modifier, 0.1% TFA (added to both the $CH_3CN$ and water) or 0.1 formic acid and basic conditions used a basic modifier, 0.1% $NH_4OH$ (added to the water) or 10 mM ammonium bicarbonate.

Analytical HPLC was run using an Agilent system, Shimadzu/Sciex LCMS with variable wavelength UV detection using reverse phase chromatography with a $CH_3CN$ and water gradient with a 0.02 or 0.1% TFA modifier (added to each solvent). LC-MS was determined using either a PE Sciex Single Quadrupole 150EX LC-MS, or Waters ZQ Single Quadrupole LC-MS or Agilent 1200 series SL (dectectors: Agilent 6140 single quadrupole and Agilent 1200 MWD SL) instruments. The compound is analyzed using a reverse phase column, e.g., Thermo Hypersil Gold C18, eluted using a gradient of $CH_3CN$ and water with a low percentage of an acid modifier such as 0.02% TFA or 0.1% formic acid or a base modifier such as 5 mM ammonium bicarbonate (adjusted to pH 10 with aqueous ammonia). When specified "acid method" refers to 0.1% formic acid in water and $CH_3CN$ gradient (1.8 min. 0.9 mL/min flow) with a Waters Acquity UPLC HSS C18; 1.8μ; 2.1×50 mm at 50° C.; "basic method" refers to 95:5 $H_2O$+0.1% $NH_4OH$:$CH_3CN$ (pH=9.4) and water gradient (1.8 min. 0.9 mL/min flow) with a Waters Acquity UPLC BEH C18; 1.7μ; 2.1×50 mm at 50° C. and "overnight basic method" refers to 95:5 $H_2O$+0.1% $NH_4OH$:$CH_3CN$ (pH=9.4) and water gradient (16 min. 0.8 mL/min flow) with a Waters Acquity UPLC BEH C18; 1.7μ; 2.1×50 mm at 50° C.

Preparative Chiral SFC was performed using a Thar/Waters Preparative SFC System with single wavelength UV detection system or PDA detector. A variety of chiral SFC columns, e.g. Chiralpak IA, IC, AY, AD. OD, OJ, C2 were used in the purification. The compounds are eluted using supercritical fluid $CO_2$ and co-solvents, such as MeOH, EtOH, IPA, and combination of these solvent in different ratio based on the compound selectivity. Modifiers (0.1% of TFA, $NH_4OH$, DEA) would be used as needed.

Analytical Chiral SFC was run using a Thar/Waters SFC system with variable wavelength UV detection or PDA detector. A variety of chiral SFC columns, e.g. Chiralpak IA, IB, IC, ID, AY, AD, AS, CCL4 were used in the purification. The compounds are eluted using supercritical fluid $CO_2$ and co-solvents, such as MeOH, EtOH, IPA, and combination of these solvent in different ratio based on the compound selectivity. Modifiers (0.1% of TFA, $NH_4OH$, DEA) would be used as needed.

Celite® is a filter aid composed of acid-washed diatomaceous silica, and is a registered trademark of Manville Corp., Denver, Colo. Isolute® is a functionalized silica gel based sorbent, and is a registered trademark of Biotage AB Corp., Sweden.

Nuclear magnetic resonance spectra were recorded at 400 MHz using a Bruker AVANCE 400 or Brucker DPX400 or Varian MR400 400 MHz spectrometer. $CDCl_3$ is deuteriochloroform, DMSO-$D_6$ is hexadeuteriodimethylsulfoxide, and MeOD is tetradeuteriomethanol, $CD_2Cl_2$ is deuteriodichloromethane. Chemical shifts are reported in parts per million (δ) downfield from the internal standard tetramethylsilane (TMS) or calibrated to the residual proton signal in the NMR solvent (e.g., $CHCl_3$ in $CDCl_3$). Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz.

Heating of reaction mixtures with microwave irradiations was carried out on a Biotage Initiator® or CEM microwave reactor, typically employing the high absorbance setting.

Cartridges or columns containing polymer based functional groups (acid, base, metal chelators, etc) can be used as part of compound workup. The "amine" columns or cartridges are used to neutralize or basify acidic reaction mixtures or products. These include $NH_2$ Aminopropyl SPE-ed SPE Cartridges available from Applied Separations and diethylamino SPE cartridges available from United Chemical Technologies, Inc.

General Methods Used in Examples

Acidic Method (Analytical)

HPLC System: Agilent 1200 series SL

Mass Spec Detector: Agilent 6140 single quadrupole

Second Detector: Agilent 1200 MWD SL

Eluent A: 0.1% Formic Acid in Water

Eluent B: $CH_3CN$

Flow Rate: 0.9 ml/min

Column: Waters Acquity UPLC HSS C18; 1.8μ; 2.1×50 mm

Column T: 50° C.

| Time (mins) | % B |
|---|---|
| 0.0 | 5 |
| 0.1 | 5 |
| 1.11 | 95 |
| 1.67 | 95 |
| 1.68 | 5 |
| 1.80 | 5 |

Capillary voltage: 3000V on ES pos (2700V on ES Neg)
Fragmentor/Gain: 190 on ES pos (160 on ES neg)
Gain: 1
Drying gas flow: 12.0 L/min
Gas Temperature: 345° C.
Nebuliser Pressure: 60 psig
Scan Range: 125-1000 amu
Ionisation Mode: ElectroSpray Positive-Negative switching
Basic Method (Analytical)
HPLC System: Agilent 1200 series SL
Mass Spec Detector: Agilent 6140 single quadrupole
Second Detector: Agilent 1200 MWD SL
Eluent A: 95:5 H2O+0.1% NH$_4$OH:CH$_3$CN (pH=9.4)
Eluent B: CH$_3$CN
Flow Rate: 0.9 ml/min
Column: Waters Acquity UPLC BEH C18; 1.7μ; 2.1×50 mm
Column T: 50° C.

| Time (mins) | % B |
|---|---|
| 0.0 | 5 |
| 0.1 | 5 |
| 1.11 | 95 |
| 1.67 | 95 |
| 1.68 | 5 |
| 1.80 | 5 |

Capillary voltage: 3000V on ES pos (2700V on ES Neg)
Fragmentor/Gain: 190 on ES pos (160 on ES neg)
Gain: 1
Drying gas flow: 12.0 L/min
Gas Temperature: 345° C.
Nebuliser Pressure: 60 psig
Scan Range: 125-1000 amu
Ionisation Mode: ElectroSpray Positive-Negative switching
Overnight Basic Method (Analytical)
HPLC System: Agilent 1200 series SL
Mass Spec Detector: Agilent 6140 single quadrupole
Second Detector: Agilent 1200 MWD SL
Eluent A: 95:5 H2O+0.1% NH$_4$OH:CH$_3$CN (pH=9.4)
Eluent B: CH$_3$CN
Flow Rate: 0.8 ml/min
Column: Waters Acquity UPLC BEH C18; 1.7μ; 2.1×50 mm
Column T: 50° C.

| Time (mins) | % B |
|---|---|
| 0.0 | 5 |
| 0.6 | 5 |
| 11.0 | 95 |
| 14.1 | 95 |
| 14.2 | 5 |
| 16 | 5 |

Capillary voltage: 3000V on ES pos (2700V on ES Neg)
Fragmentor/Gain: 190 on ES pos (160 on ES neg)
Gain: 1
Drying gas flow: 12.0 L/min
Gas Temperature: 345° C.
Nebuliser Pressure: 60 psig
Scan Range: 125-800 amu
Ionisation Mode: ElectroSpray Positive-Negative switching Abbreviations are listed in the table below. All other abbreviations are as described in the ACS Style Guide (American Chemical Society, Washington, D.C., 1986).

Table of Abbreviations

[Rh(cod)Cl]$_2$ or [RhCl(cod)]$_2$: di-μ-chlorido-bis[η$^2$,η$^2$-(cycloocta-1,5-diene)rhodium
®T3P: 2,4,6-tripropyl-1,3,5,2,4,6-trioxatriphosphorinane 2,4,6-trioxide
[C.: degree Celsius
AcOH: acetic acid
ADDP: (E)-diazene-1,2-diylbis(piperidin-1-ylmethanone)
aq = aqueous
BINAP: 2,2'-bis(diphenylphosphino)-1,1'-binaphthalene
CDI: Carbonyl dimidazole
CH$_2$Cl$_2$: dichloromethane
CH$_3$CN: acetonitrile
CHCl$_3$: chloroform
Cs$_2$CO$_3$: cesium carbonate
DBU: 1,8-diazabicyclo[5.4.0]undec-7-ene
DCE: dichloroethane
DCM: dichloromethane
DIPEA or DIEA: diisopropylethyl amine
DME: dimethyl ether
DMF: N,N-dimethylformamide
DMF-DMA or DMF-dimethyl acetal: N,N-dimethylformaide-dimethyl acetal
DMSO: dimethyl sulfoxide
EDC: 1-ethyl-3-(3-dimethylaminopropyl)carbodiimide
Et$_2$O: diethyl ether
Et$_3$N: triethylamine
EtOAc: ethyl acetate
EtOH: ethanol
g: gram(s)
h: hour(s)
HATU: O-(7-azabenzotriazol-1-yl)-N,N,N',N'-tetramethyluronium hexafluorophosphate
HBTU: N,N,N',N'-tetramethyl-O-(1H-benzotriazol-1-yl)uronium hexafluorophosphate
HCl: hydrochloric acid
HOAt: 1-hydroxy-7-azabenzotriazole
HPLC: high performance liquid chromatography
IPA: isopropyl alcohol
K$_2$CO$_3$: potassium carbonate
KOAc: potassium acetate
LAH: lithium aluminum hydride
LC: liquid chromatography
LC-MS: liquid chromatography-mass spectroscopy
LiBH$_4$: lithium borohydride
LiHMDS: lithium hexamethyldisilazane
LiOH: lithium hydroxide
M: molar
MeCN: acetonitrile
MeI: methyl iodide
MeOH: methanol
mg: milligram(s)
MgCl$_2$: magnesium chloride
MgSO$_4$: magnesium sulfate
MHz: megahertz
min: minute(s)
mL: milliliter(s)
mmol: millimole(s)
MS: mass spectroscopy
N$_2$: nitrogen gas
Na$_2$CO$_3$: sodium carbonate
Na$_2$SO$_4$: sodium sulfate
NaBH$_3$CN or NaCNBH$_3$: sodium cyanoborohydride
NaCl: sodium chloride
NaH: sodium hydride
NaHCO$_3$: sodium bicarbonate
NaHMDS: sodium hexamethyldisilazane
NaHSO$_4$: sodium bisulfate
NaOAc: sodium acetate
NaOH: sodium hydroxide

Table of Abbreviations

NBS: N-bromosuccinimide
nBuLi: n-butyl lithium
NH$_4$Cl: ammonium chloride
NMR: nuclear magnetic resonance
P(tBu)$_3$: tri-t-butyl phosphine
Pd(PhP$_3$)$_4$: tetrakistriphenylphosphine palladium
Pd/C: palladium on carbon
Pd$_2$(dba)$_3$: tris(dibenzylideneacetone)-dipalladium(0)
PdCl$_2$(dppf) or Pd(dppf)Cl$_2$: [1,1'-bis(diphenylphosphino)-ferrocene] dichloropalladium(II)
Petrol: petroleum ether
PS-PPh$_3$: polymer supported triphenylphosphine
PtO$_2$: platinum(IV) oxide
RT: room temperature
T3P: 2,4,6-tripropyl-1,3,5,2,4,6-trioxatriphosphorinane-2,4,6-trioxide solution
TEA: triethylamine
TFA: trifluoroacetic acid
TFFH: tetrafluoroformamidinium hexafluorophosphate
THF: tetrahydrofuran
triflic anhydride: trifluoromethanesulfonic anhydride
TsOH: p-toluenesulfonic acid
wt %: weight percent

Example 1. 5-Cyclopropyl-1-{3-[3-(dimethylcarbamoyl)cyclohexyl]phenyl}-1H-pyrazole-4-carboxylic Acid (cis-racemate)

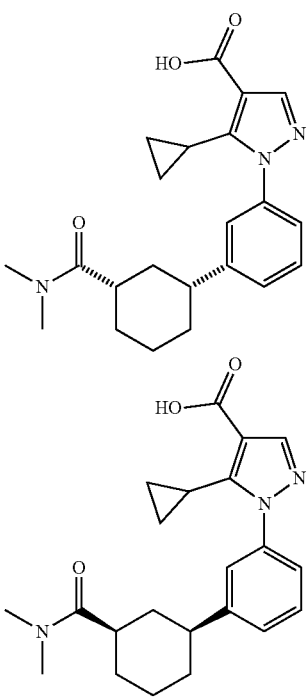

1a) 3-Oxo-cyclohexanecarboxylic acid dimethylamide

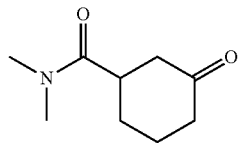

A solution of 3-oxo-cyclohexanecarboxylic acid (0.730 g, 5.13 mmol), HATU (1.95 g, 5.13 mmol), dimethylamine (2M in THF, 3.08 mL), and DIPEA (1.79 mL, 10.3 mmol) in DCM (20 mL) was stirred for 4 h. The mixture was diluted with DCM and the organic phase washed with aqueous NaHCO$_3$ and dried (MgSO$_4$), filtered, and concentrated to dryness and purified by silica chromatography (EtOAc/petrol 40-100% gradient) to give the product (0.591 g, 68%). $^1$H NMR (400 MHz, CDCl$_3$): 3.07 (3H, s), 2.98 (3H, s), 2.89 (1H, s), 2.71 (1H, dd), 2.60-2.27 (3H, m), 2.27-2.08 (1H, m), 1.97-1.86 (2H, m), 1.86-1.63 (1H, m).

1b) Trifluoromethanesulfonic acid 3-dimethylcarbamoyl-cyclohex-1-enyl ester

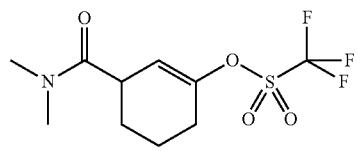 [SMILES: CN(C)C(=O)C1C=C(OS(=O)(=O)C(F)(F)F)CCC1]

A solution of 3-oxo-cyclohexanecarboxylic acid dimethylamide (0.591 g, 3.49 mmol) in dry THF (35 mL) under a flush of nitrogen at −78° C. was slowly treated with NaHMDS (1M in THF, 4.191 mL). After 20 min., a solution of N-phenyltrifluoromethanesulfonamide (1.50 g, 4.19 mmol) in THF (8 mL) was added. The mixture was allowed to warm to room temperature overnight. The reaction was quenched with water, concentrated and then partitioned between EtOAc and water. The organic phase was washed with water and aqueous NaHCO$_3$ then brine before it was dried (MgSO$_4$), filtered, and concentrated to give the crude product, used without further purification (1.35 g, quantative).

1c) 5-Cyclopropyl-1-[3-(3-dimethylcarbamoyl-cyclohex-1-enyl)-phenyl]-1H-pyrazole-4-carboxylic Acid methyl ester

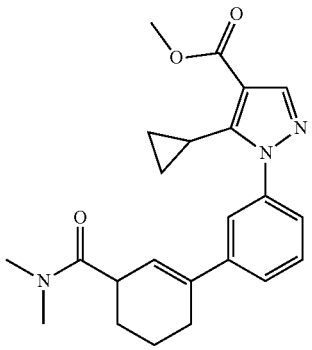 [SMILES: COC(=O)c1cnn(-c2cccc(C3=CC(C(=O)N(C)C)CCC3)c2)c1C1CC1]

A stirred mixture of trifluoromethanesulfonic acid 3-dimethylcarbamoyl-cyclohex-1-enyl ester (0.737 g, 2.45 mmol), 5-cyclopropyl-1-[3-(4,4,5,5-tetramethyl-[1,3,2]dioxaborolan-2-yl)-phenyl]-1H-pyrazole-4-carboxylic acid methyl ester (0.600 g, 1.63 mmol), aqueous Na$_2$CO$_3$ (3M, 1.640 mL) and Pd(PPh$_3$)$_4$ (0.142 g, 0.12 mmol) in EtOH (3 mL) and toluene (9 mL) was heated at reflux for 2 h. After cooling, the mixture was partitioned between EtOAc (30 mL) and water (20 mL). The organic phase was washed with water (20 mL) and brine (20 mL) before it was dried (MgSO$_4$), filtered, and concentrated. Silica purification, eluting 10-80% EtOAC/petrol gave the product, (0.160 g, 25%) used without further purification. LC-MS m/z 394 (M+H)$^+$, 1.38 (ret. time), basic method.

1d) 5-Cyclopropyl-1-{3-[3-(dimethylcarbamoyl) cyclohexyl]phenyl}-1H-pyrazole-4-carboxylic acid methyl ester (cis racemate)

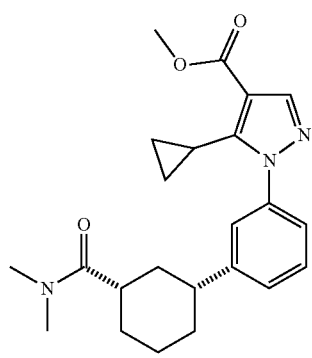 [SMILES: COC(=O)c1cnn(-c2cccc([C@@H]3CCC[C@H](C(=O)N(C)C)C3)c2)c1C1CC1]

A solution of 5-cyclopropyl-1-[3-(3-dimethylcarbamoyl-cyclohex-1-enyl)-phenyl]-1H-pyrazole-4-carboxylic acid methyl ester (0.16 g, 0.41 mmol) in EtOH (15 mL) was treated with Pd/C (16 mg) and shaken under an atmosphere of hydrogen for 2 h. The catalyst was removed by filtration and the solution was concentrated. Purified by silica column, 25 g, eluting 20-80% EtOAc/petrol to give:

Trans isomer (10 mg): LC-MS m/z 396 (M+H)$^+$, 1.40 (ret. time), basic method.

Cis isomer (80 mg): LC-MS m/z 396 (M+H)$^+$, 1.39 (ret. time), basic method.

1e) 5-Cyclopropyl-1-{3-[3-(dimethylcarbamoyl) cyclohexyl]phenyl}-1H-pyrazole-4-carboxylic Acid (cis-racemate)

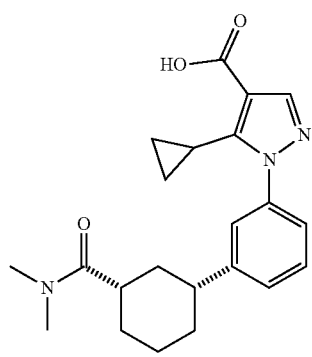

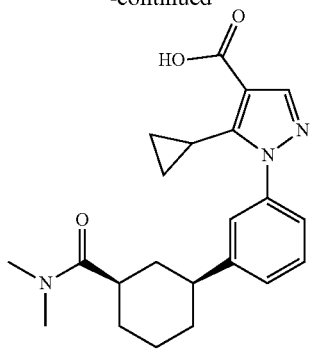

A stirred solution of 5-cyclopropyl-1-{3-[3-(dimethylcarbamoyl)cyclohexyl]phenyl}-1H-pyrazole-4-carboxylic acid methyl ester (cis racemate) (0.080 g, 0.20 mmol) in EtOH (1.5 mL) was treated with aqueous NaOH (2M, 0.51 mL). After 24 hours the mixture was partitioned between EtOAc and water. The organic phase was extracted with further water and was then discarded. The combined aqueous layer was acidified with 1N HCl and extracted into EtOAc (×2). The combined organic phases were dried (MgSO$_4$), filtered and concentrated under vacuum to give the product (0.058 g, 75%). LC-MS m/z 382 (M+H)$^+$, 1.04 (ret. time), basic method. $^1$H NMR (400 MHz, DMSO-d6): 12.25 (1H, s), 7.92 (1H, s), 7.49-7.42 (2H, m), 7.42-7.31 (2H, m), 3.03 (3H, s), 2.89-2.66 (5H, m), 2.20-2.04 (1H, m), 1.90-1.77 (3H, m), 1.71 (1H, d), 1.67-1.32 (4H, m), 0.89-0.76 (2H, m), 0.60-0.47 (2H, m).

Example 2. 5-Cyclopropyl-1-{3-[3-(4,5,6,7-tetrahydro-1H-indazol-1-yl)cyclohexyl]phenyl}-1H-pyrazole-4-carboxylic Acid (cis-racemate)

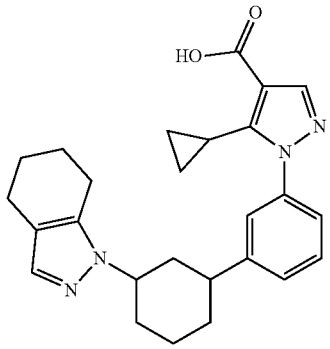 [SMILES: O=C(O)c1cnn(-c2cccc(C3CCCC(n4ncc5c4CCCC5)C3)c2)c1C1CC1]

2a) 5-Cyclopropyl-1-[3-(3-oxo-cyclohexyl)-phenyl]-1H-pyrazole-4-carboxylic acid methyl ester

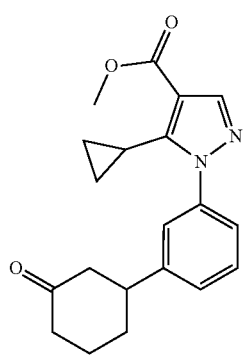 [SMILES: COC(=O)c1cnn(-c2cccc(C3CCCC(=O)C3)c2)c1C1CC1]

A mixture of 5-cyclopropyl-1-[3-(4,4,5,5-tetramethyl-[1,3,2]dioxaborolan-2-yl)-phenyl]-1H-pyrazole-4-carboxylic acid methyl ester (0.215 g, 0.60 mmol), cyclohexenone (0.048 g, 0.50 mmol), Et₃N (0.10 mL, 0.75 mmol), and [Rh(cod)Cl]₂ (0.015 g, 0.025 mmol) in dioxane (4 mL) and water (0.4 mL) was stirred under nitrogen at 90° C. for 16 h. After cooling, the mixture was diluted with water and extracted with EtOAc (×2), and the combined organic phases were dried (MgSO₄) and concentrated to dryness. The residue was purified by silica chromatography eluting with EtOAc/petrol 10-30% to give the product (0.210 g, quantative). LC-MS m/z 339 (M+H)⁺, 1.36 (ret. time).

2b) 1-{3-[3-(N'-tert-Butoxycarbonyl-hydrazino)-cyclohexyl]-phenyl}-5-cyclopropyl-1H-pyrazole-4-carboxylic Acid methyl ester

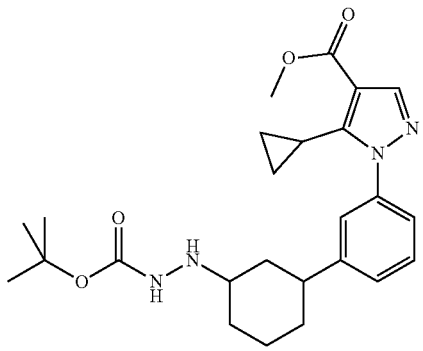 [SMILES: COC(=O)c1cnn(-c2cccc(C3CCCC(NNC(=O)OC(C)(C)C)C3)c2)c1C1CC1]

A solution of 5-cyclopropyl-1-[3-(3-oxo-cyclohexyl)-phenyl]-1H-pyrazole-4-carboxylic acid methyl ester and t-butyl carbazate in MeOH (1.8 mL) was stirred for 90 min and then concentrated to dryness under vacuum. A stirred solution of the residue in AcOH was treated with NaBH₃CN. After one hour the mixture was treated with aqueous NaOH (1M) and extracted with DCM. The organic phase was washed with saturated aqueous NaHCO₃, dried over MgSO₄, filtered, and concentrated to dryness. The residue was purified by silica chromatography eluting with EtOAc/petrol 30% to give two stereoisomers:
Fraction 1: (0.058 g, %). LC-MS m/z 455 (M+H)⁺, 1.55 (ret. time).
Fraction 2: (0.076 g, %). LC-MS m/z 455 (M+H)⁺, 1.49 (ret. time).
Fraction 2 was later shown to be a racemic mixture of cis-diastereoisomers by subsequent derivatisation and X-ray crystallography.

2c) 5-Cyclopropyl-1-[3-(3-hydrazino-cyclohexyl)-phenyl]-1H-pyrazole-4-carboxylic Acid methyl ester hydrochloride

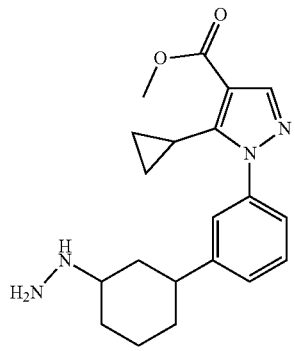 [SMILES: COC(=O)c1cnn(-c2cccc(C3CCCC(NN)C3)c2)c1C1CC1]

A solution of cis-racemic 1-{3-[3-(N'-tert-butoxycarbonyl-hydrazino)-cyclohexyl]phenyl}-5-cyclopropyl-1H-pyrazole-4-carboxylic acid methyl ester (0.076 g, 0.17 mmol) in HCl (4M in dioxane, 3 mL) was stirred for 4 hours, then concentrated to dryness under vacuum to give the product (0.067 g, quantative). LC-MS m/z 355 (M+H)⁺, 1.24 (ret. time).

2d) 5-Cyclopropyl-1-{3-[3-(4,5,6,7-tetrahydro-1H-indazol-1-yl)cyclohexyl]phenyl}-1H-pyrazole-4-carboxylic Acid (cis-racemate)

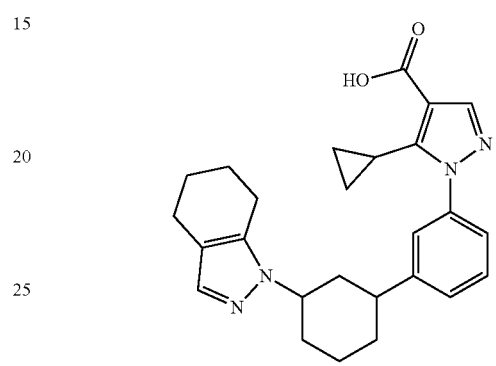

A mixture of 5-cyclopropyl-1-[3-(3-hydrazino-cyclohexyl)-phenyl]-1H-pyrazole-4-carboxylic acid methyl ester hydrochloride (50 mg, 0.13 mmol), 2-[1-dimethylamino-methylidene]-cyclohexanone (20 mg, 0.13 mmol) and NaOAc (25 mg, 0.31 mmol) in ethanol (2 mL) was stirred at 70° C. for 16 hours. The mixture was concentrated. The product was extracted with EtOAc (×3). The combined organic layers were washed with brine and dried over MgSO₄. The product was filtered and evaporated to dryness. The crude material was used for the next step without further purification. LC-MS m/z 431 (M+H)⁺, 1.18 (ret. time). ¹H NMR (400 MHz, CDCl₃): 8.09 (1H, s), 7.64 (1H, s), 7.46-7.42 (1H, m), 7.40 (1H, s), 7.38-7.34 (2H, m), 4.38-4.27 (1H, m), 2.84-2.74 (1H, m), 2.69 (2H, t), 2.55 (2H, t), 2.38 (1H, q), 2.19-2.08 (3H, m), 2.08-1.95 (3H, m), 1.95-1.85 (2H, m), 1.85-1.73 (2H, m), 1.63 (1H, d), 1.58 (1H, d), 0.98-0.89 (2H, m), 0.70-0.61 (2H, m).

Example 3. 5-Cyclopropyl-1-{3-[3-(piperidine-1-carbonyl)cyclohexyl]phenyl}-1H-pyrazole-4-carboxylic Acid (cis-racemate)

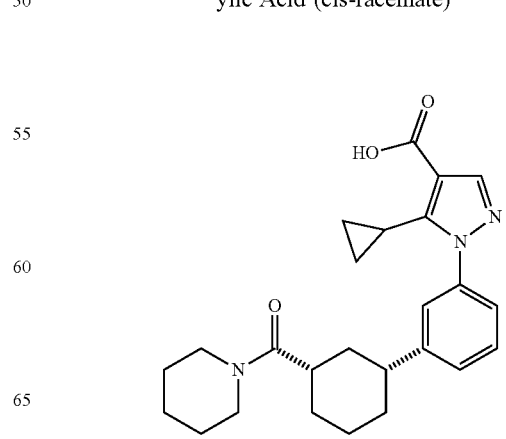

3a) 3-Oxo-cyclohexanecarboxylic Acid benzyl ester

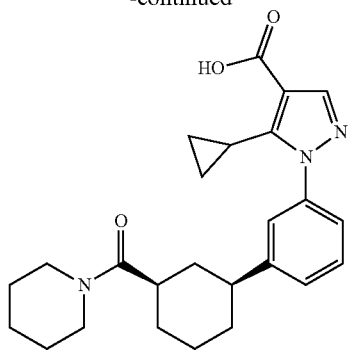

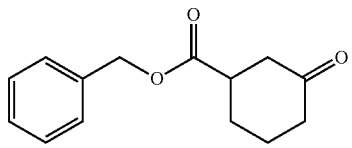 [SMILES: O=C1CCCC(C(=O)OCc2ccccc2)C1]

A stirred mixture of 3-oxo-cyclohexanecarboxylic acid (1.50 g, 10.6 mmol) and benzyl bromide (1.38 mL, 11.6 mmol) in dry MeCN (20 mL) was treated with DBU (1.66 mL, 11.1 mmol). After 18 h, the mixture was concentrated under vacuum and then diluted with EtOAc. The organic phase was washed with saturated NaHCO₃, then 1N HCl, water and then brine before it was dried (MgSO₄), filtered, and concentrated to dryness under vacuum. Purification by silica column, 50 g SNAP, eluting 5-40% EtOAc in petrol to gave the product (2.11 g, 86%). LC-MS m/z 250 (M+NH₄)⁺, 1.31 (ret. time).

3b) 3-Trifluoromethanesulfonyloxy-cyclohex-2-enecarboxylic Acid benzyl ester

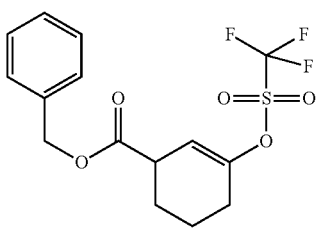 [SMILES: O=C(OCc1ccccc1)C1C=C(OS(=O)(=O)C(F)(F)F)CCC1]

A stirred solution of 3-oxo-cyclohexanecarboxylic acid benzyl ester (2.11 g, 12.5 mmol) and N-phenyltrifluoromethanesulfonamide (5.35 g, 15.0 mmol) in dry THF (100 mL) under a flush of nitrogen at −78° C. was slowly treated with NaHMDS (1M in THF, 15 mL). The solution was allowed to warm with the cold bath overnight. After quenching with a little water, the mixture was concentrated and then partitioned between Et₂O and water. The organic phase was washed with water and aqueous NaHCO₃ (×2) then brine before it was dried (MgSO₄), filtered and concentrated to give the crude product, used without further purification (4.01 g, 88%).

3c) 1-[3-(3-Benzyloxycarbonyl-cyclohex-1-enyl)-phenyl]-5-cyclopropyl-1H-pyrazole-4-carboxylic Acid methyl ester

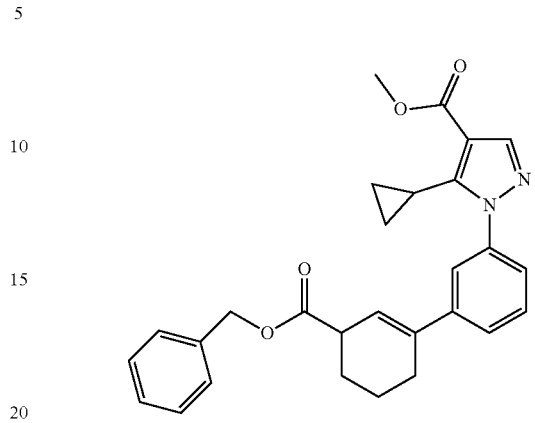

A stirred mixture of 3-trifluoromethanesulfonyloxy-cyclohex-2-enecarboxylic acid benzyl ester (2.05 g, 6.80 mmol), 5-cyclopropyl-1-[3-(4,4,5,5-tetramethyl-[1,3,2]dioxaborolan-2-yl)-phenyl]-1H-pyrazole-4-carboxylic acid methyl ester (1.67 g, 4.54 mmol), aqueous Na₂CO₃ (3M, 4.54 mL) and Pd(PPh₃)₄ (0.393 g, 0.34 mmol) in EtOH (6 mL) and toluene (20 mL) was heated at reflux for 2 h. After cooling, the mixture was partitioned between EtOAc (70 mL) and water (40 mL). The organic phase was washed with water (20 mL) and brine (20 mL) before it was dried (MgSO₄), filtered, and concentrated to dryness and purified by silica chromatography (EtOAc/petrol 5-35% gradient) to give the product (0.365 g, 33%). LC-MS m/z 457 (M+H)⁺, 1.62 (ret. time).

3d) 1-[3-((1R,3S)-3-Carboxy-cyclohexyl)-phenyl]-5-cyclopropyl-1H-pyrazole-4-carboxylic Acid methyl ester

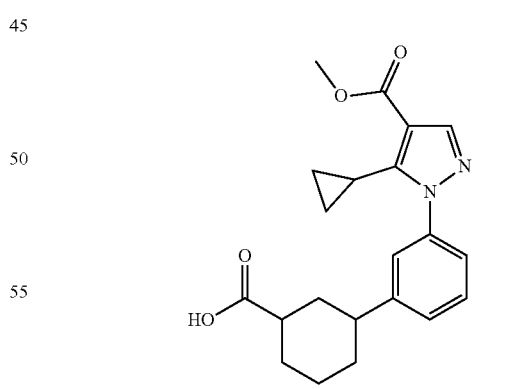

A solution of 1-[3-(3-benzyloxycarbonyl-cyclohex-1-enyl)-phenyl]-5-cyclopropyl-1H-pyrazole-4-carboxylic acid methyl ester (0.365 g, 0.80 mmol) in EtOH (30 mL) was treated with Pd/C (0.04 g) and the mixture shaken under a hydrogen atmosphere for 18 h. The catalyst was removed by filtration and the solvent evaporated to give the product (0.277 g, 94%). LC-MS m/z 369 (M+H)⁺, 1.09 (ret. time).

3e) 5-Cyclopropyl-1-{3-[3-(piperidine-1-carbonyl)cyclohexyl]phenyl}-1H-pyrazole-4-carboxylic Acid methyl ester (cis-racemate)

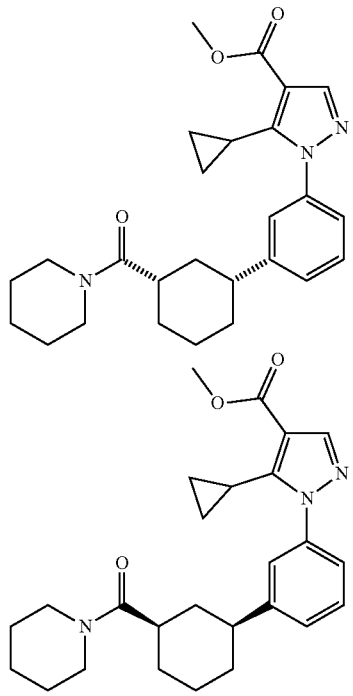

A solution of 1-[3-(3-carboxy-cyclohexyl)-phenyl]-5-cyclopropyl-1H-pyrazole-4-carboxylic acid methyl ester (0.035 g, 0.10 mmol), HATU (0.036 g, 0.10 mmol), piperidine (0.010 g, 0.11 mmol) and DIPEA (0.033 mL, 0.19 mmol) in DCM (2 mL) was stirred for 2 h. The mixture was diluted with DCM, and the organic phase washed with aqueous NaHCO₃, dried (MgSO₄), filtered, and concentrated to dryness. Silica purification eluting with EtOAc/hexane 10-50% gave the product (0.013 g, 31%), identified by NMR as the cis-isomer; the trans-isomer was not isolated. LC-MS m/z 436 (M+H)⁺, 1.51 (ret. time), basic method.

3f) 5-Cyclopropyl-1-{3-[3-(piperidine-1-carbonyl)cyclohexyl]phenyl}-1H-pyrazole-4-carboxylic Acid (cis-racemate)

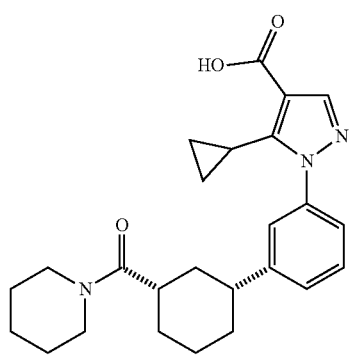

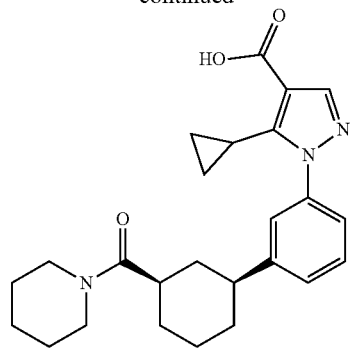

A stirred solution of 5-cyclopropyl-1-{3-[3-(piperidine-1-carbonyl)cyclohexyl]phenyl}-1H-pyrazole-4-carboxylic acid methyl ester (0.013 g, 0.03 mmol) in EtOH (0.4 mL) was treated with aqueous NaOH (2M, 0.075 mL). After 60 hours the mixture was partitioned between EtOAc and water. The organic phase was extracted with further water and then discarded. The combined aqueous layer was acidified with 1N HCl and extracted into EtOAc (×2). The combined organic phases were dried (MgSO₄), filtered and concentrated under vacuum to give the product (0.011 g, 87%). LC-MS m/z 422 (M+H)⁺ 1.11 (ret. time), basic method. ¹H NMR (400 MHz, DMSO-d6): 12.21 (1H, s), 7.94-7.89 (1H, m), 7.49-7.29 (4H, m), 3.44 (4H, d), 2.83-2.71 (2H, m), 2.15-2.04 (1H, m), 1.89-1.63 (4H, m), 1.63-1.33 (10H, m), 0.92-0.76 (2H, m), 0.62-0.47 (2H, m).

Example 4. 1-[3-(3-{7-Azaspiro[4.5]decane-7-carbonyl}cyclohexyl)phenyl]-5-cyclopropyl-1H-pyrazole-4-carboxylic Acid (cis-racemate)

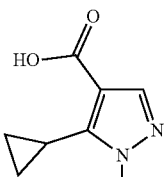
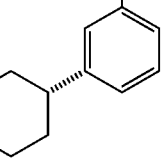
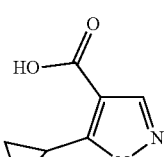
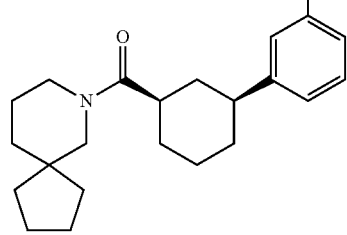

4a) 1-[3-(3-{7-Azaspiro[4.5]decane-7-carbonyl}cyclohexyl)phenyl]-5-cyclopropyl-1H-pyrazole-4-carboxylic Acid methyl ester (cis-racemate)

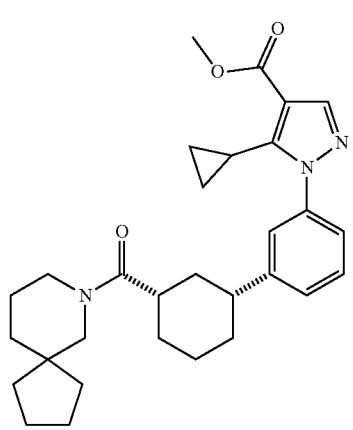

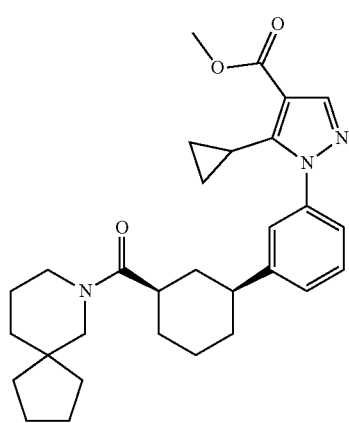

A solution of 1-[3-((1R,3S)-3-carboxy-cyclohexyl)-phenyl]-5-cyclopropyl-1H-pyrazole-4-carboxylic acid methyl ester (0.070 g, 0.19 mmol), HATU (0.072 g, 0.19 mmol), 7-azaspiro[4.5]decane (0.032 g, 0.23 mmol) and DIPEA (0.066 mL, 0.38 mmol) in DCM (1 mL) was stirred for 2 h. The mixture was diluted with DCM, and the organic phase washed with aqueous NaHCO$_3$, dried (MgSO$_4$), filtered, and concentrated to dryness. Silica purification eluting with EtOAc/hexane 10-45% gave the product (0.025 g, 27%), identified by NMR as the cis-isomer; the trans-isomer was not isolated. LC-MS m/z 490 (M+H)$^+$, 1.65 (ret. time).

4b) 1-[3-(3-{7-Azaspiro[4.5]decane-7-carbonyl}cyclohexyl)phenyl]-5-cyclopropyl-1H-pyrazole-4-carboxylic Acid (cis-racemate)

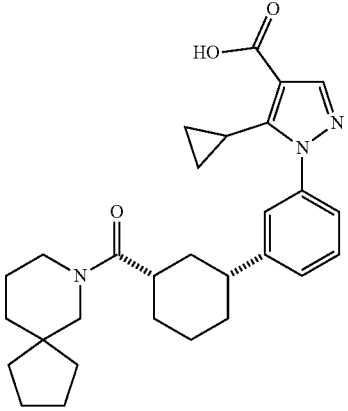

A stirred solution of 1-[3-(3-{7-azaspiro[4.5]decane-7-carbonyl}cyclohexyl)phenyl]-5-cyclopropyl-1H-pyrazole-4-carboxylic acid methyl ester (0.025 g, 0.05 mmol) in EtOH (0.5 mL) was treated with aqueous NaOH (2M, 0.128 mL). After 60 hours the mixture was partitioned between EtOAc and water. The organic phase was extracted with water and then discarded. The combined aqueous layer was acidified with 1N HCl and extracted into EtOAc (×2). The combined organic phases were dried (MgSO$_4$), filtered, and concentrated under vacuum to give the product (0.017 g, 70%). LC-MS m/z 476 (M+H)$^+$, 1.24 (ret. time), basic method. $^1$H NMR (400 MHz, DMSO-d6): 12.21 (1H, s), 7.94-7.89 (1H, m), 7.49-7.42 (2H, m), 7.42-7.28 (2H, m), 3.49-3.37 (2H, m), 3.22 (2H, s), 2.87-2.72 (2H, m), 2.15-2.01 (1H, m), 1.90-1.10 (20H, m), 0.90-0.74 (2H, m), 0.62-0.46 (2H, m).

Example 5. 5-Cyclopropyl-1-{3-[3-(2-propylpiperidine-1-carbonyl)cyclohexyl]phenyl}-1H-pyrazole-4-carboxylic Acid (cis-racemate)

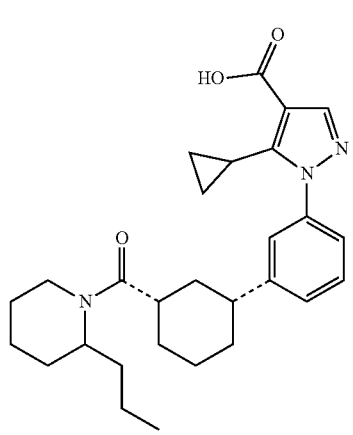 [SMILES: CCCC1CCCCN1C(=O)[C@H]1CCC[C@@H](c2cccc(-n3ncc(C(=O)O)c3C3CC3)c2)C1]

5a) 5-Cyclopropyl-1-{3-[3-(2-propylpiperidine-1-carbonyl)cyclohexyl]phenyl}-1H-pyrazole-4-carboxylic methyl ester

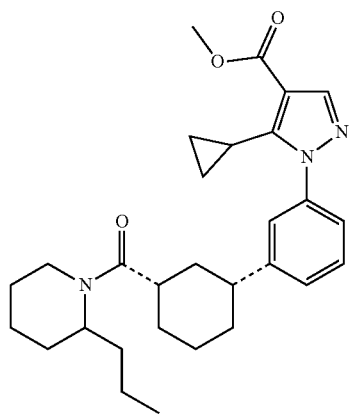 [SMILES: CCCC1CCCCN1C(=O)[C@H]1CCC[C@@H](c2cccc(-n3ncc(C(=O)OC)c3C3CC3)c2)C1]

A solution of 5-cyclopropyl-1-{3-[3-(2-propylpiperidine-1-carbonyl)cyclohexyl]phenyl}-1H-pyrazole-4-carboxylic acid methyl ester (0.050 g, 0.14 mmol), HATU (0.052 g, 0.14 mmol), 2-propylpiperidine (0.021 g, 0.16 mmol) and DIPEA (0.047 mL, 0.27 mmol) in DCM (1 mL) was stirred for 2 h. The mixture was diluted with DCM, and the organic phase washed with aqueous NaHCO$_3$, dried (MgSO$_4$), filtered, and concentrated to dryness. Silica purification eluting with EtOAc/hexane 20-40% gave the product (0.035 g, 54%), identified by NMR as 2 piperidine diastereoisomers with cis-cyclohexyl ring; the trans-isomers were not isolated. LC-MS m/z 478 (M+H)$^+$, 1.63/1.64 (ret. time).

5b) 5-Cyclopropyl-1-{3-[3-(2-propylpiperidine-1-carbonyl)cyclohexyl]phenyl}-1H-pyrazole-4-carboxylic Acid (cis-racemate)

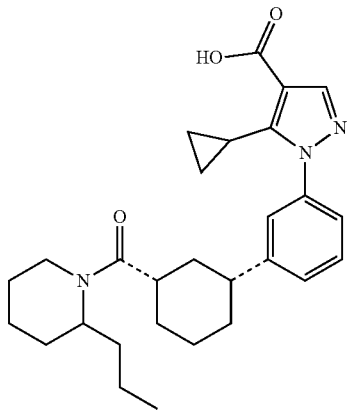 [SMILES: CCCC1CCCCN1C(=O)[C@H]1CCC[C@@H](c2cccc(-n3ncc(C(=O)O)c3C3CC3)c2)C1]

A stirred solution of 5-cyclopropyl-1-{3-[3-(2-propylpiperidine-1-carbonyl)cyclohexyl]phenyl}-1H-pyrazole-4-carboxylic acid methyl ester (0.035 g, 0.07 mmol) in EtOH (0.5 mL) was treated with aqueous NaOH (2M, 0.183 mL). After 60 hours the mixture was partitioned between EtOAc and water. The organic phase was extracted with further water and then discarded. The combined aqueous layer was acidified with 1N HCl and extracted into EtOAc (×2). The combined organic phases were dried (MgSO$_4$), filtered, and concentrated under vacuum to give the product (0.025 g, 74%): mixture of 2 piperidine diastereoisomers with cis-cyclohexyl ring. LC-MS m/z 464 (M+H)$^+$, 1.24/1.26 (ret. time), basic method. $^1$H NMR (400 MHz, DMSO-d6): 12.24 (1H, s), 7.92 (1H, s), 7.49-7.28 (4H, m), 4.64 (0.6H, s), 4.33 (0.4H, d), 4.10-3.98 (0.4H, m), 3.78 (0.6H, d), 3.13-2.90 (1H, m), 2.76 (2H, m), 2.15-2.01 (1H, m), 1.85-1.10 (18H, m), 1.00-0.72 (5H, m), 0.62-0.46 (2H, m).

Example 6. 5-cyclopropyl-1-{3-[3-(2,2-dimethylpyrrolidine-1-carbonyl)cyclohexyl]phenyl}-1H-pyrazole-4-carboxylic Acid

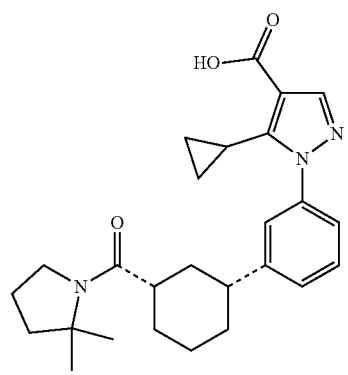 [SMILES: CC1(C)CCCN1C(=O)[C@H]1CCC[C@@H](c2cccc(-n3ncc(C(=O)O)c3C3CC3)c2)C1]

6a) 5-Cyclopropyl-1-{3-[3-(2,2-dimethylpyrrolidine-1-carbonyl)cyclohexyl]phenyl}-1H-pyrazole-4-carboxylic Acid methyl ester

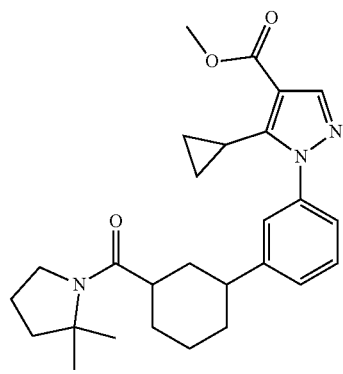 [SMILES: COC(=O)c1cnn(-c2cccc(C3CCCC(C(=O)N4CCCC4(C)C)C3)c2)c1C1CC1]

A solution of 5-cyclopropyl-1-{3-[3-(2-propylpiperidine-1-carbonyl)cyclohexyl]phenyl}-1H-pyrazole-4-carboxylic acid methyl ester (0.042 g, 0.11 mmol), HATU (0.043 g, 0.11 mmol), 2,2-dimethylpyrrolidine (0.014 g, 0.14 mmol) and DIPEA (0.040 mL, 0.23 mmol) in DCM (1 mL) was stirred for 18 h. The mixture was diluted with DCM, and the organic phase washed with aqueous NaHCO$_3$, dried (MgSO$_4$), filtered, and concentrated to dryness. Silica purification eluting with EtOAc/hexane 5-35% gave the product (0.031 g, 60%), identified by NMR as cis-cyclohexyl diastereoisomers; the trans-isomers were not isolated. LC-MS m/z 450 (M+H)$^+$, 1.57 (ret. time).

6b) 5-Cyclopropyl-1-{3-[3-(2,2-dimethylpyrrolidine-1-carbonyl)cyclohexyl]phenyl}-1H-pyrazole-4-carboxylic Acid (cis racemate)

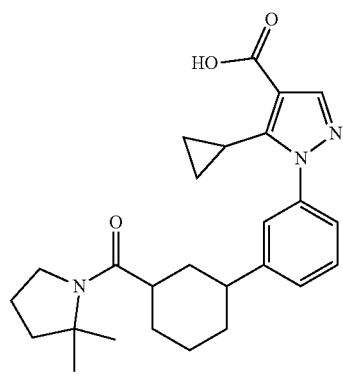 [SMILES: CC1(C)CCCN1C(=O)C1CCCC(c2cccc(-n3ncc(C(=O)O)c3C3CC3)c2)C1]

A stirred solution of 5-cyclopropyl-1-{3-[3-(2,2-dimethylpyrrolidine-1-carbonyl)cyclohexyl]phenyl}-1H-pyrazole-4-carboxylic acid methyl ester (0.031 g, 0.07 mmol) in EtOH (1 mL) was treated with aqueous NaOH (2M, 0.345 mL). After 18 hours the mixture was partitioned between EtOAc and water. The organic phase was extracted with further water and then discarded. The combined aqueous layer was acidified with 1N HCl and extracted into EtOAc (×2). The combined organic phases were dried (MgSO$_4$), filtered and concentrated under vacuum to give the product (0.018 g, 60%): cis-diastereoisomers about the cyclohexyl ring. LC-MS m/z 436 (M+H)$^+$, 1.20 (ret. time), basic method. $^1$H NMR (400 MHz, DMSO-d6): 12.23 (1H, s), 7.92 (1H, s), 7.49-7.30 (4H, m), 3.54 (2H, t), 2.78-2.66 (1H, m), 2.60-2.53 (1H, m), 2.15-1.98 (1H, m), 1.90-1.62 (8H, m), 1.62-1.38 (4H, m), 1.33 (6H, d), 0.89-0.74 (2H, m), 0.61-0.47 (2H, m).

Example 7. 1-[3-(3-{1-Azaspiro[4.5]decane-1-carbonyl}cyclohexyl)phenyl]-5-cyclopropyl-1H-pyrazole-4-carboxylic Acid (cis-racemate)

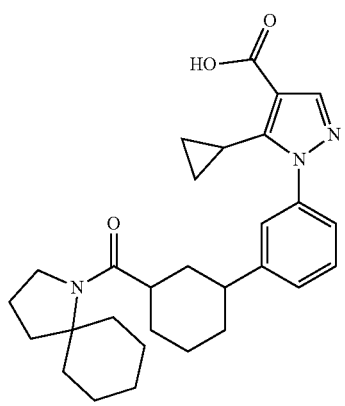 [SMILES: O=C(O)c1cnn(-c2cccc(C3CCCC(C(=O)N4CCCC45CCCCC5)C3)c2)c1C1CC1]

7a) 1-[3-(3-{1-Azaspiro[4.5]decane-1-carbonyl}cyclohexyl)phenyl]-5-cyclopropyl-1H-pyrazole-4-carboxylic Acid methyl ester

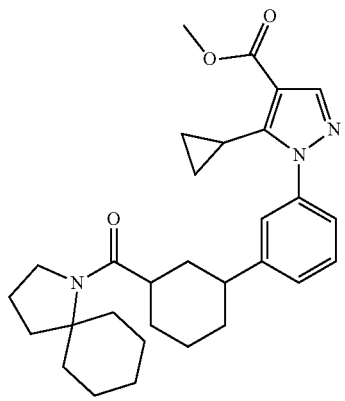 [SMILES: COC(=O)c1cnn(-c2cccc(C3CCCC(C(=O)N4CCCC45CCCCC5)C3)c2)c1C1CC1]

A solution of 5-cyclopropyl-1-{3-[3-(2-propylpiperidine-1-carbonyl)cyclohexyl]phenyl}-1H-pyrazole-4-carboxylic acid methyl ester (0.160 g, 0.43 mmol), HATU (0.165 g, 0.43 mmol), 1-azaspiro[4.5]decane (0.094 g, 0.52 mmol) and DIPEA (0.140 mL, 1.09 mmol) in DCM (4 mL) was stirred for 2 h. The mixture was diluted with DCM, and the organic phase washed with aqueous NaHCO$_3$, dried (MgSO$_4$), filtered, and concentrated to dryness. Silica purification eluting with EtOAc/hexane 10-50% gave the product (0.047 g, 22%), identified by NMR as cis-cyclohexyl diastereoisomers; the trans-isomers were not isolated. LC-MS m/z 490 (M+H)$^+$, 1.68 (ret. time).

7b) 1-[3-(3-{1-Azaspiro[4.5]decane-1-carbonyl}cyclohexyl)phenyl]-5-cyclopropyl-1H-pyrazole-4-carboxylic Acid (cis racemate)

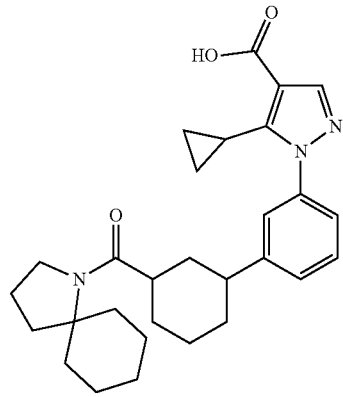 [SMILES: O=C(O)c1cnn(-c2cccc(C3CCCC(C(=O)N4CCCC45CCCCC5)C3)c2)c1C1CC1]

A stirred solution of 1-[3-(3-{1-azaspiro[4.5]decane-1-carbonyl}cyclohexyl)phenyl]-5-cyclopropyl-1H-pyrazole-4-carboxylic acid methyl ester (0.047 g, 0.10 mmol) in EtOH (1 mL) was treated with aqueous NaOH (2M, 0.240 mL). After 60 hours the mixture was partitioned between EtOAc and water. The organic phase was extracted with further water and then discarded. The combined aqueous layer was acidified with 1N HCl and extracted into EtOAc (×2). The combined organic phases were dried (MgSO$_4$), filtered, and concentrated under vacuum to give the product (0.039 g, 85%) cis-diastereoisomers about the cyclohexyl ring. LC-MS m/z 476 (M+H)$^+$, 1.27 (ret. time), basic method. $^1$H NMR (400 MHz, DMSO-d6): 12.23 (1H, s), 7.92 (1H, s), 7.49-7.42 (2H, m), 7.42-7.37 (1H, m), 7.35 (1H, d), 3.54 (2H, t), 2.79-2.66 (1H, m), 2.59 (1H, dd), 2.15-2.02 (1H, m), 1.89-1.67 (8H, m), 1.67-1.33 (7H, m), 1.33-1.15 (5H, m), 1.15-1.01 (2H, m), 0.86-0.74 (2H, m), 0.61-0.47 (2H, m).

Example 8. 1-{3-[3-(2-butylpyrrolidine-1-carbonyl)cyclohexyl]phenyl}-5-cyclopropyl-1H-pyrazole-4-carboxylic Acid (cis racemate)

8a) 1-{3-[3-(2-Butylpyrrolidine-1-carbonyl)cyclohexyl]phenyl}-5-cyclopropyl-1H-pyrazole-4-carboxylic Acid methyl ester

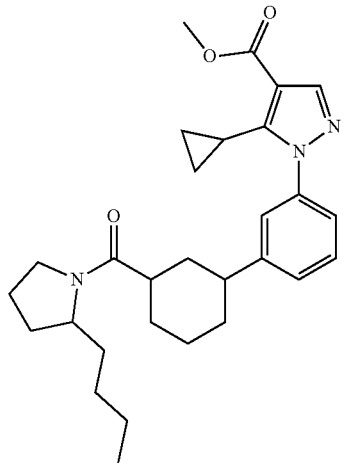

A solution of 5-cyclopropyl-1-{3-[3-(2-propylpiperidine-1-carbonyl)cyclohexyl]phenyl}-1H-pyrazole-4-carboxylic acid methyl ester (0.200 g, 0.54 mmol), HATU (0.206 g, 0.54 mmol), 2-butylpyrrolidine (0.107 g, 0.65 mmol) and DIPEA (0.236 mL, 1.36 mmol) in DCM (4 mL) was stirred for 18 h. The mixture was diluted with DCM, and the organic phase washed with aqueous NaHCO$_3$, dried (MgSO$_4$), filtered and concentrated to dryness. Silica purification eluting with EtOAc/hexane 10-60% gave the product (0.086 g, 33%), identified by NMR as cis-cyclohexyl diastereoisomers; the trans-isomers were not isolated. LC-MS m/z 478 (M+H)$^+$, 1.63 (ret. time).

8b and 8c) 1-{3-[3-(2-Butylpyrrolidine-1-carbonyl)cyclohexyl]phenyl}-5-cyclopropyl-1H-pyrazole-4-carboxylic Acid (cis racemate)

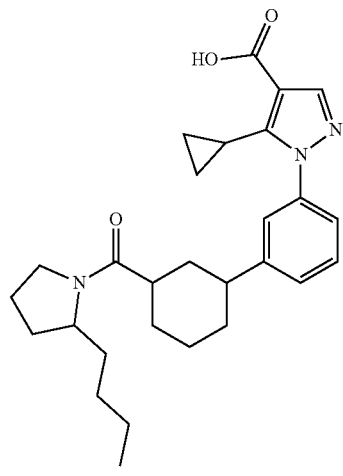

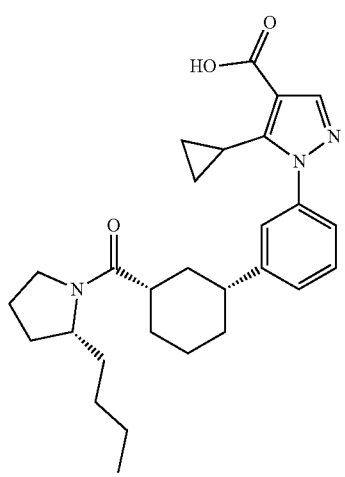 [SMILES: CCCCC1CCCN1C(=O)C1CCCC(c2cccc(-n3ncc(C(=O)O)c3C3CC3)c2)C1]

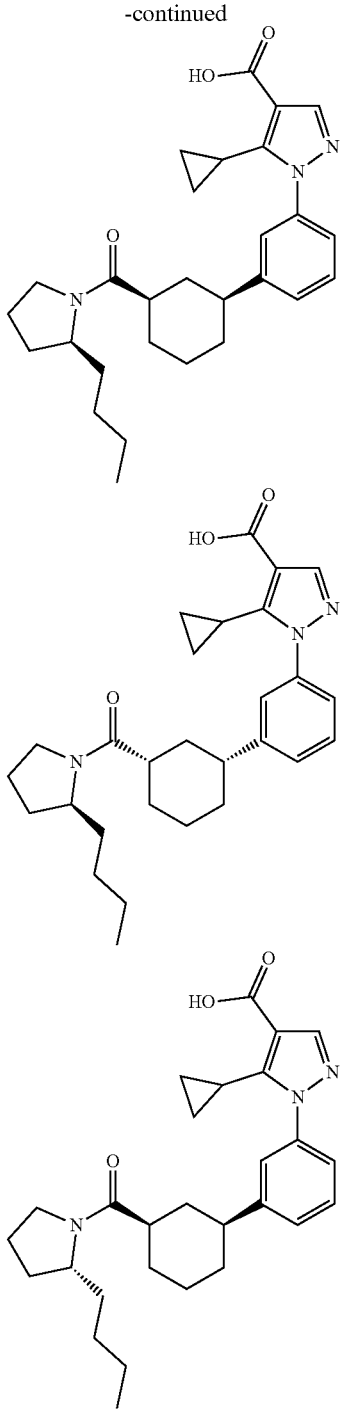

A stirred solution of 1-{3-[3-(2-butylpyrrolidine-1-carbonyl)cyclohexyl]phenyl}-5-cyclopropyl-1H-pyrazole-4-carboxylic acid methyl ester (0.086 g, 0.18 mmol) in EtOH (3 mL) was treated with aqueous NaOH (2M, 0.900 mL). After 36 hours the mixture was partitioned between EtOAc and water. The aqueous layer was acidified with 1N HCl and extracted into EtOAc (×2). The combined organic phases were dried (MgSO$_4$), filtered, and concentrated under vacuum. The residue was purified using HPLC to give the following diastereoisomeric mixtures, configurationally assigned by X-ray crystallography (cis-cyclohexyl, R, S at 2-butylpyrrolidine-1-carbonyl center, each fraction contain all four possible isomers in slightly different proportions):

Fraction 1(8b) (0.018 g, 22%): four diastereoisomers, LC-MS m/z 464 (M+H)$^+$, 4.92/5.02 (ret. time), basic method. 1H NMR (400 MHz, DMSO-d6): 12.41-12.15 (1H, m), 7.95-7.89 (1H, m), 7.55-7.31 (4H, m), 3.89 (1H, d), 3.63-3.41 (2H, m), 2.79-2.66 (1H, m), 2.58 (1H, d), 2.15-2.03 (1H, m), 1.89-1.17 (18H, m), 0.96-0.78 (5H, m), 0.60-0.48 (2H, m).

Fraction 2 (8c) (8(0.017 g, 21%): four diastereoisomers, LC-MS m/z 464 (M+H)$^+$, 4.90/5.00 (ret. time), basic method. $^1$H NMR (400 MHz, DMSO-d6): 12.42-12.12 (1H, m), 7.92 (1H, s), 7.49-7.31 (4H, m), 3.96-3.83 (1H, m), 3.56-3.43 (2H, m), 2.79-2.65 (1H, m), 2.62-2.54 (1H, m), 2.15-2.03 (1H, m), 1.92-1.71 (7H, m), 1.67-1.15 (11H, m), 0.95-0.74 (5H, m), 0.59-0.47 (2H, m)

Example 9. 1-[3-(3-{1H,4H,5H,6H,7H,8H-cyclohepta[c]pyrazol-1-yl}cyclohexyl)phenyl]-5-cyclopropyl-1H-pyrazole-4-carboxylic Acid (cis-racemate)

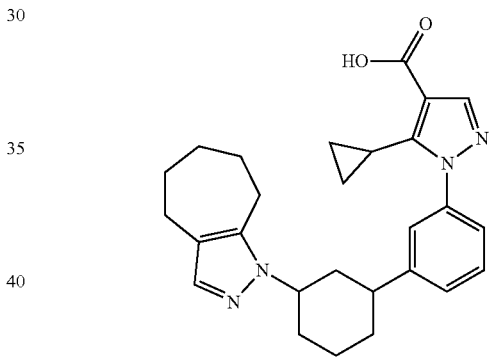

9a) 2-[1-Dimethylamino-meth-(E)-ylidene]-cycloheptanone

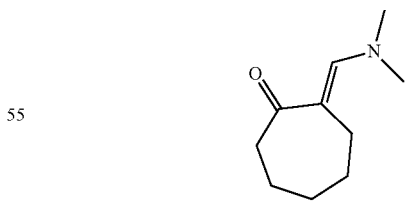

A mixture of cycloheptanone (0.50 g, 4.46 mmol) and DMF-dimethylacetal (0.53 g, 4.46 mmol) was stirred at 130° C. for 24 hours, then concentrated to dryness under vacuum. The residue was treated with toluene and again concentrated to dryness under vacuum to give the product, used without further purification. LC-MS m/z 168 (M+H)$^+$, 1.20 (ret. time).

9b) 1-[3-(3-{1H,4H,5H,6H,7H,8H-Cyclohepta[c]pyrazol-1-yl}cyclohexyl)phenyl]-5-cyclopropyl-1H-pyrazole-4-carboxylic Acid (cis-racemate)

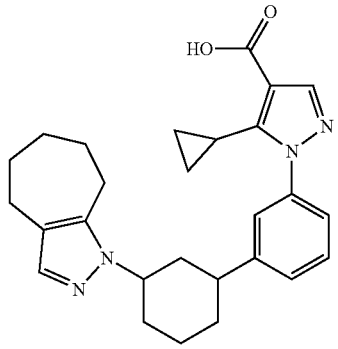 [SMILES: O=C(O)c1cnn(-c2cccc(C3CCCC(n4ncc5c4CCCCC5)C3)c2)c1C1CC1]

A mixture of 2-[1-dimethylamino-meth-(E)-ylidene]-cycloheptanone (0.043 g, 0.26 mmol), 5-cyclopropyl-1-[3-(3-hydrazino-cyclohexyl)-phenyl]-1H-pyrazole-4-carboxylic acid methyl ester hydrochloride (0.100 g, 0.26 mmol) and NaOAc (0.050 g, 0.61 mmol) in ethanol (2 mL) was stirred at 70° C. for 16 h. The mixture was concentrated, diluted with MeOH/THF (1:1, 5 mL), treated with aqueous LiOH (1M, 2 mL), and stirred at room temperature. After 24 hours the mixture was acidified with citric acid (5% aqueous) and extracted into EtOAc (×3). The combined organic phases were washed with water and brine, dried (MgSO₄), filtered, and concentrated under vacuum. The residue was purified by HPLC to give the product (0.018 g, 32%). LC-MS m/z 445 (M+H)⁺, 1.19 (ret. time). ¹H NMR (400 MHz, Me-d3-OD): 8.00 (1H, s), 7.56 (1H, s), 7.51 (1H, t), 7.49-7.38 (3H, m), 4.67-4.52 (1H, m), 3.03-2.95 (1H, m), 2.92 (2H, t), 2.67-2.60 (2H, m), 2.18-2.12 (2H, m), 2.12-1.96 (4H, m), 1.95-1.86 (3H, m), 1.80-1.74 (2H, m), 1.73-1.64 (3H, m), 1.63-1.54 (1H, m), 0.93-0.86 (2H, m), 0.64-0.59 (2H, m).

Example 10. 1-[3-(3-{1H,4H,5H,6H-cyclopenta[c]pyrazol-1-yl}cyclopentyl)phenyl]-5-cyclopropyl-1H-pyrazole-4-carboxylic Acid

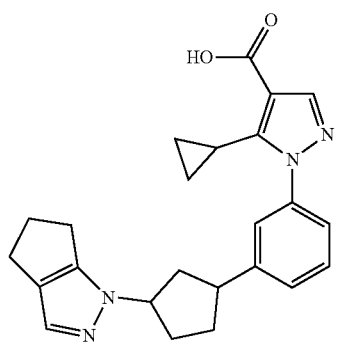 [SMILES: O=C(O)c1cnn(-c2cccc(C3CCC(n4ncc5c4CCC5)C3)c2)c1C1CC1]

10a) 2-[1-Dimethylamino-meth-(E)-ylidene]-cycloheptanone

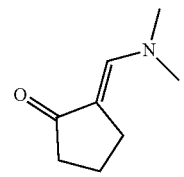

A mixture of cyclopentanone (0.50 g, 5.94 mmol) and DMF-dimethylacetal (0.71 g, 5.94 mmol) was stirred at 100° C. for 20 hours, then concentrated to dryness under vacuum. The residue was treated with toluene and again concentrated to dryness under vacuum to give the product, used without further purification. LC-MS m/z 140 (M+H)⁺, 0.93 (ret. time).

10b) 5-Cyclopropyl-1-[3-(3-oxo-cyclopentyl)-phenyl]-1H-pyrazole-4-carboxylic acid methyl ester

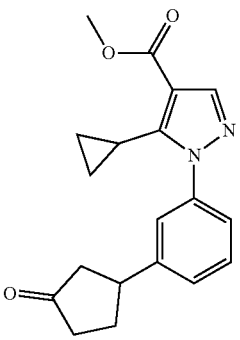 [SMILES: COC(=O)c1cnn(-c2cccc(C3CCC(=O)C3)c2)c1C1CC1]

A mixture of 5-cyclopropyl-1-[3-(4,4,5,5-tetramethyl-[1,3,2]dioxaborolan-2-yl)-phenyl]-1H-pyrazole-4-carboxylic acid methyl ester (0.215 g, 0.60 mmol), cyclopentenone (0.35 g, 4.26 mmol), Et3N (0.89 mL, 6.39 mmol) and [Rh(cod)Cl]₂ (0.11 g, 0.21 mmol) in dioxane (14 mL) and water (2 mL) was stirred under nitrogen at 100° C. for 2 h. After cooling, the mixture was diluted with water and extracted with EtOAc (×2), and the combined organic phases dried (MgSO₄) and concentrated to dryness. The residue was purified by silica chromatography eluting with EtOAc/petrol 30-60% to give the product (0.98 g, quantative). LC-MS m/z 325 (M+H)⁺, 1.25 (ret. time).

10c) 1-{3-[3-(N'-tert-Butoxycarbonyl-hydrazino)-cyclopentyl]-phenyl}-5-cyclopropyl-1H-pyrazole-4-carboxylic Acid methyl ester

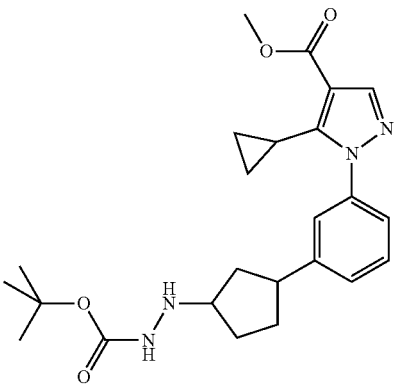 [SMILES: COC(=O)c1cnn(-c2cccc(C3CCC(NNC(=O)OC(C)(C)C)C3)c2)c1C1CC1]

A solution of 5-cyclopropyl-1-[3-(3-oxo-cyclohexyl)-phenyl]-1H-pyrazole-4-carboxylic acid methyl ester (0.98 g, 3.02 mmol) and t-butyl carbazate (0.41 g, 3.02 mmol) in MeOH (15 mL) was stirred for 90 min and then concentrated to dryness under vacuum. A stirred solution of the residue in AcOH (15 mL) was treated with NaBH₃CN (0.20 g, 3.02 mmol). After one hour the mixture was treated with aqueous NaOH (1M) and extracted with DCM. The organic phase was washed with saturated aqueous NaHCO₃, dried over MgSO₄, filtered, and concentrated to dryness. The residue was purified by silica chromatography eluting with EtOAc/petrol 30% to give the product (1.5 g, quantative) as a mixture of diastereoisomers. LC-MS m/z 441 (M+H)⁺, 1.47 (ret. time).

10d) 5-Cyclopropyl-1-[3-(3-hydrazino-cyclopentyl)-phenyl]-1H-pyrazole-4-carboxylic Acid methyl ester hydrochloride

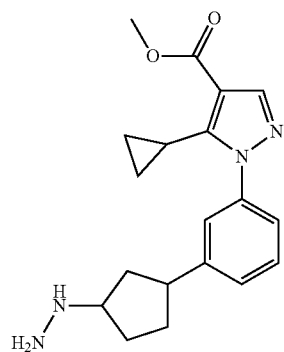 [SMILES: COC(=O)c1cnn(-c2cccc(C3CCC(NN)C3)c2)c1C1CC1]

A solution of 1-{3-[3-(N'-tert-butoxycarbonyl-hydrazino)-cyclopentyl]-phenyl}-5-cyclopropyl-1H-pyrazole-4-carboxylic acid methyl ester (1.20 g, 2.72 mmol) in HCl (4M in dioxane, 27 mL) was stirred for 5 hours and then concentrated to dryness under vacuum to give the product (1.10 g, quantative). LC-MS m/z 341 (M+H)⁺, 1.20 (ret. time).

10e) 1-[3-(3-{1H,4H,5H,6H-cyclopenta[c]pyrazol-1-yl}cyclopentyl)phenyl]-5-cyclopropyl-1H-pyrazole-4-carboxylic Acid

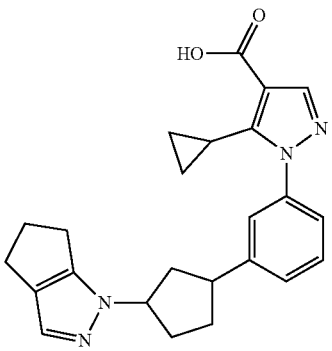 [SMILES: O=C(O)c1cnn(-c2cccc(C3CCC(n4ncc5c4CCC5)C3)c2)c1C1CC1]

A mixture of 2-[1-dimethylamino-meth-(E)-ylidene]-cyclopentanone (0.037 g, 0.27 mmol), 5-cyclopropyl-1-[3-(3-hydrazino-cyclopentyl)-phenyl]-1H-pyrazole-4-carboxylic acid methyl ester hydrochloride (0.100 g, 0.27 mmol) and NaOAc (0.052 g, 0.64 mmol) in ethanol (2 mL) was stirred at 70° C. for 16 h. The mixture was concentrated, diluted with MeOH/THF (1:1, 5 mL), treated with aqueous LiOH (1M, 2 mL) and stirred at room temperature. After 24 hours the mixture was acidified with citric acid (5% aqueous) and extracted into EtOAc (×3). The combined organic phases were washed with water and brine, dried (MgSO₄), filtered, and concentrated under vacuum. The residue was purified by silica chromatography eluting with EtOAc/MeOH (gradient) to give the product (0.025 g, 32%) as a mixture of cis- and trans-diastereoisomers. LC-MS m/z 403 (M+H)⁺, 1.10 (ret. time). ¹H NMR (400 MHz, Me-d₃-OD): 7.99 (1H, s), 7.55-7.45 (3H, m), 7.41-7.37 (1H, m), 7.15 (1H, 2×s), 4.82-4.69 (1H, m), 3.65-3.53 (0.5H, m), 2.84-2.78 (2H, m), 2.65-2.53 (4H, m), 2.49-2.15 (5H, m), 2.12-2.02 (2H, m), 1.91-1.79 (0.5H, m), 0.94-0.86 (2H, m), 0.67-0.59 (2H, m).

Example 11. 5-Cyclopropyl-1-(3-{3-[2-(3-methylbutyl)pyrrolidine-1-carbonyl]cyclohexyl}phenyl)-1H-pyrazole-4-carboxylic Acid (cis racemate)

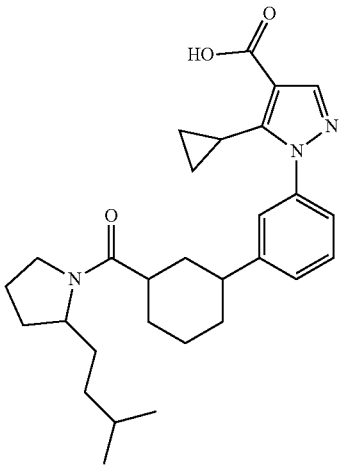 [SMILES: CC(C)CCC1CCCN1C(=O)C1CCCC(c2cccc(-n3ncc(C(=O)O)c3C3CC3)c2)C1]

11a) 5-Cyclopropyl-1-(3-{3-[2-(3-methylbutyl)pyrrolidine-1-carbonyl]cyclohexyl}phenyl)-1H-pyrazole-4-carboxylic Acid methyl ester

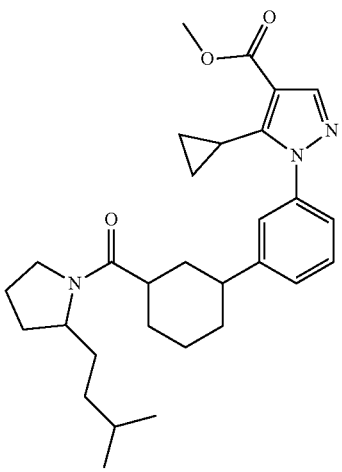 [SMILES: COC(=O)c1cnn(-c2cccc(C3CCCC(C(=O)N4CCCC4CCC(C)C)C3)c2)c1C1CC1]

A solution of 5-cyclopropyl-1-{3-[3-(2-propylpiperidine-1-carbonyl)cyclohexyl]phenyl}-1H-pyrazole-4-carboxylic acid methyl ester (0.072 g, 0.20 mmol), HATU (0.074 g, 0.20 mmol), 2-(3-methylbutyl)pyrrolidine (0.039 g, 0.27 mmol) and DIPEA (0.085 mL, 0.49 mmol) in DCM (1 mL) was stirred for 16 h. The mixture was diluted with DCM, and the organic phase washed with aqueous NaHCO₃, dried (MgSO₄), filtered and concentrated to dryness. Silica purification eluting with EtOAc/hexane 10-50% gave the product (0.030 g, 31%), identified by NMR as cis-cyclohexyl diastereoisomers; the trans-isomers were not isolated. LC-MS m/z 492 (M+H)⁺, 1.66 (ret. time), basic method.

11 b) 5-Cyclopropyl-1-(3-{3-[2-(3-methylbutyl)pyrrolidine-1-carbonyl]cyclohexyl}phenyl)-1H-pyrazole-4-carboxylic Acid (cis racemate)

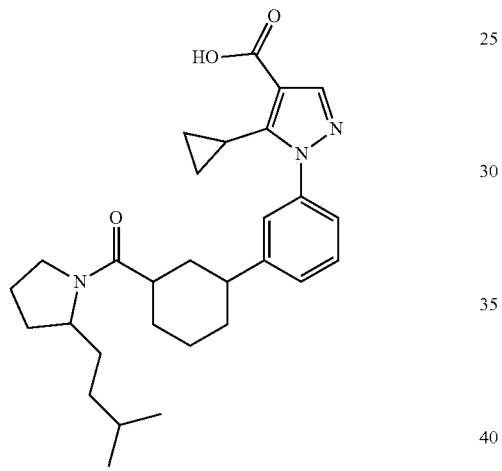

A stirred solution of 5-cyclopropyl-1-(3-{3-[2-(3-methylbutyl)pyrrolidine-1-carbonyl]cyclohexyl} phenyl)-1H-pyrazole-4-carboxylic acid methyl ester (0.030 g, 0.06 mmol) in EtOH (0.5 mL) was treated with aqueous NaOH (2M, 0.152 mL). After 60 hours the mixture was partitioned between EtOAc and water. The organic phase was extracted with further water and then discarded. The combined aqueous layer was acidified with 1N HCl and extracted into EtOAc (×2). The combined organic phases were dried (MgSO₄), filtered and concentrated under vacuum to give the product (0.017 g, 58%) as a mixture of cis diastereoisomers. LC-MS m/z 478 (M+H)⁺, 1.25/1.26 (ret. time), basic method. ¹H NMR (400 MHz, DMSO-d6): 12.37-12.10 (1H, m), 7.92 (1H, s), 7.49-7.30 (4H, m), 3.94-3.81 (1H, m), 3.56-3.43 (1H, m), 3.28-3.15 (1H, m), 2.79-2.64 (1H, m), 2.63-2.54 (1H, m), 2.15-2.03 (1H, m), 1.91-1.71 (7H, m), 1.61-1.37 (6H, m), 1.29-0.93 (4H, m), 0.93-0.79 (8H, m), 0.60-0.47 (2H, m).

Example 12. 5-cyclopropyl-1-{3-[3-(2-cyclopropylpyrrolidine-1-carbonyl)cyclohexyl]phenyl}-1H-pyrazole-4-carboxylic Acid (cis racemate)

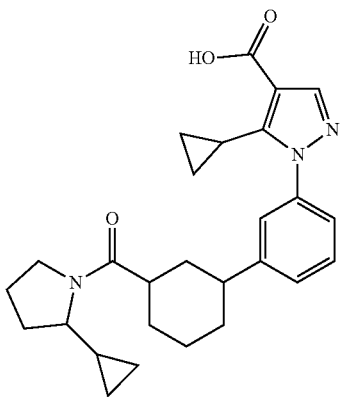 [SMILES: O=C(O)c1cnn(-c2cccc(C3CCCC(C(=O)N4CCCC4C4CC4)C3)c2)c1C1CC1]

12a) 5-Cyclopropyl-1-{3-[3-(2-cyclopropylpyrrolidine-1-carbonyl)cyclohexyl]phenyl}-1H-pyrazole-4-carboxylic Acid methyl ester

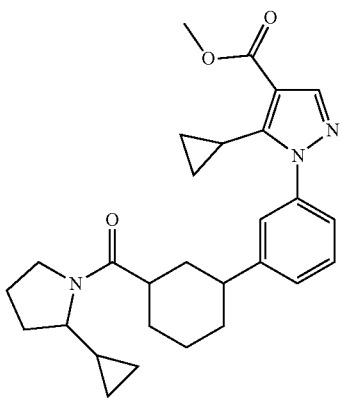 [SMILES: COC(=O)c1cnn(-c2cccc(C3CCCC(C(=O)N4CCCC4C4CC4)C3)c2)c1C1CC1]

A solution of 5-cyclopropyl-1-{3-[3-(2-propylpiperidine-1-carbonyl)cyclohexyl]phenyl}-1H-pyrazole-4-carboxylic acid methyl ester (0.072 g, 0.20 mmol), HATU (0.074 g, 0.20 mmol), 2-cyclopropylpyrrolidine (0.040 g, 0.27 mmol) and DIPEA (0.085 mL, 0.49 mmol) in DCM (1 mL) was stirred for 16 h. The mixture was diluted with DCM, and the organic phase washed with aqueous NaHCO₃, dried (MgSO₄), filtered and concentrated to dryness. Silica purification eluting with EtOAc/hexane 15-60% gave the product (0.029 g, 32%), identified by NMR as cis-cyclohexyl diastereoisomers; the trans-isomers were not isolated. LC-MS m/z 462 (M+H)⁺, 1.53 (ret. time), basic method.

12b) 5-Cyclopropyl-1-{3-[3-(2-cyclopropylpyrrolidine-1-carbonyl)cyclohexyl]phenyl}-1H-pyrazole-4-carboxylic Acid (cis racemate)

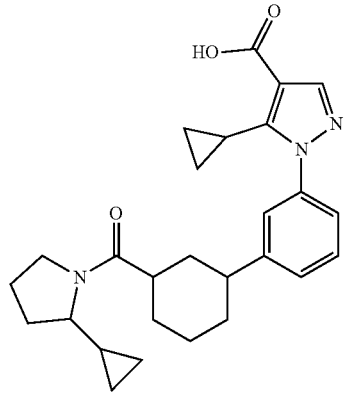 [SMILES: O=C(O)c1cnn(-c2cccc(C3CCCC(C(=O)N4CCCC4C4CC4)C3)c2)c1C1CC1]

A stirred solution of 5-cyclopropyl-1-{3-[3-(2-cyclopropylpyrrolidine-1-carbonyl)cyclohexyl] phenyl}-1H-pyrazole-4-carboxylic acid methyl ester (0.029 g, 0.06 mmol) in EtOH (0.5 mL) was treated with aqueous NaOH (2M, 0.157 mL). After 60 hours the mixture was partitioned between EtOAc and water. The organic phase was extracted with further water and then discarded. The combined aqueous layer was acidified with 1N HCl and extracted into EtOAc (×2). The combined organic phases were dried (MgSO$_4$), filtered and concentrated under vacuum to give the product (0.016 g, 57%) as a mixture of cis-diastereoisomers. LC-MS m/z 448 (M+H)$^+$, 1.13 (ret. time), basic method. $^1$H NMR (400 MHz, DMSO-d6): 12.39-12.03 (1H, m), 7.92 (1H, s), 7.49-7.30 (4H, m), 3.80-3.71 (0.5H, m), 3.69-3.58 (0.5H, m), 3.58-3.43 (1H, m), 3.43-3.34 (1H, m), 2.80-2.65 (1.5H, m), 2.63-2.55 (0.5H, m), 2.24-2.05 (1H, m), 2.03-1.94 (1H, m), 1.91-1.73 (6H, m), 1.73-1.34 (6H, m), 0.99-0.73 (3H, m), 0.55-0.41 (3H, m), 0.41-0.04 (2H, m). Peaks close to amide are rotameric.

Example 13. 1-{3-[3-(2-cyclobutylpyrrolidine-1-carbonyl)cyclohexyl]phenyl}-5-cyclopropyl-1H-pyrazole-4-carboxylic Acid (cis racemate)

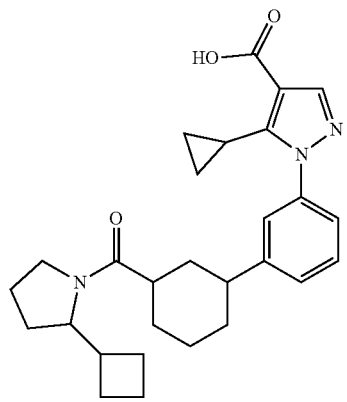 [SMILES: O=C(O)c1cnn(-c2cccc(C3CCCC(C(=O)N4CCCC4C4CCC4)C3)c2)c1C1CC1]

13a) 1-{3-[3-(2-Cyclobutylpyrrolidine-1-carbonyl)cyclohexyl]phenyl}-5-cyclopropyl-1H-pyrazole-4-carboxylic Acid methyl ester

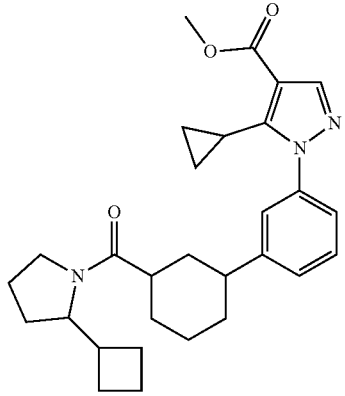 [SMILES: COC(=O)c1cnn(-c2cccc(C3CCCC(C(=O)N4CCCC4C4CCC4)C3)c2)c1C1CC1]

A solution of 5-cyclopropyl-1-{3-[3-(2-propylpiperidine-1-carbonyl)cyclohexyl]phenyl}-1H-pyrazole-4-carboxylic acid methyl ester (0.072 g, 0.20 mmol), HATU (0.074 g, 0.20 mmol), 2-cyclobutylpyrrolidine (0.034 g, 0.27 mmol), and DIPEA (0.085 mL, 0.49 mmol) in DCM (1 mL) was stirred for 16 h. The mixture was diluted with DCM, and the organic phase washed with aqueous NaHCO$_3$, dried (MgSO$_4$), filtered and concentrated to dryness. Silica purification eluting with EtOAc/hexane 15-50% gave the product (0.034 g, 37%), identified by NMR as cis-cyclohexyl diastereoisomers; the trans-isomers were not isolated. LC-MS m/z 476 (M+H)$^+$, 1.59/1.61 (ret. time), basic method.

13b) 1-{3-[3-(2-Cyclobutylpyrrolidine-1-carbonyl)cyclohexyl]phenyl}-5-cyclopropyl-1H-pyrazole-4-carboxylic Acid (cis racemate)

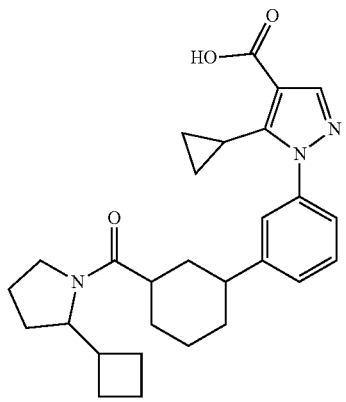 [SMILES: O=C(O)c1cnn(-c2cccc(C3CCCC(C(=O)N4CCCC4C4CCC4)C3)c2)c1C1CC1]

A stirred solution of 1-{3-[3-(2-cyclobutylpyrrolidine-1-carbonyl)cyclohexyl]phenyl}-5-cyclopropyl-1H-pyrazole-4-carboxylic acid methyl ester (0.034 g, 0.07 mmol) in EtOH (0.5 mL) was treated with aqueous NaOH (2M, 0.179 mL). After 60 hours, the mixture was partitioned between EtOAc and water. The organic phase was extracted with further water and then discarded. The combined aqueous layer was acidified with 1N HCl and extracted into EtOAc (×2). The combined organic phases were dried (MgSO$_4$), filtered, and concentrated under vacuum to give the product (0.022 g, 67%) as a mixture of cis-diastereoisomers. LC-MS m/z 462 (M+H)+, 1.17/1.19 (ret. time), basic method. ¹H NMR (400 MHz, DMSO-d6): 12.22 (1H, s), 7.92 (1H, s), 7.50-7.30 (4H, m), 4.11-3.96 (1H, m), 3.59-3.39 (2H, m), 2.83-2.66 (1H, m), 2.66-2.54 (1H, m), 2.46-2.34 (1H, m), 2.17-2.03 (1H, m), 1.90-1.29 (18H, m), 0.91-0.73 (2H, m), 0.60-0.46 (2H, m).

Example 14. 5-Cyclopropyl-1-{3-[(cis)-3-(6-methyl-5,6-dihydro-4H-cyclopentapyrazol-1-yl)-cyclohexyl]-phenyl}-1H-pyrazole-4-carboxylic Acid (cis racemic)

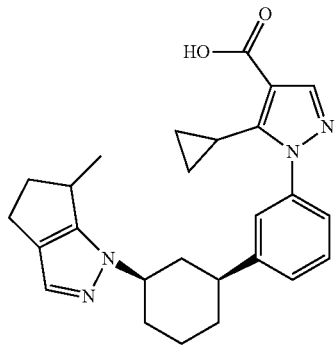 [SMILES: CC1CCc2cnn([C@@H]3CCC[C@H](c4cccc(-n5ncc(C(=O)O)c5C5CC5)c4)C3)c21]

14a) 5-Cyclopropyl-1-[3-(3-oxo-cyclohexyl)-phenyl]-1H-pyrazole-4-carboxylic acid methyl ester

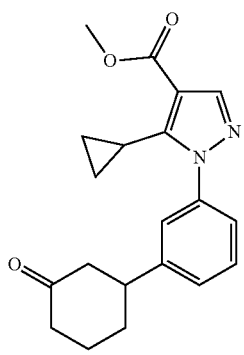 [SMILES: COC(=O)c1cnn(-c2cccc(C3CCCC(=O)C3)c2)c1C1CC1]

A mixture of 2-cyclohexen-1one (650 mg, 6.79 mmol), 5-cyclopropyl-1-[3-(4,4,5,5-tetramethyl-[1,3,2]dioxaborolan-2-yl)-phenyl]-1H-pyrazole-4-carboxylic acid methyl ester (2.50 g, 6.79 mmol), [RhCl(cod)]₂ (170 mg, 0.34 mmol) and TEA (1.41 mL, 10.19 mmol) in water (23 mL) and 1,4-dioxane (3 mL) was stirred at 100° C. for 2 hours and stirred RT for 16 hours. The reaction mixture was cooled to room temperature, and partitioned between H₂O and EtOAc. The aqueous layer was extracted with EtOAc. The organic layers were combined, dried over MgSO₄, filtered and concentrated. The product was purified by Biotage (30% to 60% EtOAc/petrol) yielded the title compound as a colorless oil (2.1 g, 92%). LC-MS m/z 339 (M+H)+, 1.39 (ret. time).

14b) 1-{3-[3-(N'-tert-Butoxycarbonyl-hydrazino)-cyclohexyl]-phenyl}-5-cyclopropyl-1H-pyrazole-4-carboxylic Acid methyl ester

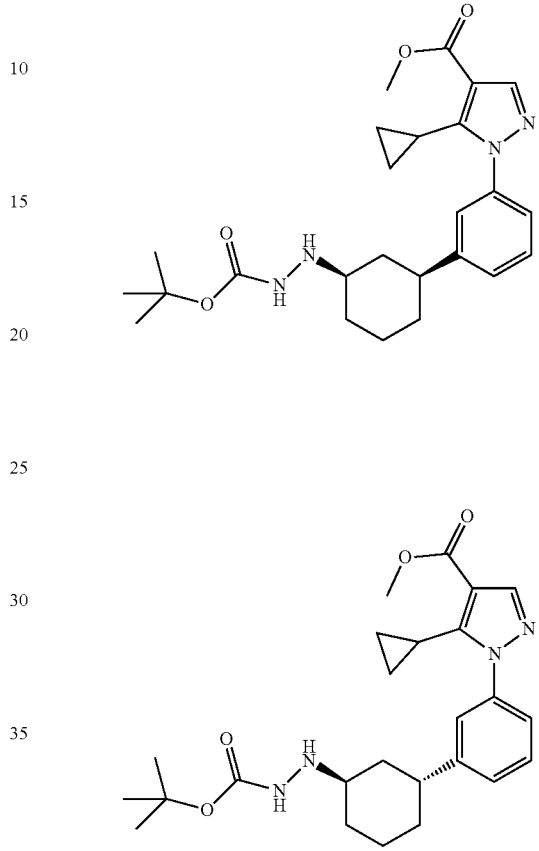

5-Cyclopropyl-1-[3-(3-oxo-cyclohexyl)-phenyl]-1H-pyrazole-4-carboxylic acid methyl ester (2.1 g, 6.21 mmol) and tert-butyl carbazate (840 mg, 6.21 mmol) in methanol (31.0 mL) were stirred at room temperature for 1.5 hours. The solvent was evaporated under vacuum and the residue dissolved in acetic acid. NaCNBH₃ (410 mg, 6.21 mmol) was added at room temperature. The mixture was stirred for 1 hour at room temperature, quenched with NaOH (1M) and extracted with dichloromethane. The organic phase was washed with a saturated solution of NaHCO₃, then brine and dried over MgSO₄. After filtration the organic layer was concentrated to dryness under vacuum. Purification by Biotage (25% EtOAc/petrol, then 40% EtOAc/petrol) separated the two diastereoisomers:

Trans diastereoisomer (1.21 g, 43%). LC-MS m/z 455 (M+H)+, 1.54 (ret. time).

Cis diastereoisomer (1.57 g, 56%). LC-MS m/z 455 (M+H)+, 1.51 (ret. time).

14c) 5-Cyclopropyl-1-[3-(3-(cis)-hydrazino-cyclohexyl)-phenyl]-1H-pyrazole-4-carboxylic acid methyl ester HCl

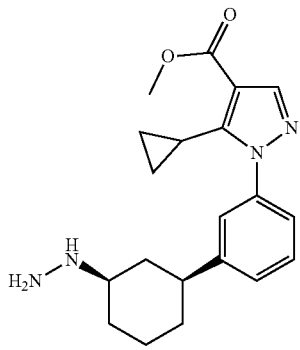 [SMILES: COC(=O)c1cnn(-c2cccc([C@H]3CCC[C@@H](NN)C3)c2)c1C1CC1]

1-{3-[3-(cis)-(N'-tert-Butoxycarbonyl-hydrazino)-cyclohexyl]-phenyl}-5-cyclopropyl-1H-pyrazole-4-carboxylic acid methyl ester (1.57 g, 3.45 mmol) was stirred in HCl in EtOAc (35 mL, saturated) for 2 hours at room temperature. The reaction was concentrated to yield the title compound as a yellow solid. HCl salt (1.2 g, 100%). LC-MS m/z 355 (M+H)$^+$, 1.28 (ret. time).

14d) 5-Cyclopropyl-1-{3-[3-(cis)-(6-methyl-5,6-dihydro-4H-cyclopentapyrazol-1-yl)-cyclohexyl]-phenyl}-1H-pyrazole-4-carboxylic Acid (cis racemate)

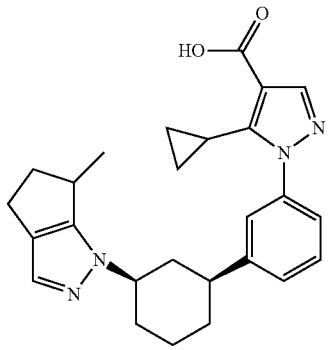 [SMILES: CC1CCc2cnn([C@@H]3CCC[C@H](c4cccc(-n5ncc(C(=O)O)c5C5CC5)c4)C3)c21]

A mixture of 2-methylcyclopentanone (0.50 g, 5.09 mmol), N,N-dimethylformamide dimethyl acetal (677 µl, 5.09 mmol) and toluene (2 mL) was heated at 100° C. for 16 hours. The reaction was concentrated to give 2-[1-dimethylamino-methylidene]-5-methylcyclopentanone which was used in the next reaction without further purification. A mixture of 5-Cyclopropyl-1-[3-(cis)-(3-hydrazino-cyclohexyl)-phenyl]-1H-pyrazole-4-carboxylic acid methyl ester HCl (100 mg, 0.26 mmol) and 2-[1-dimethylamino-methylidene]-5-methylcyclopentanone (46 mg, 0.26 mmol) in ethanol (2.0 mL) was stirred at 70° C. for 16 hours. The reaction was concentrated and the residue was treated with LiOH (2 mL, 1M, aq) and MeOH:THF (1:1, 5 mL), and stirred for 16 hours at room temperature. The mixture was diluted with water, the pH adjusted to pH 4 (citric acid 5%), and extracted with EtOAc (×3). The combined organic layers were washed with brine, dried over MgSO$_4$, filtered and evaporated to dryness under vacuum. Purification by preparative HPLC gave the product (17 mg, 11%). LC-MS m/z 431 (M+H)$^+$, 1.20 (ret. time). $^1$H NMR (400 MHz, DMSO-d$_6$): 7.92 (1H, s), 7.50-7.43 (2H, m), 7.43-7.35 (2H, m), 7.06 (1H, s), 4.24-4.15 (2H, m), 2.95-2.85 (1H, m), 2.13-2.09 (1H, m), 2.07-1.77 (8H, m), 1.55 (2H, s), 1.23 (3H, dd), 1.01 (2H, s), 0.85-0.77 (2H, m), 0.58-0.45 (2H, m).

Example 15. 5-Cyclopropyl-1-{3-[3-(4-oxo-4,5,6,7-tetrahydro-indazol-1-yl)-cyclopentyl]-phenyl}-1H-pyrazole-4-carboxylic Acid

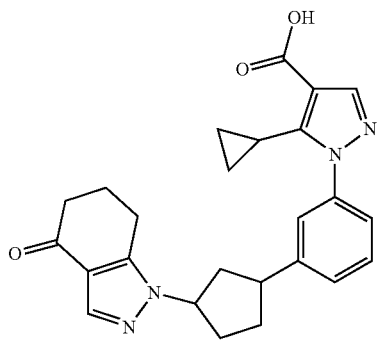 [SMILES: O=C(O)c1cnn(-c2cccc(C3CCC(n4ncc5c4CCCC5=O)C3)c2)c1C1CC1]

15a) 5-Cyclopropyl-1-[3-(3-oxo-cyclopentyl)-phenyl]-1H-pyrazole-4-carboxylic acid methyl ester

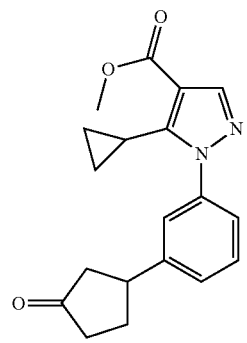 [SMILES: COC(=O)c1cnn(-c2cccc(C3CCC(=O)C3)c2)c1C1CC1]

A mixture of 2-cyclopentenone (250 mg, 3.04 mmol), 5-cyclopropyl-1-[3-(4,4,5,5-tetramethyl-[1,3,2]dioxaborolan-2-yl)-phenyl]-1H-pyrazole-4-carboxylic acid methyl ester (1.12 g, 3.04 mmol), [RhCl(cod)]$_2$ (80 mg, 0.15 mmol) and TEA (0.63 mL, 4.57 mmol) in water (10 mL) and 1,4-dioxane (2 mL) was stirred at 100° C. for 2 hours and RT for 16 hours. The mixture was partitioned between H$_2$O and EtOAc. The aqueous layer was extracted with EtOAc. The organic layers were combined, dried over MgSO$_4$, filtered and concentrated to dryness under vacuum. Silica chromatography (30% to 60% EtOAc/petrol) gave the product (0.98 g, 100%). LC-MS m/z 325 (M+H)$^+$, 1.25 (ret. time).

15b) 1-{3-[3-(N'-tert-Butoxycarbonyl-hydrazino)-cyclopentyl]-phenyl}-5-cyclopropyl-1H-pyrazole-4-carboxylic Acid methyl ester

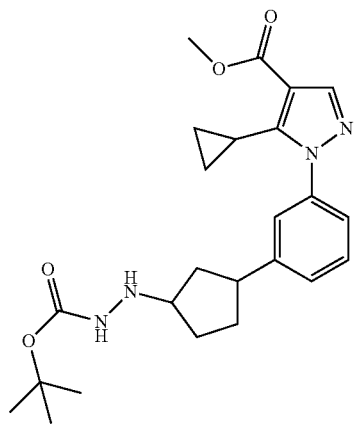 [SMILES: COC(=O)c1cnn(-c2cccc(C3CCC(NNC(=O)OC(C)(C)C)C3)c2)c1C1CC1]

5-Cyclopropyl-1-[3-(3-oxo-cyclopentyl)-phenyl]-1H-pyrazole-4-carboxylic acid methyl ester (980 mg, 3.02 mmol) and tert-butyl carbazate (410 mg, 3.02 mmol) in methanol (15.1 mL) were stirred at room temperature for 1.5 hours. The solvent was evaporated under vacuum and the residue dissolved in acetic acid. NaCNBH$_3$ (200 mg, 3.02 mmol) was added at room temperature. The mixture was stirred for 1 hour at room temperature, quenched with NaOH (1M) and extracted with dichloromethane. The organic phase was washed with saturated aqueous NaHCO$_3$ followed by brine, dried over MgSO$_4$, filtered and concentrated to dryness under vacuum to yield the product (1.5 g, 100%). LC-MS m/z 441 (M+H)$^+$, 1.47 (ret. time).

15c) 5-Cyclopropyl-1-[3-(3-hydrazino-cyclopentyl)-phenyl]-1H-pyrazole-4-carboxylic Acid methyl ester

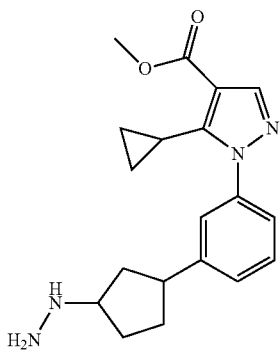 [SMILES: COC(=O)c1cnn(-c2cccc(C3CCC(NN)C3)c2)c1C1CC1]

1-{3-[3-(N'-tert-Butoxycarbonyl-hydrazino)-cyclopentyl]-phenyl}-5-cyclopropyl-1H-pyrazole-4-carboxylic acid methyl ester (1.2 g, 2.72 mmol) was stirred in HCl in EtOAc (saturated) for 2 hours at room temperature. The reaction was concentrated to dryness under vacuum to yield the title compound as a yellow solid. HCl salt. (1.1 g, 100%). LC-MS m/z 341 (M+H)$^+$, 1.20 (ret. time).

15d) 5-Cyclopropyl-1-{3-[3-(4-oxo-4,5,6,7-tetrahydro-indazol-1-yl)-cyclopentyl]-phenyl}-1H-pyrazole-4-carboxylic Acid methyl ester

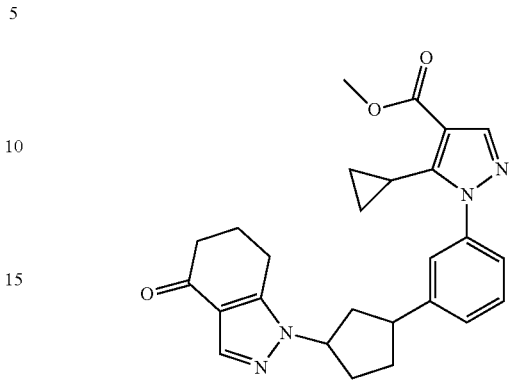

A stirred solution of 2-dimethylaminomethylene-cyclohexane-1,3-dione [J. Med. Chem., 2011, 54(14), 5070] (337 mg, 0.90 mmol) in MeOH (3 mL) was treated with cis and trans 5-cyclopropyl-1-[3-(3-hydrazino-cyclopentyl)-phenyl]-1H-pyrazole-4-carboxylic acid methyl ester (150 mg, 0.90 mmol). The mixture was heated to reflux for 5 hours, then cooled to room temperature and filtered. Purification by Biotage (100% EtOAc) gave the product (200 mg, 50%). LC-MS m/z 445 (M+H)$^+$, 1.39 (ret. time).

15e) 5-Cyclopropyl-1-{3-[3-(4-oxo-4,5,6,7-tetrahydro-indazol-1-yl)-cyclopentyl]-phenyl}-1H-pyrazole-4-carboxylic Acid

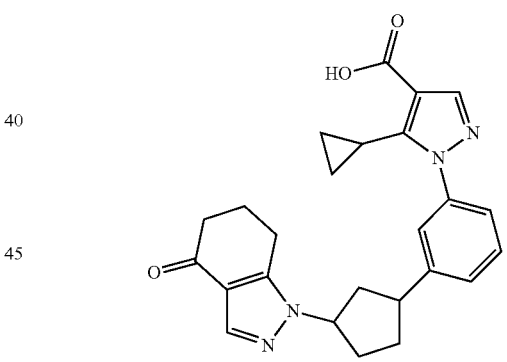

A stirred mixture of 5-cyclopropyl-1-{3-[3-(4-oxo-4,5,6,7-tetrahydro-indazol-1-yl)-cyclopentyl]-phenyl}-1H-pyrazole-4-carboxylic acid methyl ester (48 mg, 0.09 mmol) in THF:MeOH (1:1, 2 mL) and water (2 mL) was treated with LiOH (18 mg, 0.43 mmol). After 24 hours, the reaction was diluted with water and the pH adjusted to pH4 (citric acid 5%). The product was extracted with EtOAc (×3). The combined organic layers were washed with brine, dried over MgSO$_4$, filtered and concentrated to dryness under vacuum. Purification by preparative HPLC gave the product (46 mg, 100%). LC-MS m/z 431 (M+H)$^+$, 1.04 (ret. time). $^1$H NMR (400 MHz, Me-d$_3$-OD): 8.00 (1H, s), 7.88 (1H, s), 7.60 (0.6H, s), 7.54-7.46 (2.4H, m), 7.44-7.37 (1H, m), 5.08-5.00 (0.4H, m), 5.00-4.91 (0.6H, m), 3.77-3.67 (0.4H, m), 3.43-3.37 (0.6H, m), 3.00-2.95 (2H, m), 2.67-2.59 (0.6H, m), 2.54-2.12 (9H, m), 2.12-2.01 (1H, m), 1.95-1.83 (0.4H, m), 0.94-0.88 (2H, m), 0.66-0.61 (2H, m).

Example 16. 5-Cyclopropyl-1-[3-(3-{6-propyl-1H,4H,5H,6H-cyclopenta[c]pyrazol-1-yl}cyclohexyl)phenyl]-1H-pyrazole-4-carboxylic Acid (cis racemic)

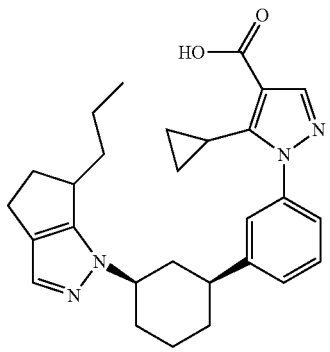 [SMILES: CCCC1CCc2cnn([C@@H]3CCC[C@H](c4cccc(-n5ncc(C(=O)O)c5C5CC5)c4)C3)c21]

A stirred mixture of 2-propylcyclopentanone (0.50 g, 3.96 mmol), N,N-dimethylformamide dimethyl acetal (526 µl, 3.96 mmol) and toluene (1 mL) was heated at 100° C. for 16 hours. The reaction was concentrated to give 2-[1-dimethylamino-methylidene]-5-propylcyclopentanone which was used in the next reaction without further purification. A stirred mixture of 5-cyclopropyl-1-[3-(3-hydrazino-cyclohexyl)-phenyl]-1H-pyrazole-4-carboxylic acid methyl ester HCl (100 mg, 0.26 mmol) and 2-[1-dimethylamino-methylidene]-5-propyl-cyclopentanone (46 mg, 0.26 mmol) in ethanol (2.0 mL) was heated to 70° C. for 16 hours. The reaction was concentrated and the residue treated with LiOH (2 mL, 1M, aq) and MeOH:THF (1:1, 5 mL), and stirred for 16 hours at room temperature. The reaction was diluted with water and the pH adjusted to pH4 (citric acid 5%). The product was extracted with EtOAc (×3). The combined organic layers were washed with brine, dried over MgSO$_4$, filtered and concentrated to dryness under vacuum. Purification by preparative HPLC gave the product (65 mg, 53%). LC-MS m/z 459 (M+H)$^+$, 1.25 (ret. time). $^1$H NMR (400 MHz, Me-d$_3$-OD): 7.99 (1H, d), 7.54-7.37 (4H, m), 7.27 (1H, s), 4.32 (1H, s), 3.25 (1H, s), 2.99-2.88 (1H, m), 2.79-2.62 (2H, m), 2.61-2.50 (1H, m), 2.33-2.24 (1H, m), 2.17 (2H, t), 2.13-1.93 (5H, m), 1.80-1.50 (4H, m), 1.48-1.36 (2H, m), 0.98 (3H, q), 0.92-0.86 (2H, m), 0.66-0.58 (2H, m).

Example 17. 1-{3-3-[2-butylpyrrolidine-1-carbonyl]cyclohexyl]phenyl}-5-cyclopropyl-1H-pyrazole-4-carboxylic Acid

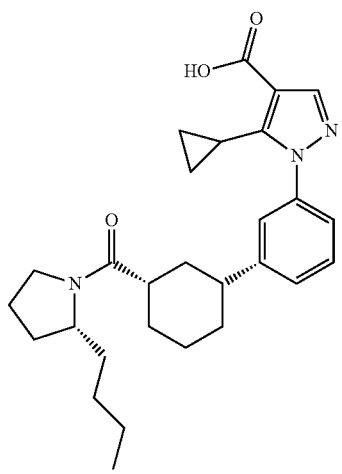

17a) 3-(2-Butyl-pyrrolidine-1-carbonyl)-cyclohexanone

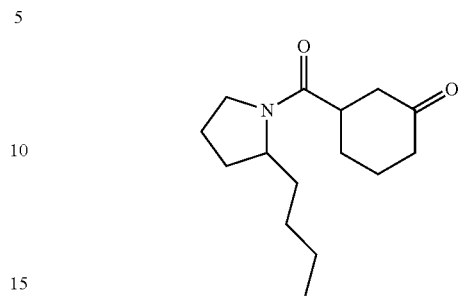

A solution of 3-oxo-cyclohexanecarboxylic acid (0.750 g, 5.27 mmol), HATU (2.01 g, 5.27 mmol), 2-butylpyrrolidine (0.863 g, 5.27 mmol) and DIPEA (1.70 g, 13.2 mmol) in DCM (20 mL) was stirred for 4 h. The mixture was washed with aqueous NaHCO$_3$ and dried (MgSO$_4$). Concentration to dryness followed by silica column purification (EtOAc/petrol 5-50% gradient) gave the product (0.939 g, 71%). $^1$H NMR (400 MHz, CDCl$_3$): 4.13-4.04 (0.7H, m), 3.88-3.72 (0.3H, m), 3.59-3.39 (2H, m), 2.91-2.84 (1H, m), 2.78-2.61 (1H, m), 2.46-2.30 (3H, m), 2.26-2.05 (1H, m), 2.05-1.67 (7H, m), 1.56-1.12 (6H, m), 0.98-0.84 (3H, m).

17b) Trifluoro-methanesulfonic acid 3-(2-butyl-pyrrolidine-1-carbonyl)-cyclohex-1-enyl ester (Mixture of alkene isomers)

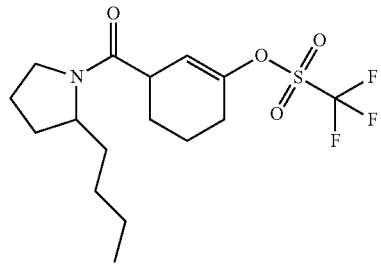 [SMILES: CCCCC1CCCN1C(=O)C1C=C(OS(=O)(=O)C(F)(F)F)CCC1]

NaHMDS (4.30 mL, 1M in THF, 4.30 mmol) was added slowly to a solution of 3-(2-butyl-pyrrolidine-1-carbonyl)-cyclohexanone (0.939 g, 3.74 mmol) and N-phenyltrifluoromethanesulfonamide (1.54 g, 4.30 mmol) in dry THF (40 mL) at −78° C. under nitrogen. The solution was allowed to warm with the cold bath over 18 h. The reaction mixture was quenched with a little water, concentrated and then partitioned between Et$_2$O and water. The organic phase was washed with water, aqueous sodium bicarbonate and brine before it was dried (MgSO$_4$), filtered and concentrated to dryness to give crude product (1.62 g, quantitative) used without purification.

17c) 1-{3-[3-(2-Butyl-pyrrolidine-1-carbonyl)-cyclohex-1-enyl]-phenyl}-5-cyclopropyl-1H-pyrazole-4-carboxylic acid methyl ester (Mixture of alkene isomers)

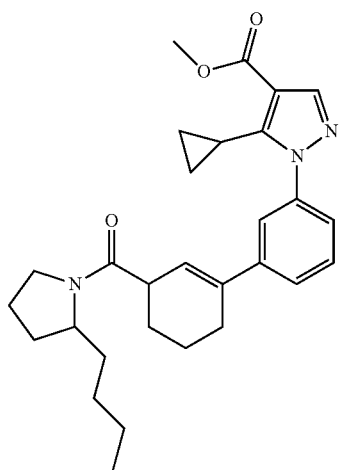 [SMILES: CCCCC1CCCN1C(=O)C1C=C(c2cccc(-n3ncc(C(=O)OC)c3C3CC3)c2)CCC1]

A stirred mixture of trifluoro-methanesulfonic acid 3-(2-butyl-pyrrolidine-1-carbonyl)-cyclohex-1-enyl ester (1.62 g, assumed 4.24 mmol), 5-cyclopropyl-1-[3-(4,4,5,5-tetramethyl-[1,3,2]dioxaborolan-2-yl)-phenyl]-1H-pyrazole-4-carboxylic acid methyl ester (1.2 g, 3.26 mmol), aqueous $Na_2CO_3$ (3M, 3.26 mL, 9.78 mmol) and $Pd(PPh_3)_4$ (0.188 g, 0.160 mol) in EtOH (7 mL) and toluene (21 mL) was heated at reflux for 2 h. After cooling, the mixture was partitioned between EtOAc (70 mL) and water (40 mL) and the organic phase washed with water (20 mL) and brine (20 mL) before it was dried ($MgSO_4$), filtered and concentrated. The crude product was purified by silica chromatography (EtOAc/petrol 10-40% gradient) to give the product (0.588 g, 34%). LC-MS m/z 476 (M+H)$^+$, 1.65 (ret. time), basic method.

17d) 1-{3-[3-(2-Butyl-pyrrolidine-1-carbonyl)-cyclohexyl]-phenyl}-5-cyclopropyl-1H-pyrazole-4-carboxylic Acid methyl ester

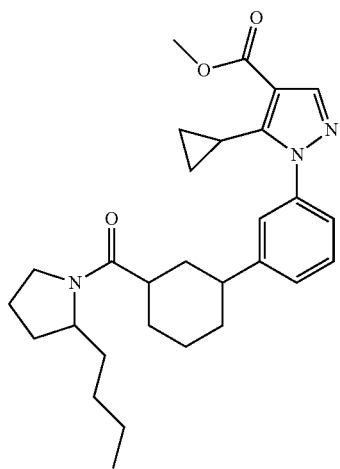 [SMILES: CCCCC1CCCN1C(=O)C1CCCC(c2cccc(-n3ncc(C(=O)OC)c3C3CC3)c2)C1]

A solution of 1-{3-[3-(2-Butyl-pyrrolidine-1-carbonyl)-cyclohex-1-enyl]-phenyl}-5-cyclopropyl-1H-pyrazole-4-carboxylic acid methyl ester (0.588 g, 1.24 mmol) in ethanol (50 mL) was treated with Pd/C (10%, 0.060 g) and the mixture shaken under an atmosphere of hydrogen for 4 h. The catalyst was removed by filtration and the solution concentrated to dryness. The crude product was purified by silica chromatography (EtOAc/petrol 15-40% gradient). Two batches of cis product were collected, but further reaction was required to remove remaining starting material. The process was repeated on both batches, with a 6 h hydrogenation. Purification by silica chromatography (EtOAc/petrol 20-40% gradient) provided material for chiral preparative HPLC purification of stereoisomers. Three batches were obtained:

Batch 1: Single stereoisomer (29 mg). LC-MS m/z 478 (M+H)$^+$, 7.61 (ret. time), overnight basic method.

Batch 2: mixture of 2 stereoisomers (not racemate) (60 mg).). LC-MS m/z 478 (M+H)$^+$7.52 (53%) and 7.60 (47%) (ret. time), overnight basic method.

Batch 3: Single stereoisomer (28 mg). LC-MS m/z 478 (M+H)$^+$, 7.53 (ret. time), overnight basic method.

17e) 1-{3-[(1R,3S)-3-[(2S)-2-butylpyrrolidine-1-carbonyl]cyclohexyl]phenyl}-5-cyclopropyl-1H-pyrazole-4-carboxylic Acid

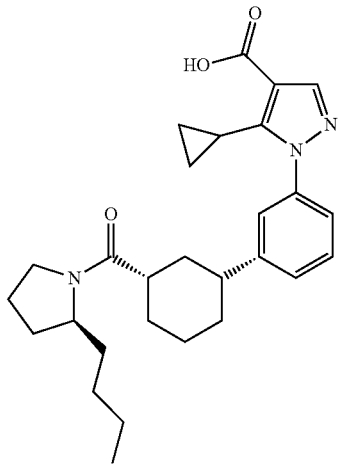

A solution of 1-{3-[3-(2-Butyl-pyrrolidine-1-carbonyl)-cyclohexyl]-phenyl}-5-cyclopropyl-1H-pyrazole-4-carboxylic acid methyl ester (Batch 1) (0.029 g, 0.06 mmol) in EtOH (0.5 mL) was treated with aqueous NaOH (2M, 0.152 mL). After 60 hours the mixture was concentrated to dryness and then partitioned between EtOAc and water, acidifying with 1N HCl. The aqueous layer was extracted with further EtOAc. The combined organic phases were dried ($MgSO_4$), filtered and to dryness to give the product (0.026 g, 92%). LC-MS m/z 464 (M+H)$^+$, 1.25 (ret. time), basic method. $^1$H NMR (400 MHz, DMSO-d6): 12.23 (1H, s), 7.92 (1H, s), 7.49-7.42 (2H, m), 7.42-7.37 (1H, m), 7.35 (1H, d), 3.95-3.83 (1H, m), 3.56-3.41 (1H, m), 3.41-3.33 (0.5H, m), 3.27-3.17 (0.5H, m), 2.77-2.65 (1H, m), 2.62-2.54 (1H, m), 2.15-2.02 (1H, m), 1.91-1.70 (7H, m), 1.65-1.18 (11H, m), 0.94-0.79 (5H, m), 0.60-0.45 (2H, m).

17f) 1-{3-[(1R,3S)-3-[(2R)-2-Butylpyrrolidine-1-carbonyl]cyclohexyl]phenyl}-5-cyclopropyl-1H-pyrazole-4-carboxylic Acid and 17g) 1-{3-[(1S,3R)-3-[(2R)-2-Butylpyrrolidine-1-carbonyl]cyclohexyl]phenyl}-5-cyclopropyl-1H-pyrazole-4-carboxylic Acid A solution of 1-{3-[3-(2-butyl-pyrrolidine-1-carbonyl)-cyclohexyl]-phenyl}-5-cyclopropyl-1H-pyrazole-4-carboxylic acid methyl ester (Batch 2) (0.060 g, 0.13 mmol) in EtOH (0.5 mL) was treated with aqueous NaOH (2M, 0.314 mL). After 60 hours the mixture was concentrated to dryness and then partitioned between EtOAc and water, acidifying with 1N HCl. The aqueous layer was extracted with further EtOAc. The combined organic phases were dried (MgSO$_4$), filtered and concentrated to dryness (53 mg). The two stereoisomers were then separated by chiral preparative HPLC to give:

1-{3-[(1R,3S)-3-[(2R)-2-butylpyrrolidine-1-carbonyl]cyclohexyl]phenyl}-5-cyclopropyl-1H-pyrazole-4-carboxylic Acid

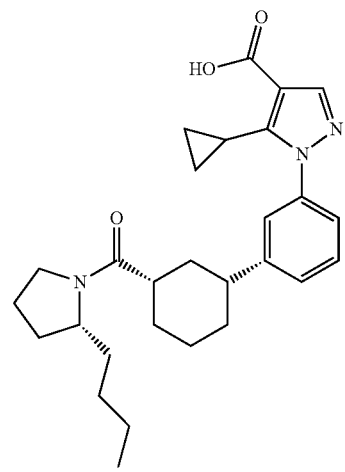

White solid (17 mg, 28%). LC-MS m/z 464 (M+H)$^+$, 1.25 (ret. time), basic method. $^1$H NMR (400 MHz, DMSO-d6): 12.43-12.09 (1H, m), 7.92 (1H, s), 7.49-7.42 (2H, m), 7.42-7.32 (2H, m), 4.06-3.84 (1H, m), 1H under water peak, 3.36-3.17 (1H, m), 2.80-2.69 (1H, m), 2.62-2.55 (1H, m), 2.16-2.05 (1H, m), 2.05-1.65 (7H, m), 1.65-1.15 (11H, m), 0.97-0.72 (5H, m), 0.59-0.46 (2H, m).

1-{3-[(1S,3R)-3-[(2R)-2-butylpyrrolidine-1-carbonyl]cyclohexyl]phenyl}-5-cyclopropyl-1H-pyrazole-4-carboxylic Acid

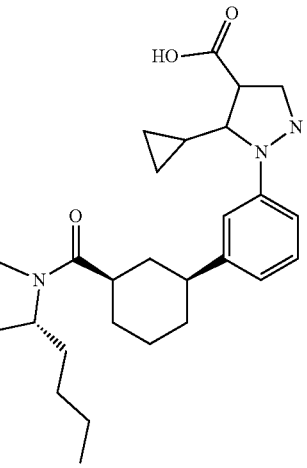

White solid (19 mg, 32%). LC-MS m/z 464 (M+H)$^+$, 1.24 (ret. time), basic method. $^1$H NMR (400 MHz, DMSO-d6): 12.47-12.06 (1H, m), 7.92 (1H, s), 7.49-7.42 (2H, m), 7.42-7.37 (1H, m), 7.37-7.31 (1H, m), 3.95-3.82 (1H, m), 1H under water peak, 3.40-3.17 (1H, m), 2.77-2.65 (1H, m), 2.62-2.54 (1H, m), 2.16-2.03 (1H, m), 1.94-1.70 (7H, m), 1.70-0.99 (11H, m), 0.95-0.69 (5H, m), 0.59-0.46 (2H, m).

17h) 1-{3-[(1S,3R)-3-[(2S)-2-Butylpyrrolidine-1-carbonyl]cyclohexyl]phenyl}-5-cyclopropyl-1H-pyrazole-4-carboxylic Acid A solution of 1-{3-[3-(2-butyl-pyrrolidine-1-carbonyl)-cyclohexyl]-phenyl}-5-cyclopropyl-1H-pyrazole-4-carboxylic acid methyl ester (Batch 3) (0.028 g, 0.06 mmol) in EtOH (0.5 mL) was treated with aqueous NaOH (2M, 0.147 mL). After 60 hours the mixture was concentrated to dryness and then partitioned between EtOAc and water, acidifying with 1N HCl. The aqueous layer was extracted with further EtOAc. The combined organic phases were dried (MgSO$_4$), filtered and concentrated to dryness to give the product (0.024 g, 88%). LC-MS m/z 462 (M−H), 1.23 (ret. time), basic method. $^1$H NMR (400 MHz, DMSO-d6): 12.26 (1H, s), 7.92 (1H, s), 7.49-7.42 (2H, m), 7.42-7.30 (2H, m), 3.97-3.83 (1H, m), 3.54-3.43 (1H, m), 3.29-3.16 (1H, m), 2.74 (1H, d), 2.62-2.53 (1H, m), 2.16-2.04 (1H, m), 2.04-1.67 (7H, m), 1.63-1.16 (11H, m), 0.95-0.77 (5H, m), 0.56-0.45 (2H, m).

Example 18. 5-Cyclopropyl-1-(3-{3-[(2S)-2-(ethoxymethyl)pyrrolidine-1-carbonyl]cyclohexyl}phenyl)-1H-pyrazole-4-carboxylic Acid AT30524/GSK3236253A Examples 72-73

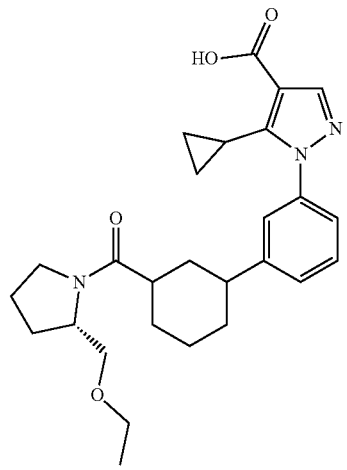 [SMILES: CCOC[C@@H]1CCCN1C(=O)C1CCCC(c2cccc(-n3ncc(C(=O)O)c3C3CC3)c2)C1]

18a) (S)-1-Benzyl-2-ethoxymethyl-pyrrolidine

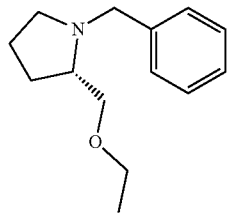 [SMILES: CCOC[C@@H]1CCCN1Cc1ccccc1]

Sodium hydride (0.465 g, 11.6 mmol) was added to a solution of N-benzyl-(S)-prolinol (2.02 g, 10.6 mmol) in dry DMF (30 mL) at 0° C. under a flush of nitrogen. After 20 minutes, ethyl bromide (1.50 g, 13.7 mmol) was added and the reaction stirred at rt for 18 h. The mixture was partitioned between Et$_2$O and water and the aqueous phase extracted with further Et$_2$O. The combined organic phase was washed with water and brine before it was dried (MgSO$_4$), filtered, and concentrated to dryness to give the crude product (2.5 g, quantative). $^1$H-NMR (400 MHz, CDCl$_3$): 7.46-7.13 (5H, m), 4.16 (1H, d), 3.73-3.26 (5H, m), 3.08-2.88 (1H, m), 2.78 (1H, s), 2.41-2.12 (1H, m), 2.12-1.84 (1H, m), 1.84-1.48 (3H, m), 1.22 (3H, t).

18b) (S)-2-Ethoxymethyl-pyrrolidine hydrochloride Salt

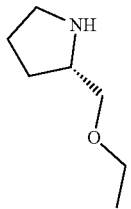

A solution of (S)-1-benzyl-2-ethoxymethyl-pyrrolidine (2.50 g, 11.4 mmol) in ethanol (125 mL) was treated with Pd/C (10%, 0.20 g) and the mixture shaken under an atmosphere of hydrogen for 4 h. The catalyst was removed by filtration and the filtrate treated with HCl in Et$_2$O (2M, 6 mL) before the mixture was concentrated to dryness to give the product as the HCl salt (1.84 g, 97%). $^1$H NMR (400 MHz, DMSO-d6): 9.45 (1H, s), 8.76 (1H, s), 3.79-3.22 (5H, m), 3.22-2.92 (2H, m), 2.11-1.70 (3H, m), 1.70-1.46 (1H, m), 1.15 (3H, t).

18c) 3-((S)-2-Ethoxymethyl-pyrrolidine-1-carbonyl)-cyclohexanone

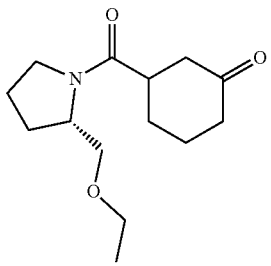 [SMILES: CCOC[C@@H]1CCCN1C(=O)C1CCCC(=O)C1]

A solution of 3-oxo-cyclohexanecarboxylic acid (0.0.754 g, 5.30 mmol), HATU (2.02 g, 5.30 mmol), (S)-2-ethoxymethyl-pyrrolidine.HCl (0.0.879 g, 5.30 mmol) and DIPEA (1.71 g, 13.3 mmol) in DCM (20 mL) was stirred for 4 h. The mixture was washed with aqueous NaHCO$_3$ and dried (MgSO$_4$). Concentration to dryness followed by silica column purification (EtOAc/petrol 5-100% gradient) gave the product (1.39 g, quantative). $^1$H-NMR (400 MHz, DMSO-d6): 4.17-3.96 (1H, m), 3.53-3.35 (4H, m), 3.30-3.17 (2H, m), 3.17-2.91 (1H, m), 2.87 (1H, s), 2.48-2.08 (4H, m), 2.08-1.56 (8H, m), 1.15-1.03 (3H, m).

18d) Trifluoro-methanesulfonic acid 3-((S)-2-ethoxymethyl-pyrrolidine-1-carbonyl)-cyclohex-1-enyl ester

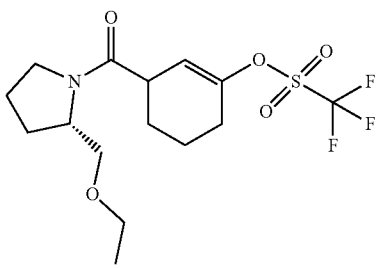 [SMILES: CCOC[C@@H]1CCCN1C(=O)C1C=C(OS(=O)(=O)C(F)(F)F)CCC1]

NaHMDS (2.07 mL, 1M in THF, 2.07 mmol) was added slowly to a solution of 3-((S)-2-ethoxymethyl-pyrrolidine-1-carbonyl)-cyclohexanone (0.40 g, 1.59 mmol) and N-phenyltrifluoromethanesulfonamide (0.654 g, 1.83 mmol) in dry THF (20 mL) at −78° C. under nitrogen. After 2 h, further N-phenyltrifluoromethanesulfonamide (0.284 g, 0.80 mmol) and NaHMDS (1.20 mL, 1.2 mmol) was added and the reaction stirred for a further 1 h at −78° C. The reaction mixture was quenched with a little water, warmed to rt, concentrated and then partitioned between Et₂O and water. The organic phase was washed with water, aqueous sodium bicarbonate and brine before it was dried (MgSO₄), filtered and concentrated to dryness to give crude product (0.544 g, 89%) used without purification.

18e) 5-Cyclopropyl-1-{3-[3-((S)-2-ethoxymethyl-pyrrolidine-1-carbonyl)-cyclohex-1-enyl]-phenyl}-1H-pyrazole-4-carboxylic acid ethyl ester

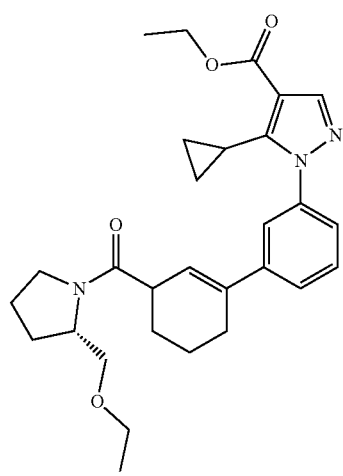 [SMILES: CCOC[C@@H]1CCCN1C(=O)C1C=C(c2cccc(-n3ncc(C(=O)OCC)c3C3CC3)c2)CCC1]

A stirred mixture of trifluoromethanesulfonic acid 3-((S)-2-ethoxymethyl-pyrrolidine-1-carbonyl)-cyclohex-1-enyl ester (0.544 g, assumed 1.41 mmol), 5-cyclopropyl-1-[3-(4,4,5,5-tetramethyl-[1,3,2]dioxaborolan-2-yl)-phenyl]-1H-pyrazole-4-carboxylic acid ethyl ester (0.54 g, 1.41 mmol), aqueous Na₂CO₃ (3M, 1.41 mL, 4.24 mmol) and Pd(PPh₃)₄ (0.082 g, 0.07 mol) in EtOH (3 mL) and toluene (10 mL) was heated at reflux for 2 h. After cooling, the mixture was partitioned between EtOAc (40 mL) and water (20 mL) and the organic phase washed with water (20 mL) and brine (20 mL) before it was dried (MgSO4), filtered and concentrated. The crude product was purified by silica chromatography (EtOAc/petrol 50-100% gradient) to give the product (0.259 g, 37%). LC-MS m/z 492 (M+H)⁺, 1.56 (ret. time), basic method.

18f) 5-Cyclopropyl-1-{3-[3-((S)-2-ethoxymethyl-pyrrolidine-1-carbonyl)-cyclohexyl]-phenyl}-1H-pyrazole-4-carboxylic Acid ethyl ester

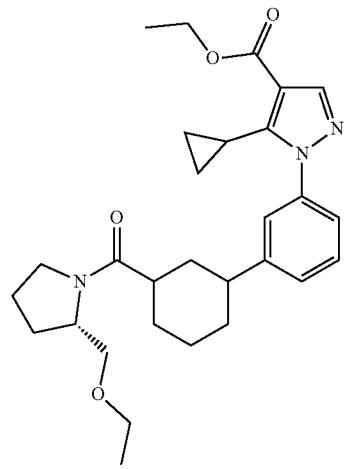 [SMILES: CCOC[C@@H]1CCCN1C(=O)C1CCCC(c2cccc(-n3ncc(C(=O)OCC)c3C3CC3)c2)C1]

A solution of 5-cyclopropyl-1-{3-[3-((S)-2-ethoxymethyl-pyrrolidine-1-carbonyl)-cyclohex-1-enyl]-phenyl}-1H-pyrazole-4-carboxylic acid ethyl ester (0.259 g, 0.53 mmol) in ethanol (20 mL) was treated with Pd/C (10%, 0.030 g) and the mixture shaken under an atmosphere of hydrogen for 4 h. The catalyst was removed by filtration and the solution concentrated to dryness. The crude product was purified by silica chromatography (EtOAc/petrol 20-90% gradient) to isolate a mixture of the two cis cyclohexyl diastereoisomers (0.141 g, 54%). LC-MS m/z 494 (M+H)⁺, 1.56 (ret. time), basic method.

18g and 18h) 5-Cyclopropyl-1-(3-{3-[(2S)-2-(ethoxymethyl)pyrrolidine-1-carbonyl]cyclohexyl}phenyl)-1H-pyrazole-4-carboxylic Acid (Resolved cis diastereoisomers)

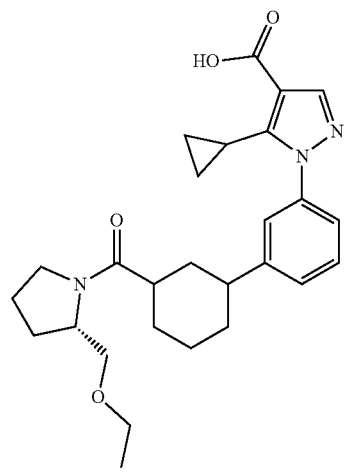

A solution of 5-cyclopropyl-1-{3-[3-((S)-2-ethoxymethyl-pyrrolidine-1-carbonyl)-cyclohexyl]-phenyl}-1H-pyrazole-4-carboxylic acid ethyl ester (0.141 g, 0.29 mmol) in EtOH (4.3 mL) was treated with aqueous NaOH (2M, 1.43 mL). After 72 hours the mixture was concentrated to dryness and then partitioned between EtOAc and water, acidifying with 1N HCl. The aqueous layer was extracted with further EtOAc. The combined organic phase was dried (MgSO₄), filtered and concentrated to dryness. The two cis diastereoisomers were separated by chiral preparative HPLC to give the 2 single diastereomer products:

18g) Cis stereoisomer 1 (0.025 g, 19%). LC-MS m/z 466 (M+H)$^+$, 1.42 (ret. time), acidic method. $^1$H NMR (400 MHz, CDCl₃): 8.08 (1H, s), 7.44-7.34 (4H, m), 3.57-3.44 (6H, m), 3.38 (1H, s), 2.75-2.57 (2H, m), 2.08-1.67 (11H, m), 1.51 (2H, d), 1.18 (3H, s), 1.01-0.91 (2H, m), 0.71-0.66 (2H, m).

18h) Cis stereoisomer 2. (0.028 g, 21%). LC-MS m/z 466 (M+H)$^+$, 1.44 (ret. time), acidic method. $^1$H NMR (400 MHz, CDCl₃): 8.10 (1H, s), 7.46-7.32 (4H, m), 3.60-3.49 (4H, m), 2.99 (3H, s), 2.65 (2H, d), 2.09-1.85 (10H, m), 1.71-1.59 (1H, m), 1.52 (2H, d), 1.19 (3H, t), 0.97-0.89 (2H, m), 0.70-0.63 (2H, m).

Example 19. 1-(5'-(Azepane-1-carbonyl)-2',3',4',5'-tetrahydro-[1,1'-biphenyl]-3-yl)-5-cyclopropyl-1H-pyrazole-4-carboxylic Acid

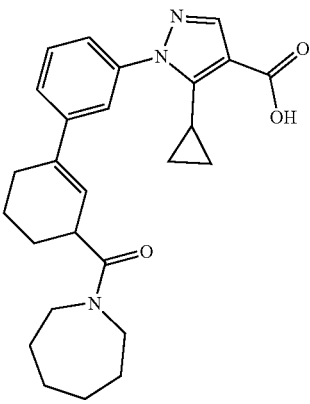 [SMILES: O=C(O)c1cnn(-c2cccc(C3=CC(C(=O)N4CCCCCC4)CCC3)c2)c1C1CC1]

19a) 3-(Azepane-1-carbonyl)cyclohexanone

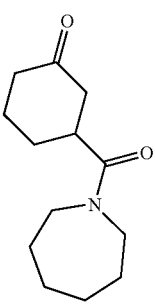 [SMILES: O=C1CCCC(C(=O)N2CCCCCC2)C1]

3-Oxocyclohexanecarboxylic acid (1 g, 7.03 mmol) and HATU (2.67 g, 7.03 mmol) in dichloromethane (DCM) (15 mL) was stirred for 10 min at RT. Azepane (0.698 g, 7.03 mmol) was added, followed by DIPEA (3.07 mL, 17.59 mmol). The reaction mixture was stirred at RT for 4 h. It was diluted with water, extracted with DCM. The organic layer was washed with NaHCO₃ and then brine. It was dried over Na₂SO₄ and filtrated. The filtrate was concentrated. It was purified with silica gel chromatography by eluting with EtOAC/Hexane (3:7). Desired fractions were concentrated to give the title compound (800 mg, 3.58 mmol, 50.9% yield) $^1$H NMR (400 MHz, CDCl₃) δ: 3.63-3.54 (m, 1H), 3.53-3.36 (m, 3H), 3.05-2.94 (m, 1H), 2.73 (dd, J=14.4, 11.2 Hz, 1H), 2.41-2.30 (m, 3H), 2.18-2.08 (m, 1H), 1.96-1.86 (m, 2H), 1.79-1.64 (m, 5H), 1.63-1.49 (m, 4H).

19b) 3-(Azepane-1-carbonyl)cyclohex-1-en-1-yl trifluoromethanesulfonate

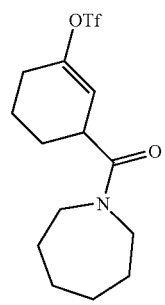 [SMILES: O=C(C1C=C(OS(=O)(=O)C(F)(F)F)CCC1)N1CCCCCC1]

To a solution of 3-(azepane-1-carbonyl)cyclohexanone (800 mg, 3.58 mmol) and N-phenyltrifluoromethanesulfonamide (1535 mg, 4.30 mmol) in dry tetrahydrofuran (THF) (20 mL) was added NaHMDS (788 mg, 4.30 mmol) slowly at −78° C. Then the reaction mixture was allowed to warm to RT and stirred for 19 h. The reaction mixture was quenched with water (30 mL) and extracted with diethyl ether (2×20 mL). The combined organic layer was washed with NaHCO₃ solution (20 mL), brine solution (20 mL) and dried under anhydrous Na₂SO₄ and filtered, The filtrate was concentrated under vacuum to gave 3-(azepane-1-carbonyl) cyclohex-1-en-1-yl trifluoromethanesulfonate (800 mg, 1.455 mmol, 40.6% yield) as crude material. The crude product was carried to the next step without further purification. LC-MS m/z 355.91 (M+H)$^+$, 2.761 min (ret. time)

19c) Ethyl 1-(5'-(azepane-1-carbonyl)-2',3',4',5'-tetrahydro-[1,1'-biphenyl]-3-yl)-5-cyclopropyl-1H-pyrazole-4-carboxylate

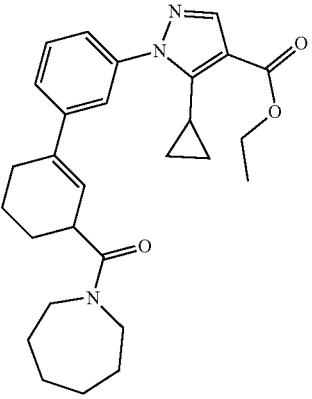 [SMILES: CCOC(=O)c1cnn(-c2cccc(C3=CC(C(=O)N4CCCCCC4)CCC3)c2)c1C1CC1]

To a solution of 3-(azepane-1-carbonyl)cyclohex-1-en-1-yltrifluoromethanesulfonate (800 mg, 2.251 mmol) and ethyl 5-cyclopropyl-1-(3-(4,4,5,5-tetramethyl-1,3,2-dioxaborolan-2-yl)phenyl)-1H-pyrazole-4-carboxylate (861 mg, 2.251 mmol) in ethanol (4.5 mL) and toluene (13.5 mL) at RT was added a solution of 3M Na$_2$CO$_3$ (2.251 mL, 6.75 mmol). The reaction mixture was heated at reflux for 2 h. It was diluted with water and extracted with ether. The organic layer was washed with NaHCO$_3$, and then brine solution. The organic layer was dried over anhydrous Na$_2$SO$_4$, filtrated and concentrated. The crude product was purified with silica gel chromatography by eluting with EtOAC/Hexane (3:7). Desired fractions were concentrated to give the title compound (400 mg, 0.839 mmol, 37.3% yield). LC-MS m/z 462.28 (M+H)$^+$, 2.81 min (ret. time).

19d) 1-(5'-(Azepane-1-carbonyl)-2',3',4',5'-tetrahydro-[1,1'-biphenyl]-3-yl)-5-cyclopropyl-1H-pyrazole-4-carboxylic Acid

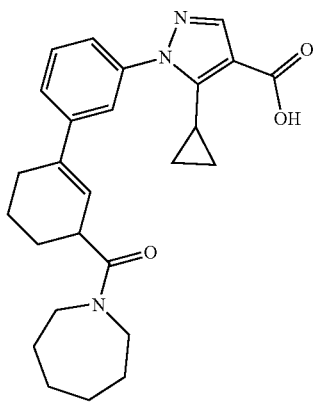 [SMILES: O=C(O)c1cnn(-c2cccc(C3=CC(C(=O)N4CCCCCC4)CCC3)c2)c1C1CC1]

To a solution of ethyl 1-(5'-(azepane-1-carbonyl)-2',3',4',5'-tetrahydro-[1,1'-biphenyl]-3-yl)-5-cyclopropyl-1H-pyrazole-4-carboxylate (100 mg, 0.217 mmol) in Ethanol (5 mL) was added 1M NaOH (0.218 mL, 0.217 mmol) and the reaction mixture was stirred at 25° C. for 3 h. The reaction mixture was concentrated and cooled to 0° C. It was neutralized with 1N HCl and then extracted with EtOAc. The organic layer was dried over Na$_2$SO$_4$, filtrated and concentrated. The crude product was purified with silica gel chromatography by eluting with 1:9 ratio of MeOH:DCM. Desired fractions were concentrated to give the title compound (33 mg, 0.074 mmol, 33.9% yield) as white solid. LC-MS m/z 433.9 (M+H)$^+$, 3.005 min (ret. time).

Example 20. 1-(3-(3-(Azepane-1-carbonyl)cyclohexyl)phenyl)-5-cyclopropyl-1H-pyrazole-4-carboxylic Acid A1 Tindy/GVK Example 1

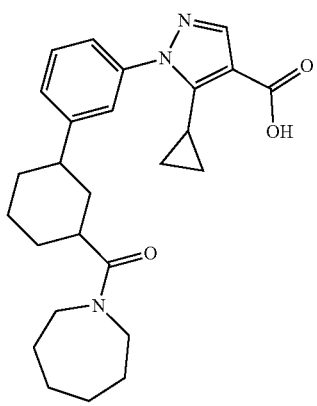 [SMILES: O=C(O)c1cnn(-c2cccc(C3CCCC(C(=O)N4CCCCCC4)C3)c2)c1C1CC1]

20a) Ethyl 1-(3-(3-(azepane-1-carbonyl)cyclohexyl)phenyl)-5-cyclopropyl-1H-pyrazole-4-carboxylate

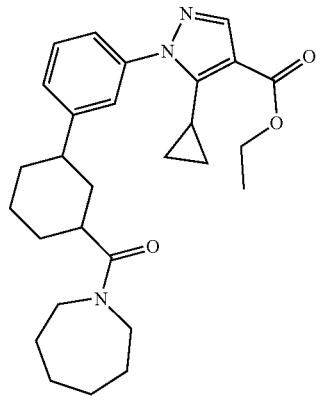 [SMILES: CCOC(=O)c1cnn(-c2cccc(C3CCCC(C(=O)N4CCCCCC4)C3)c2)c1C1CC1]

To a solution of ethyl 1-(5'-(azepane-1-carbonyl)-2',3',4',5'-tetrahydro-[1,1'-biphenyl]-3-yl)-5-cyclopropyl-1H-pyrazole-4-carboxylate (300 mg, 0.650 mmol) in ethanol (40 mL) was added palladium on carbon (40 mg, 0.376 mmol). The reaction mixture was stirred under hydrogen atmosphere at 25° C. for 6 h. The reaction mixture was filtered through Celite® and the filtrate was concentrated. It was purified with silica gel chromatography by eluting with 3:7 ratio of EtOAC:Hexane. Desired fractions were concentrated to give the title compound (200 mg, 0.402 mmol, 61.9% yield). LC-MS m/z 464.0 (M+H)$^+$, 4.131 min (ret. time).

20b) 1-(3-(3-(Azepane-1-carbonyl)cyclohexyl)phenyl)-5-cyclopropyl-1H-pyrazole-4-carboxylic Acid

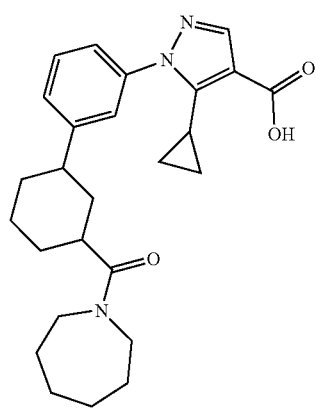 [SMILES: O=C(O)c1cnn(-c2cccc(C3CCCC(C(=O)N4CCCCCC4)C3)c2)c1C1CC1]

To a solution of ethyl 1-(3-(3-(azepane-1-carbonyl)cyclohexyl)phenyl)-5-cyclopropyl-1H-pyrazole-4-carboxylate (200 mg, 0.431 mmol) in ethanol (5 mL) was added 1M NaOH (0.431 mL, 0.431 mmol). The reaction mixture was stirred at 25° C. for 3 h. The reaction mixture was concentrated and cool to 0° C. It was neutralized with 1N HCl and then extracted with EtOAc. The organic layer was dried over Na$_2$SO$_4$, filtrated and concentrated. It was purified with silica gel chromatography by eluting with 1:9 ratio of MeOH:DCM. Desired fractions were concentrated to give the title compound (170 mg, 0.384 mmol, 89% yield) as white solid. LC-MS m/z 436.25 (M+H)+, 2.35 min (ret. time).

Example 21. 1-(3-(3-(Cyclohexyl(methyl)carbamoyl)cyclohexyl)phenyl)-5-cyclopropyl-1H-pyrazole-4-carboxylic Acid

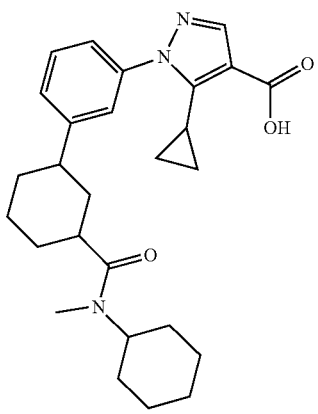 [SMILES: CN(C(=O)C1CCCC(c2cccc(-n3ncc(C(=O)O)c3C3CC3)c2)C1)C1CCCCC1]

21a) N-Cyclohexyl-N-methyl-3-oxocyclohexanecarboxamide

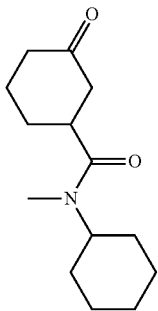 [SMILES: CN(C(=O)C1CCCC(=O)C1)C1CCCCC1]

To a solution of 3-oxocyclohexanecarboxylic acid (1 g, 7.03 mmol) in dichloromethane (DCM) (15 mL) was added HATU (2.67 g, 7.03 mmol). It was stirred for 30 min, and then N-methylcyclohexanamine (0.796 g, 7.03 mmol) was added followed by addition of DIPEA (1.229 mL, 7.03 mmol). The reaction mixture was stirred for 4 h. It was diluted with NaHCO₃ solution and then extracted with EtOAc (2×20 mL). The combined organic layer was washed with brine solution (20 mL) and dried over anhydrous Na₂SO₄, filtered and concentrated. It was purified with silica gel chromatography by eluting with EtOAc:Hexane (4:6). Desired fractions were concentrated to give the title compound (800 mg, 3.37 mmol, 47.9% yield) as clear liquid. This material was carried to next step without further purification.

21b) 3-(Cyclohexyl(methyl)carbamoyl)cyclohex-1-en-1-yltrifluoromethanesulfonate

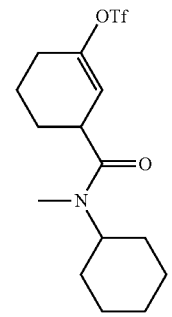 [SMILES: CN(C(=O)C1C=C(OS(=O)(=O)C(F)(F)F)CCC1)C1CCCCC1]

To a solution of N-cyclohexyl-N-methyl-3-oxocyclohexanecarboxamide (800 mg, 3.37 mmol) and 1,1,1-trifluoro-N-phenyl-N-((trifluoromethyl)sulfonyl)methanesulfonamide (1204 mg, 3.37 mmol) in tetrahydrofuran (THF) (10 mL) at −78° C. was added NaHMDS (618 mg, 3.37 mmol) slowly. The reaction mixture was allowed to stir at RT for 20 h. It was diluted with ice water and extracted with EtOAc (2×20 mL). The combined organic layer was washed with brine solution (20 mL) and dried over anhydrous Na₂SO₄, filtered and concentrated to give the title compound (800 mg, 2.166 mmol, 64.2% yield) as gammy crude. LC-MS m/z 369.97 (M+H)+, 2.70 min (ret. time).

21c) Ethyl 1-(5'-(cyclohexyl(methyl)carbamoyl)-2',3',4',5'-tetrahydro-[1,1'-biphenyl]-3-yl)-5-cyclopropyl-1H-pyrazole-4-carboxylate To solution of ethyl 5-cyclopropyl-1-(3-(4,4,5,5-tetramethyl-1,3,2-dioxaborolan-2-yl)phenyl)-1H-pyrazole-4-carboxylate (500 mg, 1.308 mmol) and 3-(cyclohexyl(methyl)carbamoyl)cyclohex-1-en-1-yltrifluoromethanesulfonate (773 mg, 2.093 mmol) in ethanol (1 mL) and toluene (3.00 mL) was added sodium carbonate (1.308 mL, 3.92 mmol). The reaction mixture was degassed with argon for 20 min and then tetrakis(triphenylphosphine)palladium(0) (76 mg, 0.065 mmol) was added. The reaction mixture was stirred at 100° C. for 3 h. The reaction was cooled to RT and diluted with water, then extracted with EtOAc (2×20 mL). The combined organic layer was washed with brine solution (20 mL) and dried over anhydrous Na₂SO₄, filtered, and concentrated. It was purified with silica gel chromatography by eluting with EtOAc:Hexane (6:4) to give the title compound (300 mg, 0.499 mmol, 38.1% yield) as gummy. LC-MS m/z 476.27 (M+H)⁺, 4.07 min (ret. time).

21d) Ethyl 1-(3-(3-(cyclohexyl(methyl)carbamoyl) cyclohexyl)phenyl)-5-cyclopropyl-1H-pyrazole-4-carboxylate

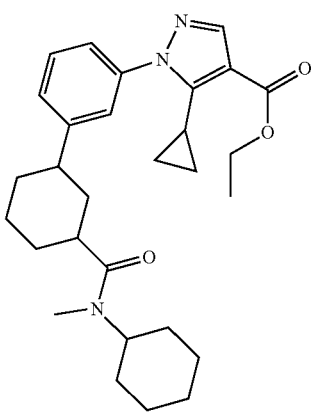 [SMILES: CCOC(=O)c1cnn(-c2cccc(C3CCCC(C(=O)N(C)C4CCCCC4)C3)c2)c1C1CC1]

To a solution of ethyl 1-(5'-(cyclohexyl(methyl)carbamoyl)-2',3',4',5'-tetrahydro-[1,1'-biphenyl]-3-yl)-5-cyclopropyl-1H-pyrazole-4-carboxylate (300 mg, 0.631 mmol) in ethanol (5 mL) was added palladium (67.1 mg, 0.631 mmol). The reaction mixture was stirred under Hydrogen atmosphere (50 psi) at 25° C. for 8 h. It was filtered through Celite® pad and washed with ethanol. The filtrate was concentrated to give crude product. It was purified with silica gel chromatography by eluting with EtOAc:Hexane (4:6). Desired fractions were concentrated to give the title compound (200 mg, 0.376 mmol, 59.5% yield) as color less liquid. LC-MS m/z 478.12 (M+H)⁺, 3.02 min (ret. time).

21e) 1-(3-(3-(Cyclohexyl(methyl)carbamoyl)cyclohexyl)phenyl)-5-cyclopropyl-1H-pyrazole-4-carboxylic Acid

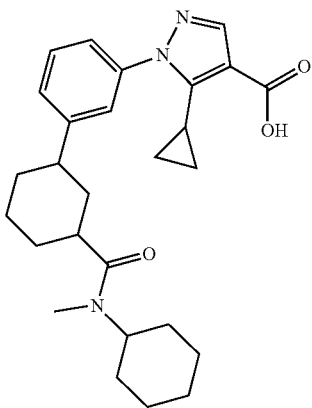 [SMILES: CN(C(=O)C1CCCC(c2cccc(-n3ncc(C(=O)O)c3C3CC3)c2)C1)C1CCCCC1]

To a solution of ethyl 1-(3-(3-(cyclohexyl(methyl)carbamoyl)cyclohexyl)phenyl)-5-cyclopropyl-1H-pyrazole-4-carboxylate (200 mg, 0.419 mmol) in ethanol (5 mL) was added 2 M NaOH (0.419 mL, 0.837 mmol). It was stirred for 5 h and then concentrated. The residue was diluted with ice water and acidified with 2N HCl to pH 2. The aqueous layer was extracted with DCM (2×20 mL). The combined organic layer was washed with brine solution (20 mL) and dried over anhydrous Na₂SO₄, filtered and concentrated. The crude residue was purified with silica gel chromatography by eluting with MeOH:DCM (0.5:9.5). Desired fractions were concentrated to give the title compound (56 mg, 0.122 mmol, 29.2% yield) as off-white solid. LC-MS m/z 450.26 (M+H)⁺, 2.53 min (ret. time).

Example 22. 5-Cyclopropyl-1-(3-(3-(methyl(2-propylcyclohexyl)carbamoyl)cyclohexyl)phenyl)-1H-pyrazole-4-carboxylic Acid

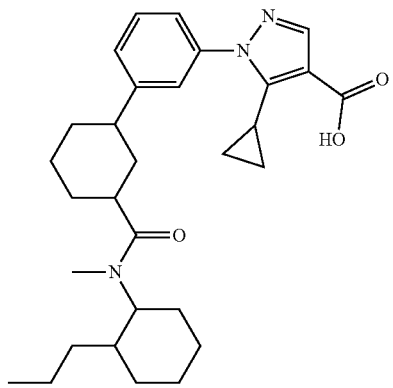 [SMILES: CCCC1CCCCC1N(C)C(=O)C1CCCC(c2cccc(-n3ncc(C(=O)O)c3C3CC3)c2)C1]

22a) N-Methyl-3-oxo-N-(2-propylcyclohexyl)cyclohexanecarboxamide

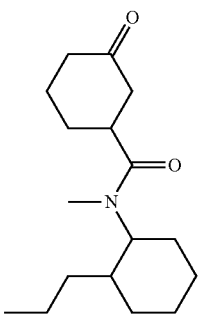 [SMILES: CCCC1CCCCC1N(C)C(=O)C1CCCC(=O)C1]

To a solution of 3-oxocyclohexanecarboxylic acid (550 mg, 3.87 mmol) in dichloromethane (DCM) (15 mL) was added HATU (1471 mg, 3.87 mmol) and stirred for 30 min. Then N-methyl-2-propylcyclohexanamine (601 mg, 3.87 mmol) was added, followed by addition of DIPEA (1.689 mL, 9.67 mmol). The reaction mixture was stirred for 4 h. The reaction mixture was diluted with NaHCO₃ solution and extracted with EtOAc (2×20 mL). The combined organic layer was washed with brine solution (20 mL) and dried over anhydrous Na2SO4, filtered and concentrated. It was purified with silica gel chromatography by eluting with EtOAc: Hexane (4:6). Desired fractions were concentrated to give the title compound (400 mg, 1.432 mmol, 37.0% yield) as clear liquid. This material was carried to next step without further purification.

22b) 3-(Methyl(2-propylcyclohexyl)carbamoyl)cyclohex-1-en-1-yl trifluoromethanesulfonate

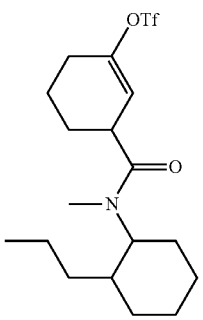 [SMILES: CCCC1CCCCC1N(C)C(=O)C1C=C(OS(=O)(=O)C(F)(F)F)CCC1]

To a solution of N-methyl-3-oxo-N-(2-propylcyclohexyl)cyclohexanecarboxamide (400 mg, 1.432 mmol) and 1,1,1-trifluoro-N-phenyl-N-((trifluoromethyl)sulfonyl)methanesulfonamide (511 mg, 1.432 mmol) in tetrahydrofuran (THF) (10 mL) at −78° C. was added NaHMDS (0.716 mL, 1.432 mmol) slowly. The reaction mixture was allowed to stir at RT for 20 h. The reaction was diluted with water (30 mL) and extracted with EtOAc (2×20 mL). The combined organic layer was washed with brine solution (20 mL) and dried over anhydrous $Na_2SO_4$, filtered and concentrated to give the title compound (1.2 g, 2.92 mmol, 204% yield) as brown gummy material. This crude product was carried to next step without further purification. LC-MS m/z 412.05 (M+H)$^+$, 3.110 min (ret. time).

22c) Ethyl 5-cyclopropyl-1-(5'-(methyl(2-propylcyclohexyl)carbamoyl)-2',3',4',5'-tetrahydro-[1,1'-biphenyl]-3-yl)-1H-pyrazole-4-carboxylate

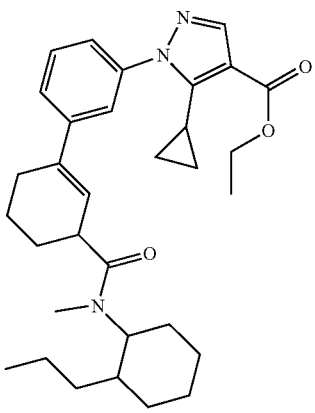 [SMILES: CCCC1CCCCC1N(C)C(=O)C1C=C(c2cccc(-n3ncc(C(=O)OCC)c3C3CC3)c2)CCC1]

To solution of ethyl 5-cyclopropyl-1-(3-(4,4,5,5-tetramethyl-1,3,2-dioxaborolan-2-yl)phenyl)-1H-pyrazole-4-carboxylate (150 mg, 0.392 mmol) and 3-(methyl(2-propylcyclohexyl)carbamoyl)cyclohex-1-en-1-yltrifluoromethanesulfonate (194 mg, 0.471 mmol) in ethanol (1 mL) and toluene (3.00 mL) was added sodium carbonate (0.392 mL, 1.177 mmol). The reaction mixture was degassed with argon for 20 min and then tetrakis(triphenylphosphine)palladium (0) (22.67 mg, 0.020 mmol) was added. The reaction mixture and stirred at 100° C. for 3 h. It was cooled to RT and diluted with water and extracted with EtOAc (2×20 mL). The combined organic layer was washed with brine solution (20 mL) and dried over anhydrous $Na_2SO_4$, filtered and concentrated. It was purified with silica gel chromatography by eluting with EtOAc:Hexane (6:4) to give the title compound (250 mg, 0.325 mmol, 83% yield) as gummy material. LC-MS m/z 518.4 (M+H)$^+$, 4.55 min (ret. time).

22d) Ethyl 5-cyclopropyl-1-(3-(3-(methyl(2-propylcyclohexyl)carbamoyl)cyclohexyl)phenyl)-1H-pyrazole-4-carboxylate

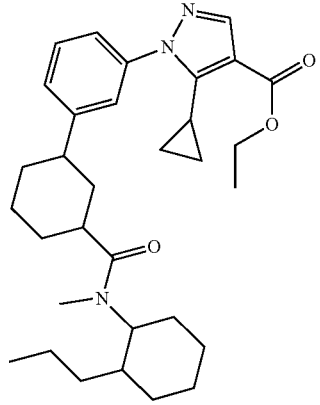 [SMILES: CCCC1CCCCC1N(C)C(=O)C1CCCC(c2cccc(-n3ncc(C(=O)OCC)c3C3CC3)c2)C1]

To a solution of ethyl 5-cyclopropyl-1-(5'-(methyl(2-propylcyclohexyl)carbamoyl)-2',3',4',5'-tetrahydro-[1,1'-biphenyl]-3-yl)-1H-pyrazole-4-carboxylate (250 mg, 0.483 mmol) in ethanol (5 mL) was added palladium (51.4 mg, 0.483 mmol) under nitrogen atmosphere. The reaction mixture was stirred under Hydrogen atmosphere (50 psi) at 25° C. for 8 h. The reaction filtered through Celite® pad and washed with ethanol. The filtrate was concentrated under vacuum to give the crude product. It was purified with silica gel chromatography by eluting with EtOAc:Hexane (4:6). Desired fractions were concentrated to give the title compound (110 mg, 0.169 mmol, 35.0% yield) as a colorless gummy liquid. LC-MS m/z 520.48 (M+H)$^+$, 4.57 min (ret. time).

22e) 5-Cyclopropyl-1-(3-(3-(methyl(2-propylcyclohexyl)carbamoyl)cyclohexyl)phenyl)-1H-pyrazole-4-carboxylic Acid

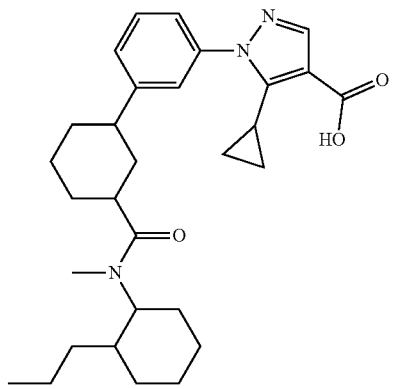 [SMILES: CCCC1CCCCC1N(C)C(=O)C1CCCC(c2cccc(-n3ncc(C(=O)O)c3C3CC3)c2)C1]

121

To a solution of ethyl 5-cyclopropyl-1-(3-(3-(methyl(2-propylcyclohexyl)carbamoyl)cyclohexyl)phenyl)-1H-pyrazole-4-carboxylate (110 mg, 0.212 mmol) in ethanol (5 mL) was added 2 M NaOH (0.212 mL, 0.423 mmol). It was stirred for 5 h and then concentrated. The residue was diluted with ice water and acidified with 2N HCl to pH 2. Aqueous layer was extracted with DCM (2×20 mL). The combined organic layer was washed with brine solution (20 mL) and dried over anhydrous $Na_2SO_4$, filtered and concentrated. The crude residue was purified with silica gel chromatography by eluting with MeOH:DCM (0.5:9.5). The eluted fractions were concentrated to give the title compound (56 mg, 0.107 mmol, 50.3% yield) as off-white solid. LC-MS m/z 492.31 (M+H)$^+$, 2.88 min and 2.92 min (ret. time).

Example 23. 5-Cyclopropyl-1-(3-(t-3-(6,6-dimethyl-5,6-dihydrocyclopenta[c]pyrazol-1(4H)-yl)cyclohexyl)phenyl)-1H-pyrazole-4-carboxylic Acid (trans racemic)

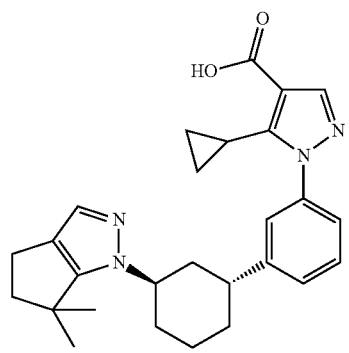 [SMILES: CC1(C)CCc2cnn([C@@H]3CCC[C@@H](c4cccc(-n5ncc(C(=O)O)c5C5CC5)c4)C3)c21]

23a) 5-((Dimethylamino)methylene)-2,2-dimethyl-cyclopentanone

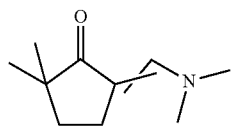

To a solution of 2,2-dimethylcyclopentanone (200 mg, 1.783 mmol) in toluene (1 mL) was added N,N-dimethylformamide dimethyl acetal (0.239 mL, 1.783 mmol). The reaction mixture was stirred at 100° C. for 22 h. The reaction mixture was concentrated to afford the title compound 5-((dimethylamino)methylene)-2,2-dimethylcyclopentanone (288.8 mg, 1.727 mmol, 97% yield) which was carried forward without further purification. LC-MS m/z 167.9 (M+H)$^+$, 0.69 min (ret. time).

122

23b) Ethyl 5-cyclopropyl-1-(3-(3-oxocyclohexyl)phenyl)-1H-pyrazole-4-carboxylate

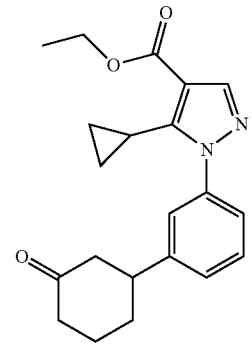 [SMILES: CCOC(=O)c1cnn(-c2cccc(C3CCCC(=O)C3)c2)c1C1CC1]

To a solution of ethyl 5-cyclopropyl-1-(3-(4,4,5,5-tetramethyl-1,3,2-dioxaborolan-2-yl)phenyl)-1H-pyrazole-4-carboxylate (1 g, 2.62 mmol), [RhCl(cod)]$_2$ (0.064 g, 0.131 mmol), and cyclohex-2-enone (0.252 mL, 2.62 mmol) in 1,4-dioxane (13.20 mL) and water (4 mL) was added triethylamine (0.729 mL, 5.23 mmol). The reaction mixture was stirred at 95° C. for 1.5 hr. The reaction mixture was diluted with H$_2$O (15 mL), filtered, and extracted with EtOAc (3×15 mL). The combined organic layer was dried over MgSO$_4$, filtered and concentrated to afford the crude product. The crude product was purified with silica gel chromatography to afford the title compound ethyl 5-cyclopropyl-1-(3-(3-oxocyclohexyl)phenyl)-1H-pyrazole-4-carboxylate (1.02 g, 2.89 mmol, 111% yield) which was carried forward without further purification. LC-MS m/z 353.3 (M+H)$^+$, 1.02 min (ret. time).

23c) Ethyl 1-(3-(3-(2-(tert-butoxycarbonyl)hydrazinyl)cyclohexyl)phenyl)-5-cyclopropyl-1H-pyrazole-4-carboxylate (trans racemate)

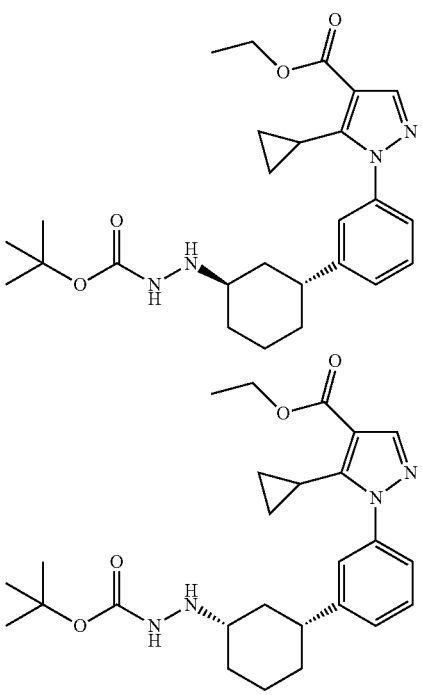

To a solution of ethyl 5-cyclopropyl-1-(3-(3-oxocyclohexyl)phenyl)-1H-pyrazole-4-carboxylate (1.0692 g, 3.03 mmol), acetic acid (0.208 mL, 3.64 mmol) and sodium triacetoxyborohydride (0.772 g, 3.64 mmol) in dichloromethane (10 mL) was added tert-butyl hydrazinecarboxylate (0.401 g, 3.03 mmol). The reaction mixture was stirred at ambient temperature for 1.5 h. To the reaction mixture was added tert-butyl hydrazinecarboxylate (0.2005 g, 1.515 mmol). The reaction mixture was stirred at ambient temperature for 68 hr. The reaction mixture was diluted with H$_2$O (15 mL) and extracted with DCM (3×15 mL). The combined organic layer was washed with brine, dried over MgSO$_4$, filtered and concentrated to afford the crude product. The crude product was purified with silica gel chromatography to afford the cis racemic (348.3 mg, 0.743 mmol, 24.50% yield) and trans racemate (690 mg, 1.473 mmol, 48.5% yield) products. LC-MS cis racemate: m/z 469.5 (M+H)$^+$, 1.05 min (ret. time); trans racemic: m/z 469.6 (M+H)$^+$, 1.14 min (ret. time).

23d) Ethyl 5-cyclopropyl-1-(3-(-3-hydrazinylcyclohexyl)phenyl)-1H-pyrazole-4-carboxylate hydrochloride (trans racemate)

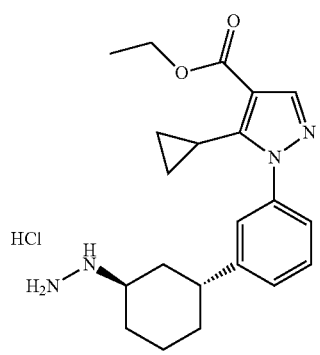 [SMILES: Cl ; CCOC(=O)c1cnn(-c2cccc([C@@H]3CCC[C@@H](NN)C3)c2)c1C1CC1]

To a solution of ethyl 1-(3-(-3-(2-(tert-butoxycarbonyl)hydrazinyl)cyclohexyl)phenyl)-5-cyclopropyl-1H-pyrazole-4-carboxylate (trans racemate, 690 mg, 1.473 mmol) in dichloromethane (8 mL) was added HCl in dioxane (1.104 mL, 4.42 mmol). The reaction mixture was stirred at ambient temperature for 16.5 h. To the reaction mixture was added HCl in dioxane (4M, 0.500 mL). The reaction mixture was stirred at ambient temperature for an additional 1.5 hr. The reaction mixture was concentrated to afford the title compound ethyl 5-cyclopropyl-1-(3-(-3-hydrazinylcyclohexyl)phenyl)-1H-pyrazole-4-carboxylate hydrochloride (trans racemate, 615.1 mg, 1.519 mmol, 103% yield) which was carried forward without further purification. LC-MS m/z 369.1 (M+H)$^+$, 0.80 min (ret. time). $^1$H NMR (400 MHz, methanol-d$_4$) δ ppm 0.60 (d, J=5.52 Hz, 2H) 0.92 (d, J=7.28 Hz, 2H) 1.40 (t, J=7.03 Hz, 3H) 1.67-1.89 (m, 4H) 1.90-2.23 (m, 5H) 2.98-3.12 (m, 1H) 3.44 (br. s., 1H) 3.68 (s, 4H) 4.34 (q, J=7.03 Hz, 2H) 7.36-7.59 (m, 4H) 8.02 (s, 1H).

23e) Ethyl 5-cyclopropyl-1-(3-(-3-(6,6-dimethyl-5,6-dihydrocyclopenta[c]pyrazol-1(4H)-yl)cyclohexyl)phenyl)-1H-pyrazole-4-carboxylate (trans racemate)

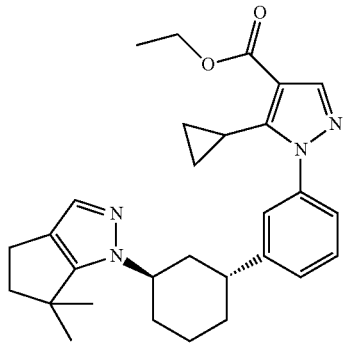 [SMILES: CCOC(=O)c1cnn(-c2cccc([C@@H]3CCC[C@@H](n4ncc5c4C(C)(C)CC5)C3)c2)c1C1CC1]

To a solution of ethyl 5-cyclopropyl-1-(3-(-3-hydrazinylcyclohexyl)phenyl)-1H-pyrazole-4-carboxylate hydrochloride (trans racemate, 40 mg, 0.109 mmol) in acetic acid (1.5 mL) was added 5-((dimethylamino)methylene)-2,2-dimethylcyclopentanone (18.16 mg, 0.109 mmol). The reaction mixture was stirred at 100° C. for 3.5 h. The reaction mixture was concentrated to remove excess solvent. The crude product was dissolved in DMSO (2 mL) and purified with reverse-phase HPLC under neutral conditions to afford the title compound, ethyl 5-cyclopropyl-1-(3-(-3-(6,6-dimethyl-5,6-dihydrocyclopenta[c]pyrazol-1(4H)-yl)cyclohexyl)phenyl)-1H-pyrazole-4-carboxylate (trans racemate, 25.7 mg, 0.054 mmol, 50.1% yield). LC-MS m/z 473.3 (M+H)$^+$, 1.34 min (ret. time).

23f) 5-Cyclopropyl-1-(3-(-3-(6,6-dimethyl-5,6-dihydrocyclopenta[c]pyrazol-1(4H)-yl)cyclohexyl)phenyl)-1H-pyrazole-4-carboxylic Acid (trans racemate)

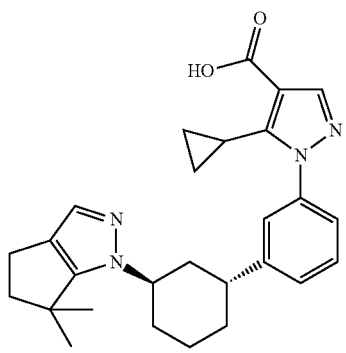

To a solution of ethyl 5-cyclopropyl-1-(3-(-3-(6,6-dimethyl-5,6-dihydrocyclopenta[c]pyrazol-1(4H)-yl)cyclohexyl)phenyl)-1H-pyrazole-4-carboxylate (trans racemate, 25.7 mg, 0.054 mmol) in methanol (0.5 mL) was added 2M LiOH (0.163 mL, 0.326 mmol). The reaction vessel was heated in a Biotage microwave at high absorption for 30 min at 80° C. The reaction mixture was neutralized with 1 N HCl (~1 mL) and concentrated. The crude product was dissolved in DMSO (2 mL) and purified with reverse-phase HPLC under acidic conditions to afford the title compound 5-cyclopropyl-1-(3-(-3-(6,6-dimethyl-5,6-dihydrocyclopenta[c]pyrazol-1(4H)-yl)cyclohexyl)phenyl)-1H-pyrazole-4-carboxylic acid (trans racemate, 21.4 mg, 0.048 mmol, 89% yield). LC-MS m/z 445.4 (M+H)+, 1.09 min (ret. time). $^1$H NMR (400 MHz, methanol-d$_4$) δ ppm 0.58-0.72 (m, 2H) 0.84-0.99 (m, 2H) 1.17 (s, 3H) 1.24 (s, 3H) 1.76 (d, J=7.28 Hz, 1H) 1.93-2.12 (m, 5H) 2.19 (br. s., 1H) 2.30-2.37 (m, 2H) 2.41 (t, J=5.77 Hz, 2H) 2.56-2.63 (m, 2H) 3.59 (br. s., 1H) 4.33 (br. s., 1H) 7.28 (s, 1H) 7.44 (d, J=5.77 Hz, 1H) 7.56 (s, 3H) 8.00 (s, 1H).

Example 24. 5-Cyclopropyl-1-(3-(-3-(6,6-dimethyl-5,6-dihydrocyclopenta[c]pyrazol-1(4H)-yl)cyclohexyl)phenyl)-1H-pyrazole-4-carboxylic Acid (cis racemate)

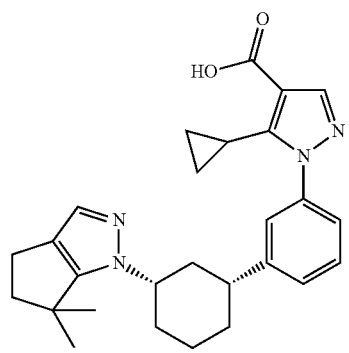 [SMILES: CC1(C)CCc2cnn([C@H]3CCC[C@@H](c4cccc(-n5ncc(C(=O)O)c5C5CC5)c4)C3)c21]

24a) 5-((Dimethylamino)methylene)-2,2-dimethylcyclopentanone

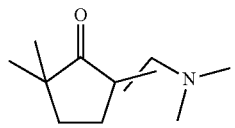

To a solution of 2,2-dimethylcyclopentanone (200 mg, 1.783 mmol) in toluene (1 mL) was added N,N-dimethylformamide dimethyl acetal (0.239 mL, 1.783 mmol). The reaction mixture was stirred at 100° C. for 22 h. The reaction mixture was concentrated to afford the title compound 5-((dimethylamino)methylene)-2,2-dimethylcyclopentanone (288.8 mg, 1.727 mmol, 97% yield) which was carried forward without further purification. LC-MS m/z 167.9 (M+H)+, 0.69 min (ret. time).

24b) Ethyl 5-cyclopropyl-1-(3-(3-oxocyclohexyl)phenyl)-1H-pyrazole-4-carboxylate

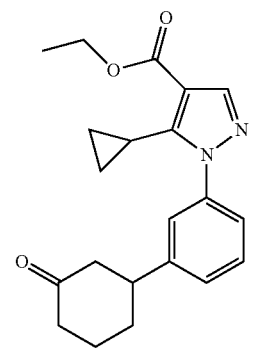 [SMILES: CCOC(=O)c1cnn(-c2cccc(C3CCCC(=O)C3)c2)c1C1CC1]

To a solution of ethyl 5-cyclopropyl-1-(3-(4,4,5,5-tetramethyl-1,3,2-dioxaborolan-2-yl)phenyl)-1H-pyrazole-4-carboxylate (1 g, 2.62 mmol), [RhCl(cod)]$_2$ (0.064 g, 0.131 mmol), and cyclohex-2-enone (0.252 mL, 2.62 mmol) in 1,4-dioxane (13.20 mL) and water (4 mL) was added triethylamine (0.729 mL, 5.23 mmol). The reaction mixture was stirred at 95° C. for 1.5 hr. The reaction mixture was diluted with H$_2$O (15 mL), filtered, and extracted with EtOAc (3×15 mL). The combined organic layer was dried over MgSO$_4$, filtered and concentrated to afford the crude product. The crude product was purified with silica gel chromatography to afford the title compound ethyl 5-cyclopropyl-1-(3-(3-oxocyclohexyl)phenyl)-1H-pyrazole-4-carboxylate (1.02 g, 2.89 mmol, 111% yield) which was carried forward without further purification. LC-MS m/z 353.3 (M+H)+, 1.02 min (ret. time).

24c) Ethyl 1-(3-(-3-(2-(tert-butoxycarbonyl)hydrazinyl)cyclohexyl)phenyl)-5-cyclopropyl-1H-pyrazole-4-carboxylate (cis racemate)

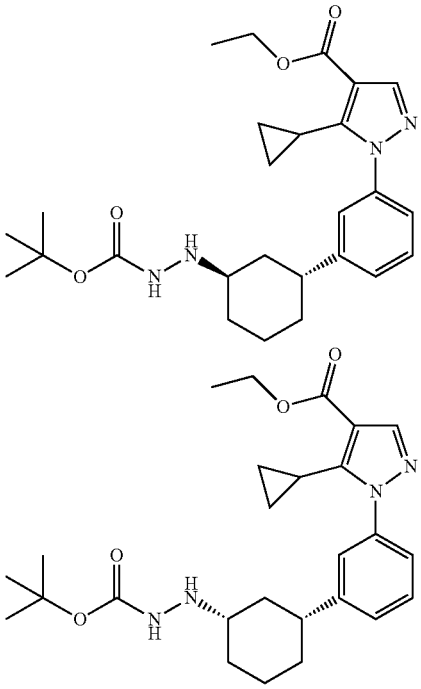

To a solution of ethyl 5-cyclopropyl-1-(3-(3-oxocyclohexyl)phenyl)-1H-pyrazole-4-carboxylate (1.0692 g, 3.03 mmol), acetic acid (0.208 mL, 3.64 mmol) and sodium triacetoxyborohydride (0.772 g, 3.64 mmol) in dichloromethane (10 mL) was added tert-butyl hydrazinecarboxylate (0.401 g, 3.03 mmol). The reaction mixture was stirred at ambient temperature for 1.5 h. To the reaction mixture was added tert-butyl hydrazinecarboxylate (0.2005 g, 1.515 mmol). The reaction mixture was stirred at ambient temperature for 68 hr. The reaction mixture was diluted with H$_2$O (15 mL) and extracted with DCM (3×15 mL). The combined organic layer was washed with brine, dried over MgSO$_4$, filtered and concentrated to afford the crude product. The crude product was purified with silica gel chromatography to afford the cis racemate (348.3 mg, 0.743 mmol, 24.50% yield) and trans racemic (690 mg, 1.473 mmol, 48.5% yield) products. LC-MS cis racemate: m/z 469.5 (M+H)$^+$, 1.05 min (ret. time); trans racemate: m/z 469.6 (M+H)$^+$, 1.14 min (ret. time).

24d) Ethyl 5-cyclopropyl-1-(3-(-3-hydrazinylcyclohexyl)phenyl)-1H-pyrazole-4-carboxylate hydrochloride (cis racemate)

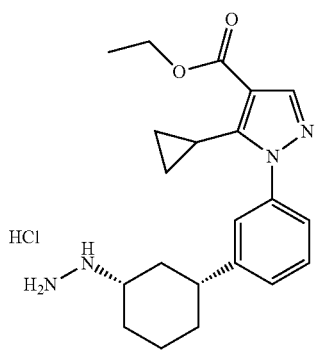 [SMILES: Cl ; CCOC(=O)c1cnn(-c2cccc([C@@H]3CCC[C@H](NN)C3)c2)c1C1CC1]

To a solution of ethyl 1-(3-(-3-(2-(tert-butoxycarbonyl)hydrazinyl)cyclohexyl)phenyl)-5-cyclopropyl-1H-pyrazole-4-carboxylate (cis racemate, 348.3 mg, 0.743 mmol) in dichloromethane (8 mL) was added HCl in dioxane (0.557 mL, 2.228 mmol). The reaction mixture was stirred at ambient temperature for 16.5 h. To the reaction mixture was added HCl in dioxane (4M, 0.250 mL). The reaction mixture was stirred at ambient temperature for an additional 5.5 hr. The reaction mixture was concentrated to afford the title compound ethyl 5-cyclopropyl-1-(3-(-3-hydrazinylcyclohexyl)phenyl)-1H-pyrazole-4-carboxylate hydrochloride (cis racemate, 239.7 mg, 0.592 mmol, 80% yield) which was carried forward without further purification. LC-MS m/z 369.1 (M+H)$^+$, 0.81 min (ret. time). $^1$H NMR (400 MHz, chloroform-d) δ ppm 0.73 (d, J=15.56 Hz, 2H) 0.84-1.10 (m, 2H) 1.16-1.59 (m, 5H) 1.78-2.15 (m, 3H) 2.32-2.91 (m, 2H) 3.61-4.01 (m, 2H) 4.35 (t, J=6.65 Hz, 2H) 6.61 (br. s., 7H) 7.32-7.55 (m, 3H) 8.15-8.34 (m, 1H).

24e) Ethyl 5-cyclopropyl-1-(3-(-3-(6,6-dimethyl-5,6-dihydrocyclopenta[c]pyrazol-1(4H)-yl)cyclohexyl)phenyl)-1H-pyrazole-4-carboxylate (cis racemate)

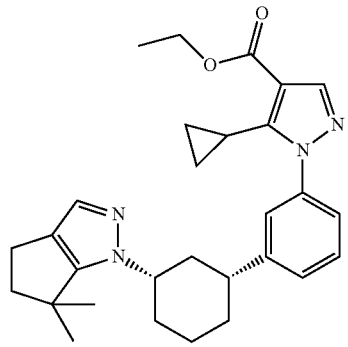 [SMILES: CCOC(=O)c1cnn(-c2cccc([C@@H]3CCC[C@H](n4ncc5c4C(C)(C)CC5)C3)c2)c1C1CC1]

To a solution of ethyl 5-cyclopropyl-1-(3-(-3-hydrazinylcyclohexyl)phenyl)-1H-pyrazole-4-carboxylate hydrochloride (cis racemate, 80 mg, 0.217 mmol) in acetic acid (1.5 mL) was added 5-((dimethylamino)methylene)-2,2-dimethylcyclopentanone (36.3 mg, 0.217 mmol). The reaction mixture was stirred at 100° C. for 3.5 h. The reaction mixture was concentrated to remove excess solvent. The crude product was dissolved in DMSO (2 mL) and purified with reverse-phase HPLC under neutral conditions to afford the title compound, ethyl 5-cyclopropyl-1-(3-(-3-(6,6-dimethyl-5,6-dihydrocyclopenta[c]pyrazol-1(4H)-yl)cyclohexyl)phenyl)-1H-pyrazole-4-carboxylate (cis racemate, 38.1 mg, 0.081 mmol, 37.1% yield). LC-MS m/z 473.4 (M+H)$^+$, 1.29 min (ret. time).

24f) 5-Cyclopropyl-1-(3-(-3-(6,6-dimethyl-5,6-dihydrocyclopenta[c]pyrazol-1(4H)-yl)cyclohexyl)phenyl)-1H-pyrazole-4-carboxylic Acid (cis racemate)

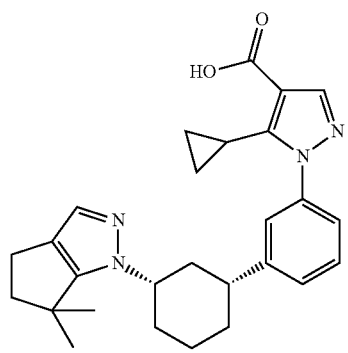 [SMILES: CC1(C)CCc2cnn([C@H]3CCC[C@@H](c4cccc(-n5ncc(C(=O)O)c5C5CC5)c4)C3)c21]

To a solution of ethyl 5-cyclopropyl-1-(3-(-3-(6,6-dimethyl-5,6-dihydrocyclopenta[c]pyrazol-1(4H)-yl)cyclohexyl)phenyl)-1H-pyrazole-4-carboxylate (cis racemate, 38.1 mg, 0.081 mmol) in methanol (0.5 mL) was added 2M LiOH (0.242 mL, 0.484 mmol). The reaction vessel was heated in a Biotage microwave at high absorption for 30 min at 80° C. The reaction mixture was neutralized with 1 N HCl (~1 mL) and concentrated. The crude product was dissolved in DMSO (2 mL) and purified with reverse-phase HPLC under acidic conditions to afford the title compound 5-cyclopropyl-1-(3-(-3-(6,6-dimethyl-5,6-dihydrocyclopenta[c]

pyrazol-1(4H)-yl)cyclohexyl)phenyl)-1H-pyrazole-4-carboxylic acid (cis racemate, 35.80 mg, 0.081 mmol, 100% yield). LC-MS m/z 445.4 (M+H)+, 1.08 min (ret. time). ¹H NMR (400 MHz, methanol-d4) δ ppm 0.62 (d, J=5.27 Hz, 2H) 0.90 (d, J=8.28 Hz, 2H) 1.44 (d, J=5.77 Hz, 6H) 1.54-1.80 (m, 2H) 1.92-2.13 (m, 5H) 2.13-2.28 (m, 2H) 2.38-2.45 (m, 2H) 2.60-2.70 (m, 2H) 2.98 (br. s., 1H) 4.39 (t, J=11.42 Hz, 1H) 7.34 (s, 1H) 7.38-7.55 (m, 4H) 8.00 (s, 1H).

Example 25. 5-Cyclopropyl-1-{3-[3-(3-methyl-pyrrolidine-1-carbonyl)-cyclohexyl]-phenyl}-1H-pyrazole-4-carboxylic Acid 25a) 5-Cyclopropyl-1-{3-[3-(3-methyl-pyrrolidine-1-carbonyl)-cyclohexyl]-phenyl}-1H-pyrazole-4-carboxylic Acid methyl ester

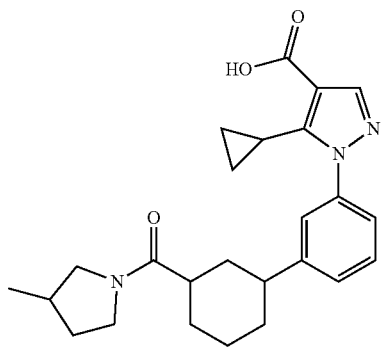 [SMILES: CC1CCN(C(=O)C2CCCC(c3cccc(-n4ncc(C(=O)O)c4C4CC4)c3)C2)C1]

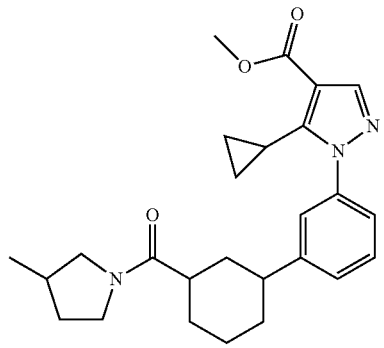 [SMILES: COC(=O)c1cnn(-c2cccc(C3CCCC(C(=O)N4CCC(C)C4)C3)c2)c1C1CC1]

A solution of 1-[3-(3-carboxy-cyclohexyl)-phenyl]-5-cyclopropyl-1H-pyrazole-4-carboxylic acid methyl ester (0.030 g, 0.08 mmol), HATU (0.031 g, 0.08 mmol), 3-methylpyrrolidine (0.012 g, 0.10 mmol) and DIPEA (0.035 mL, 0.20 mmol) in DCM (1 mL) was stirred for 2 h. The mixture was diluted with DCM, and the organic phase washed with aq. NaHCO₃, dried (MgSO₄), filtered, and concentrated to dryness. Silica purification eluting with EtOAc/hexane 20-65% gave the product (0.010 g, 28%), identified by NMR as cis-cyclohexyl diastereoisomers; the trans-isomers were not isolated. LC-MS m/z 436 (M+H)+, 1.48 (ret. time).

25b) 5-Cyclopropyl-1-{3-[3-(3-methyl-pyrrolidine-1-carbonyl)-cyclohexyl]-phenyl}-1H-pyrazole-4-carboxylic Acid (cis racemic)

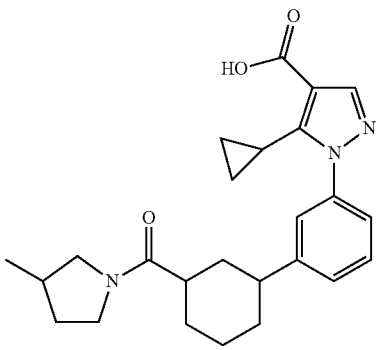 [SMILES: CC1CCN(C(=O)C2CCCC(c3cccc(-n4ncc(C(=O)O)c4C4CC4)c3)C2)C1]

A stirred solution of 5-cyclopropyl-1-{3-[3-(3-methyl-pyrrolidine-1-carbonyl)-cyclohexyl]-phenyl}-1H-pyrazole-4-carboxylic acid methyl ester (0.010 g, 0.02 mmol) in EtOH (0.3 mL) was treated with aq. NaOH (2M, 0.057 mL). After 60 hours, the mixture was partitioned between EtOAc and water. The organic phase was extracted with further water and then discarded. The combined aqueous layer was acidified with 1N HCl and extracted into EtOAc (×2). The combined organic phases were dried (MgSO₄), filtered and concentrated under vacuum to give the product (0.009 g, 93%): cis-diastereoisomers about the cyclohexyl ring. LC-MS m/z 422 (M+H)+, 1.09 (ret. time), basic method. ¹H NMR (400 MHz, DMSO-d6): 12.39-12.10 (1H, m), 7.92 (1H, s), 7.49-7.42 (2H, m), 7.37 (2H, dd), 3.74-3.54 (2H, m), 3.24-3.07 (1H, m), 3.07-2.95 (1H, m), 2.81-2.71 (1H, m), 2.63-2.55 (1H, m), 2.31-2.00 (3H, m), 1.91-1.70 (4H, m), 1.66-1.30 (5H, m), 1.08-0.89 (3H, m), 0.89-0.74 (2H, m), 0.60-0.46 (2H, m).

Example 26. 1-(3-(1-(tert-butoxycarbonyl)piperidin-3-yl)phenyl)-5-((1R,2R)-2-(1-methyl-1H-1,2,3-triazol-4-yl)cyclopropyl)-1H-pyrazole-4-carboxylic Acid

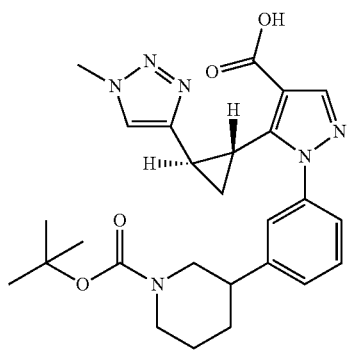 [SMILES: Cn1cc([C@@H]2C[C@H]2c2c(C(=O)O)cnn2-c2cccc(C3CCCN(C(=O)OC(C)(C)C)C3)c2)nn1]

26a) tert-Butyl 3-(3-(4-(ethoxycarbonyl)-5-((1R, 2R)-2-(1-methyl-1H-1,2,3-triazol-4-yl)cyclopropyl)-1H-pyrazol-1-yl)phenyl)-5,6-dihydropyridine-1(2H)-carboxylate

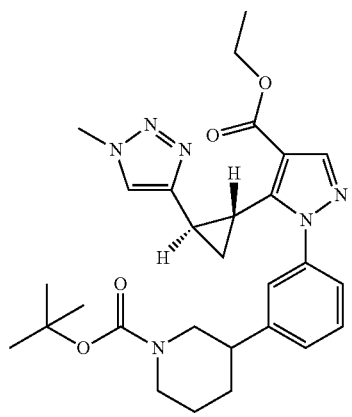 [SMILES: CCOC(=O)c1cnn(-c2cccc(C3CCCN(C(=O)OC(C)(C)C)C3)c2)c1[C@@H]1C[C@H]1c1cn(C)nn1]

Weighed out ethyl 1-(3-bromophenyl)-5-((1R,2R)-2-(1-methyl-1H-1,2,3-triazol-4-yl)cyclopropyl)-1H-pyrazole-4-carboxylate (600 mg, 1.441 mmol), tert-butyl 3-(4,4,5,5-tetramethyl-1,3,2-dioxaborolan-2-yl)-5,6-dihydropyridine-1(2H)-carboxylate (535 mg, 1.730 mmol) and cesium carbonate (939 mg, 2.88 mmol). Added 1,4-Dioxane (15 mL) followed by Water (3 mL), then the flask was flushed with nitrogen. Tetrakis (83 mg, 0.072 mmol) was added and the reaction was sealed and heated to 80° C. for 22 h. The reaction was cooled to RT and concentrated down under reduced pressure. The residue was purified by flash chromatography on silica running from 100% Hex to 100% EtOAc. The desired fractions were concentrated down to give the title compound (608.2 mg, 81 yield). LC-MS m/z 519.1 (M+H)$^+$, 1.22 min (ret. time).

26b) tert-Butyl 3-(3-(4-(ethoxycarbonyl)-5-((1R, 2R)-2-(1-methyl-1H-1,2,3-triazol-4-yl)cyclopropyl)-1H-pyrazol-1-yl)phenyl)piperidine-1-carboxylate

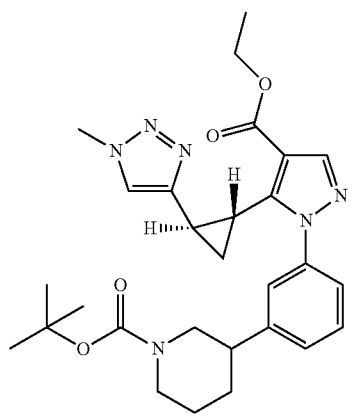 [SMILES: CCOC(=O)c1cnn(-c2cccc(C3CCCN(C(=O)OC(C)(C)C)C3)c2)c1[C@@H]1C[C@H]1c1cn(C)nn1]

Weighed out tert-butyl 3-(3-(4-(ethoxycarbonyl)-5-((1R, 2R)-2-(1-methyl-1H-1,2,3-triazol-4-yl)cyclopropyl)-1H-pyrazol-1-yl)phenyl)-5,6-dihydropyridine-1(2H)-carboxylate (560.4 mg, 1.081 mmol) and dissolved in Ethanol (25 mL). The reaction was flushed with nitrogen, then added 10% Pd/C (115 mg, 0.108 mmol). The reaction was flushed with nitrogen then flushed with hydrogen, and allowed to stir under a hydrogen balloon for 18 h. Starting material was still present in the reaction. The reaction was flushed with nitrogen and filtered. The reaction was flushed with nitrogen, and added 10% Pd/C (300 mg, 0.282 mmol). The reaction was flushed with nitrogen, then hydrogen and left to stir under hydrogen balloon for 4 h. The reaction was flushed with nitrogen, then filtered. The resulting solution was concentrated in vacuo to give the title compound (456.8 mg, 81% yield). LC-MS m/z 521.2 (M+H)$^+$, 1.17 min (ret. time).

26c) 1-(3-(1-(tert-butoxycarbonyl)piperidin-3-yl)phenyl)-5-((1R,2R)-2-(1-methyl-1H-1,2,3-triazol-4-yl)cyclopropyl)-1H-pyrazole-4-carboxylic Acid carboxylate

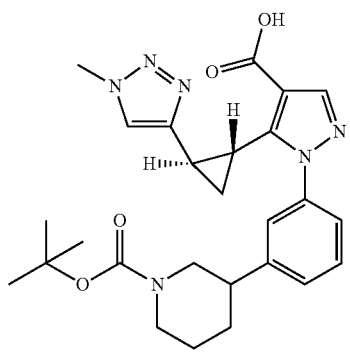 [SMILES: Cn1cc([C@@H]2C[C@H]2c2c(C(=O)O)cnn2-c2cccc(C3CCCN(C(=O)OC(C)(C)C)C3)c2)nn1]

To a solution of tert-butyl 3-(3-(4-(ethoxycarbonyl)-5-((1R,2R)-2-(1-methyl-1H-1,2,3-triazol-4-yl)cyclopropyl)-1H-pyrazol-1-yl)phenyl)piperidine-1-carboxylate (74.7 mg, 0.143 mmol) in a mix of Methanol (1.25 mL) and Tetrahydrofuran (THF) (0.625 mL) was added LiOH (65 mg, 1.549 mmol) and Water (0.250 mL). The reaction was heated at 50° C. for 17 h. The reaction was concentrated. To the residue was added acetonitrile (5 mL), then the reaction was acidified with formic acid (88%) to pH=3. The reaction was concentrated down. The crude product was dissolved in DMSO (2 mL) and purified with reverse-phase HPLC under acidic conditions (formic acid) to afford the title compound (33.9 mg, 48%). LC-MS m/z 493.2 (M+H)$^+$, 1.01 min (ret. time). $^1$H NMR (400 MHz, DMSO-d$_6$) δ: 12.37 (br. s., 1H), 7.98 (s, 1H), 7.60 (s, 1H), 7.48-7.31 (m, 4H), 4.00-3.80 (m, 5H), 2.77 (br. s., 2H), 2.60 (d, J=10.3 Hz, 1H), 2.48-2.41 (m, 1H), 2.23 (br. s., 1H), 1.79-1.62 (m, 2H), 1.60-1.48 (m, 1H), 1.40 (br. s., 10H), 1.36-1.19 (m, 2H).

Example 27. 1-(3-(1-(tert-Butoxycarbonyl)piperidin-3-yl)phenyl)-5-cyclopropyl-1H-pyrazole-4-carboxylic Acid

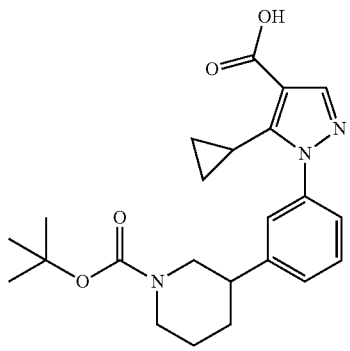 [SMILES: CC(C)(C)OC(=O)N1CCCC(c2cccc(-n3ncc(C(=O)O)c3C3CC3)c2)C1]

27a) tert-Butyl 3-(3-(5-cyclopropyl-4-(ethoxycarbonyl)-1H-pyrazol-1-yl)phenyl)-5,6-dihydropyridine-1(2H)-carboxylate

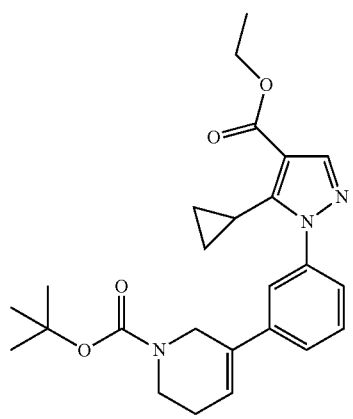 [SMILES: CCOC(=O)c1cnn(-c2cccc(C3=CCCN(C(=O)OC(C)(C)C)C3)c2)c1C1CC1]

Weighed out ethyl 1-(3-bromophenyl)-5-cyclopropyl-1H-pyrazole-4-carboxylate (1.01 g, 3.01 mmol), tert-butyl 3-(4,4,5,5-tetramethyl-1,3,2-dioxaborolan-2-yl)-5,6-dihydropyridine-1(2H)-carboxylate (1.029 g, 3.33 mmol) and cesium carbonate (2.05 g, 6.29 mmol). Added 1,4-Dioxane (25 mL) followed by Water (5.00 mL). The flask was flushed with nitrogen and tetrakis (0.174 g, 0.151 mmol) was added. The reaction was sealed and heated to 80° C. for 2 days. The reaction was concentrated down under reduced pressure. The compound was purified by flash chromatography on silica running from 100% Hex to 100% EtOAc. The desired fractions were concentrated to give the title compound (818.0 mg, 62.0% yield). LC-MS m/z 438.0 (M+H)$^+$, 1.45 min (ret. time).

27b) tert-Butyl 3-(3-(5-cyclopropyl-4-(ethoxycarbonyl)-1H-pyrazol-1-yl)phenyl)piperidine-1-carboxylate

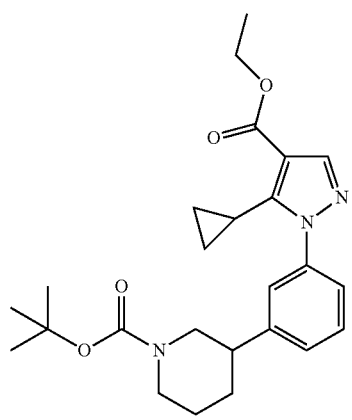 [SMILES: CCOC(=O)c1cnn(-c2cccc(C3CCCN(C(=O)OC(C)(C)C)C3)c2)c1C1CC1]

Tert-butyl 3-(3-(5-cyclopropyl-4-(ethoxycarbonyl)-1H-pyrazol-1-yl)phenyl)-5,6-dihydropyridine-1(2H)-carboxylate (729.9 mg, 1.668 mmol) was dissolved in Ethanol (25 mL). The flask was flushed with nitrogen, and added 10% Pd/C (178 mg, 0.167 mmol). The flask was flushed with nitrogen, flushed hydrogen, and allowed to stir under a hydrogen balloon. The reaction was stirred for 19 h, then the reaction was flushed with nitrogen, and filtered. The flask was flushed with nitrogen, Pd/C (500 mg, 0.470 mmol) was added. The flask was flushed with hydrogen and left to stir under hydrogen balloon. After 3 h, the reaction was flushed with nitrogen, and filtered. The solution was concentrated down to give the title compound (528.5 mg, 72.1% yield). LC-MS m/z 440.2 (M+H)$^+$, 1.38 min (ret. time).

27c) 1-(3-(1-(tert-butoxycarbonyl)piperidin-3-yl)phenyl)-5-cyclopropyl-1H-pyrazole-4-carboxylic Acid

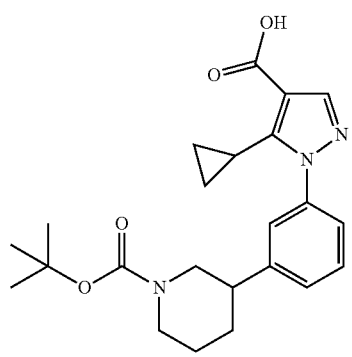 [SMILES: CC(C)(C)OC(=O)N1CCCC(c2cccc(-n3ncc(C(=O)O)c3C3CC3)c2)C1]

To a solution of tert-butyl 3-(3-(5-cyclopropyl-4-(ethoxycarbonyl)-1H-pyrazol-1-yl)phenyl)piperidine-1-carboxylate (72.7 mg, 0.165 mmol) in a mix of Methanol (1.25 mL) and Tetrahydrofuran (THF) (0.625 mL) was added LiOH (75 mg, 1.787 mmol) and Water (0.250 mL). The reaction was stirred at 50° C. for 17 h and then concentrated. To the residue was added acetonitrile (5 mL), then the reaction was acidified with formic acid (88%) to pH=3. The reaction was concentrated down. The crude product was dissolved in DMSO (2 mL) and purified with reverse-phase HPLC under acidic conditions (formic acid) to afford the title compound (40.1 mg, 58.9%). LC-MS m/z 412.3 (M+H)$^+$, 1.13 min (ret. time). $^1$H NMR (400 MHz, DMSO-d$_6$) δ: 12.29 (s, 1H), 7.94 (s, 1H), 7.53-7.42 (m, 3H), 7.39 (d, J=7.3 Hz, 1H), 3.95 (d, J=12.3 Hz, 2H), 2.75 (d, J=11.0 Hz, 3H), 2.17-2.05 (m, 1H), 1.94 (d, J=10.3 Hz, 1H), 1.71 (d, J=11.5 Hz, 2H), 1.49-1.35 (m, 10H), 0.83 (d, J=8.3 Hz, 2H), 0.51 (d, J=5.0 Hz, 2H).

Example 28. 1-(3-(1-(cyclohexylmethyl)piperidin-3-yl)phenyl)-5-cyclopropyl-1H-pyrazole-4-carboxylic Acid, Hydrochloride

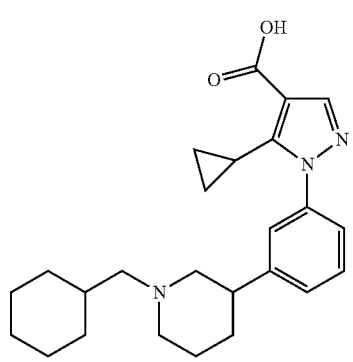 [SMILES: O=C(O)c1cnn(-c2cccc(C3CCCN(CC4CCCCC4)C3)c2)c1C1CC1]

28a) Ethyl 5-cyclopropyl-1-(3-(piperidin-3-yl)phenyl)-1H-pyrazole-4-carboxylate, Hydrochloride

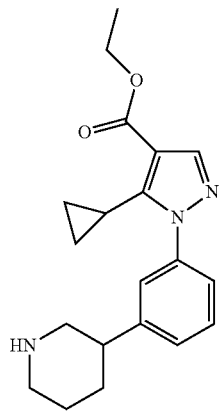 [SMILES: CCOC(=O)c1cnn(-c2cccc(C3CCCNC3)c2)c1C1CC1]

Tert-butyl 3-(3-(5-cyclopropyl-4-(ethoxycarbonyl)-1H-pyrazol-1-yl)phenyl)piperidine-1-carboxylate (452.8 mg, 1.030 mmol) was dissolved in Dichloromethane (DCM) (10 mL) and Methanol (1 mL). Added 4M HCl in 1,4-dioxane (2.58 mL, 10.30 mmol). After stirring for 16 h, the reaction was concentrated in vacuo to give the title compound (383.0 mg, 99 yield). LC-MS m/z 340.1 (M+H)+, 0.83 min (ret. time).

28b) ethyl 1-(3-(1-(cyclohexylmethyl)piperidin-3-yl)phenyl)-5-cyclopropyl-1H-pyrazole-4-carboxylate

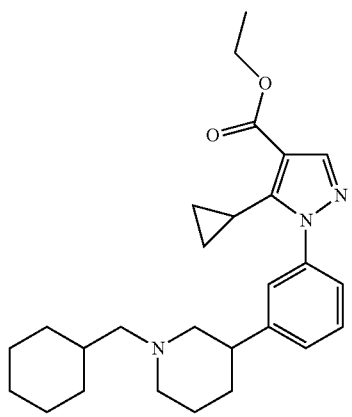 [SMILES: CCOC(=O)c1cnn(-c2cccc(C3CCCN(CC4CCCCC4)C3)c2)c1C1CC1]

Ethyl 5-cyclopropyl-1-(3-(piperidin-3-yl)phenyl)-1H-pyrazole-4-carboxylate, Hydrochloride (89.7 mg, 0.239 mmol) was dissolved in Dichloromethane (DCM) (6 mL). Added TEA (0.1 mL, 0.717 mmol) and allowed the reaction to stir for 5 min, then added cyclohexanecarbaldehyde (0.034 mL, 0.286 mmol). The reaction was stirred for 5 min then sodium triacetoxyborohydride (152 mg, 0.716 mmol) was added. The reaction was stirred for 16 h, then quenched with NaHCO₃ (5 mL), and diluted with DCM (15 mL). The organic layer was dried through a phase separator and concentrated. The compound was purified by flash chromatography on silica running from 100% Hex to 100% EtOAc. The desired fractions were concentrated to give the title compound (77.8 mg, 74.8% yield). LC-MS m/z 436.3 (M+H)+, 1.01 min (ret. time).

28c) 1-(3-(1-(Cyclohexylmethyl)piperidin-3-yl)phenyl)-5-cyclopropyl-1H-pyrazole-4-carboxylic Acid, Hydrochloride

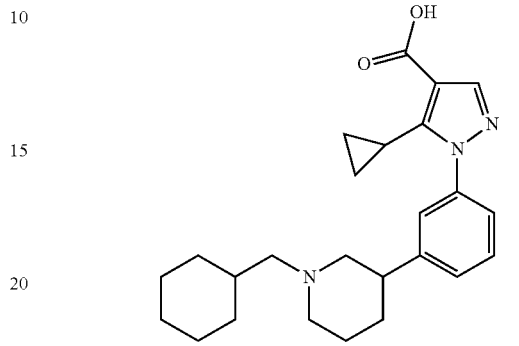

To a solution of ethyl 1-(3-(1-(cyclohexylmethyl)piperidin-3-yl)phenyl)-5-cyclopropyl-1H-pyrazole-4-carboxylate (77.8 mg, 0.179 mmol) in a mix of Methanol (1.25 mL) and Tetrahydrofuran (THF) (0.625 mL) was added LiOH (93 mg, 2.216 mmol) and Water (0.250 mL). The reaction stirred at 50° C. for 15 h, then concentrated. To the residue was added acetonitrile (5 mL), then the reaction was acidified with 1 M HCl to pH=3. The reaction was concentrated down. The crude product was dissolved in DMSO (2 mL) and purified with reverse-phase HPLC under acidic conditions (0.1% TFA). The desired fractions were concentrated down, then taken back up in acetonitrile and added 4M HCl in 1,4-dioxane (1.0 mL) and concentrated (performed 3×-traded the TFA for HCl) to give the title compound (61.2 mg, 77% yield). LC-MS m/z 408.2 (M+H)+, 0.84 min (ret. time). ¹H NMR (DMSO-d₆) δ: 9.75 (br. s., 1H), 7.96 (s, 1H), 7.49-7.57 (m, 3H), 7.40 (d, J=6.0 Hz, 1H), 3.70 (dd, J=11.8, 4.3 Hz, 1H), 3.45-3.59 (m, 3H), 3.28-3.38 (m, 1H), 3.18 (t, J=10.9 Hz, 1H), 2.91 (br. s., 3H), 2.09-2.18 (m, 1H), 1.75-2.06 (m, 6H), 1.61-1.72 (m, 4H), 1.08-1.22 (m, 2H), 0.92-1.02 (m, 2H), 0.52 (d, J=5.3 Hz, 2H).

Example 29. 5-((1R,2R)-2-(1-Methyl-1H-1,2,3-triazol-4-yl)cyclopropyl)-1-(3-(1-phenethylpiperidin-3-yl)phenyl)-1H-pyrazole-4-carboxylic Acid, Hydrochloride

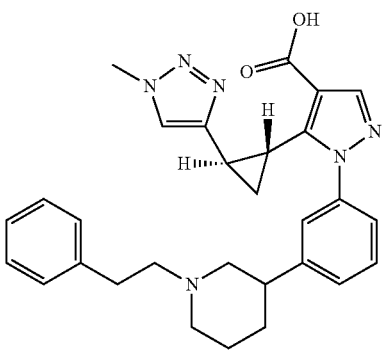 [SMILES: Cn1cc([C@@H]2C[C@H]2c2c(C(=O)O)cnn2-c2cccc(C3CCCN(CCc4ccccc4)C3)c2)nn1]

29a) Ethyl 5-cyclopropyl-1-(3-(piperidin-3-yl)phenyl)-1H-pyrazole-4-carboxylate, Hydrochloride

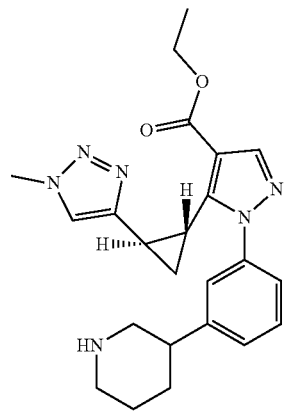 [SMILES: CCOC(=O)c1cnn(-c2cccc(C3CCCNC3)c2)c1[C@@H]1C[C@H]1c1cn(C)nn1]

Tert-butyl 3-(3-(4-(ethoxycarbonyl)-5-((1R,2R)-2-(1-methyl-1H-1,2,3-triazol-4-yl)cyclopropyl)-1H-pyrazol-1-yl)phenyl)piperidine-1-carboxylate (380.1 mg, 0.730 mmol) was dissolved in Dichloromethane (DCM) (10 mL) and Methanol (1 mL). Added 4M HCl in 1,4-dioxane (2.0 mL, 8.00 mmol). The reaction was stirred for 16 h, and then concentrated in vacuo to give the title compound (361.7 mg, 108% yield). LC-MS m/z 421.2 (M+H)+, 0.75 min (ret. time).

29b) Ethyl 5-((1R,2R)-2-(1-methyl-1H-1,2,3-triazol-4-yl)cyclopropyl)-1-(3-(1-phenethylpiperidin-3-yl)phenyl)-1H-pyrazole-4-carboxylate

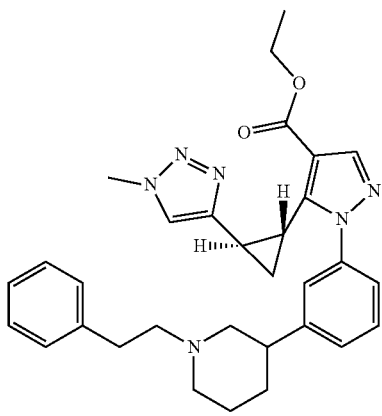 [SMILES: CCOC(=O)c1cnn(-c2cccc(C3CCCN(CCc4ccccc4)C3)c2)c1[C@@H]1C[C@H]1c1cn(C)nn1]

Ethyl 5-((1R,2R)-2-(1-methyl-1H-1,2,3-triazol-4-yl)cyclopropyl)-1-(3-(piperidin-3-yl)phenyl)-1H-pyrazole-4-carboxylate, Hydrochloride (62 mg, 0.136 mmol) was dissolved in Dichloromethane (DCM) (8 mL). Added TEA (0.05 mL, 0.359 mmol) and allowed the reaction to stir for 5 min. Then added 2-phenylacetaldehyde (0.02 mL, 0.171 mmol), and allowed the reaction to stir for 5 min, then added sodium triacetoxyborohydride (99 mg, 0.467 mmol). The reaction was stirred for 21 h, then quenched with NaHCO$_3$ (satd, 5 mL) and diluted with DCM (15 mL). The organic phase was passed through a phase separator and concentrated. The compound was purified by flash chromatography on silica running from 100% Hex to 100% EtOAc, then the solvent was switched to 100% DCM to 20% (90% MeOH/10% NH$_4$OH)/80% DCM. The desired fractions were concentrated down to give the title compound (37.7 mg, 53.0% yield). LC-MS m/z 525.3 (M+H)+, 0.93 min (ret. time).

29c) 5-((1R,2R)-2-(1-Methyl-1H-1,2,3-triazol-4-yl)cyclopropyl)-1-(3-(1-phenethylpiperidin-3-yl)phenyl)-1H-pyrazole-4-carboxylic Acid, Hydrochloride

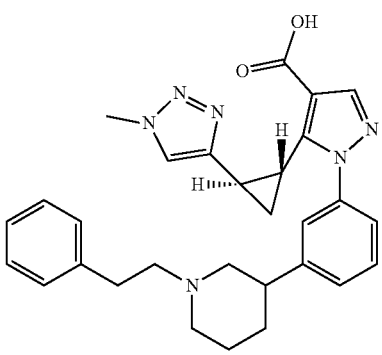 [SMILES: Cn1cc([C@@H]2C[C@H]2c2c(C(=O)O)cnn2-c2cccc(C3CCCN(CCc4ccccc4)C3)c2)nn1]

To a solution of ethyl 5-((1R,2R)-2-(1-methyl-1H-1,2,3-triazol-4-yl)cyclopropyl)-1-(3-(1-phenethylpiperidin-3-yl)phenyl)-1H-pyrazole-4-carboxylate (37.7 mg, 0.072 mmol) in a mix of Methanol (1.25 mL) and Tetrahydrofuran (THF) (0.625 mL) was added LiOH (35 mg, 0.834 mmol) and Water (0.250 mL). The reaction was stirred at 50° C. for 14 h then concentrated. To the residue was added ACN (5 mL), then the reaction was acidified with 1 M HCl to pH=3. The reaction was concentrated. The crude product was dissolved in DMSO (2 mL) and purified with reverse-phase HPLC under acidic conditions (0.1% TFA). The desired fractions were concentrated down, then taken back up in acetonitrile and added 4M HCl in 1,4-dioxane (1.0 mL) and concentrated (performed 3×-traded the TFA for HCl) to give the title compound (22.6 mg, 59.0% yield). LC-MS m/z 497.2 (M+H)+, 0.76 min (ret. time). $^1$H NMR (DMSO-d$_6$) δ: 10.84 (br. s., 1H), 8.00 (s, 1H), 7.63 (d, J=7.0 Hz, 1H), 7.46-7.52 (m, 3H), 7.22-7.41 (m, 7H), 3.96 (d, J=4.3 Hz, 3H), 3.66-3.75 (m, 4H), 3.59 (d, J=11.0 Hz, 2H), 3.49 (dd, J=11.3, 4.0 Hz, 3H), 3.08-3.19 (m, 3H), 2.95 (d, J=10.0 Hz, 1H), 2.12-2.21 (m, 1H), 1.95 (br. s., 2H), 1.73-1.83 (m, 1H).

Example 30. 5-((1R,2R)-2-(1-methyl-1H-1,2,3-triazol-4-yl)cyclopropyl)-1-(3-(1-(phenylsulfonyl)piperidin-3-yl)phenyl)-1H-pyrazole-4-carboxylic Acid

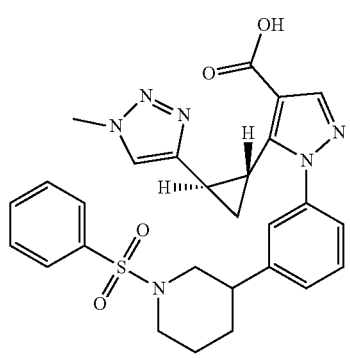 [SMILES: Cn1cc([C@@H]2C[C@H]2c2c(C(=O)O)cnn2-c2cccc(C3CCCN(S(=O)(=O)c4ccccc4)C3)c2)nn1]

30a) Ethyl 5-((1R,2R)-2-(1-methyl-1H-1,2,3-triazol-4-yl)cyclopropyl)-1-(3-(1-(phenylsulfonyl)piperidin-3-yl)phenyl)-1H-pyrazole-4-carboxylate

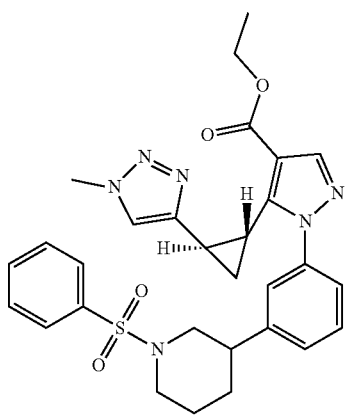 [SMILES: CCOC(=O)c1cnn(-c2cccc(C3CCCN(S(=O)(=O)c4ccccc4)C3)c2)c1[C@@H]1C[C@H]1c1cn(C)nn1]

Dissolved ethyl 5-((1R,2R)-2-(1-methyl-1H-1,2,3-triazol-4-yl)cyclopropyl)-1-(3-(piperidin-3-yl)phenyl)-1H-pyrazole-4-carboxylate, Hydrochloride (75 mg, 0.164 mmol) in Dichloromethane (DCM) (2 mL). Added TEA (0.050 mL, 0.361 mmol) and stirred for 5 min, then added benzenesulfonyl chloride (0.025 mL, 0.195 mmol). The reaction was stirred for 2 days, and then concentrated. The compound was purified by flash chromatography on silica running from 100% Hex to 100% EtOAc. The desired fractions were concentrated down to give the title compound (53.7 mg, 58.4% yield). LC-MS m/z 561.2 (M+H)$^+$, 1.11 min (ret. time).

30b) 5-((1R,2R)-2-(1-Methyl-1H-1,2,3-triazol-4-yl)cyclopropyl)-1-(3-(1-(phenylsulfonyl)piperidin-3-yl)phenyl)-1H-pyrazole-4-carboxylic Acid

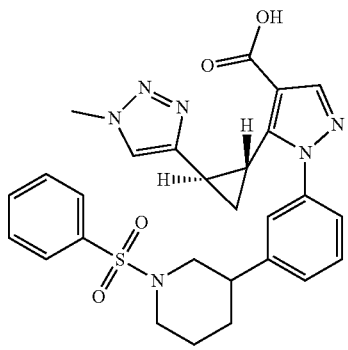 [SMILES: Cn1cc([C@@H]2C[C@H]2c2c(C(=O)O)cnn2-c2cccc(C3CCCN(S(=O)(=O)c4ccccc4)C3)c2)nn1]

To a solution of ethyl 5-((1R,2R)-2-(1-methyl-1H-1,2,3-triazol-4-yl)cyclopropyl)-1-(3-(1-(phenylsulfonyl)piperidin-3-yl)phenyl)-1H-pyrazole-4-carboxylate (53.7 mg, 0.096 mmol) in a mix of Methanol (1.25 mL) and Tetrahydrofuran (THF) (0.625 mL) was added LiOH (40.2 mg, 0.958 mmol) and Water (0.250 mL). The reaction was stirred at 50° C. for 17 h then concentrated. To the residue was added acetonitrile (5 mL), then the reaction was acidified with 1 M HCl to pH=3. The reaction was concentrated down. The crude product was dissolved in DMSO (2 mL) and purified with reverse-phase HPLC under acidic conditions to afford the title compound (33.0 mg, 64.7%). LC-MS m/z 533.1 (M+H)$^+$, 0.91 min (ret. time). $^1$H NMR (400 MHz, DMSO-d$_6$) δ: 12.67-11.99 (m, 1H), 7.97 (s, 1H), 7.78-7.68 (m, 3H), 7.67-7.60 (m, 2H), 7.57 (d, J=11.5 Hz, 1H), 7.47-7.39 (m, 3H), 7.35 (d, J=6.0 Hz, 1H), 3.95 (d, J=3.3 Hz, 3H), 3.65 (d, J=11.0 Hz, 2H), 2.78 (d, J=8.8 Hz, 1H), 2.48-2.25 (m, 3H), 2.15 (d, J=5.8 Hz, 1H), 1.75 (br. s., 1H), 1.68-1.27 (m, 4H), 1.23 (dd, J=5.4, 8.7 Hz, 1H).

Example 31. 1-(3-(1-(2-cyclohexylacetyl)piperidin-3-yl)phenyl)-5-((1R,2R)-2-(1-methyl-1H-1,2,3-triazol-4-yl)cyclopropyl)-1H-pyrazole-4-carboxylic Acid

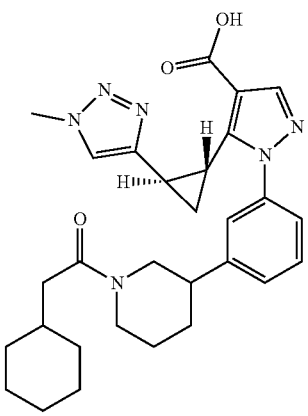 [SMILES: Cn1cc([C@@H]2C[C@H]2c2c(C(=O)O)cnn2-c2cccc(C3CCCN(C(=O)CC4CCCCC4)C3)c2)nn1]

31a) Ethyl 1-(3-(1-(2-cyclohexylacetyl)piperidin-3-yl)phenyl)-5-((1R,2R)-2-(1-methyl-1H-1,2,3-triazol-4-yl)cyclopropyl)-1H-pyrazole-4-carboxylate

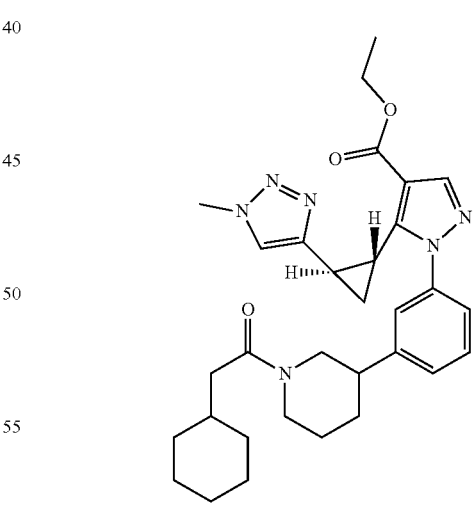

Ethyl 5-((1R,2R)-2-(1-methyl-1H-1,2,3-triazol-4-yl)cyclopropyl)-1-(3-(piperidin-3-yl)phenyl)-1H-pyrazole-4-carboxylate, Hydrochloride (75 mg, 0.164 mmol) was dissolved in Dichloromethane (DCM) (2 mL). Added 2-cyclohexylacetic acid (25.1 mg, 0.177 mmol) followed by TEA (0.069 mL, 0.492 mmol) then propylphosphonic anhydride solution 50% wt in EtOAc (0.147 mL, 0.246 mmol). The reaction was stirred for 2 days then quenched with NaHCO₃ (satd, 0.5 mL), then diluted with DCM (15 mL) and washed with citric acid (satd, 5 mL). The organic layer was separated and concentrated. The compound was purified on silica running from 100% Hex to 100% EtOAc. The desired fractions were concentrated down to give the title compound (53.7 mg, 60.1% yield). LC-MS m/z 545.4 (M+H)⁺, 1.15 min (ret. time).

31 b) 1-(3-(1-(2-Cyclohexylacetyl)piperidin-3-yl)phenyl)-5-((1R,2R)-2-(1-methyl-1H-1,2,3-triazol-4-yl)cyclopropyl)-1H-pyrazole-4-carboxylic Acid

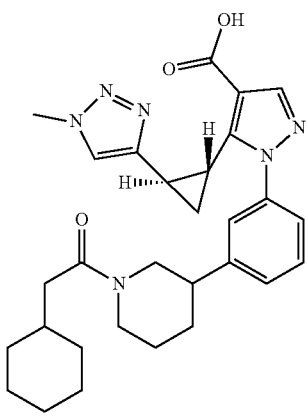 [SMILES: Cn1cc([C@@H]2C[C@H]2c2c(C(=O)O)cnn2-c2cccc(C3CCCN(C(=O)CC4CCCCC4)C3)c2)nn1]

To a solution of ethyl 1-(3-(1-(2-cyclohexylacetyl)piperidin-3-yl)phenyl)-5-((1R,2R)-2-(1-methyl-1H-1,2,3-triazol-4-yl)cyclopropyl)-1H-pyrazole-4-carboxylate (53.7 mg, 0.099 mmol) in a mix of Methanol (1.25 mL) and Tetrahydrofuran (THF) (0.625 mL) was added LiOH (41.4 mg, 0.986 mmol) and Water (0.250 mL). The reaction was stirred at 50° C. for 15 h then concentrated. To the residue was added acetonitrile (5 mL), then the reaction was acidified with 1 M HCl to pH=3. The reaction was concentrated down. The crude product was dissolved in DMSO (2 mL) and purified with reverse-phase HPLC under acidic conditions to afford the title compound (36.3 mg, 71.3%). LC-MS m/z 517.3 (M+H)⁺, 1.02 min (ret. time). ¹H NMR (DMSO-d₆) δ: 7.98 (br. s., 1H), 7.55-7.64 (m, 1H), 7.33-7.48 (m, 4H), 4.25-4.50 (m, 2H), 3.85-3.98 (m, 5H), 3.80 (d, J=12.3 Hz, 1H), 3.01 (d, J=12.3 Hz, 1H), 2.62 (d, J=11.8 Hz, 1H), 2.21 (br. s., 3H), 1.66 (d, J=13.3 Hz, 10H), 1.34 (d, J=6.3 Hz, 2H), 1.06-1.19 (m, 2H), 0.90-0.98 (m, 2H).

Example 32. 5-((1R,2R)-2-(1-methyl-1H-1,2,3-triazol-4-yl)cyclopropyl)-1-(3-(1-pivaloylpiperidin-3-yl)phenyl)-1H-pyrazole-4-carboxylic Acid

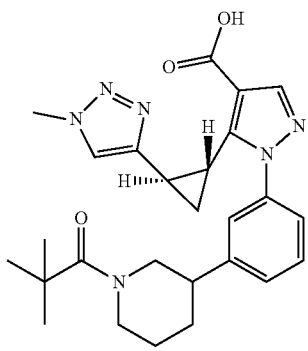 [SMILES: Cn1cc([C@@H]2C[C@H]2c2c(C(=O)O)cnn2-c2cccc(C3CCCN(C(=O)C(C)(C)C)C3)c2)nn1]

32a) Ethyl 5-((1R,2R)-2-(1-methyl-1H-1,2,3-triazol-4-yl)cyclopropyl)-1-(3-(1-pivaloylpiperidin-3-yl)phenyl)-1H-pyrazole-4-carboxylate

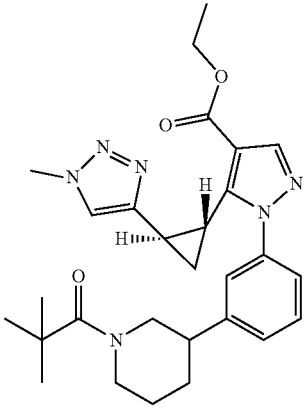 [SMILES: CCOC(=O)c1cnn(-c2cccc(C3CCCN(C(=O)C(C)(C)C)C3)c2)c1[C@@H]1C[C@H]1c1cn(C)nn1]

Ethyl 5-((1R,2R)-2-(1-methyl-1H-1,2,3-triazol-4-yl)cyclopropyl)-1-(3-(piperidin-3-yl)phenyl)-1H-pyrazole-4-carboxylate, Hydrochloride (75 mg, 0.164 mmol) was dissolved in Dichloromethane (DCM) (2 mL). Added TEA (0.069 mL, 0.492 mmol) and stirred for 5 min, then added pivaloyl chloride (0.022 mL, 0.181 mmol). The reaction was stirred for 2 days then quenched with NaHCO₃ (0.5 mL), then diluted with DCM (15 mL) and washed with citric acid (satd, 5 mL). The organic layer was separated and concentrated. The compound was purified on silica running from 100% Hex to 100% EtOAc. The desired fractions were concentrated down to give the title compound (58.2 mg, 70.3% yield). LC-MS m/z 505.4 (M+H)⁺, 1.05 min (ret. time).

32b) 5-((1R,2R)-2-(1-Methyl-1H-1,2,3-triazol-4-yl)cyclopropyl)-1-(3-(1-pivaloylpiperidin-3-yl)phenyl)-1H-pyrazole-4-carboxylic Acid

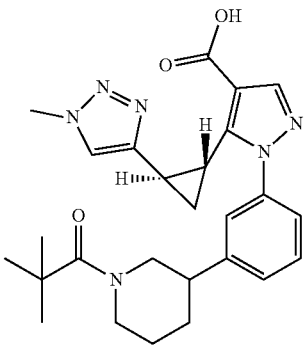 [SMILES: Cn1cc([C@@H]2C[C@H]2c2c(C(=O)O)cnn2-c2cccc(C3CCCN(C(=O)C(C)(C)C)C3)c2)nn1]

To a solution of ethyl 5-((1R,2R)-2-(1-methyl-1H-1,2,3-triazol-4-yl)cyclopropyl)-1-(3-(1-pivaloylpiperidin-3-yl)phenyl)-1H-pyrazole-4-carboxylate (58.2 mg, 0.115 mmol) in a mix of Methanol (1.25 mL) and Tetrahydrofuran (THF) (0.625 mL) was added LiOH (48.4 mg, 1.153 mmol) and Water (0.250 mL). The reaction was stirred at 50° C. for 15 h then concentrated. To the residue was added acetonitrile (5 mL), then the reaction was acidified with 1 M HCl to pH=3. The reaction was concentrated down. The crude product was dissolved in DMSO (2 mL) and purified with reverse-phase HPLC under acidic conditions to afford the title compound (26.1 mg, 47.5%). LC-MS m/z 477.2 (M+H)+, 0.90 min (ret. time). ¹H NMR (DMSO-d₆) δ: 7.98 (s, 1H), 7.61 (s, 1H), 7.40-7.49 (m, 3H), 7.37 (br. s., 1H), 4.19-4.35 (m, 2H), 3.95 (s, 3H), 2.82 (d, J=12.5 Hz, 2H), 2.60 (d, J=8.8 Hz, 2H), 2.12-2.25 (m, 1H), 1.68-1.81 (m, 3H), 1.28-1.37 (m, 3H), 1.21 (s, 9H).

Example 33. 1-(3-(1-benzoylpiperidin-3-yl)phenyl)-5-((1R,2R)-2-(1-methyl-1H-1,2,3-triazol-4-yl)cyclopropyl)-1H-pyrazole-4-carboxylic Acid

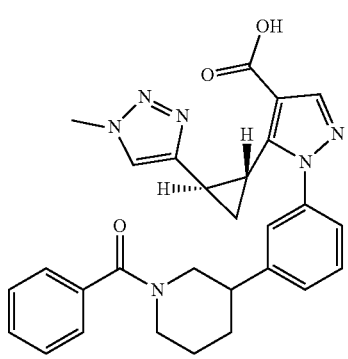 [SMILES: Cn1cc([C@@H]2C[C@H]2c2c(C(=O)O)cnn2-c2cccc(C3CCCN(C(=O)c4ccccc4)C3)c2)nn1]

33a) Ethyl 5-((1R,2R)-2-(1-methyl-1H-1,2,3-triazol-4-yl)cyclopropyl)-1-(3-(1-pivaloylpiperidin-3-yl)phenyl)-1H-pyrazole-4-carboxylate

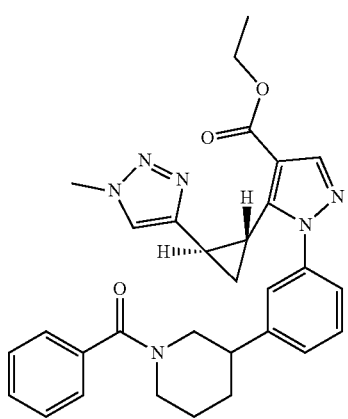 [SMILES: CCOC(=O)c1cnn(-c2cccc(C3CCCN(C(=O)c4ccccc4)C3)c2)c1[C@@H]1C[C@H]1c1cn(C)nn1]

Ethyl 5-((1R,2R)-2-(1-methyl-1H-1,2,3-triazol-4-yl)cyclopropyl)-1-(3-(piperidin-3-yl)phenyl)-1H-pyrazole-4-carboxylate, Hydrochloride (75 mg, 0.164 mmol) was dissolved in Dichloromethane (DCM) (2 mL). Added benzoic acid (20.04 mg, 0.164 mmol) and TEA (0.069 mL, 0.492 mmol) followed by propylphosphonic anhydride solution 50% wt in EtOAc (0.147 mL, 0.246 mmol). The reaction was stirred for 2 days then quenched with NaHCO₃ (0.5 mL), then diluted with DCM (15 mL) and washed with citric acid (satd, 5 mL). The organic layer was separated and concentrated. The compound was purified on silica running from 100% Hex to 100% EtOAc. The desired fractions were concentrated down to give the title compound (53.3 mg, 61.9% yield). LC-MS m/z 525.3 (M+H)+, 1.03 min (ret. time).

33b) 1-(3-(1-Benzoylpiperidin-3-yl)phenyl)-5-((1R,2R)-2-(1-methyl-1H-1,2,3-triazol-4-yl)cyclopropyl)-1H-pyrazole-4-carboxylic Acid

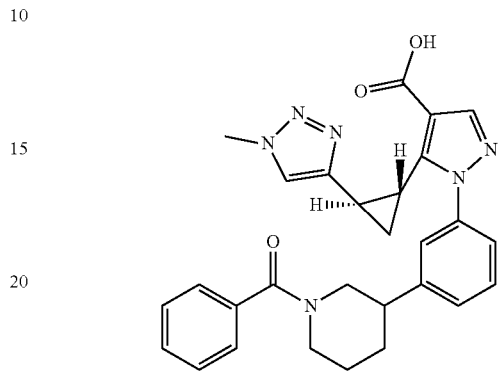

To a solution of ethyl 1-(3-(1-benzoylpiperidin-3-yl)phenyl)-5-((1R,2R)-2-(1-methyl-1H-1,2,3-triazol-4-yl)cyclopropyl)-1H-pyrazole-4-carboxylate (53.3 mg, 0.102 mmol) in a mix of Methanol (1.25 mL) and Tetrahydrofuran (THF) (0.625 mL) was added LiOH (42.6 mg, 1.016 mmol) and Water (0.250 mL). The reaction was stirred at 50° C. for 15 h then concentrated. To the residue was added acetonitrile (5 mL), then the reaction was acidified with 1 M HCl to pH=3. The reaction was concentrated down. The crude product was dissolved in DMSO (2 mL) and purified with reverse-phase HPLC under acidic conditions to afford the title compound (29.2 mg, 57.9%). LC-MS m/z 497.2 (M+H)+, 0.89 min (ret. time). ¹H NMR (400 MHz, DMSO-d6) δ=7.98 (br. s., 1H), 7.60 (br. s., 1H), 7.42 (br. s., 9H), 3.95 (s, 3H), 3.63-3.50 (m, 1H), 3.15-3.00 (m, 1H), 2.76 (br. s., 2H), 2.21 (br. s., 1H), 1.82 (d, J=11.8 Hz, 1H), 1.72-1.43 (m, 3H), 1.26 (br. s., 3H), 0.90-0.80 (m, 1H).

Example 34. 5-((1R,2R)-2-(1-Methyl-1H-1,2,3-triazol-4-yl)cyclopropyl)-1-(3-(1-((R)-2-propylpiperidine-1-carbonyl)piperidin-3-yl)phenyl)-1H-pyrazole-4-carboxylic Acid

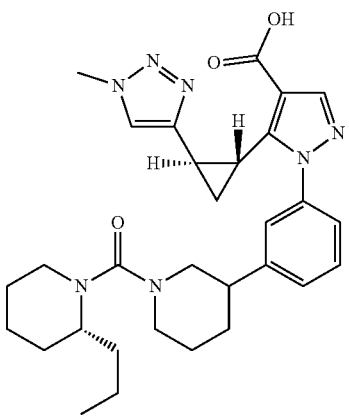 [SMILES: CCC[C@@H]1CCCCN1C(=O)N1CCCC(c2cccc(-n3ncc(C(=O)O)c3[C@@H]3C[C@H]3c3cn(C)nn3)c2)C1]

34a) ethyl 5-((1R,2R)-2-(1-methyl-1H-1,2,3-triazol-4-yl)cyclopropyl)-1-(3-(1-((R)-2-propylpiperidine-1-carbonyl)piperidin-3-yl)phenyl)-1H-pyrazole-4-carboxylate

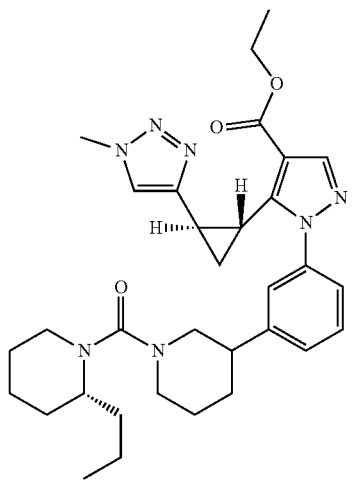 [SMILES: CCC[C@@H]1CCCCN1C(=O)N1CCCC(c2cccc(-n3ncc(C(=O)OCC)c3[C@@H]3C[C@H]3c3cn(C)nn3)c2)C1]

Ethyl 5-((1R,2R)-2-(1-methyl-1H-1,2,3-triazol-4-yl)cyclopropyl)-1-(3-(piperidin-3-yl)phenyl)-1H-pyrazole-4-carboxylate, Hydrochloride (50 mg, 0.109 mmol) was dissolved in Dichloromethane (DCM) (1.5 mL). Added TEA (0.046 mL, 0.328 mmol). The reaction was flushed with nitrogen and then triphosgene (10.71 mg, 0.036 mmol) was added. After stirring for 15 min, (R)-2-propylpiperidine (15.31 mg, 0.120 mmol) was added. The reaction was stirred for 18 h at RT, and then heated to 45° C. for 21 h. The reaction was concentrated and purified by flash chromatography on silica running from 100% Hex to 100% EtOAc. The desired fractions were concentrated to give the title compound (22.5 mg, 35.8% yield). LC-MS m/z 574.4 (M+H)⁺, 1.21 min (ret. time).

34b) 5-((1R,2R)-2-(1-Methyl-1H-1,2,3-triazol-4-yl)cyclopropyl)-1-(3-(1-((R)-2-propylpiperidine-1-carbonyl)piperidin-3-yl)phenyl)-1H-pyrazole-4-carboxylic Acid

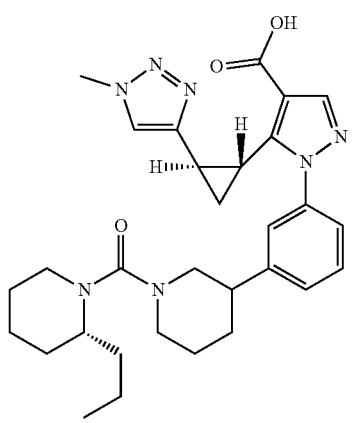 [SMILES: CCC[C@@H]1CCCCN1C(=O)N1CCCC(c2cccc(-n3ncc(C(=O)O)c3[C@@H]3C[C@H]3c3cn(C)nn3)c2)C1]

To a solution of ethyl 5-((1R,2R)-2-(1-methyl-1H-1,2,3-triazol-4-yl)cyclopropyl)-1-(3-(1-((R)-2-propylpiperidine-1-carbonyl)piperidin-3-yl)phenyl)-1H-pyrazole-4-carboxylate (22.5 mg, 0.039 mmol) in a mix of Methanol (1.25 mL) and Tetrahydrofuran (THF) (0.625 mL) was added LiOH (16.46 mg, 0.392 mmol) and water (0.250 mL). The reaction was stirred at 50° C. for 17 h then concentrated. To the residue was added acetonitrile (5 mL), then the reaction was acidified with 1 M HCl to pH=3. The reaction was concentrated down. The crude product was dissolved in DMSO (2 mL) and purified with reverse-phase HPLC under acidic conditions to afford the title compound (13.3 mg, 62.2%). LC-MS m/z 546.4 (M+H)⁺, 1.06 min (ret. time). ¹H NMR (DMSO-d₆) δ: 7.98 (s, 1H), 7.60 (d, J=5.3 Hz, 1H), 7.32-7.48 (m, 4H), 3.95 (s, 3H), 3.82 (br. s., 1H), 3.29-3.56 (m, 3H), 2.87-2.98 (m, 1H), 2.57-2.80 (m, 3H), 2.11-2.24 (m, 1H), 1.46-1.81 (m, 11H), 1.16-1.36 (m, 8H).

Example 35. 1-(3-(3-(2-cyclohexylethyl)piperidin-1-yl)phenyl)-5-((1R,2R)-2-(1-methyl-1H-1,2,3-triazol-4-yl)cyclopropyl)-1H-pyrazole-4-carboxylic Acid

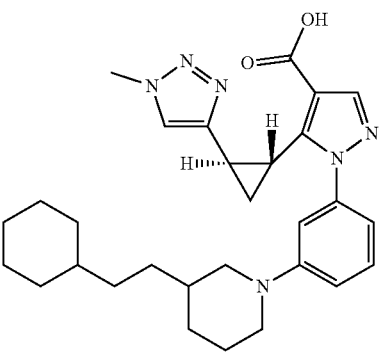 [SMILES: Cn1cc([C@@H]2C[C@H]2c2c(C(=O)O)cnn2-c2cccc(N3CCCC(CCC4CCCCC4)C3)c2)nn1]

35a) (E)-3-(2-Cyclohexylvinyl)pyridine

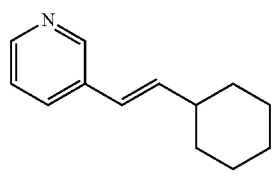 [SMILES: C(=C\C1CCCCC1)/c1cccnc1]

Weighed out (E)-(2-cyclohexylvinyl)boronic acid (3.05 g, 19.80 mmol), 3-bromopyridine (1.80 ml, 18.34 mmol) and cesium carbonate (12.05 g, 37.0 mmol). Added 1,4-Dioxane (150 ml) followed by Water (30.0 ml), then the flask was flushed with nitrogen. Tetrakis (2.25 g, 1.947 mmol) was added and the reaction was sealed and heated to 80° C. for 21 h. The reaction was concentrated down in vacuo. The residue was taken back up in DCM (250 mL) and washed with water (50 mL). The organic phase was concentrated and the compound was purified by flash chromatography on silica running from 100% Hex to 40% EtOAc/60% Hexane. The desired fractions were concentrated down to give the title compound (3.3568 g, 98% yield). LC-MS m/z 188.1 (M+H)⁺, 0.61 min (ret. time).

35b) 3-(2-Cyclohexylethyl)piperidine

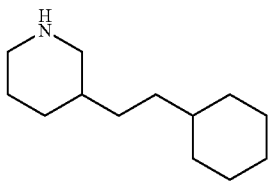 [SMILES: C1CCC(CCC2CCCNC2)CC1]

Dissolved (E)-3-(2-cyclohexylvinyl)pyridine (3.25 g, 17.35 mmol) in Ethanol (250 ml) and added AcOH (1.1 ml, 19.22 mmol). The reaction was run through the H-cube on continuous loop using a Rh catalyst (5%) at 80 bar and 100° C. at 1 mL/min for 24 h. The resulting solution was concentrated and then the residue was taken back up in DCM and washed once with satd NaHCO$_3$. The organic layer was dried with MgSO$_4$, filtered and concentrated in vacuo to give the title compound (3.2393 g, 96% yield). LC-MS m/z 196.0 (M+H)$^+$, 0.68 min (ret. time).

35c) Methyl 1-(3-(3-(2-cyclohexylethyl)piperidin-1-yl)phenyl)-5-((1R,2R)-2-(1-methyl-1H-1,2,3-triazol-4-yl)cyclopropyl)-1H-pyrazole-4-carboxylate

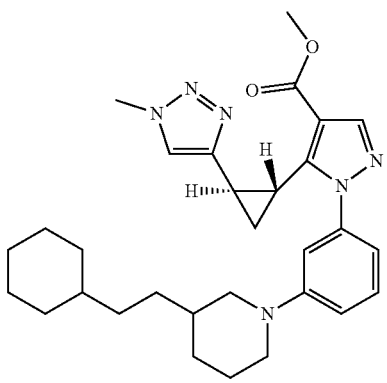 [SMILES: COC(=O)c1cnn(-c2cccc(N3CCCC(CCC4CCCCC4)C3)c2)c1[C@@H]1C[C@H]1c1cn(C)nn1]

To a suspension of methyl 1-(3-bromophenyl)-5-((1R,2R)-2-(1-methyl-1H-1,2,3-triazol-4-yl)cyclopropyl)-1H-pyrazole-4-carboxylate (439.2 mg, 1.092 mmol), 3-(2-cyclohexylethyl)piperidine (215 mg, 1.101 mmol), Pd$_2$(dba)$_3$ (60.0 mg, 0.066 mmol) and X-phos (85 mg, 0.178 mmol) in 1,4-dioxane (10 mL) was added K$_3$PO$_4$ (348 mg, 1.638 mmol). The reaction was then heated to 95° C. for 21 h. The reaction was cooled to room temp and more Pd$_2$(dba)$_3$ (55 mg, 0.061 mmol) and X-phos (85 mg, 0.178 mmol) were added and the reaction was heated for 3 days. The reaction was concentrated and purified by flash chromatography on silica running from 100% Hex to 100% EtOAc. The desired fractions were concentrated to give the title compound (236.1 mg, 41.9% yield). LC-MS m/z 517.5 (M+H)$^+$, 1.31 min (ret. time).

35d) 1-(3-(3-(2-Cyclohexylethyl)piperidin-1-yl)phenyl)-5-((1R,2R)-2-(1-methyl-1H-1,2,3-triazol-4-yl)cyclopropyl)-1H-pyrazole-4-carboxylic Acid

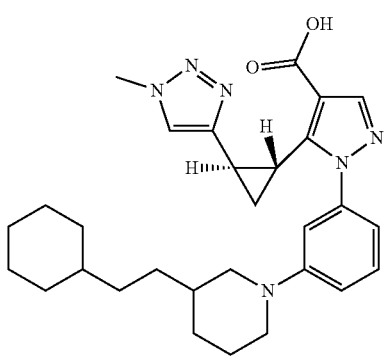 [SMILES: Cn1cc([C@@H]2C[C@H]2c2c(C(=O)O)cnn2-c2cccc(N3CCCC(CCC4CCCCC4)C3)c2)nn1]

To a solution of methyl 1-(3-(3-(2-cyclohexylethyl)piperidin-1-yl)phenyl)-5-((1R,2R)-2-(1-methyl-1H-1,2,3-triazol-4-yl)cyclopropyl)-1H-pyrazole-4-carboxylate (236.1 mg, 0.457 mmol) in a mix of Methanol (2.0 mL) and Tetrahydrofuran (THF) (1.000 mL) was added LiOH (192 mg, 4.57 mmol) and Water (0.400 mL). The reaction was heated at 50° C. for 17 h. The reaction was concentrated. To the residue was added acetonitrile (5 mL), then the reaction was acidified with 6N HCl to pH=3. The reaction was concentrated down. The crude product was dissolved in DMSO (4 mL) and purified with reverse-phase HPLC under acidic conditions (0.1% TFA). The desired fractions were concentrated down, and the resulting solid was taken up in water and lyophilized overnight to give the title compound (225.3 mg, 98% yield). LC-MS m/z 503.4 (M+H)$^+$, 1.18 min (ret. time). $^1$H NMR (DMSO-d$_6$) δ: 7.96 (s, 1H), 7.59 (s, 1H), 7.30-7.38 (m, 1H), 7.05-7.13 (m, 2H), 6.96 (d, J=7.0 Hz, 1H), 3.95 (s, 3H), 3.54 (t, J=11.8 Hz, 2H), 2.62-2.73 (m, 1H), 2.35-2.48 (m, 2H), 2.16-2.26 (m, 1H), 1.80 (d, J=12.3 Hz, 1H), 1.57-1.73 (m, 6H), 1.52 (d, J=11.0 Hz, 2H), 1.11-1.40 (m, 11H), 0.79-0.93 (m, 2H).

Example 36c 1-(3-((S)-3-(2-Cyclohexylethyl)piperidin-1-yl)phenyl)-5-((1R,2R)-2-(1-methyl-1H-1,2,3-triazol-4-yl)cyclopropyl)-1H-pyrazole-4-carboxylic Acid and

Example 36d 1-(3-((R)-3-(2-cyclohexylethyl)piperidin-1-yl)phenyl)-5-((1R,2R)-2-(1-methyl-1H-1,2,3-triazol-4-yl)cyclopropyl)-1H-pyrazole-4-carboxylic Acid

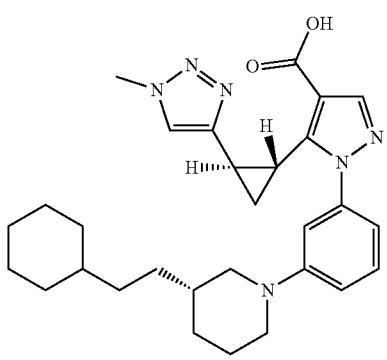 [SMILES: Cn1cc([C@@H]2C[C@H]2c2c(C(=O)O)cnn2-c2cccc(N3CCC[C@H](CCC4CCCCC4)C3)c2)nn1]

-continued

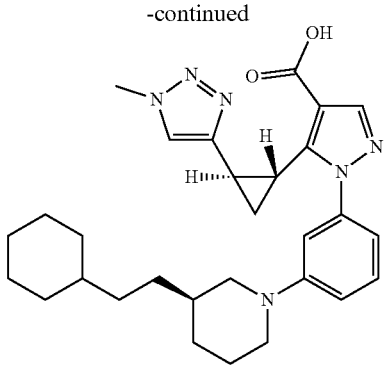

36a) Methyl 1-(3-((S)-3-(2-cyclohexylethyl)piperidin-1-yl)phenyl)-5-((1R,2R)-2-(1-methyl-1H-1,2,3-triazol-4-yl)cyclopropyl)-1H-pyrazole-4-carboxylate
and 36b) Methyl 1-(3-((R)-3-(2-cyclohexylethyl)piperidin-1-yl)phenyl)-5-((1R,2R)-2-(1-methyl-1H-1,2,3-triazol-4-yl)cyclopropyl)-1H-pyrazole-4-carboxylate

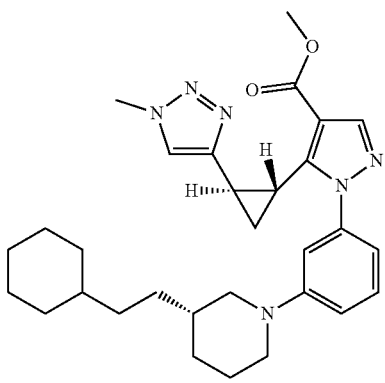

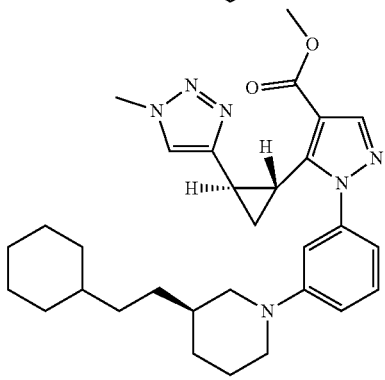

Methyl 1-(3-(3-(2-cyclohexylethyl)piperidin-1-yl)phenyl)-5-((1R,2R)-2-(1-methyl-1H-1,2,3-triazol-4-yl)cyclopropyl)-1H-pyrazole-4-carboxylate (181.9 mg) was separated into its enantiomers using the SFC system with a Chiralpak IB, 20×250 mm, 5u column and 30% ethanol as co-solvent and a flow rate of 50 g/min and backpressure of 100 bar. The desired fractions were concentrated to give the two isomers. Compound 36a, 40.0 mg, LC-MS m/z 517.4 (M+H)⁺, 1.29 min (ret. time)) and Compound 36b, 38.7 mg, LC-MS m/z 517.4 (M+H)⁺, 1.30 min (ret. time). The absolute configuration of each enantiomer was confirmed by VCD analysis.

36c) 1-(3-((S)-3-(2-Cyclohexylethyl)piperidin-1-yl)phenyl)-5-((1R,2R)-2-(1-methyl-1H-1,2,3-triazol-4-yl)cyclopropyl)-1H-pyrazole-4-carboxylic Acid

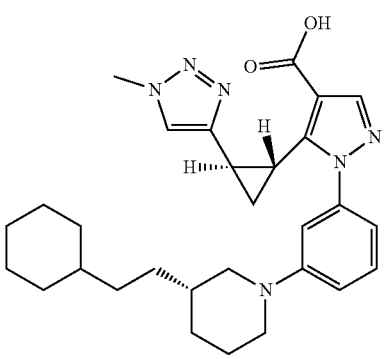

To a solution of methyl 1-(3-((S)-3-(2-cyclohexylethyl)piperidin-1-yl)phenyl)-5-((1R,2R)-2-(1-methyl-1H-1,2,3-triazol-4-yl)cyclopropyl)-1H-pyrazole-4-carboxylate (32.7 mg, 0.063 mmol) in a mix of Methanol (2.0 mL) and Tetrahydrofuran (THF) (1.000 mL) was added LiOH (26.6 mg, 0.633 mmol) and Water (0.400 mL). The reaction was stirred at 50° C. for 20 h then concentrated. To the residue was added acetonitrile (5 mL), then the reaction was acidified with 6 N HCl to pH=3. The reaction was concentrated down. The crude product was dissolved in DMSO (2 mL) and purified with reverse-phase HPLC under acidic conditions to afford the title compound (31.9 mg, 100%). LC-MS m/z 503.4 (M+H)⁺, 1.15 min (ret. time). ¹H NMR (DMSO-d₆) δ: 7.95 (s, 1H), 7.59 (s, 1H), 7.33 (s, 1H), 7.02-7.12 (m, 2H), 6.94 (d, J=6.8 Hz, 1H), 3.95 (s, 3H), 3.55 (t, J=8.9 Hz, 2H), 2.59-2.70 (m, 1H), 2.31-2.48 (m, 2H), 2.22 (d, J=8.0 Hz, 1H), 1.75-1.83 (m, 1H), 1.67 (t, J=12.3 Hz, 7H), 1.50 (br. s., 3H), 1.11-1.39 (m, 11H).

36d) 1-(3-((R)-3-(2-Cyclohexylethyl)piperidin-1-yl)phenyl)-5-((1R,2R)-2-(1-methyl-1H-1,2,3-triazol-4-yl)cyclopropyl)-1H-pyrazole-4-carboxylic Acid

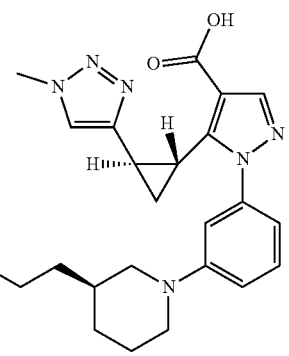

To a solution of methyl 1-(3-((R)-3-(2-cyclohexylethyl)piperidin-1-yl)phenyl)-5-((1R,2R)-2-(1-methyl-1H-1,2,3-triazol-4-yl)cyclopropyl)-1H-pyrazole-4-carboxylate (31.4 mg, 0.061 mmol) in a mix of Methanol (2.0 mL) and Tetrahydrofuran (THF) (1.000 mL) was added LiOH (25.5 mg, 0.608 mmol) and Water (0.400 mL).). The reaction was stirred at 50° C. for 20 h then concentrated. To the residue was added acetonitrile (5 mL), then the reaction was acidified with 6 N HCl to pH=3. The reaction was concentrated down. The crude product was dissolved in DMSO (2 mL) and purified with reverse-phase HPLC under acidic conditions to afford the title compound (26.4 mg, 86%). LC-MS m/z 503.4 (M+H)$^+$, 1.16 min (ret. time). $^1$H NMR (DMSO-d$_6$) δ: 7.96 (s, 1H), 7.59 (s, 1H), 7.35 (t, J=7.8 Hz, 1H), 7.06-7.13 (m, 2H), 6.97 (d, J=6.0 Hz, 1H), 3.95 (s, 3H), 3.54 (t, J=13.2 Hz, 2H), 2.68 (br. s., 1H), 2.32-2.47 (m, 2H), 2.15-2.24 (m, 1H), 1.79 (d, J=12.0 Hz, 1H), 1.57-1.73 (m, 7H), 1.52 (d, J=10.0 Hz, 2H), 1.34-1.40 (m, 1H), 1.10-1.31 (m, 11H).

Example 37. 1-(3-((1,3-cis)-3-(6-Butyl-5,6-dihydro-cyclopenta[c]pyrazol-1(4H)-yl)cyclohexyl)phenyl)-5-cyclopropyl-1H-pyrazole-4-carboxylic Acid

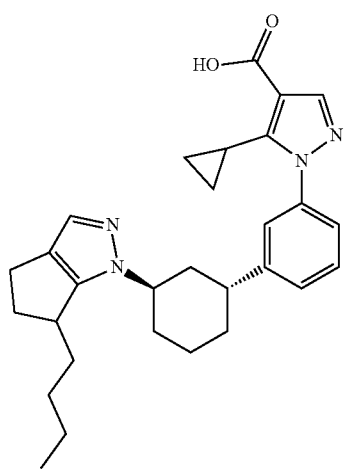 [SMILES: CCCCC1CCc2cnn([C@@H]3CCC[C@@H](c4cccc(-n5ncc(C(=O)O)c5C5CC5)c4)C3)c21]

37a) 2-Butyl-5-((dimethylamino)methylene)cyclopentanone

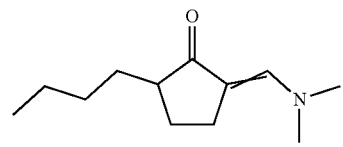

1-tert-butoxy-N,N,N',N'-tetramethylmethanediamine (186 mg, 1.070 mmol) was added dropwise to 2-butylcyclopentanone (150 mg, 1.070 mmol) under nitrogen atmosphere at ambient temperature. The reaction mixture was stirred at ambient temperature under nitrogen for 1 h, then at 110° C. for 2.5 h. The reaction mixture was stored in the refrigerator overnight. The crude product was carried forward. LC-MS m/z 196.1 (M+H)$^+$, 0.91 min (ret. time).

37b) Ethyl 1-(3-((1,3-cis)-3-(6-butyl-5,6-dihydrocyclopenta[c]pyrazol-1(4H)-yl)cyclohexyl)phenyl)-5-cyclopropyl-1H-pyrazole-4-carboxylate

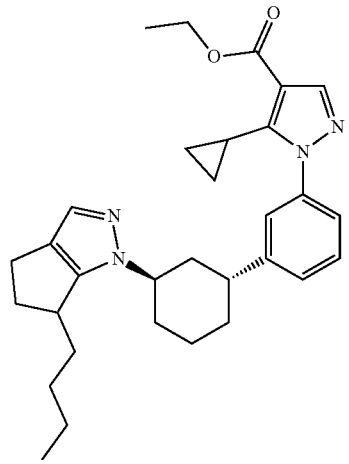 [SMILES: CCCCC1CCc2cnn([C@@H]3CCC[C@@H](c4cccc(-n5ncc(C(=O)OCC)c5C5CC5)c4)C3)c21]

To a solution of ethyl 5-cyclopropyl-1-(3-((1,3-cis)-3-hydrazinylcyclohexyl)phenyl)-1H-pyrazole-4-carboxylate hydrochloride (60 mg, 0.148 mmol) in acetic acid (1.5 mL) was added 2-butyl-5-((dimethylamino)methylene)cyclopentanone (28.9 mg, 0.148 mmol). The reaction mixture was stirred at reflux for 3 h. The reaction mixture was allowed to cool to ambient temperature and stirred for 86 h. The reaction mixture was concentrated and the crude product was dissolved in DMSO (2 mL) and purified on a Gilson HPLC, eluting at 20 mL/min with a linear gradient running from 60% CH$_3$CN/H$_2$O to 100% CH$_3$CN/H$_2$O. The desired fractions were concentrated to afford the title compound (32.5 mg, 0.065 mmol, 43.8% yield). LC-MS m/z 501.2 (M+H)$^+$, 1.54 min (ret. time).

37c) 1-(3-((1,3-cis)-3-(6-Butyl-5,6-dihydrocyclopenta[c]pyrazol-1(4H)-yl)cyclohexyl)phenyl)-5-cyclopropyl-1H-pyrazole-4-carboxylic Acid

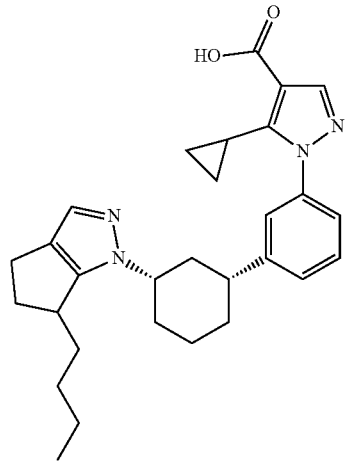 [SMILES: CCCCC1CCc2cnn([C@H]3CCC[C@@H](c4cccc(-n5ncc(C(=O)O)c5C5CC5)c4)C3)c21]

To a solution of ethyl 1-(3-((1,3-cis)-3-(6-butyl-5,6-dihydrocyclopenta[c]pyrazol-1(4H)-yl)cyclohexyl)phenyl)-5-cyclopropyl-1H-pyrazole-4-carboxylate (32.5 mg, 0.065 mmol) in methanol (0.5 mL) was added 2M LiOH (0.195 mL, 0.389 mmol). The reaction vessel was heated in a Biotage microwave at high absorption for 30 min at 80° C. The reaction vessel was heated in a Biotage microwave at high absorption for 30 min at 80° C. LCMS showed evidence of further hydrolysis however the reaction was incomplete. To the reaction mixture was added 2M LiOH (0.1 mL). The reaction vessel was heated in a Biotage microwave at high absorption for 30 min at 80° C. The reaction vessel was heated in a Biotage microwave at high absorption for 30 min at 100° C. LCMS showed reaction nearly complete. The reaction mixture was stirred at ambient temperature for 23.5 h. LCMS showed methyl ester still remained. The reaction vessel was heated in a Biotage microwave at high absorption for 15 min at 100° C. The reaction mixture was concentrated and the crude product dissolved in DMSO (2 mL). It was purified by Gilson HPLC under acidic conditions (0.1% TFA as modifier) to give the title compound (8.89 mg, 0.019 mmol, 29.0% yield). LC-MS m/z 473.3 (M+H)+, 1.22 min (ret. time) $^1$H NMR (400 MHz, methanol-d$_4$) δ ppm: 0.62 (d, J=5.27 Hz, 2H) 0.85-0.97 (m, 5H) 1.26-1.47 (m, 4H) 1.55-2.37 (m, 13H) 2.58-2.82 (m, 4H) 2.97 (t, J=11.67 Hz, 1H) 4.49 (t, J=11.42 Hz, 1H) 7.40-7.57 (m, 5H) 8.00 (s, 1H).

Example 38. 1-(3-((1,3-trans)-3-(6-Butyl-5,6-dihydrocyclopenta[c]pyrazol-1(4H)-yl)cyclohexyl)phenyl)-5-cyclopropyl-1H-pyrazole-4-carboxylic Acid

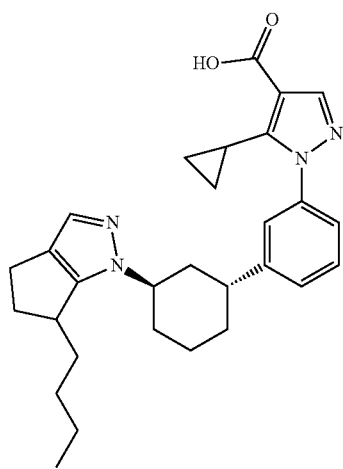 [SMILES: CCCCC1CCc2cnn([C@@H]3CCC[C@@H](c4cccc(-n5ncc(C(=O)O)c5C5CC5)c4)C3)c21]

38a) Ethyl 1-(3-((1,3-trans)-3-(6-butyl-5,6-dihydrocyclopenta[c]pyrazol-1(4H)-yl)cyclohexyl)phenyl)-5-cyclopropyl-1H-pyrazole-4-carboxylate

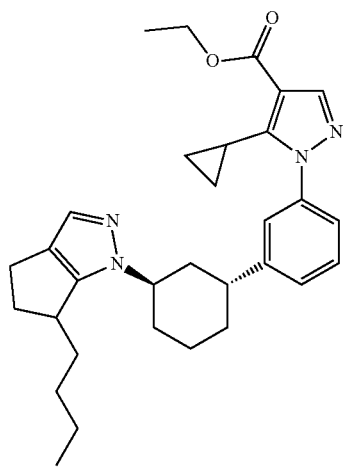 [SMILES: CCCCC1CCc2cnn([C@@H]3CCC[C@@H](c4cccc(-n5ncc(C(=O)OCC)c5C5CC5)c4)C3)c21]

To a solution of ethyl 5-cyclopropyl-1-(3-((1S,3S)-3-hydrazinylcyclohexyl)phenyl)-1H-pyrazole-4-carboxylate hydrochloride (80 mg, 0.198 mmol) in acetic acid (1.5 mL) was added 2-butyl-5-((dimethylamino)methylene)cyclopentanone (38.6 mg, 0.198 mmol). The reaction mixture was stirred at reflux for 2.5 h. The reaction mixture was concentrated and the crude product was dissolved in DCM (1 mL). The crude product was purified on a silica cartridge (12 g) with a Combiflash Companion, eluting at 20 mL/min with a gradient running from 50% EtOAc/hexanes to 90% EtOAc/hexanes over 35 min. The desired fractions were concentrated to afford the title compound (75.2 mg, 0.150 mmol, 76% yield). LC-MS m/z 501.2 (M+H)+, 1.48 min (ret. time).

38b) 1-(3-((1,3-trans)-3-(6-Butyl-5,6-dihydrocyclopenta[c]pyrazol-1(4H)-yl)cyclohexyl)phenyl)-5-cyclopropyl-1H-pyrazole-4-carboxylic Acid

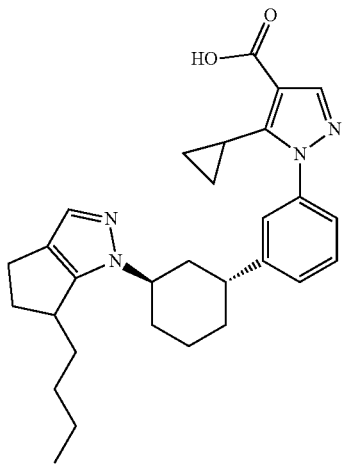 [SMILES: CCCCC1CCc2cnn([C@@H]3CCC[C@@H](c4cccc(-n5ncc(C(=O)O)c5C5CC5)c4)C3)c21]

To a solution of ethyl 1-(3-((1,3-trans)-3-(6-butyl-5,6-dihydrocyclopenta[c]pyrazol-1(4H)-yl)cyclohexyl)phenyl)-5-cyclopropyl-1H-pyrazole-4-carboxylate (75.2 mg, 0.150 mmol) in methanol (0.5 mL) was added LiOH (0.451 mL, 0.901 mmol). The reaction vessel was heated in a Biotage microwave at high absorption for 30 min at 80° C. After cooling the reaction LCMS showed evidence of methyl ester and carboxylic acid hydrolysis products. The reaction vessel was heated in a Biotage microwave at high absorption for 30 min at 100° C. LCMS showed minor evidence of methyl ester remaining. The reaction vessel was heated in a Biotage microwave at high absorption for 30 min at 100° C. LCMS showed good conversion. The reaction mixture was neutralized with 1 N HCl and concentrated to afford the crude product. The crude product was dissolved in DMSO (2 mL) and purified on a Gilson HPLC eluting at 20 mL/min with a linear gradient running from 40% CH$_3$CN/H$_2$O (0.1% TFA) to 90% CH$_3$CN/H$_2$O (0.1% TFA) over 15 min. The desired fractions were concentrated to afford the title compound (38.51 mg, 0.081 mmol, 54.2% yield). LC-MS m/z 473.3 (M+H)+, 1.25 min (ret. time) $^1$H NMR (400 MHz, methanol-d4) δ ppm: 0.63 (d, J=5.27 Hz, 2H) 0.82-0.97 (m, 5H) 1.12-1.35 (m, 4H) 1.37-1.68 (m, 2H) 1.75 (m, J=8.30 Hz, 2H) 1.91-2.15 (m, 5H) 2.19-2.42 (m, 3H) 2.48-2.62 (m, 1H) 2.68 (m, J=8.40, 8.40 Hz, 2H) 3.14 (m, J=7.80 Hz, 1H) 3.48-3.56 (m, 1H) 4.40 (br. s., 1H) 7.32 (s, 1H) 7.43 (d, J=7.03 Hz, 1H) 7.49-7.58 (m, 3H) 8.01 (s, 1H).

Example 39. 1-(3-((1R,3S)-3-(6,6-Dimethyl-5,6-dihydrocyclopenta[c]pyrazol-1(4H)-yl)cyclohexyl)phenyl)-5-(2-(1-methyl-1H-1,2,3-triazol-4-yl)cyclopropyl)-1H-pyrazole-4-carboxylic Acid

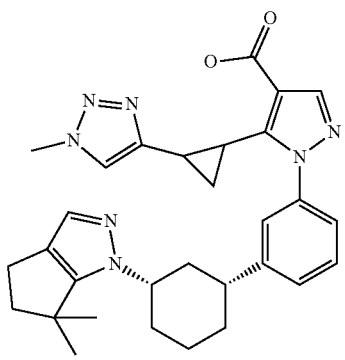 [SMILES: Cn1cc(C2CC2c2c(C(=O)O)cnn2-c2cccc([C@@H]3CCC[C@H](n4ncc5c4C(C)(C)CC5)C3)c2)nn1]

39a) 4-(Diethoxymethyl)-1-methyl-1H-1,2,3-triazole

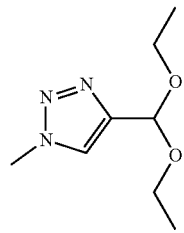

A solution of iodomethane (166 g, 1170 mmol) in tert-butanol (500 mL) was added to NaHCO₃ (98 g, 1170 mmol), copper(II) sulfate (12.45 g, 78 mmol), sodium azide (76 g, 1170 mmol) and sodium (R)-2-((S)-1,2-dihydroxyethyl)-4-hydroxy-5-oxo-2,5-dihydrofuran-3-olate (30.9 g, 156 mmol) in water (500 mL) slowly at room temperature. Then 3,3-diethoxyprop-1-yne (50 g, 390 mmol) was added. The reaction mixture was stirred at 60° C. for 16 h. The reaction mixture was extracted with ethyl acetate (3×1000 mL). The combined organic layer was dried with MgSO₄ and concentrated to obtain the title compound 4-(diethoxymethyl)-1-methyl-1H-1,2,3-triazole (46 g, 236 mmol, 60.5% yield) which was carried over to next step without further purification. LC-MS m/z 186.1 (M+H)⁺, 1.46 min (ret. time).

39b) 1-Methyl-1H-1,2,3-triazole-4-carbaldehyde

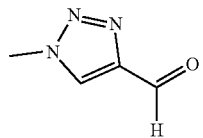

To a solution of 4-(diethoxymethyl)-1-methyl-1H-1,2,3-triazole (46 g, 248 mmol) in water (200 mL), TFA (100 mL, 649 mmol) was added. The reaction mixture was stirred at room temperature for 1 h. The water was evaporated and dried under vacuum to get the title compound, 1-methyl-1H-1,2,3-triazole-4-carbaldehyde (26 g, 234 mmol, 94% yield) as a yellow solid. LC-MS m/z 112.2 (M+H)⁺, 0.51 min (ret. time).

39c) (E)-tert-Butyl 3-(1-methyl-1H-1,2,3-triazol-4-yl)acrylate

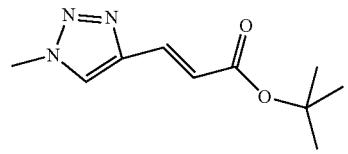

To a solution of tert-butyl 2-(diethoxyphosphoryl)acetate (62.4 g, 248 mmol) in tetrahydrofuran (500 mL), sodium hydride (10.80 g, 270 mmol, 60%) was added at 0° C. The reaction mixture was stirred at 0° C. under N₂ for 10 min. Then a solution of 1-methyl-1H-1,2,3-triazole-4-carbaldehyde (25 g, 225 mmol) in THF (500 mL) was added dropwise and the reaction mixture was stirred at 0° C. for 15 min. Water (500 mL) was added and extracted with ethyl acetate (3×300 mL). The combined organic layer was washed with water (2×100 mL) and brine (2×100 mL), dried over Na₂SO₄ and concentrated. The crude product was purified by Combiflash chromatography (hexane:ethyl acetate=1:5) to give the title compound (E)-tert-butyl 3-(1-methyl-1H-1,2,3-triazol-4-yl)acrylate (40 g, 184 mmol, 82% yield) as an oil. LC-MS m/z 210.1 (M+H)⁺, 1.73 min (ret. time).

39d) tert-Butyl 2-(1-methyl-1H-1,2,3-triazol-4-yl)cyclopropanecarboxylate

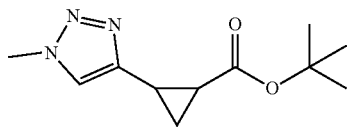 [SMILES: Cn1cc(C2CC2C(=O)OC(C)(C)C)nn1]

To a solution of trimethylsulfoxonium iodide (126 g, 573 mmol) in dimethyl sulfoxide (300 mL), sodium hydride (16.06 g, 401 mmol) was added at 0° C. The reaction mixture was stirred at room temperature under N₂ for 1 h. Then a solution of (E)-tert-butyl 3-(1-methyl-1H-1,2,3-triazol-4-yl)acrylate (40 g, 191 mmol) in tetrahydrofuran (300 mL) was added dropwise. The reaction mixture was stirred at room temperature for 1 hr and heated to 50° C. for another 1 h. Then 200 mL of ethyl acetate and 250 mL of water were added. The water layer was extracted with ethyl acetate (3×250 mL), the combined organic layer was dried with Na₂SO₄ and concentrated to give the title compound (36 g, 144 mmol, 75% yield). LC-MS m/z 224.1 (M+H)⁺, 1.69 min (ret. time).

39e) 2-(1-Methyl-1H-1,2,3-triazol-4-yl)cyclopropanecarboxylic Acid

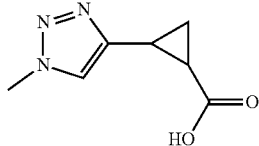

A solution of tert-butyl 2-(1-methyl-1H-1,2,3-triazol-4-yl)cyclopropanecarboxylate (36 g, 161 mmol) in dichloromethane (400 mL), TFA (200 mL, 2596 mmol) was added slowly under nitrogen at room temperature. The reaction mixture was stirred at room temperature for 4 h. It was concentrated. 100 mL of ethyl acetate and 100 mL of water were added to residue. The water layer was extracted with ethyl acetate (3×100 mL). The combined organic phase was dried with MgSO$_4$ and concentrated to get title compound 2-(1-methyl-1H-1,2,3-triazol-4-yl)cyclopropanecarboxylic acid (24 g, 134 mmol, 83% yield) as a white solid. LC-MS m/z 168.1 (M+H)$^+$, 1.16 min (ret. time).

39f) Methyl 3-(2-(1-methyl-1H-1,2,3-triazol-4-yl)cyclopropyl)-3-oxopropanoate

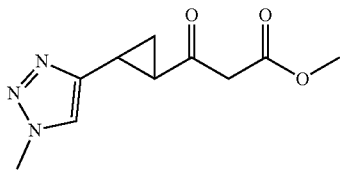 [SMILES: COC(=O)CC(=O)C1CC1c1cn(C)nn1]

To a solution of 2-(1-methyl-1H-1,2,3-triazol-4-yl)cyclopropanecarboxylic acid (24 g, 144 mmol) in tetrahydrofuran (700 mL), was added CDI (30.3 g, 215 mmol) was added. The reaction mixture was stirred at room temperature for 2 h. Then potassium 3-methoxy-3-oxopropanoate (67.3 g, 431 mmol) was added. The reaction mixture was stirred at room temperature for 18 h. The solvent was evaporated and re-dissolved in ethyl acetate (200 mL). Then it was washed with 1 M KHSO$_4$ (150 mL), saturated NaHCO$_3$ (150 mL) and brine (150 mL). The organic layer was dried with Na$_2$SO$_4$ and concentrated to obtain the title compound methyl 3-(2-(1-methyl-1H-1,2,3-triazol-4-yl)cyclopropyl)-3-oxopropanoate (20 g, 85 mmol, 59.3% yield) as an oil. LC-MS m/z 224.1 (M+H)$^+$, 1.39 min (ret. time).

39g) Methyl 1-(3-bromophenyl)-5-(2-(1-methyl-1H-1,2,3-triazol-4-yl)cyclopropyl)-1H-pyrazole-4-carboxylate

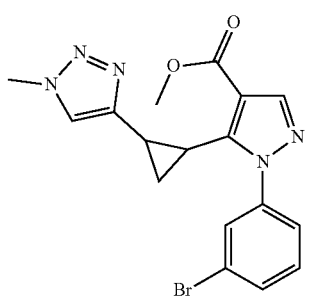 [SMILES: COC(=O)c1cnn(-c2cccc(Br)c2)c1C1CC1c1cn(C)nn1]

A solution of methyl 3-(dimethylamino)-2-(2-(1-methyl-1H-1,2,3-triazol-4-yl)cyclopropanecarbonyl)acrylate (10 g, 35.9 mmol) in acetonitrile (100 mL) was added to (3-bromophenyl)hydrazine hydrochloride (9.64 g, 43.1 mmol) slowly under nitrogen at room temperature. The reaction mixture was stirred at room temperature for 16 h. Then 200 mL of water was added and extracted with ethyl acetate (3×500 mL). The combined organic layer was dried with Na$_2$SO$_4$ and concentrated. The crude product was purified by Combiflash chromatography (hexane:ethyl acetate=4:1) to give the title compound methyl 1-(3-bromophenyl)-5-(2-(1-methyl-1H-1,2,3-triazol-4-yl)cyclopropyl)-1H-pyrazole-4-carboxylate (14 g, 34.8 mmol, 97% yield). LC-MS m/z 204.1 (M+H)$^+$, 1.81 min (ret. time).

39h) Methyl 5-(2-(1-methyl-1H-1,2,3-triazol-4-yl)cyclopropyl)-1-(3-(4,4,5,5-tetramethyl-1,3,2-dioxaborolan-2-yl)phenyl)-1H-pyrazole-4-carboxylate

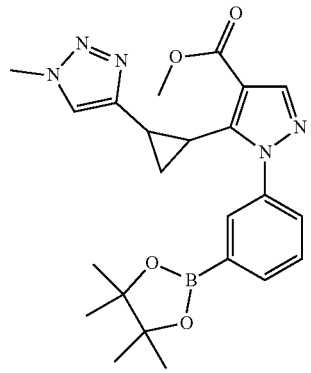 [SMILES: COC(=O)c1cnn(-c2cccc(B3OC(C)(C)C(C)(C)O3)c2)c1C1CC1c1cn(C)nn1]

To a solution of methyl 1-(3-bromophenyl)-5-(2-(1-methyl-1H-1,2,3-triazol-4-yl)cyclopropyl)-1H-pyrazole-4-carboxylate (14 g, 34.8 mmol) in 1,4-dioxane (200 mL) was added potassium acetate (6.83 g, 69.6 mmol), bis(pinacolato)diboron (13.26 g, 52.2 mmol) and the reaction mixture was degassed with argon for 30 min and then PdCl$_2$(dppf)-CH$_2$Cl$_2$ adduct (2.84 g, 3.48 mmol) was added. The reaction mixture was stirred at 100° C. for 16 h. After it was cooled to room temperature, it was filtered through Celite pad and the filtrate was concentrated. The crude product was purified by Combiflash chromatography (hexane:ethyl acetate=2:1) to get the title compound methyl 5-(2-(1-methyl-1H-1,2,3-triazol-4-yl)cyclopropyl)-1-(3-(4,4,5,5-tetramethyl-1,3,2-dioxaborolan-2-yl)phenyl)-1H-pyrazole-4-carboxylate (15 g, 23.37 mmol, 67.1% yield) as white solid. LC-MS m/z 450.1 (M+H)$^+$, 1.69 min (ret. time).

39i) Methyl 5-(2-(1-methyl-1H-1,2,3-triazol-4-yl)cyclopropyl)-1-(3-(3-oxocyclohexyl)phenyl)-1H-pyrazole-4-carboxylate

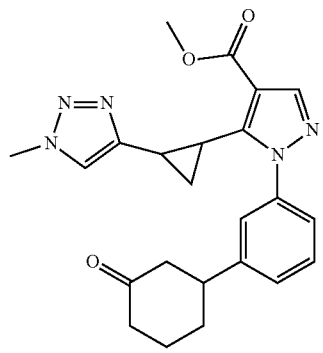 [SMILES: COC(=O)c1cnn(-c2cccc(C3CCCC(=O)C3)c2)c1C1CC1c1cn(C)nn1]

To a solution of methyl 5-(2-(1-methyl-1H-1,2,3-triazol-4-yl)cyclopropyl)-1-(3-(4,4,5,5-tetramethyl-1,3,2-dioxaborolan-2-yl)phenyl)-1H-pyrazole-4-carboxylate (1.5 g, 3.34 mmol), [RhCl(cod)]$_2$ (0.082 g, 0.167 mmol), and cyclohex-2-enone (0.321 g, 3.34 mmol) in 1,4-dioxane (13.20 mL) and water (4 mL) was added triethylamine (0.931 mL, 6.68 mmol). The reaction mixture was stirred at 95° C. for 90 min. The reaction mixture was filtered, diluted with H$_2$O (15 mL) and extracted with EtOAc (3×15 mL). The combined organic layer was dried over MgSO$_4$, filtered and concentrated to afford the crude product. The crude product was purified on a silica cartridge (24 g) with a Combiflash Companion, eluting at 35 mL/min with a gradient running from 0% EtOAc/hexanes to 90 EtOAc/hexanes over 65.5 min. The desired fractions were concentrated to afford the title compound (1.13 g, 2.69 mmol, 81% yield). LC-MS m/z 420.2 (M+H)$^+$, 0.84 min (ret. time).

39j) Methyl 1-(3-(-3-(2-(tert-butoxycarbonyl)hydrazinyl)cyclohexyl)phenyl)-5-(2-(1-methyl-1H-1,2,3-triazol-4-yl)cyclopropyl)-1H-pyrazole-4-carboxylate and methyl 1-(3-((1S,3S)-3-(2-(tert-butoxycarbonyl)hydrazinyl)cyclohexyl)phenyl)-5-(2-(1-methyl-1H-1,2,3-triazol-4-yl)cyclopropyl)-1H-pyrazole-4-carboxylate

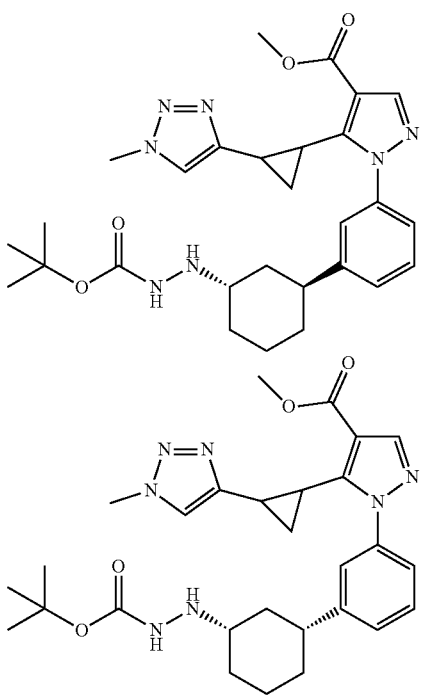

To a solution of methyl 5-(2-(1-methyl-1H-1,2,3-triazol-4-yl)cyclopropyl)-1-(3-(3-oxocyclohexyl)phenyl)-1H-pyrazole-4-carboxylate (1.13 g, 2.69 mmol), acetic acid (0.185 mL, 3.23 mmol) and sodium triacetoxyborohydride (0.685 g, 3.23 mmol) in dichloromethane (DCM) (10 mL) was added tert-butyl hydrazinecarboxylate (0.356 g, 2.69 mmol). The reaction mixture was stirred at ambient temperature for 1.5 h. LCMS showed starting material remained. The reaction mixture was stirred at ambient temperature for 15.5 h. LCMS showed similar conversion. To the reaction mixture was added tert-butyl hydrazine carboxylate (0.178 g, 1.345 mmol) and sodium triacetoxyborohydride (0.342 g, 1.62 mmol). The reaction mixture was stirred at ambient temperature for 3 h. LCSM showed further conversion, however starting material still remained. The reaction mixture was stirred at ambient temperature for 70 h (over the weekend). LCMS showed minor evidence of starting material. To the reaction mixture was added sodium triacetoxyborohydride (0.342 g, 1.62 mmol) and acetic acid (0.092 mL, 1.62 mmol). The reaction mixture was stirred at ambient temperature for 4 h. LCMS (3) showed reaction nearly complete. The reaction mixture was diluted with H$_2$O (15 mL) and extracted with DCM (3×15 mL). The combined organic layer was washed with brine, dried over MgSO$_4$, filtered and concentrated to afford the crude product. The crude product was purified on a silica cartridge (40 g) with a Combiflash Companion, eluting at 30 mL/min with a gradient running from 0 EtOAc/hexanes to 40% EtOAc/hexanes over 40 min. The desired fractions were concentrated to afford the title compounds methyl 1-(3-((1R,3S)-3-(2-(tert-butoxycarbonyl)hydrazinyl)cyclohexyl)phenyl)-5-(2-(1-methyl-1H-1,2,3-triazol-4-yl)cyclopropyl)-1H-pyrazole-4-carboxylate (cis) (260 mg, 0.485 mmol, 18.02% yield) LC-MS m/z 536.3 (M+H)$^+$, 0.97 min (ret. time) and methyl 1-(3-((1S,3S)-3-(2-(tert-butoxycarbonyl)hydrazinyl)cyclohexyl)phenyl)-5-(2-(1-methyl-1H-1,2,3-triazol-4-yl)cyclopropyl)-1H-pyrazole-4-carboxylate (trans) (780 mg, 1.456 mmol, 54.1% yield) LC-MS m/z 536.3 (M+H)$^+$, 0.92 min (ret. time).

39k) Methyl 1-(3-((1,3-cis)-3-hydrazinylcyclohexyl)phenyl)-5-(2-(1-methyl-1H-1,2,3-triazol-4-yl)cyclopropyl)-1H-pyrazole-4-carboxylate hydrochloride

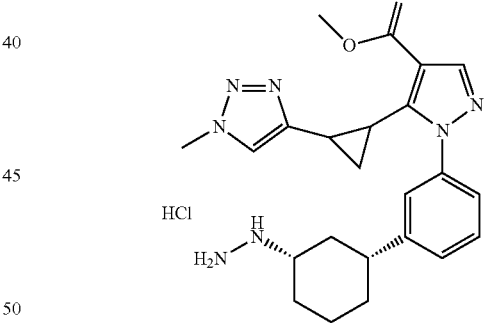

To a solution of methyl 1-(3-((1,3 cis)-3-(2-(tert-butoxycarbonyl)hydrazinyl)cyclohexyl)phenyl)-5-(2-(1-methyl-1H-1,2,3-triazol-4-yl)cyclopropyl)-1H-pyrazole-4-carboxylate (260 mg, 0.485 mmol) in dichloromethane (DCM) (4 mL) was added 4M HCl in dioxane (0.400 mL, 1.602 mmol). The reaction mixture was stirred at ambient temperature for 16.5 h. LCMS showed good conversion although some starting material remained. To the reaction mixture was added HCl in dioxane (4M, 0.500 mL). The reaction mixture was stirred at ambient temperature for an additional 1.5 h. The reaction mixture was concentrated to afford the title compound (115.9 mg, 0.246 mmol, 50.6% yield) an HCl salt. LC-MS m/z 436.3 (M+H)$^+$, 0.67 min (ret. time).

39l) 5-((Dimethylamino)methylene)-2,2-dimethylcyclopentanone

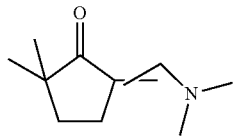

1-tert-butoxy-N,N,N',N'-tetramethylmethanediamine (368 μL, 1.783 mmol) was added dropwise to a vial containing 2,2-dimethylcyclopentanone (200 mg, 1.783 mmol) under nitrogen atmosphere at ambient temperature. The reaction mixture was stirred at ambient temperature under nitrogen atmosphere for 45 min, then at 110° C. for 2 h. LCMS showed evidence of desired product. The crude product (282.4 mg, 1.689 mmol, 95% yield) was carried forward to subsequent reactions. LC-MS m/z 167.9 (M+H)+, 0.64 min (ret. time).

39m) Methyl 1-(3-((1,3-cis)-3-(6,6-dimethyl-5,6-dihydrocyclopenta[c]pyrazol-1(4H)-yl)cyclohexyl)phenyl)-5-(2-(1-methyl-1H-1,2,3-triazol-4-yl)cyclopropyl)-1H-pyrazole-4-carboxylate

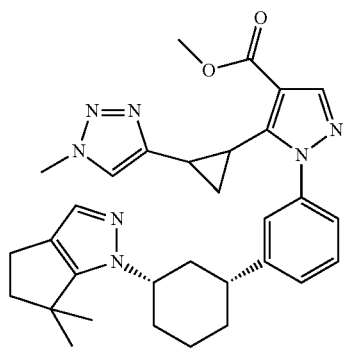 [SMILES: COC(=O)c1cnn(-c2cccc([C@@H]3CCC[C@H](n4ncc5c4C(C)(C)CC5)C3)c2)c1C1CC1c1cn(C)nn1]

To a solution of methyl 1-(3-((1,3-cis)-3-hydrazinylcyclohexyl)phenyl)-5-(2-(1-methyl-1H-1,2,3-triazol-4-yl)cyclopropyl)-1H-pyrazole-4-carboxylate hydrochloride (50 mg, 0.106 mmol) in acetic acid (1 mL) was added 5-((dimethylamino)methylene)-2,2-dimethylcyclopentanone (17.72 mg, 0.106 mmol). The reaction mixture was stirred at reflux for 2 h. The reaction mixture was neutralized with NaOH and concentrated. The remaining solid residue was diluted with water and extracted with EtOAc (3×). The combined organic layers were concentrated. The crude product was dissolved in DMSO (2 mL) and purified on a Gilson HPLC, eluting at 20 mL/min with a linear gradient running from 40% CH₃CN/H₂O to 90% CH₃CN/H₂O over 15 min. The desired fractions were concentrated to afford the title compound (14.6 mg, 0.027 mmol, 25.5% yield). LC-MS m/z 540.4 (M+H)+, 1.13 min (ret. time).

39n) 1-(3-((1,3-cis)-3-(6,6-Dimethyl-5,6-dihydrocyclopenta[c]pyrazol-1(4H)-yl)cyclohexyl)phenyl)-5-(2-(1-methyl-1H-1,2,3-triazol-4-yl)cyclopropyl)-1H-pyrazole-4-carboxylic Acid

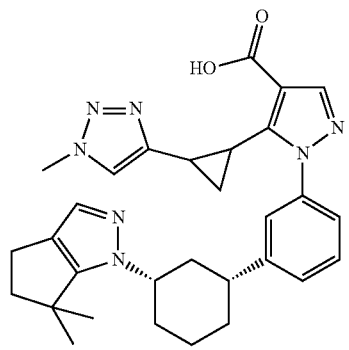 [SMILES: Cn1cc(C2CC2c2c(C(=O)O)cnn2-c2cccc([C@@H]3CCC[C@H](n4ncc5c4C(C)(C)CC5)C3)c2)nn1]

To a solution of methyl 1-(3-((1,3-cis)-3-(6,6-dimethyl-5,6-dihydrocyclopenta[c]pyrazol-1 (4H)-yl)cyclohexyl)phenyl)-5-(2-(1-methyl-1H-1,2,3-triazol-4-yl)cyclopropyl)-1H-pyrazole-4-carboxylate (14.6 mg, 0.027 mmol) in methanol (0.25 mL) was added LiOH (0.081 mL, 0.162 mmol). The reaction mixture was stirred at ambient temperature for 18 h. The reaction mixture was neutralized with 1 N HCl and concentrated to afford the crude product. The crude product was dissolved in DMSO (2 mL) and purified on a Gilson HPLC, eluting at 20 mL/min with a linear gradient running from 40% CH₃CN/H₂O (0.1% TFA) to 90% CH₃CN/H₂O (0.1% TFA) over 15 min. The desired fraction was concentrated to afford the title compound (12.53 mg, 0.024 mmol, 88% yield). LC-MS m/z 526.4 (M+H)+, 1.04 min (ret. time). ¹H NMR (400 MHz, methanol-d₄) δ ppm: 1.33 (m, J=5.80 Hz, 1H) 1.46 (s, 9H) 1.70 (m, J=13.10 Hz, 1H) 1.78-1.89 (m, 1H) 1.90-1.98 (m, 1H) 2.01-2.17 (m, 3H) 2.17-2.30 (m, 1H) 2.44 (m, J=7.00 Hz, 3H) 2.63-2.73 (m, 2H) 2.89 (m, J=1.00, 1.00 Hz, 1H) 3.97 (d, J=14.30 Hz, 3H) 4.36-4.50 (m, 1H) 7.37-7.58 (m, 7H) 8.04 (s, 1H).

Example 40. 1-(3-((1,3-trans)-3-(6,6-Dimethyl-5,6-dihydrocyclopenta[c]pyrazol-1(4H)-yl)cyclohexyl)phenyl)-5-(2-(1-methyl-1H-1,2,3-triazol-4-yl)cyclopropyl)-1H-pyrazole-4-carboxylic Acid

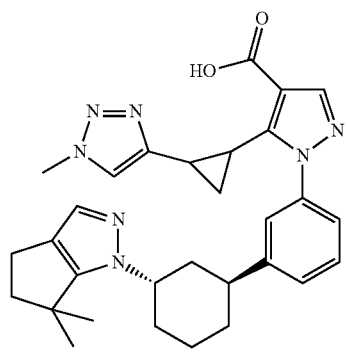 [SMILES: Cn1cc(C2CC2c2c(C(=O)O)cnn2-c2cccc([C@H]3CCC[C@H](n4ncc5c4C(C)(C)CC5)C3)c2)nn1]

40a) Methyl 1-(3-((1,3-trans)-3-hydrazinylcyclohexyl)phenyl)-5-(2-(1-methyl-1H-1,2,3-triazol-4-yl)cyclopropyl)-1H-pyrazole-4-carboxylate hydrochloride

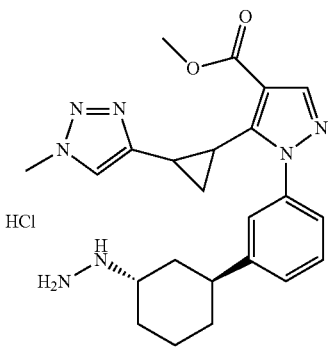 [SMILES: Cl ; COC(=O)c1cnn(-c2cccc([C@H]3CCC[C@H](NN)C3)c2)c1C1CC1c1cn(C)nn1]

To a solution of methyl 1-(3-((1,3-trans)-3-(2-(tert-butoxycarbonyl)hydrazinyl)cyclohexyl)phenyl)-5-(2-(1-methyl-1H-1,2,3-triazol-4-yl)cyclopropyl)-1H-pyrazole-4-carboxylate (780 mg, 1.456 mmol) in dichloromethane (DCM) (8 mL) was added HCl in dioxane (2.184 mL, 8.74 mmol). The reaction mixture was stirred at ambient temperature for 16.5 h. LCMS showed good conversion although some starting material remained. To the reaction mixture was added HCl in dioxane (4M, 0.500 mL). The reaction mixture was stirred at ambient temperature for an additional 1.5 h. LCMS showed desired product. The reaction mixture was concentrated to afford the title compound (740.5 mg, 1.569 mmol, 108% yield) an HCl salt. LC-MS m/z 436.3 (M+H)$^+$, 0.65 min (ret. time).

40b) Methyl 1-(3-((1,3-trans)-3-(6,6-dimethyl-5,6-dihydrocyclopenta[c]pyrazol-1(4H)-yl)cyclohexyl)phenyl)-5-(2-(1-methyl-1H-1,2,3-triazol-4-yl)cyclopropyl)-1H-pyrazole-4-carboxylate

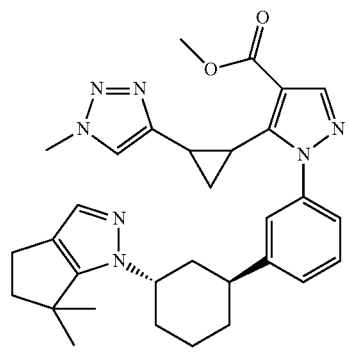 [SMILES: COC(=O)c1cnn(-c2cccc([C@H]3CCC[C@H](n4ncc5c4C(C)(C)CC5)C3)c2)c1C1CC1c1cn(C)nn1]

To a solution of methyl 1-(3-((1S,3S)-3-hydrazinylcyclohexyl)phenyl)-5-(2-(1-methyl-1H-1,2,3-triazol-4-yl)cyclopropyl)-1H-pyrazole-4-carboxylate hydrochloride (80 mg, 0.169 mmol) in Acetic Acid (1 mL) was added 5-((dimethylamino)methylene)-2,2-dimethylcyclopentanone (28.3 mg, 0.169 mmol). The reaction mixture was stirred at reflux for 3 h. The reaction mixture was neutralized with 1N NaOH and concentrated. The crude product was dissolved in DMSO (2 mL) and purified on a Gilson HPLC, eluting at 20 mL/min with a linear gradient running from 40% CH$_3$CN/H$_2$O to 90% CH$_3$CN/H$_2$O over 15 min. The desired fractions were concentrated to afford the title compound (33.7 mg, 0.062 mmol, 36.8% yield). LC-MS m/z 540.2 (M+H)$^+$, 1.14 min (ret. time).

40c) 1-(3-((1,3-trans)-3-(6,6-Dimethyl-5,6-dihydrocyclopenta[c]pyrazol-1(4H)-yl)cyclohexyl)phenyl)-5-(2-(1-methyl-1H-1,2,3-triazol-4-yl)cyclopropyl)-1H-pyrazole-4-carboxylic Acid

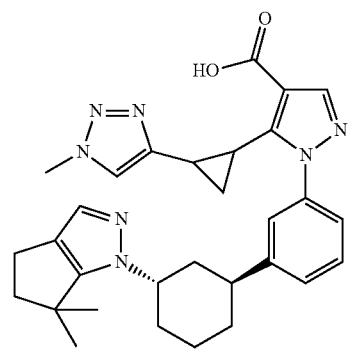 [SMILES: Cn1cc(C2CC2c2c(C(=O)O)cnn2-c2cccc([C@H]3CCC[C@H](n4ncc5c4C(C)(C)CC5)C3)c2)nn1]

To a solution of methyl 1-(3-((1S,3S)-3-(6,6-dimethyl-5,6-dihydrocyclopenta[c]pyrazol-1(4H)-yl)cyclohexyl)phenyl)-5-(2-(1-methyl-1H-1,2,3-triazol-4-yl)cyclopropyl)-1H-pyrazole-4-carboxylate (33.7 mg, 0.062 mmol) in methanol (0.5 mL) was added LiOH (0.031 mL, 0.062 mmol). The reaction vessel was heated in a Biotage microwave at high absorption for 30 min at 80° C. The reaction mixture was neutralized with 1 N HCl and concentrated. The crude product was dissolved in DMSO (2 mL) and purified on a Gilson HPLC, eluting at 20 mL/min with a linear gradient running from 40% CH$_3$CN/H$_2$O (0.1% TFA) to 90% CH$_3$CN/H$_2$O (0.1% TFA) over 15 min. The desired fractions were concentrated to afford the title compound (17.96 mg, 0.034 mmol, 54.7% yield). LC-MS m/z 526.2 (M+H)$^+$, 1.04 min (ret. time) $^1$H NMR (400 MHz, methanol-d4) δ ppm: 1.10-1.27 (m, 6H) 1.35 (br. s., 2H) 1.63-1.78 (m, 1H) 1.97 (br. s., 3H) 2.04-2.15 (m, 1H) 2.33 (d, J=5.02 Hz, 5H) 2.48 (br. s., 1H) 2.60 (d, J=6.78 Hz, 2H) 2.67 (s, 2H) 3.44 (br. s., 1H) 4.02 (d, J=6.78 Hz, 3H) 4.31 (br. s., 1H) 7.35 (br. s., 1H) 7.37-7.45 (m, 1H) 7.51 (d, J=10.29 Hz, 4H) 8.04 (s, 1H).

Example 41. 1-(3-(3-((2-Butylcyclopentyl)(methyl)carbamoyl)cyclohexyl)phenyl)-5-cyclopropyl-1H-pyrazole-4-carboxylic Acid

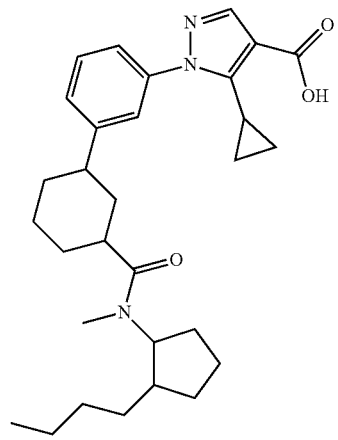 [SMILES: CCCCC1CCCC1N(C)C(=O)C1CCCC(c2cccc(-n3ncc(C(=O)O)c3C3CC3)c2)C1]

41a) 2-Butyl-N-methylcyclopentanamine

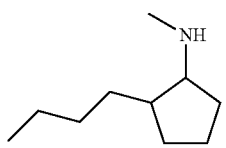

To a mixture of 2-butylcyclopentanone (1 g, 7.13 mmol) and methanamine (14.26 mL, 14.26 mmol) in tetrahydrofuran (THF) (5 mL) at 20° C. was added AcOH (0.082 mL, 1.426 mmol) following by addition of sodium triacetoxyborohydride (3.02 g, 14.26 mmol). It was stirred for 10 h. The reaction was diluted with NaHCO$_3$ solution and extracted with EtOAc (2×20 mL). The combined organic layer was washed with brine solution (20 mL), dried over anhydrous Na2SO$_4$, filtered and concentrated to give the title compound (650 mg, 4.19 mmol, 58.7% yield) as a gammy solid. It was carried to the next step. $^1$H NMR (400 MHz, DMSO-d$_6$) δ ppm: 0.78-0.93 (m, 3H) 1.05-1.33 (m, 6H) 1.34-1.49 (m, 2H) 1.51-1.65 (m, 2H) 1.66-1.83 (m, 2H) 1.83-1.93 (m, 1H) 1.97-2.21 (m, 2H) 2.22-2.30 (m, 3H) 2.52-2.56 (m, 0.5H) 2.75-2.83 (m, 0.5H) 3.57-3.65 (m, 1H).

41b) N-(2-Butylcyclopentyl)-N-methyl-3-oxocyclohexanecarboxamide

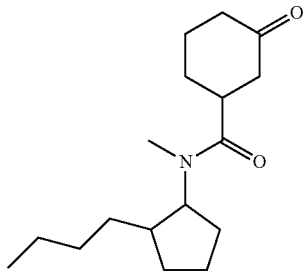 [SMILES: CCCCC1CCCC1N(C)C(=O)C1CCCC(=O)C1]

To a solution of 3-oxocyclohexanecarboxylic acid (600 mg, 4.22 mmol) in dichloromethane (DCM) (15 mL) was added HATU (1605 mg, 4.22 mmol). It was stirred at ambient temperature for 30 min. 2-Butyl-N-methylcyclopentanamine (655 mg, 4.22 mmol) was added followed by addition of DIPEA (1.843 mL, 10.55 mmol). It was stirred for 4 h. The reaction was diluted with NaHCO$_3$ solution and extracted with EtOAc (2×20 mL). The combined organic layer was washed with brine solution (20 mL), dried over anhydrous Na$_2$SO$_4$, filtered and concentrated. The crude residue was purified on flash column chromatography eluting with EtOAc:hexane (4:6). Desired fractions were concentrated to give the title compound (400 mg, 0.747 mmol, 17.69% yield) as a color less liquid. LC-MS m/z 280.0 (M+H)$^+$, 3.822 min (ret. time).

41c) 3-((2-Butylcyclopentyl)(methyl)carbamoyl)cyclohex-1-en-1-yl trifluoromethanesulfonate

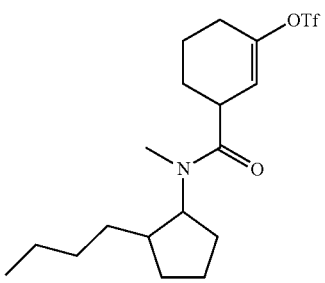 [SMILES: CCCCC1CCCC1N(C)C(=O)C1C=C(OS(=O)(=O)C(F)(F)F)CCC1]

To a solution of N-(2-butylcyclopentyl)-N-methyl-3-oxocyclohexanecarboxamide (400 mg, 1.432 mmol) and 1,1,1-trifluoro-N-phenyl-N-((trifluoromethyl)sulfonyl)methanesulfonamide (511 mg, 1.432 mmol) in tetrahydrofuran (THF) (10 mL) at −78° C. was added NaHMDS (0.716 mL, 1.432 mmol) slowly. The reaction mixture was allowed to stir at ambient temperature for 20 h. The reaction was diluted with water (30 mL) and extracted with EtOAc (2×20 mL). The combined organic layer was washed with brine solution (20 mL), dried over anhydrous Na$_2$SO$_4$, filtered and concentrated to give the title compound (1 g, 2.430 mmol, 170% yield). LC-MS m/z 412.1 (M+H)$^+$, 4.662 min (ret. time).

41d) Ethyl 1-(5'-((2-butylcyclopentyl)(methyl)carbamoyl)-2',3',4',5'-tetrahydro-[1,1'-biphenyl]-3-yl)-5-cyclopropyl-1H-pyrazole-4-carboxylate

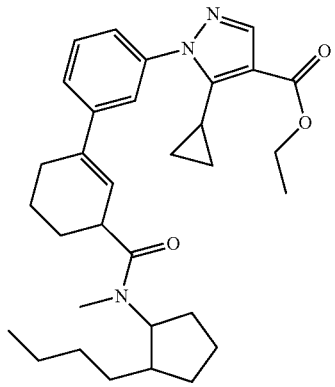 [SMILES: CCCCC1CCCC1N(C)C(=O)C1C=C(c2cccc(-n3ncc(C(=O)OCC)c3C3CC3)c2)CCC1]

To solution of ethyl 5-cyclopropyl-1-(3-(4,4,5,5-tetramethyl-1,3,2-dioxaborolan-2-yl)phenyl)-1H-pyrazole-4-carboxylate (150 mg, 0.392 mmol) and 3-((2-butylcyclopentyl)(methyl)carbamoyl)cyclohex-1-en-1-yltrifluoromethanesulfonate (194 mg, 0.471 mmol) in ethanol (1 mL) and toluene (3.00 mL) was added sodium carbonate (0.392 mL, 1.177 mmol). The reaction mixture was degassed with argon for 20 min, then tetrakis(triphenylphosphine)palladium(0) (22.67 mg, 0.020 mmol) was added. It was heated at 100° C. for 3 h. The reaction was cooled to RT and diluted with water. It was extracted with EtOAc (2×20 mL). The combined organic layer was washed with brine solution (20 mL), dried over anhydrous Na$_2$SO$_4$, filtered and concentrated. The crude residue was purified on flash column chromatography eluting with EtOAc:hexane (6:4) to give the title compound (250 mg, 0.331 mmol, 84% yield). LCMS m/z 518.2 (M+H)⁺, 4.598 min (ret. time).

41e) Ethyl 1-(3-(3-((2-butylcyclopentyl)(methyl)carbamoyl)cyclohexyl)phenyl)-5-cyclopropyl-1H-pyrazole-4-carboxylate

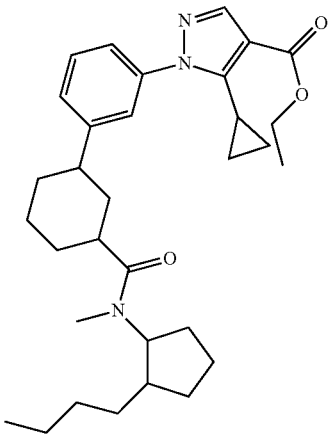 [SMILES: CCCCC1CCCC1N(C)C(=O)C1CCCC(c2cccc(-n3ncc(C(=O)OCC)c3C3CC3)c2)C1]

To a solution of ethyl 1-(5'-((2-butylcyclopentyl)(methyl)carbamoyl)-2',3',4',5'-tetrahydro-[1,1'-biphenyl]-3-yl)-5-cyclopropyl-1H-pyrazole-4-carboxylate (250 mg, 0.483 mmol) in ethanol (5 mL) was added palladium (51.4 mg, 0.483 mmol) under Nitrogen atmosphere. The reaction mixture was stirred under Hydrogen atmosphere (50 psi) at 25° C. for 8 h. The reaction mixture was filtered through celite pad and the filtrate was concentrated to give the title compound (110 mg, 0.164 mmol, 33.9% yield) as a gammy liquid. LCMS m/z 520.2 (M+H)⁺, 4.609 min (ret. time).

41f) 1-(3-(3-((2-Butylcyclopentyl)(methyl)carbamoyl)cyclohexyl)phenyl)-5-cyclopropyl-1H-pyrazole-4-carboxylic Acid

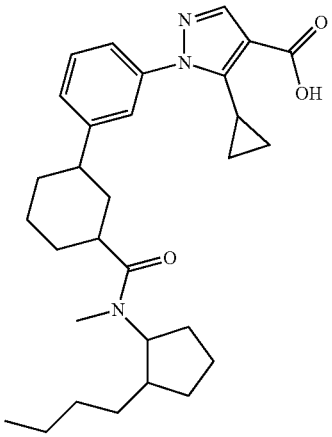 [SMILES: CCCCC1CCCC1N(C)C(=O)C1CCCC(c2cccc(-n3ncc(C(=O)O)c3C3CC3)c2)C1]

To a solution of ethyl 1-(3-(3-((2-butylcyclopentyl)(methyl)carbamoyl)cyclohexyl)phenyl)-5-cyclopropyl-1H-pyrazole-4-carboxylate (110 mg, 0.212 mmol) in ethanol (5 mL) was added 2N NaOH (0.212 mL, 0.423 mmol). It was stirred for 5 h and then concentrated. The residue was diluted with ice water and acidified with 2N HCl to pH 2. The aqueous layer was extracted with DCM (2×20 mL). The combined organic layer was washed with brine solution (20 mL) and dried over anhydrous Na₂SO₄, filtered and concentrated. The crude residue was purified on flash column chromatography eluting with MeOH:DCM (0.5:9.5). Desired fractions were concentrated to give the title compound (28 mg, 0.052 mmol, 24.43% yield) as a pale yellow solid. LC-MS m/z 492.41, 492.45 & 492.41 (M+H)⁺, 6.50, 6.57 & 6.62 min (ret. time).

Example 42. 1-(3-(3-(2-Butylpyrrolidine-1-carbonyl)cyclohexyl)phenyl)-5-(2-(1-methyl-1H-1,2,3-triazol-4-yl)cyclopropyl)-1H-pyrazole-4-carboxylic Acid

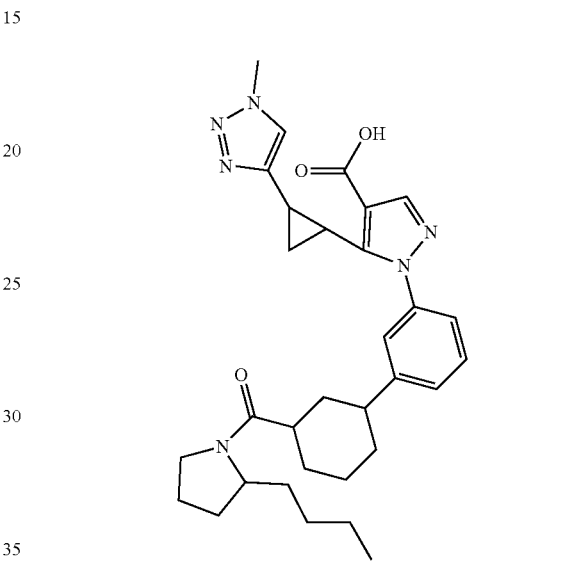

42a) Ethyl 1-(5'-(2-butylpyrrolidine-1-carbonyl)-2',3',4',5'-tetrahydro-[1,1'-biphenyl]-3-yl)-5-(2-(1-methyl-1H-1,2,3-triazol-4-yl)cyclopropyl)-1H-pyrazole-4-carboxylate

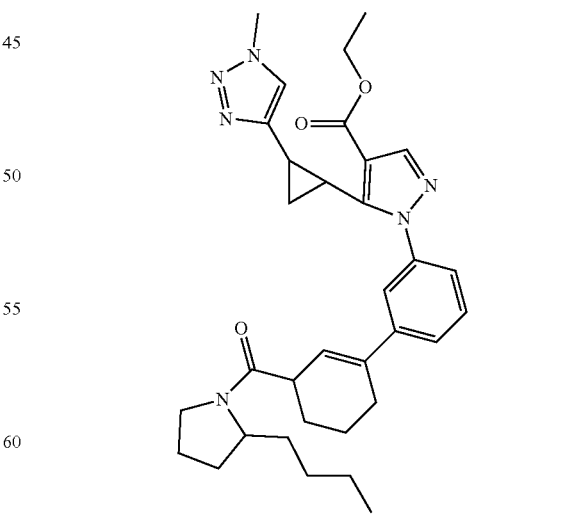

To a solution of ethyl 5-(2-(1-methyl-1H-1,2,3-triazol-4-yl)cyclopropyl)-1-(3-(4,4,5,5-tetramethyl-1,3,2-dioxaborolan-2-yl)phenyl)-1H-pyrazole-4-carboxylate (300 mg, 0.647 mmol) in a mixture of N,N-dimethylformamide (DMF) (3 mL) and water (0.5 mL), 3-(2-butylpyrrolidine-1-carbonyl)cyclohex-1-en-1-yltrifluoromethanesulfonate (745 mg, 1.942 mmol), Na$_2$CO$_3$ (206 mg, 1.942 mmol) and PdCl$_2$(dppf)-CH$_2$Cl$_2$ adduct (52.9 mg, 0.065 mmol) were added. The reaction mixture was stirred at 100° C. for 4 h. The solvent was evaporated under Biotage V-10 and was purified by reverse-phase HPLC under acidic condition to obtain the title compound (150 mg, 0.263 mmol, 40.6% yield). LC-MS m/z 571.4 (M+H)$^+$, 1.19 min (ret. time).

42b) Ethyl 1-(3-(3-(2-butylpyrrolidine-1-carbonyl)cyclohexyl)phenyl)-5-(2-(1-methyl-1H-1,2,3-triazol-4-yl)cyclopropyl)-1H-pyrazole-4-carboxylate

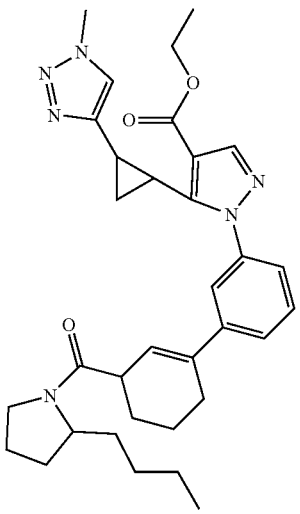 [SMILES: CCCCC1CCCN1C(=O)C1C=C(c2cccc(-n3ncc(C(=O)OCC)c3C3CC3c3cn(C)nn3)c2)CCC1]

To a solution of ethyl 1-(5'-(2-butylpyrrolidine-1-carbonyl)-2',3',4',5'-tetrahydro-[1,1'-biphenyl]-3-yl)-5-(2-(1-methyl-1H-1,2,3-triazol-4-yl)cyclopropyl)-1H-pyrazole-4-carboxylate (150 mg, 0.263 mmol) in ethanol (10 mL), Pd/C (10%, 28.0 mg, 0.026 mmol) was added. Then the reaction mixture was hydrogenated under H$_2$ parr for 6 h. Pd was filtered through celite. The filtrate was concentrated to obtain the title compound (140 mg, 0.244 mmol, 93% yield) which was used in next step without further purification. LC-MS m/z 5713.5 (M+H)$^+$, 1.19 min (ret. time).

42c) 1-(3-(3-(2-Butylpyrrolidine-1-carbonyl)cyclohexyl)phenyl)-5-(2-(1-methyl-1H-1,2,3-triazol-4-yl)cyclopropyl)-1H-pyrazole-4-carboxylic Acid

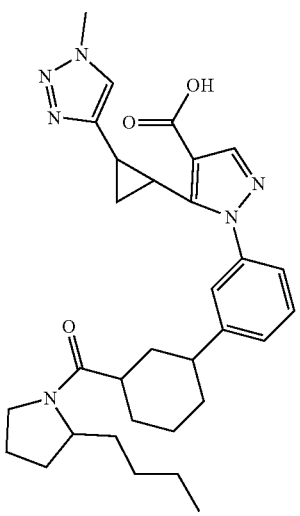 [SMILES: CCCCC1CCCN1C(=O)C1CCCC(c2cccc(-n3ncc(C(=O)O)c3C3CC3c3cn(C)nn3)c2)C1]

To a solution of ethyl 1-(3-(3-(2-butylpyrrolidine-1-carbonyl)cyclohexyl)phenyl)-5-(2-(1-methyl-1H-1,2,3-triazol-4-yl)cyclopropyl)-1H-pyrazole-4-carboxylate (140 mg, 0.244 mmol) in methanol (2 mL), LiOH (29.3 mg, 1.222 mmol) and 5 drop of water were added. The reaction mixture was stirred at room temperature for 16 h. Then 1N of HCl was added until pH=1. All the solvent was evaporated under Biotage v-10. The crude product was purified by reverse-phase HPLC to obtain the title compound (27.8 mg, 0.051 mmol, 20.8% yield). LC-MS m/z 545.3 (M+H)$^+$, 1.03 min (ret. time).

Example 43. 1-(3-((R)-3-(Cyclohexylmethoxy)piperidin-1-yl)phenyl)-5-((1R,2R)-2-(1-methyl-1H-1,2,3-triazol-4-yl)cyclopropyl)-1H-pyrazole-4-carboxylic Acid

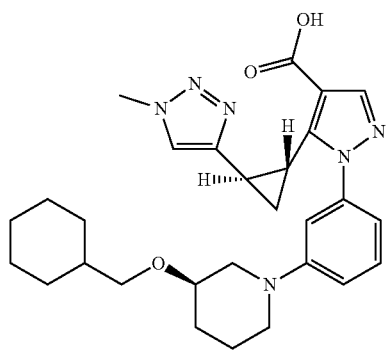

1-(3-((R)-3-(cyclohexylmethoxy)piperidin-1-yl)phenyl)-5-((1R,2R)-2-(1-methyl-1H-1,2,3-triazol-4-yl)cyclopropyl)-1H-pyrazole-4-carboxylic acid 43a) ((R)-3-((tert-Butyldiphenylsilyl)oxy)piperidine

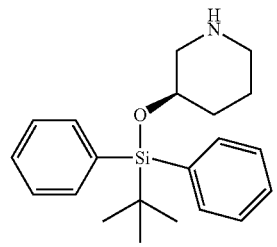 [SMILES: CC(C)(C)[Si](O[C@@H]1CCCNC1)(c1ccccc1)c1ccccc1]

Dissolved (R)-tert-butyl 3-hydroxypiperidine-1-carboxylate (626.3 mg, 3.11 mmol) in Dichloromethane (DCM) (14 mL). Added imidazole (233 mg, 3.42 mmol) and DMAP (19.01 mg, 0.156 mmol), then added TBDPS-Cl (0.879 mL, 3.42 mmol) slowly. The reaction was stirred for 17 h, and then diluted with DCM (25 mL). The organic layer was washed with water (15 mL), 10% citric acid (15 mL) and brine (15 mL). The organic layer was dried MgSO$_4$, filtered and concentrated in vacuo. The compound was purified by flash chromatography on silica running from 100% Hexane to 40% EtOAc/60% Hexane. The desired fractions were concentrated down to give (R)-tert-butyl 3-((tert-butyldiphenylsilyl)oxy)piperidine-1-carboxylate (1.3758 g, 101% yield). %). LC-MS 1.75 min (ret. time).

Dissolved (R)-tert-butyl 3-((tert-butyldiphenylsilyl)oxy) piperidine-1-carboxylate (1.3758 g, 3.13 mmol) in dichloromethane (DCM) (14 mL). Added 4M HCl in 1,4-dioxane (7.82 mL, 31.3 mmol). The reaction was stirred for 16 h, and then concentrated in vacuo to give (R)-3-((tert-butyldiphenylsilyl)oxy)piperidine, Hydrochloride (1.2072 g, 3.21 mmol, 103% yield). LC-MS m/z 340.0 (M+H)+, 1.09 min (ret. time). The HCl salt was taken up in EtOAc (100 mL) and then washed twice with $K_2CO_3$ (1M, 50 mL). The organic layer was dried with $MgSO_4$, filtered and concentrated in vacuo to give the title compound (911.3 mg, 86% yield). LC-MS m/z 340.1 (M+H)+, 1.08 min (ret. time).

43b) Cyclohexylmethyl Methanesulfonate

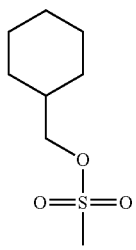

Dissolved cyclohexylmethanol (1.071 ml, 8.76 mmol) in Dichloromethane (DCM) (60 ml). Added TEA (2.441 ml, 17.52 mmol) and chilled the reaction in an ice bath to 0° C. Methanesulfonyl chloride (0.817 ml, 10.51 mmol) was added and the reaction was stirred for 16 h. The organic layer was washed with $NaHCO_3$, followed by brine. The organic layer was dried $MgSO_4$, filtered and concentrated to give the title compound (1.6218 g, 8.43 mmol, 96% yield). $^1H$ NMR (chloroform-d) δ: 4.04 (d, J=6.0 Hz, 2H), 3.01 (s, 3H), 1.67-1.84 (m, 6H), 1.15-1.35 (m, 3H), 0.96-1.09 (m, 2H).

43c) Ethyl 1-(3-((R)-3-((tert-butyldiphenylsilyl)oxy) piperidin-1-yl)phenyl)-5-((1R,2R)-2-(1-methyl-1H-1,2,3-triazol-4-yl)cyclopropyl)-1H-pyrazole-4-carboxylate

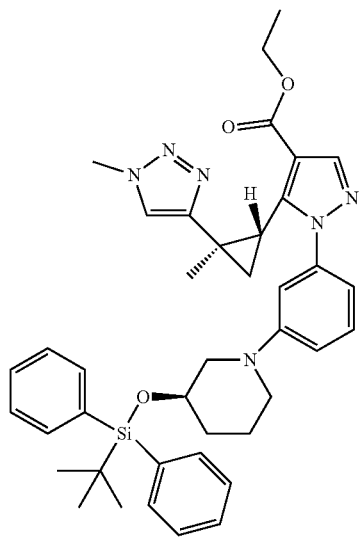 [SMILES: CCOC(=O)c1cnn(-c2cccc(N3CCC[C@@H](O[Si](c4ccccc4)(c4ccccc4)C(C)(C)C)C3)c2)c1[C@@H]1C[C@@]1(C)c1cn(C)nn1]

To a suspension of ethyl 1-(3-bromophenyl)-5-((1R,2R)-2-(1-methyl-1H-1,2,3-triazol-4-yl)cyclopropyl)-1H-pyrazole-4-carboxylate (416 mg, 0.999 mmol), (R)-3-((tert-butyldiphenylsilyl)oxy)piperidine (353 mg, 1.040 mmol), and XPhos Pd G3 (55 mg, 0.065 mmol) in 1,4-Dioxane (10 mL) was added $K_3PO_4$ (339 mg, 1.597 mmol). The reaction was then heated to 95° C. for 19 h. More XPhos Pd G3 (55 mg, 0.065 mmol) was then added and reheated for 24 h. The reaction was diluted with DCM (100 mL) and concentrated in vacuo. The compound was purified by flash chromatography on silica running from 100% Hex to 100% EtOAc. The desired fractions were concentrated to give the title compound (268.7 mg, 39.8% yield).). LC-MS m/z 675.5 (M+H)+, 1.66 min (ret. time).

43d) Ethyl 1-(3-((R)-3-hydroxypiperidin-1-yl)phenyl)-5-((1R,2R)-2-(1-methyl-1H-1,2,3-triazol-4-yl)cyclopropyl)-1H-pyrazole-4-carboxylate

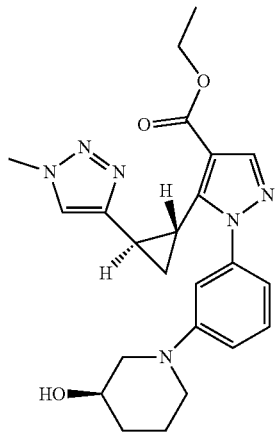 [SMILES: CCOC(=O)c1cnn(-c2cccc(N3CCC[C@@H](O)C3)c2)c1[C@@H]1C[C@H]1c1cn(C)nn1]

Ethyl 1-(3-((R)-3-((tert-butyldiphenylsilyl)oxy)piperidin-1-yl)phenyl)-5-((1R,2R)-2-(1-methyl-1H-1,2,3-triazol-4-yl)cyclopropyl)-1H-pyrazole-4-carboxylate (268.7 mg, 0.398 mmol) was dissolved in Tetrahydrofuran (THF) (4 mL). Added 1M TBAF in THF (0.44 mL, 0.440 mmol). The reaction was stirred for 80 min, then diluted with DCM (15 mL) and concentrated. The compound was purified by flash chromatography on silica running from 100% Hex to 100% EtOAc, then switched the solvents to 100% DCM to 80% DCM \ 20% (90% MeOH/10% $NH_4OH$). The desired fractions were concentrated down to give the title compound (146.3 mg, 84% yield). LC-MS m/z 437.3 (M+H)+, 0.83 min (ret. time).

43e) 1-(3-((R)-3-(Cyclohexylmethoxy)piperidin-1-yl)phenyl)-5-((1R,2R)-2-(1-methyl-1H-1,2,3-triazol-4-yl)cyclopropyl)-1H-pyrazole-4-carboxylic Acid

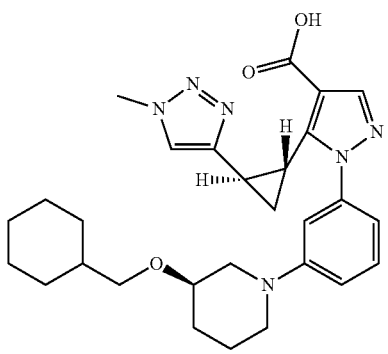 [SMILES: Cn1cc([C@@H]2C[C@H]2c2c(C(=O)O)cnn2-c2cccc(N3CCC[C@@H](OCC4CCCCC4)C3)c2)nn1]

Weighed out ethyl 1-(3-((R)-3-hydroxypiperidin-1-yl)phenyl)-5-((1R,2R)-2-(1-methyl-1H-1,2,3-triazol-4-yl)cyclopropyl)-1H-pyrazole-4-carboxylate (46.7 mg, 0.107 mmol) and dissolved in N,N-Dimethylformamide (DMF) (1.0 mL). Added 60% NaH in oil (10 mg, 0.250 mmol). The reaction was stirred for 15 min, then added cyclohexylmethyl methanesulfonate (38 mg, 0.198 mmol) and heated the reaction to 70° C. for 20 h. The reaction was filtered and then purified by reverse-phase HPLC under acidic conditions to afford the title compound (8.3 mg, 15.37% yield). LC-MS m/z 505.4 (M+H)$^+$, 1.13 min (ret. time). $^1$H NMR (400 MHz, DMSO-d$_6$) δ: 7.95 (s, 1H), 7.60 (s, 1H), 7.33-7.26 (m, 1H), 7.05-6.97 (m, 2H), 6.86 (d, J=7.5 Hz, 1H), 3.96 (s, 3H), 3.63-3.56 (m, 1H), 3.38-3.20 (m, 4H), 2.78-2.60 (m, 2H), 2.47-2.41 (m, 1H), 2.27-2.19 (m, 1H), 1.97-1.88 (m, 1H), 1.77-1.57 (m, 5H), 1.46 (d, J=9.5 Hz, 2H), 1.38-1.24 (m, 3H), 1.22-1.12 (m, 3H), 0.92-0.82 (m, 3H).

The invention claimed is:
1. A compound of Formula (I)

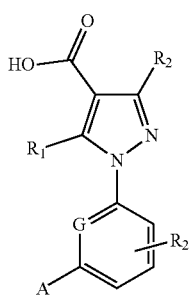

(I)

wherein:
R$_1$ is —CF$_3$, —C$_{3-7}$cycloalkyl, or —C$_{4-7}$heterocycloalkyl, wherein the —C$_{3-7}$cycloalkyl, and —C$_{4-7}$heterocycloalkyl is unsubstituted or substituted by one or two substituents independently selected from —C$_{1-3}$alkyl, phenyl, triazolyl, pyridyl, pyridazinyl, imidazolyl, pyrazolyl, isoxazolyl, halo, —NR$_9$—C(O)—R$_{10}$ and —C(O)R$_{10}$, and wherein the phenyl, triazolyl, pyridyl, pyridazinyl, imidazolyl, pyrazolyl and isoxazolyl is unsubstituted or substituted by one or two substituents independently selected from —C$_{1-3}$alkyl and halo; or
R$_1$ is —C$_{2-3}$alkyl-R$_{11}$;
Each R$_2$ is independently hydrogen, halo, or —C$_{1-3}$alkyl;
G is CH or N;
A is

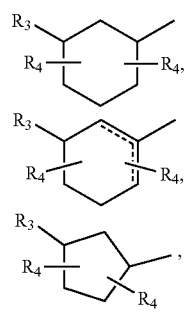

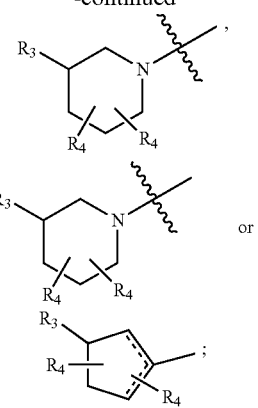

R$_3$ is —(CH$_2$)$_n$—C(O)N(R$_5$)(R$_6$),

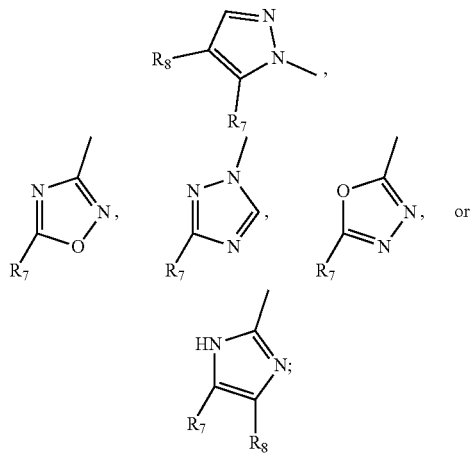

or R$_3$ is —O—C$_{1-3}$alkyl, —C$_{1-6}$alkyl, —C$_{4-7}$heterocycloalkyl, —O—C$_{4-7}$heterocycloalkyl, —C$_{3-7}$cycloalkyl, —O—C$_{3-7}$cycloalkyl, —C(O)—O—C$_{1-5}$alkyl, —C(O)—C$_{1-5}$alkyl, —C(O)-aryl, —S—C$_{1-3}$alkyl, —S—C$_{4-7}$heterocycloalkyl, —S—C$_{3-7}$cycloalkyl, —S(O)—C$_{1-3}$alkyl, —S(O)—C$_{4-7}$heterocycloalkyl, —S(O)—C$_{3-7}$cycloalkyl, —S(O)$_2$—C$_{1-3}$alkyl, —S(O)$_2$—C$_{4-7}$heterocycloalkyl, —S(O)$_2$—C$_{3-7}$cycloalkyl, —S(O)$_2$-aryl, wherein each of —O—C$_{1-3}$alkyl, —C$_{1-6}$alkyl, —C$_{4-7}$heterocycloalkyl, —O—C$_{4-7}$heterocycloalkyl, —C$_{3-7}$cycloalkyl, —O—C$_{3-7}$cycloalkyl, —C(O)—C$_{1-5}$alkyl, —C(O)-aryl, —S—C$_{1-3}$alkyl, —S—C$_{4-7}$heterocycloalkyl, —S—C$_{3-7}$cycloalkyl, —S(O)—C$_{1-3}$alkyl, —S(O)—C$_{4-7}$heterocycloalkyl, —S(O)—C$_{3-7}$cycloalkyl, —S(O)$_2$—C$_{1-3}$alkyl, —S(O)$_2$—C$_{4-7}$heterocycloalkyl, —S(O)$_2$—C$_{3-7}$cycloalkyl —S(O)$_2$-aryl, is unsubstituted or substituted by one or two substituents independently selected from —C$_{1-7}$alkyl, —C$_{3-7}$cycloalkyl, —OH, =O, —O—C$_{1-5}$alkyl, —C$_{4-7}$heterocycloalkyl, phenyl, pyridyl, pyrazolyl, pyridazinyl, pyrimidinyl, pyrazinyl, and triazolyl, and wherein the —C$_{1-7}$alkyl, —C$_{3-7}$cycloalkyl, —O—C$_{1-3}$alkyl, —C$_{4-7}$heterocycloalkyl, phenyl, pyridyl, pyrazolyl, pyridazinyl, pyrimidinyl, pyrazinyl, or triazolyl is further unsubstituted or substituted by one or two substituents independently selected from C$_{1-5}$ alkyl and halo;

Each $R_4$ is independently hydrogen, halo or —$C_{1-3}$alkyl;

$R_5$ and $R_6$ are independently H, —$C_{1-6}$alkyl, —$C_{3-7}$cycloalkyl or —$C_{4-7}$heterocycloalkyl, wherein each of —$C_{1-6}$alkyl, —$C_{3-7}$cycloalkyl or —$C_{4-7}$heterocycloalkyl is unsubstituted or substituted by one or two substituents independently selected from F, —CH—F$_2$, —CF$_3$, —(CH$_2$)$_n$—O—(CH$_2$)$_m$—CH$_3$, and —$C_{3-7}$cycloalkyl;

or $R_5$ and $R_6$ together with the nitrogen atom to which they are attached form a 5-8-membered ring or an 8-10-membered bicyclic ring or a 9-10-membered bridged bicyclic ring, wherein each 5-8-membered ring, 8-11-membered bicyclic ring, or 9-10-membered bridged bicyclic ring optionally includes one or more oxygen ring atoms or another nitrogen ring atom, and wherein each 5-8-membered ring, 8-11-membered bicyclic ring, or 9-10-membered bridged bicyclic ring is unsubstituted or substituted by one or two substituents independently selected from —$C_{1-5}$alkyl, —$C_{3-7}$cycloalkyl, —$C_{4-7}$heterocycloalkyl, F, —CHF$_2$, —CF$_3$, and —(CH$_2$)$_n$—O—(CH$_2$)$_m$—CH$_3$;

$R_5$ and $R_6$ together with the nitrogen atom to which they are attached form 4-azaspiro[2.5]octane, 7-azaspiro[4.5]decane, 2-oxa-8-azaspiro[5.5]undecane, 6-oxa-9-azaspiro[4.5]decane, 2-oxa-8-azaspiro[5.5]undecane, or 1-azaspiro[4.5]decane;

$R_7$ and $R_8$ are independently H, —$C_{1-6}$alkyl, —$C_{3-7}$cycloalkyl or —$C_{4-7}$heterocycloalkyl wherein each of —$C_{1-6}$ alkyl, —$C_{3-7}$ cycloalkyl or —$C_{4-7}$ heterocycloalkyl is unsubstituted or substituted by one or two substituents independently selected from F, CHF$_2$, CF$_3$, and (CH$_2$)$_n$—O—(CH$_2$)$_m$—CH$_3$, or $R_7$ and $R_8$ together with the carbon atoms to which they are attached form a 5-8-membered ring, which optionally includes one or more oxygen or nitrogen atoms as ring atoms, and wherein the 5-8-membered ring is unsubstituted or substituted by one or two substituents independently selected from —$C_{1-5}$alkyl, —$C_{3-7}$cycloalkyl, —$C_{4-7}$heterocycloalkyl, F, —CHF$_2$, —CF$_3$, =O, and —(CH$_2$)$_n$—O—(CH$_2$)$_m$—CH$_3$;

$R_9$ is H or —$C_{1-3}$alkyl;

$R_{10}$ is —$C_{1-3}$ alkyl;

$R_{11}$ is phenyl, triazolyl, pyridyl, pyridazinyl, imidazolyl, or pyrazolyl, wherein each of phenyl, triazolyl, pyridyl, pyridazinyl, imidazolyl, or pyrazolyl is unsubstituted or substituted by one or two substituents independently selected from $C_{1-3}$alkyl and halo;

Each n is independently 0 or 1;

Each m is independently 0 or 1;

or a pharmaceutically acceptable salt thereof.

2. The compound of Formula (I) according to claim 1, wherein:

$R_1$ is —CF$_3$ or —$C_{3-7}$cycloalkyl, wherein the —$C_{3-7}$cycloalkyl, is unsubstituted or substituted by one or two substituents selected from —$C_{1-3}$alkyl and halo, or wherein the —$C_{3-7}$cycloalkyl is substituted by one substituent selected from triazolyl, pyridyl, pyridazinyl, imidazolyl, pyrazolyl and isoxazolyl, and wherein the triazolyl, pyridyl, pyridazinyl, imidazolyl, pyrazolyl and isoxazolyl is unsubstituted or substituted by one or two substituents selected from —$C_{1-3}$alkyl and halo;

$R_2$ is hydrogen;

G is CH;

A is

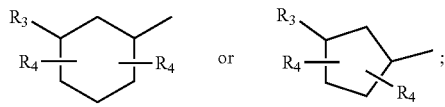

$R_3$ is —(CH$_2$)$_n$—C(O)N($R_5$)($R_6$), or

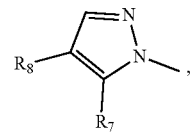

$R_3$ is —O—$C_{1-3}$alkyl, —$C_{1-6}$alkyl, —$C_{4-7}$heterocycloalkyl, —O—$C_{4-7}$heterocycloalkyl, —$C_{3-7}$cycloalkyl, or —O—$C_{3-7}$cycloalkyl, wherein each of —O—$C_{1-3}$alkyl, —$C_{1-6}$alkyl, —$C_{4-7}$heterocycloalkyl, —O—$C_{4-7}$heterocycloalkyl, —$C_{3-7}$cycloalkyl, or —O—$C_{3-7}$cycloalkyl, is unsubstituted or substituted by one or two substituents selected from —$C_{1-7}$alkyl, —$C_{3-7}$cycloalkyl, —OH, =O, —O—$C_{1-5}$alkyl, —$C_{4-7}$heterocycloalkyl, phenyl, pyridyl, pyrazolyl, pyridazinyl, pyrimidinyl, pyrazinyl, and triazolyl, and wherein the —$C_{1-7}$alkyl, —$C_{3-7}$cycloalkyl, —O—$C_{1-3}$alkyl, —$C_{4-7}$heterocycloalkyl, phenyl, pyridyl, pyrazolyl, pyridazinyl, pyrimidinyl, pyrazinyl, or triazolyl is unsubstituted or further substituted by one or two substituents independently selected from —$C_{1-5}$alkyl and halo;

Each $R_4$ is independently hydrogen, halo, or —$C_{1-3}$alkyl;

$R_5$ and $R_6$ are independently H, —$C_{1-6}$alkyl, —$C_{3-7}$cycloalkyl or —$C_{4-7}$heterocycloalkyl, wherein each of —$C_{1-6}$alkyl, —$C_{3-7}$cycloalkyl or —$C_{4-7}$heterocycloalkyl is unsubstituted or substituted by one or two substituents independently selected from F, —CH—F$_2$, —CF$_3$, —(CH$_2$)—O—(CH$_2$)$_m$—CH$_3$, and —$C_{3-7}$cycloalkyl;

or $R_5$ and $R_6$ together with the nitrogen atom to which they are attached form a 5-8-membered ring or an 8-10-membered bicyclic ring or a 9-10-membered bridged bicyclic ring, wherein each 5-8-membered ring, 8-11-membered bicyclic ring, or 9-10-membered bridged bicyclic ring optionally includes one or more oxygen ring atoms or another nitrogen ring atom, and wherein each 5-8-membered ring, 8-11-membered bicyclic ring, or 9-10-membered bridged bicyclic ring is unsubstituted or substituted by one or two substituents independently selected from —$C_{1-5}$alkyl, —$C_{3-7}$cycloalkyl, —$C_{4-7}$heterocycloalkyl, F, —CHF$_2$, —CF$_3$, and —(CH$_2$)$_n$—O—(CH$_2$)$_m$—CH$_3$;

$R_5$ and $R_6$ together with the nitrogen atom to which they are attached form 4-azaspiro[2.5]octane, 7-azaspiro[4.5]decane, 2-oxa-8-azaspiro[5.5]undecane, 6-oxa-9-azaspiro[4.5]decane, 2-oxa-8-azaspiro[5.5]undecane, or 1-azaspiro[4.5]decane;

$R_7$ and $R_8$ are independently H, —$C_{1-6}$alkyl, —$C_{3-7}$cycloalkyl or —$C_{4-7}$heterocycloalkyl wherein each of —$C_{1-6}$ alkyl, —$C_{3-7}$ cycloalkyl or —$C_{4-7}$ heterocycloalkyl is unsubstituted or substituted by one or two substituents independently selected from F, —CHF$_2$, —CF$_3$, and —(CH$_2$)$_n$—O—(CH$_2$)$_m$—CH$_3$;

or $R_7$ and $R_8$ together with the carbon atoms to which they are attached form a 5-8-membered ring, which optionally includes one or more oxygen or nitrogen atoms as ring atoms, and wherein the 5-8-membered ring is unsubstituted or substituted by one or two substituents independently selected from —$C_{1-5}$alkyl, —$C_{3-7}$cycloalkyl, —$C_{4-7}$heterocycloalkyl, F, —$CHF_2$, —$CF_3$, =O, and —$(CH_2)_n$—O—$(CH_2)_m$—$CH_3$;

Each n is independently 0 or 1;

Each m is independently 0 or 1;

or a pharmaceutically acceptable salt thereof.

3. The compound of claim 1 selected from:

5-Cyclopropyl-1-{3-[3-(dimethylcarbamoyl)cyclohexyl]phenyl}-1H-pyrazole-4-carboxylic acid (cis-racemate);

5-Cyclopropyl-1-{3-[3-(4,5,6,7-tetrahydro-1H-indazol-1-yl)cyclohexyl]phenyl}-1H-pyrazole-4-carboxylic acid;

5-Cyclopropyl-1-{3-[3-(piperidine-1-carbonyl)cyclohexyl]phenyl}-1H-pyrazole-4-carboxylic acid (cis-racemate);

1-[3-(3-{7-Azaspiro[4.5]decane-7-carbonyl}cyclohexyl)phenyl]-5-cyclopropyl-1H-pyrazole-4-carboxylic acid (cis-racemate);

5-Cyclopropyl-1-{3-[3-(2-propylpiperidine-1-carbonyl)cyclohexyl]phenyl}-1H-pyrazole-4-carboxylic acid;

5-cyclopropyl-1-{3-[3-(2,2-dimethylpyrrolidine-1-carbonyl)cyclohexyl]phenyl}-1H-pyrazole-4-carboxylic acid;

1-[3-(3-{1-Azaspiro[4.5]decane-1-carbonyl}cyclohexyl)phenyl]-5-cyclopropyl-1H-pyrazole-4-carboxylic acid;

1-{3-[3-(2-butylpyrrolidine-1-carbonyl)cyclohexyl]phenyl}-5-cyclopropyl-1H-pyrazole-4-carboxylic acid;

1-[3-(3-{1H,4H,5H,6H,7H,8H-cyclohepta[c]pyrazol-1-yl}cyclohexyl)phenyl]-5-cyclopropyl-1H-pyrazole-4-carboxylic acid;

1-[3-(3-{1H,4H,5H,6H-cyclopenta[c]pyrazol-1-yl}cyclopentyl)phenyl]-5-cyclopropyl-1H-pyrazole-4-carboxylic acid;

5-Cyclopropyl-1-(3-{3-[2-(3-methylbutyl)pyrrolidine-1-carbonyl]cyclohexy}phenyl)-1H-pyrazole-4-carboxylic acid;

5-Cyclopropyl-1-{3-[3-(2-cyclopropylpyrrolidine-1-carbonyl)cyclohexyl]phenyl}-1H-pyrazole-4-carboxylic acid;

1-{3-[3-(2-cyclobutylpyrrolidine-1-carbonyl)cyclohexyl]phenyl}-5-cyclopropyl-1H-pyrazole-4-carboxylic acid;

5-Cyclopropyl-1-{3-[(cis)-3-(6-methyl-5,6-dihydro-4H-cyclopentapyrazol-1-yl)-cyclohexyl]-phenyl}-1H-pyrazole-4-carboxylic acid (cis racemic);

5-Cyclopropyl-1-{3-[3-(4-oxo-4,5,6,7-tetrahydro-indazol-1-yl)-cyclopentyl]-phenyl}-1H-pyrazole-4-carboxylic acid;

5-Cyclopropyl-1-[3-(3-{6-propyl-1H,4H,5H,6H-cyclopenta[c]pyrazol-1-yl}cyclohexyl)phenyl]-1H-pyrazole-4-carboxylic acid (cis racemic);

1-{3-3-[2-butylpyrrolidine-1-carbonyl]cyclohexyl]phenyl}-5-cyclopropyl-1H-pyrazole-4-carboxylic acid;

5-Cyclopropyl-1-(3-{3-[(2S)-2-(ethoxymethyl)pyrrolidine-1-carbonyl]cyclohexyl}phenyl)-1H-pyrazole-4-carboxylic acid (cis stereoisomer 1);

5-Cyclopropyl-1-(3-{3-[(2S)-2-(ethoxymethyl)pyrrolidine-1-carbonyl]cyclohexyl}phenyl)-1H-pyrazole-4-carboxylic acid (cis stereoisomer 2);

1-(5'-(Azepane-1-carbonyl)-2',3',4',5'-tetrahydro-[1,1'-biphenyl]-3-yl)-5-cyclopropyl-1H-pyrazole-4-carboxylic acid;

1-(3-(3-(Azepane-1-carbonyl)cyclohexyl)phenyl)-5-cyclopropyl-1H-pyrazole-4-carboxylic acid;

1-(3-(3-(Cyclohexyl(methyl)carbamoyl)cyclohexyl)phenyl)-5-cyclopropyl-1H-pyrazole-4-carboxylic acid;

5-Cyclopropyl-1-(3-(3-(methyl(2-propylcyclohexyl)carbamoyl)cyclohexyl)phenyl)-1H-pyrazole-4-carboxylic acid;

5-Cyclopropyl-1-(3-(t-3-(6,6-dimethyl-5,6-dihydrocyclopenta[c]pyrazol-1(4H)-yl)cyclohexyl)phenyl)-1H-pyrazole-4-carboxylic acid (trans racemic);

5-Cyclopropyl-1-(3-(-3-(6,6-dimethyl-5,6-dihydrocyclopenta[c]pyrazol-1(4H)-yl)cyclohexyl)phenyl)-1H-pyrazole-4-carboxylic acid (cis racemate);

5-Cyclopropyl-1-{3-[3-(3-methyl-pyrrolidine-1-carbonyl)-cyclohexyl]-phenyl}-1H-pyrazole-4-carboxylic acid;

1-(3-(1-(tert-butoxycarbonyl)piperidin-3-yl)phenyl)-5-((1R,2R)-2-(1-methyl-1H-1,2,3-triazol-4-yl)cyclopropyl)-1H-pyrazole-4-carboxylic acid;

1-(3-(1-(tert-Butoxycarbonyl)piperidin-3-yl)phenyl)-5-cyclopropyl-1H-pyrazole-4-carboxylic acid;

1-(3-(1-(cyclohexylmethyl)piperidin-3-yl)phenyl)-5-cyclopropyl-1H-pyrazole-4-carboxylic acid, Hydrochloride;

5-((1R,2R)-2-(1-Methyl-1H-1,2,3-triazol-4-yl)cyclopropyl)-1-(3-(1-phenethylpiperidin-3-yl)phenyl)-1H-pyrazole-4-carboxylic acid, Hydrochloride;

5-((1R,2R)-2-(1-methyl-1H-1,2,3-triazol-4-yl)cyclopropyl)-1-(3-(1-(phenylsulfonyl)piperidin-3-yl)phenyl)-1H-pyrazole-4-carboxylic acid;

1-(3-(1-(2-cyclohexylacetyl)piperidin-3-yl)phenyl)-5-((1R,2R)-2-(1-methyl-1H-1,2,3-triazol-4-yl)cyclopropyl)-1H-pyrazole-4-carboxylic acid;

5-((1R,2R)-2-(1-methyl-1H-1,2,3-triazol-4-yl)cyclopropyl)-1-(3-(1-pivaloylpiperidin-3-yl)phenyl)-1H-pyrazole-4-carboxylic acid;

1-(3-(1-benzoylpiperidin-3-yl)phenyl)-5-((1R,2R)-2-(1-methyl-1H-1,2,3-triazol-4-yl)cyclopropyl)-1H-pyrazole-4-carboxylic acid;

5-((1R,2R)-2-(1-Methyl-1H-1,2,3-triazol-4-yl)cyclopropyl)-1-(3-(1-((R)-2-propylpiperidine-1-carbonyl)piperidin-3-yl)phenyl)-1H-pyrazole-4-carboxylic acid;

1-(3-(3-(2-cyclohexylethyl)piperidin-1-yl)phenyl)-5-((1R,2R)-2-(1-methyl-1H-1,2,3-triazol-4-yl)cyclopropyl)-1H-pyrazole-4-carboxylic acid;

1-(3-((S)-3-(2-Cyclohexylethyl)piperidin-1-yl)phenyl)-5-((1R,2R)-2-(1-methyl-1H-1,2,3-triazol-4-yl)cyclopropyl)-1H-pyrazole-4-carboxylic acid;

1-(3-((R)-3-(2-cyclohexylethyl)piperidin-1-yl)phenyl)-5-((1R,2R)-2-(1-methyl-1H-1,2,3-triazol-4-yl)cyclopropyl)-1H-pyrazole-4-carboxylic acid;

1-(3-((1R,3 S)-3-(6-Butyl-5,6-dihydrocyclopenta[c]pyrazol-1(4H)-yl)cyclohexyl)phenyl)-5-cyclopropyl-1H-pyrazole-4-carboxylic acid;

1-(3-((1,3-trans)-3-(6-Butyl-5,6-dihydrocyclopenta[c]pyrazol-1(4H)-yl)cyclohexyl)phenyl)-5-cyclopropyl-1H-pyrazole-4-carboxylic acid;

1-(3-((1,3-cis)-3-(6,6-Dimethyl-5,6-dihydrocyclopenta[c]pyrazol-1(4H)-yl)cyclohexyl)phenyl)-5-(2-(1-methyl-1H-1,2,3-triazol-4-yl)cyclopropyl)-1H-pyrazole-4-carboxylic acid;

1-(3-((1,3-trans)-3-(6,6-Dimethyl-5,6-dihydrocyclopenta[c]pyrazol-1(4H)-yl)cyclohexyl)phenyl)-5-(2-(1-methyl-1H-1,2,3-triazol-4-yl)cyclopropyl)-1H-pyrazole-4-carboxylic acid;

1-(3-(3-((2-Butylcyclopentyl)(methyl)carbamoyl)cyclohexyl)phenyl)-5-cyclopropyl-1H-pyrazole-4-carboxylic acid;

1-(3-(3-(2-Butylpyrrolidine-1-carbonyl)cyclohexyl)phenyl)-5-(2-(1-methyl-1H-1,2,3-triazol-4-yl)cyclopropyl)-1H-pyrazole-4-carboxylic acid; and 1-(3-((R)-3-(Cyclohexylmethoxy)piperidin-1-yl)phenyl)-5-((1R,2R)-2-(1-methyl-1H-1,2,3-triazol-4-yl)cyclopropyl)-1H-pyrazole-4-carboxylic acid.

4. A pharmaceutical composition comprising a compound of claim 1 and a pharmaceutically acceptable carrier or excipient.

5. A method for therapeutically treating COPD which comprises administering to a human in need thereof, a compound of claim 1.

6. The method according to claim 5 wherein the compound is administered orally.

7. The method according to claim 5 wherein the compound is administered intravenously.

8. The method according to claim 5 wherein the compound is administered by inhalation.

* * * * *